Figure 1:
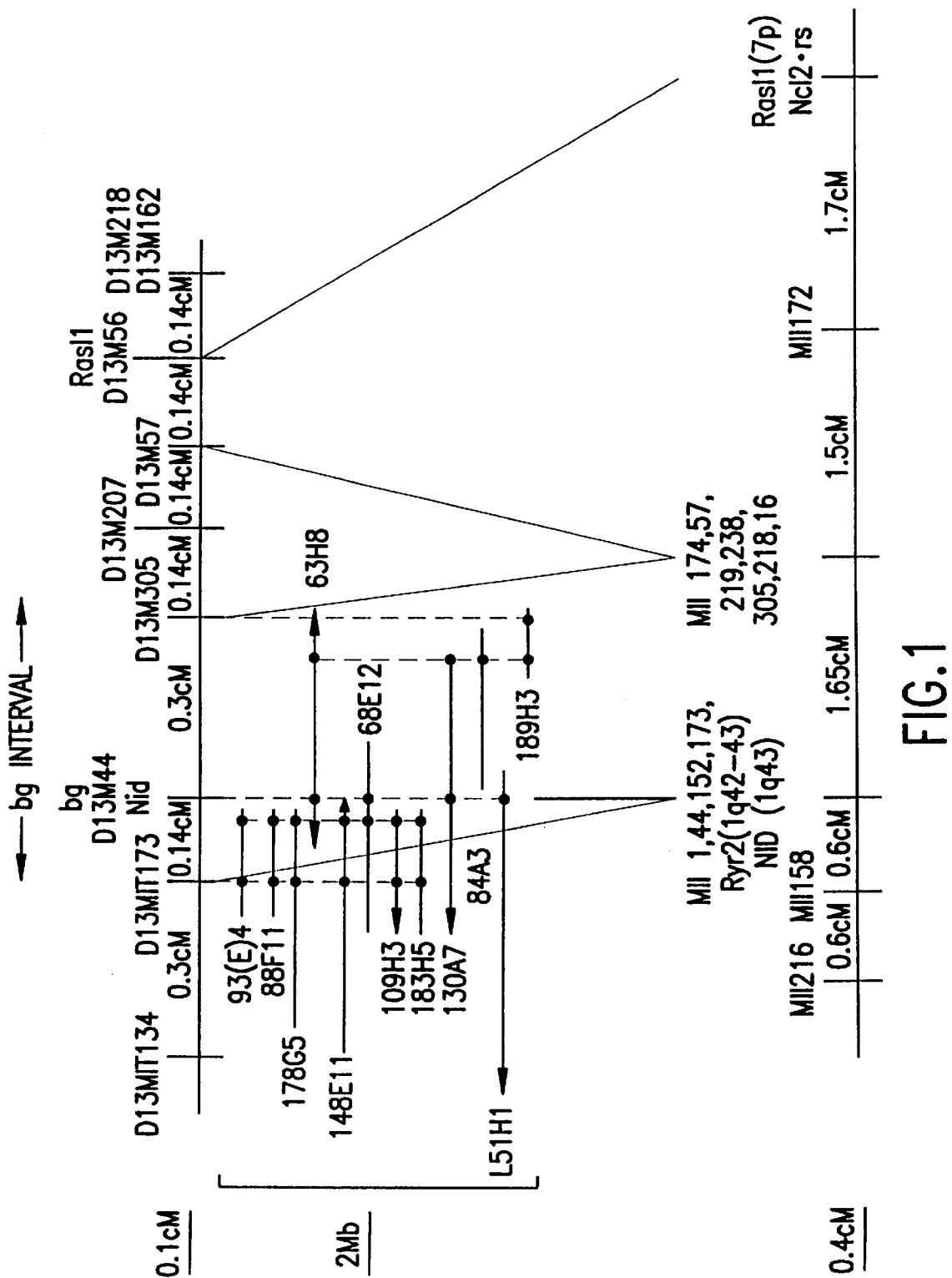

United States Patent [19]
Kaplan et al.

[11] Patent Number: 5,952,223
[45] Date of Patent: Sep. 14, 1999

[54] COMPOSITIONS FOR THE DIAGNOSIS AND TREATMENT OF CHEDIAK-HIGASHI SYNDROME

[75] Inventors: Jerry Kaplan; Charles M. Perou, both of Salt Lake City, Utah; Karen J. Moore, Maynard, Mass.

[73] Assignees: Millennium Pharmaceuticals, Cambridge, Mass.; The University of Utah Research Foundation, Salt Lake City, Utah

[21] Appl. No.: 08/822,445

[22] Filed: Mar. 21, 1997

Related U.S. Application Data

[60] Provisional application No. 60/021,064, Jul. 1, 1996, provisional application No. 60/015,673, Apr. 19, 1996, and provisional application No. 60/013,883, Mar. 22, 1996.

[51] Int. Cl.$^6$ .................................................. C12N 15/85
[52] U.S. Cl. ........................... 435/325; 435/6; 435/320.1; 536/23.5
[58] Field of Search ................................ 536/23.5, 23.51; 435/6, 172.3, 69.1, 325, 320.1

[56] References Cited

PUBLICATIONS

Rieger, R. et al. (eds.), *Glossary of Genetics and Cytogenetics*, Springer–Verlag, New York, 1976, pp. 17–18.
Barrat, F.J. et al.,*Am. J. Hum. Genet.*, 59:625–32, Sep. 1996.
Ramsay, M., *Nature Genetics*, 14:242–245, Nov. 1996.
Nagle, D.L. et al., *Nature Genetics*, 14:307–311, Nov. 1996.
Barbosa, M. et al., 1996, "Identification of the Homologous Beige and Chediak–Higashi Syndrome Genes", Nature 382:262–265.
Cockett, M. et al., 1991, "The Use of Engineered E1A Genes to Transactivate the hCMV–MIE Promoter in Permanent CHO Cell Lines", Nucleic Acids Research 19:319–325.
Duronio, R., 1992, "Comparative Analysis of the β Transducin Family with Identification of Several New Members Including *PWP1*, a Nonessential Gene of *Saccharomyces cerevisiae* that is Divergently Transcribed from *NMT1*", Proteins: Structure, Function, and Genetics 13:41–56.

Jenkins, N. et al., 1991, "Nidogen/Enactin (Nid) Maps to the Proximal End of Mouse Chromosome 13 Linked to Beige (bg) and Identifies a New Region of Homology between Mouse and Human Chromosomes", Genomics 9:401–403.
Johnstone and Thorpe, 1987, "Production of Antibodies" in Immunochemistry in Practice, Johnstone and Thorpe, eds. Blackwell Scientific Publications, Oxford, U.K., pp. 30–47.
Perou, C. et al., 1996, "Identification of the Murine Beige Gene by YAC Complementation and Positional Cloning", Nature Genetics 13:303–308.
Perou and Kaplan, 1993, "Complementation Analysis of Chediak–Higashi Syndrome: The Same Gene may be Responsible for the Defect in All Patients and Species", Somatic Cell and Molecular Genetics 19:459–468.
Perou and Kaplan, 1993, "Chediak–Higashi Syndrome is Not Due to a Defect in Microtubule–Based Lysosomal Mobility", J. of Cell Science 106:99–107.
Schlegel and Rechsteiner, 1975, "Microinjection of Thymidine Kinase and Bovine Serum Albumin into Mammalian Cells by Fusion with Red Blood Cells", Cell 5:371–379.
van der Voorn and Ploegh, 1992, "The WD–40 Repeat", FEBS Letters 307:131–134.
Wang, D.S. et al., 1994, "Binding of pH Domains of β–Adrenergic Receptor Kinase and β–Spectrin to WD40/β–Transducin Repeat Containing Regions of the β–Subunit of Trimeric G–Proteins", Biochem. Biophys. Res. Comm. 203:29–35.

*Primary Examiner*—Marianne P. Allen
*Attorney, Agent, or Firm*—Pennie & Edmonds LLP

[57] ABSTRACT

The present invention relates to the identification of novel nucleic acid molecules and proteins encoded by such nucleic acid molecules or degenerate variants thereof, that participate in the differentiation and/or function of intracellular vesicles. The nucleic acid molecules of the present invention represent the genes corresponding to the mammalian bg gene, a gene that, when mutated, is responsible for the human Chediak-Higashi syndrome.

20 Claims, 91 Drawing Sheets

FIG. 2B

| YAC NAME | #FULL/TOTAL | COMPLEMENTS |
|---|---|---|
| 151.H1 | 2/2 | NO |
| 195.A8 | 3/7 | YES |
| 113.G6 | 1/2 | YES |
| 137.A10 | 1/2 | NO |

```
A    R    G    E    I    S    I    W    V    S    G    Q    R    K    T    D    V    I    L    D      20
GCA CGA GGG GAA ATC TCC ATA TGG GTC TCT GGG CAG AGG AAG ACT GAT GTC ATC TTG GAT              60

F    V    L    P    R    K    T    S    L    S    S    D    S    N    K    T    F    C    M    I      40
TTT GTG CTC CCA AGA AAA ACA AGC TTA TCA TCA GAC AGC AAT AAA ACA TTT TGC ATG ATT             120

G    H    C    L    T    S    Q    E    E    S    L    Q    L    A    G    K    W    D    L    G      60
GGT CAT TGC TTA ACA TCC CAA GAA GAG TCT CTG CAA TTA GCT GGA AAA TGG GAC CTG GGG             180

N    L    L    F    N    G    A    K    I    S    Q    E    A    F    F    L    Y    A      80
AAC TTG CTC CTC TTC AAT GGA GCT AAA ATT GGC TCA CAA GAG GCC TTT TTC CTG TAT GCT             240

C    G    P    N    Y    T    S    I    M    P    C    K    Y    G    Q    P    V    I    D    Y     100
TGT GGA CCC AAC TAC ACA TCC ATC ATG CCG TGT AAA TAT GGA CAG CCA GTC ATT GAC TAC             300

S    K    Y    I    N    K    D    I    L    R    C    D    E    I    F    M    T     120
TCC AAA TAC ATT AAT AAA GAC ATT TTG AGA TGT GAT GAA ATC AGA GAC CTT TTT ATG ACC             360

K    K    E    V    D    V    G    L    L    I    E    S    L    S    V    V    Y    T    C     140
AAG AAA GAA GTG GAT GTT GGT CTC TTA ATT GAA AGT CTT TCA GTT GTT TAT ACA ACT TGC             420

C    P    A    Q    Y    T    I    Y    E    P    V    I    R    L    K    G    Q    V    K    T     160
TGT CCT GCT CAG TAC ACC ATC TAT GAA CCA GTG ATT CGA CTC AAG GGC CAA GTG AAA ACT             480

Q    P    S    Q    R    P    F    S    S    K    E    A    Q    S    I    L    L    E    P    S     180
CAG CCC TCT CAA AGA CCC TTC AGC AGC AAG GAA GCC CAG AGC ATC TTG CTA GAA CCT TCT             540
```

FIG. 4A

```
Q   L   K   G   L   Q   P   T   E   C   K   A   I   Q   G   I   L   H   E   I      200
CAA CTC AAA GGC CTC CAA CCT ACG GAA TGT AAA GCC ATC CAG GGC ATT CTG CAT GAG ATT     600

G   A   G   T   F   V   F   L   A   R   V   V   L   E   L   S   C   S   E          220
GGT GGG GCT GGC ACA TTT GTT CTC GCT AGG GTT GTT CTT GAA CTT AGT AGC TGT GAA         660

E   T   Q   A   L   A   L   R   V   I   L   S   L   Y   S   Q   Q   R              240
GAA ACT CAA GCA TTA GCA CTG CGG GTT ATA CTG TCT TTA ATT AAG TAC AGC CAA CAG AGA     720

T   Q   E   L   E   N   C   N   G   L   S   M   I   H   Q   V   L   V   K   Q      260
ACA CAG GAA CTG GAA AAT TGT AAT GGA CTC TCT ATG ATT CAC CAA GTG TTG GTC AAA CAG     780

K   C   I   V   G   F   H   I   L   K   T   L   L   E   G   C   C   G   E   E      280
AAA TGC ATT GTT GGC TTT CAC ATT TTG AAG ACC CTT CTT GAA GGT TGC TGC GGT GAA GAA     840

V   I   H   V   S   E   H   Q   L   L   D   V   D   W   K   I   S   H   A   E      300
GTT ATC CAC GTC AGT GAG CAT CAG CTG CTG GAT GTT GAT TGG AAG ATA TCT CAT GCT ATA     900

Q   D   V   K   L   Q   L   L   A   L   E   V   L   R   V   E   H   H             320
ATC CAA GAT GTT AAG CTG CAG CTG CTA GCA GCT TTG GAA GTC CTC ATC CGG GTA GAG GCA CAC 960

G   V   W   E   T   L   A   L   N   A   H   V   H   H   F   L   L                 340
CAA GGT GTG TGG GAG ACT CTG GCA AAC GCC CAC GTG CAC CAC TTC CTA CTG                 1020

Q   Q   F   N   I   K   Q   L                                                       360
CAG CAG CAG TTT AAT ATT AAG CAG TTG                                                 1080
```

FIG.4B

```
T   C   Q   V   L   Q   E   H   R   E   G   Q   L   T   S   M   P   R   E   V     380
ACC TGT CAG GTT TTA CAG GAA CAC AGA GAG GGG CAG CTT ACA TCT ATG CCC CGA GAA GTT    1140

C   R   S   F   V   K   I   I   A   E   V   L   A   V   S   P   P   D   L   L     400
TGT AGA TCA TTT GTG AAA ATC ATT GCA GAA GTC CTT GCA GTC TCT CCT CCA GAC TTG TTA    1200

L   T   V   I   F   N   F   L   L   Y   S   L   R   H   P   P   T   N   T   Y     420
TTG ACA GTT ATT TTC AAT TTC CTG TTA TAC TCT CTG CGG CAT CCT CCT ACT AAT ACT TAT    1260

V   C   H   N   P   T   N   F   Y   L   R   H   S   S   A   F   T   I   F   Q     440
GTT TGT CAC AAT CCC ACA AAC TTC TAC CTG AGG CAT AGC TCT GCC TTT ACT ATC TTT CAG    1320

E   K   V   Q   S   L   A   Y   L   R   H   S   S   G   G   G   Q   Q   A   G     460
GAG AAA GTG CAG TCA CTC GCG TAC CTG AGG CAT AGC AGC GGA GGG GGG CAA CAA GCA GGA    1380

E   P   S   G   F   L   V   I   S   P   S   A   F   T   A   P   P   E   G   T     480
GAG CCT AGC GGA TTC CTG GTA ATA AGC CCA TCT GCC TTT ACT GCA CCT CCT GAA GGA ACC    1440

S   L   P   A   S   N   I   V   P   Q   R   M   A   Q   M   V   R   S   L   A     500
AGT CTA CCA GCA AGT AAT ATT GTT CCA CAG CGG ATG GCT CAG ATG GTT CGA TCT CTG GCT    1500

K   L   G   F   S   F   P   T   Y   L   P   L   I   R   A   Q   K   A   A   S     520
AAA CTG GGT TTT AGT TTT CCT ACT TAT TTA CCA CTA ATA CGA GCA CAA AAA GCT GCA AGT    1560

L   G   R   V   D   K   L   Q   N   I   A   D   A   N   P   E   K   Q   N   L     540
TTG GGT AGA GTT GAC AAG TTA CAA AAT ATT GCA GAT GCC AAC CCA GAG AAA CAG AAT CTT    1620
```

FIG. 4C

| | | | | | | | | | | |
|---|---|---|---|---|---|---|---|---|---|---|
| P | Y | A | L | K | T | S | K | E | E | A | F | I | S | S | C | E | S | A | K | 560 |
| CCC | TAC | GCA | CTG | AAA | ACA | AGC | AAA | GAG | GAA | GCA | TTC | ATC | AGC | AGC | TGT | GAG | TCT | GCA | AAG | 1680 |

```
P   Y   A   L   K   T   S   K   E   E   A   F   I   S   S   C   E   S   A   K       560
CCC TAC GCA CTG AAA ACA AGC AAA GAG GAA GCA TTC ATC AGC AGC TGT GAG TCT GCA AAG      1680

T   V   C   E   M   E   A   L   G   A   H   A   S   A   N   G   V   E   P   R       580
ACT GTT TGT GAA ATG GAG GCT CTT CTT GGA GCC CAC GCC TCT GCC AAT GGG GTT TCC AGA     1740

G   S   P   R   F   P   R   A   R   V   D   H   K   D   V   G   T   E   P   R       600
GGA TCA CCG AGG TTC CCC AGG GCC AGA GTA GAT CAC AAA GAT GTG GGA ACA GAG CCC AGA     1800

S   D   D   D   S   P   G   D   E   S   Y   P   R   R   P   D   N   L   K   G       620
TCA GAT GAC GAC AGT CCT GGG GAT GAG TCT TAC CCA CGT CGG CCT GAC AAC CTC AAG GGA     1860

L   A   S   F   Q   R   S   Q   A   S   R   S   L   G   L   D   R   N   A   D       640
CTG GCC TCA TTC CAG CGA AGC CAA AGC AGC CTT GGG CTG GAT AGG AAT GCT GAT             1920

F   P   S
                                                                        TTT CCC TCT

Q   N   G   S   A   V   F   T   S   R   W   P   E   A   Y   N   R   A   T   S   T   660
CAG AAT GGA TCT GCA GTT ACC TTT TCT GCT AGG TGG CCA GAG GCT TAT AAC CGA GCC ACA AGC ACC 1980

W   E   N   F   T   I   E   D   C   L   I   P   I   C   C   G   L   Y   E   L   L   S   680
TGG GAG AAC TTT ACC ATT GAA GAC TGT CTG ATA CCT ATC TGC TGT GGA TTA TAT GAA CTC TTA AGT 2040

H   S   V   I   E   D   A   M   L   E   D   V   M   D   R   I   Q       700
CAC AGT GTC ATT GAA GAC GCT ATG CTT GAA GAT GTG ATG GAC AGG ATT CAA     2100

G   V   L   L   V   L   P   D   A                                      720
GGG GTT CTT CTT GTC CTG CCT GAT GCT                                    2160
```

FIG.4D

| | | | | | | | | | | | | | | | | |
|---|---|---|---|---|---|---|---|---|---|---|---|---|---|---|---|---|
| A | D | I | L | L | V | N | H | P | S | P | A | I | Q | Q | G | V | I | 740 |
| GCA | GAT | ATT | CTT | CTA | GTC | AAC | CAC | CCA | TCA | CCT | GCT | ATC | CAG | CAA | GGA | GTA | ATT | 2220 |

| K | L | H | A | Y | I | N | R | A | S | K | E | Q | D | K | F | L | K | 760 |
|---|---|---|---|---|---|---|---|---|---|---|---|---|---|---|---|---|---|---|
| AAA | CTG | TTA | CAT | GCA | TAC | ATT | AAT | AGA | GCA | TCA | AAG | GAG | CAA | GAC | AAG | TTT | CTG | AAG | 2280 |

| N | R | G | F | S | L | L | A | N | Q | L | Y | L | H | R | G | T | Q | E | L | 780 |
|---|---|---|---|---|---|---|---|---|---|---|---|---|---|---|---|---|---|---|---|---|
| AAC | CGT | GGC | TTT | TCC | TTA | TTA | GCC | AAC | CAG | TTG | TAT | CTT | CAT | AGG | GGA | ACT | CAG | GAG | TTG | 2340 |

| L | E | C | F | V | E | M | F | F | G | R | P | I | G | L | D | E | E | F | D | 800 |
|---|---|---|---|---|---|---|---|---|---|---|---|---|---|---|---|---|---|---|---|---|
| TTG | GAG | TGC | TTT | GTT | GAA | ATG | TTC | TTT | GGT | CGA | CCG | ATT | GGC | CTG | GAT | GAA | GAA | TTT | GAT | 2400 |

| L | E | V | K | H | M | E | L | F | Q | K | W | S | V | I | P | V | L | G | 820 |
|---|---|---|---|---|---|---|---|---|---|---|---|---|---|---|---|---|---|---|---|
| CTG | GAG | GTG | AAG | CAC | ATG | GAA | CTG | TTC | CAG | AAG | TGG | TCT | GTC | ATT | CCC | GTT | CTC | GGA | 2460 |

| L | I | E | T | S | L | Y | D | N | V | L | H | N | A | L | D | N | G | L | L | Y | 840 |
|---|---|---|---|---|---|---|---|---|---|---|---|---|---|---|---|---|---|---|---|---|---|
| CTA | ATA | GAG | ACC | TCT | CTC | TAT | GAC | AAT | GTC | CTC | CAC | AAT | GCT | CTT | GAC | AAT | GGT | CTA | CTC | CTG | 2520 |

| Q | V | L | N | S | C | S | K | V | A | D | M | L | E | K | N | I | P | V | N | E | 860 |
|---|---|---|---|---|---|---|---|---|---|---|---|---|---|---|---|---|---|---|---|---|---|
| CAA | GTT | TTA | AAC | TCT | TGT | TCC | AAG | GTA | GCA | GAC | ATG | CTA | GAA | AAG | AAT | ATT | CCT | GTG | AAC | GAA | 2580 |

| V | L | C | N | T | V | A | A | L | N | G | L | F | I | A | V | T | I | H | A | C | 880 |
|---|---|---|---|---|---|---|---|---|---|---|---|---|---|---|---|---|---|---|---|---|---|
| GTA | TTA | TGT | AAT | ACA | GTA | GCA | GCC | CTG | AAT | GGA | TTA | TTC | ATA | GCA | GTT | ACA | ATT | CAT | GCT | TGC | 2640 |

| Y | K | L | A | C | D | I | Q | L | F | I | Q | L | A | C | V | T | N | E | 900 |
|---|---|---|---|---|---|---|---|---|---|---|---|---|---|---|---|---|---|---|---|---|
| TAC | AAA | TTG | CTC | GCA | TGT | GAT | ATA | CAG | CTT | TTC | ATA | | | | | | | | 2700 |

FIG.4E

| | | | | | | | | | | | | |
|---|---|---|---|---|---|---|---|---|---|---|---|---|
| S | S | S | G | T | Q | Y | F | R | V | I | E | D | L | I | V | L | G | Y | 920 |
| AGT | TCC | TCA | GGC | ACA | CAG | TAT | TTT | AGA | GTG | ATT | GAA | GAC | CTT | ATT | GTA | CTT | GGA | TAT | 2760 |

| L | H | N | S | K | N | K | R | T | Q | N | M | A | L | A | L | Q | R | V | 940 |
|---|---|---|---|---|---|---|---|---|---|---|---|---|---|---|---|---|---|---|---|
| CTT | CAT | AAT | AGC | AAA | AAC | AAG | AGG | ACA | CAA | AAT | ATG | GCT | TTG | GCC | CTG | CAG | CTT | AGA | GTT | 2820 |

| L | Q | A | A | L | E | F | I | R | S | T | A | N | H | D | S | E | S | P | V | 960 |
|---|---|---|---|---|---|---|---|---|---|---|---|---|---|---|---|---|---|---|---|
| CTC | CAG | GCT | GCT | TTG | GAA | TTT | ATA | AGG | AGC | ACA | GCC | AAT | CAT | GAC | TCT | GAA | AGT | CCA | GTG | 2880 |

| H | S | P | S | A | H | R | H | S | V | P | K | R | R | S | I | A | G | S | 980 |
|---|---|---|---|---|---|---|---|---|---|---|---|---|---|---|---|---|---|---|---|
| CAC | TCG | CCT | TCT | GCC | CAT | CGC | CAC | TCA | GTG | CCT | AAG | CGG | AGA | AGC | ATT | GCT | GGT | TCT | 2940 |

| R | K | F | P | L | A | Q | T | E | S | L | M | K | R | S | V | A | S | 1000 |
|---|---|---|---|---|---|---|---|---|---|---|---|---|---|---|---|---|---|---|
| CGC | AAA | TTC | CCT | CTG | GCT | CAG | ACA | GAG | TCT | CTG | ATG | AAG | CGC | TCA | GTG | GCC | AGC | 3000 |

| D | E | L | H | S | M | Q | R | M | R | S | Q | E | H | P | S | Q | A | S | 1020 |
|---|---|---|---|---|---|---|---|---|---|---|---|---|---|---|---|---|---|---|---|
| GAT | GAG | CTA | CAC | TCT | ATG | CAG | AGG | ATG | AGG | AGC | CAA | GAG | CAC | CCC | AGC | CAG | GCC | TCG | 3060 |

| E | A | E | L | Q | R | L | Q | R | L | T | I | L | A | V | N | R | T | I | 1040 |
|---|---|---|---|---|---|---|---|---|---|---|---|---|---|---|---|---|---|---|---|
| GAG | GCA | GAG | CTC | GCT | CAG | AGG | CTG | CAG | AGG | CTC | ACC | ATC | TTA | GCT | GTG | AAC | AGG | ATT | ATT | 3120 |

| Y | Q | E | L | N | S | D | I | I | D | L | R | T | P | E | N | T | S | Q | 1060 |
|---|---|---|---|---|---|---|---|---|---|---|---|---|---|---|---|---|---|---|---|
| TAC | CAA | GAG | TTG | AAT | TCA | GAT | ATT | ATT | GAC | CTT | AGA | ACT | CCA | GAA | AAT | ACA | TCC | CAA | 3180 |

| S | K | T | S | V | S | Q | T | E | I | S | E | E | D | M | H | E | Q | P | 1080 |
|---|---|---|---|---|---|---|---|---|---|---|---|---|---|---|---|---|---|---|---|
| AGC | AAG | ACC | TCA | GTT | TCT | CAG | ACT | GAA | ATT | TCT | GAA | GAA | GAC | ATG | CAT | GAG | CAA | CCT | 3240 |

FIG. 4F

```
S   V   Y   N   P   F   Q   K   E   M   L   T   Y   L   L   D   G   F   K   V      1100
TCT GTA TAT AAT CCA TTT CAA AAA GAA ATG TTA ACC TAT CTG TTG GAT GGC TTC AAA GTG      3300

C   I   G   S   K   T   S   V   S   K   Q   W   T   K   I   L   G   S             1120
TGT ATT GGT TCA AGT ACT AGC GTT TCT AAG CAG CAG TGG ACT AAA ATC CTG GGG TCT         3360

C   K   E   T   L   R   D   Q   L   G   R   L   A   H   I   L   S   P   T         1140
TGT AAA GAA ACC CTC CGA GAC CAG CTT GGA AGA TTG CTA GCG CAT ATT TCT CCA ACC         3420

H   T   V   Q   E   R   K   Q   L   E   I   V   H   E   P   A   H   Q   D         1160
CAC ACT GTA CAA GAA CGG AAG CAG CAG CTT GAG ATA GTT CAT GAA CCA GCT CAC CAG GAT     3480

I   L   R   D   C   L   S   P   S   Q   H   G   A   K   L   V   L   Y   L         1180
ATA CTT CGT GAC TGT CTT AGC CCC TCC CAA CAT GGA GCC AAG TTG GTT TTG TAT TTG         3540

S   E   L   H   N   A   L   K   I   L   G   H   K   C   I   P   P   S   A   P   S 1200
TCA GAG TTG CAT AAT GCT CTA AAG ATC CTA TGT GGC CAC AAG TGC ATC CCG CCC AGT GCC CCT TCC 3600

L   M   N   A   L   K   I   I   R   E   E   Q   K   Y   E   S   E   E   S         1220
CTG ATG AAT GCT CTA AAG ATC ATC AGA GAG GAG CAA AAG TAT GAA AGT GAA GAG AGT         3660

K   P   E   L   I   K   I   I   R   E   E   Q   K   Y   E   S   E   E   S         1240
AAA CCA GAG CTC ATT AAG ATC ATC AGA GAG GAG CAA AAG TAT GAA AGT GAA GAG AGT         3720

V   S   K   G   S   W   Q   K   T   V   N   N   Q   Q   S   L   F   Q   R         1260
GTG AGC AAA GGC TCA TGG CAG AAA ACG GTG AAC AAC CAG CAA AGT CTC TTC CAG AGG         3780
```

FIG.4G

```
L   D   F   K   S   K   D   I   S   K   I   A   A   D   I   T   Q   A   V   S      1280
CTC GAT TTC AAA TCC AAG GAT ATA TCT AAA ATC GCT GCA GAC ATC ACC CAG GCT GTA TCA     3840

L   S   Q   G   I   E   R   K   K   V   I   Q   H   I   R   G   M   Y   K   V      1300
CTC TCC CAA GGC ATT GAA AGG AAG AAG GTG ATC CAG CAC ATC AGA GGG ATG TAC AAA GTT     3900

D   L   S   A   S   R   H   W   Q   E   C   I   Q   Q   L   T   H   D   R   A      1320
GAC CTG AGT GCC AGC AGG CAC TGG CAG GAA TGC ATC CAG CAG CTG ACA CAT GAC AGA GCA     3960

V   W   Y   D   P   I   Y   Y   P   T   S   W   Q   L   D   P   T   E   G   P      1340
GTC TGG TAT GAC CCA ATC TAC TAT CCA ACT TCA TGG CAG TTG GAT CCA ACA GAA GGG CCA     4020

N   R   E   R   R   Q   R   L   Q   R   C   Y   L   T   I   P   N   K   L   L      1360
AAC CGA GAG AGG AGA CGT TTG CAG AGA TGC TAT CTA ACT ATT CCC AAT AAG TAC CTC CTG     4080

R   D   R   Q   K   S   E   G   V   V   S   S   T   V   K   D   K   A   I   R      1380
AGG GAC AGA CAG AAG TCA GAA GGT GTG TCC TCT ACT GTC AAA GAC AAA GCT ATC AGA         4140

K   T   H   S   S   F   F   S   I   S   V   A   P   S   R   E   T   A   G   D      1400
AAA ACT CAT TCT TCC TTC TCC ATC AGT GCA CCA AGA GAG ACA GCT GGG GAA TCC ATC AGA     4200

V   N   R   C   I   S   V   A   P   S   R   E   D   N   A   S   D   A   V   E      1420
GTG AAT CGA TGT ATC AGT GTT GCA CCA AGA GAG GAC AAT GCC TCT GAC GCA GTT GAA         4260

G   K   C   G   M   Y   F   V   E   D   N   A   S   D   A   V   E   S   S   L      1440
GGT AAA TGT GGG ATG TAC TTT GTG GAA GAC AAT GCC TCT GAC GCA GTT GAA AGC TCG AGC     4320
```

FIG. 4H

| | | | | | | | | | | | | |
|---|---|---|---|---|---|---|---|---|---|---|---|---|
| L | Q | G | E | L | E | P | A | S | F | S | W | T | Y | E | E | I | K | E | V | 1460 |
| CTC | CAA | GGG | GAG | TTA | GAG | CCG | GCA | TCA | TTT | TCT | TGG | ACA | TAT | GAG | GAA | ATT | AAA | GAA | GTT | 4380 |

| H | R | W | Q | L | R | D | N | A | V | E | I | F | L | T | N | G | R | 1480 |
| CAC | AGG | CGC | TGG | CAA | CTA | AGA | GAT | AAT | GCT | GTA | GAA | ATC | TTT | TTA | ACA | AAT | GGC | AGA | 4440 |

| T | L | L | A | F | D | N | N | K | V | R | D | D | V | Y | Q | S | I | L | 1500 |
| ACA | CTC | CTA | TTA | GCA | TTT | GAC | AAT | AAC | AAG | GTT | CGT | GAT | GAC | GTG | TAC | CAG | AGC | ATC | CTC | 4500 |

| T | N | L | P | N | L | E | Y | G | N | I | T | A | L | T | N | L | W | 1520 |
| ACA | AAT | CTC | CCA | AAT | CTT | CTG | GAG | TAC | GGC | AAC | ATC | ACC | GCT | CTG | ACA | AAC | CTG | TGG | 4560 |

| Y | S | Q | I | T | N | F | E | Y | L | T | H | L | N | K | H | A | G | R | 1540 |
| TAT | TCT | CAA | ATT | ACC | AAT | TTT | GAA | TAT | TTG | ACT | CAT | TTA | AAC | AAG | CAT | GCG | GGC | CGG | 4620 |

| S | F | N | D | L | M | Q | D | P | S | I | L | S | K | Y | V | S | 1560 |
| TCC | TTC | AAT | GAT | CTC | ATG | CAG | GAT | CCA | TCT | ATC | CTT | TCT | AAG | TAT | GTT | AGT | 4680 |

| E | T | L | D | L | N | R | Y | V | D | T | Y | K | L | E | E | I | A | V | 1580 |
| GAG | ACT | CTT | GAC | CTC | AAT | AGA | TAC | GTT | GAC | ACA | TAC | AAG | TTG | GAG | GAG | ATA | GCT | GTG | 4740 |

| Q | Y | K | E | K | D | P | M | P | P | V | Q | L | E | E | Y | 1600 |
| CAG | TAT | AAA | GAA | AAA | GAC | CCC | ATG | CCT | CCT | GTG | CAA | CCC | TAC | CAC | TAT | 4800 |

| R | K | G | A | R | E | D | D | P | M | P | P | V | Q | P | Y | H | Y | G | S | 1620 |
| CGC | AAG | GGA | GCT | CGA | GAG | GAT | GAC | CCC | ATG | CCT | CCT | GTG | CAA | CCC | TAC | CAC | TAT | GGC | TCC | 4860 |

FIG. 4I

```
  H   Y   S   N   S   G   T   V   L   H   F   L   V   R   M   P   P   F   T   K     1640
CAC TAC TCC AAC AGC GGC ACC GTG CTC CAC TTC CTG GTC AGG ATG CCG CCT TTC ACT AAA      4920

M   F   L   A   Y   Q   D   Q   S   F   D   I   P   D   R   T   F   H   S   T     1660
ATG TTT CTA GCC TAT CAA GAT CAG AGT TTC GAC ATT CCA GAC CGA ACA TTT CAT TCT ACA      4980

N   T   T   W   R   L   S   S   F   E   S   M   T   D   V   K   E   L   I   P     1680
AAC ACA ACT TGG CGC CTC TCC TCC TTT GAG TCC ATG ACT GAT GTG AAG GAG CTG ATT CCA      5040

E   F   F   Y   L   P   E   F   L   V   N   R   E   G   D   F   G   V   R         1700
GAG TTT TTC TAT CTT CCT GAG TTC TTA GTG AAC CGT GAA GGC GAC TTC GGT GTT CGT          5100

Q   N   G   E   R   V   N   H   R   Q   A   L   Y   G   W   A   R   N   D   P     1720
CAG AAT GGA GAG CGG GTT AAC CAC CGG CAA GCA CTA TAC GGC TGG GCA CGC AAT GAT CCT      5160

L   F   I   I   L   I   H   R   Q   F   G   Y   F   P   W   S   H   V   S   R     1740
CTG TTC ATC CTT ATT CAC CGG CAA TTT GGC TAC TTT CCC TGG TCT GAC CAT GTG TCC CGG      5220

H   W   I   D   L   V   G   M   D   V   F   G   Y   K   Q   K   A   S   A   V     1760
CAC TGG ATC GAC TTA GTG GGA ATG GAT GTC TCT GGC TAC AAG CAA AAG GCG TCT GCA GTT      5280

N   V   F   H   P   A   T   Y   F   G   M   D   V   S   A   V   E   D   P   V     1780
AAT GTC TTC CAC CCT GCT ACA TAT TTT GGA ATG GAT GTC TCT GCA GTT GAA GAT CCA GTG      5340

Q   R   R   A   L   E   T   M   I   K   T   Y   G   Q   T   P   R   Q   L   F     1800
CAG AGA CGG GCT TTA GAA ACC ATG ATA AAA ACC TAC GGG CAG ACC CCA CGT CAG TTG TTC      5400
```

FIG.4J

| | | | | | | | | | | | | | | | | | | | | |
|---|---|---|---|---|---|---|---|---|---|---|---|---|---|---|---|---|---|---|---|---|
| H | T | A | H | A | S | R | P | G | A | K | L | N | I | E | G | E | L | P | A | 1820 |
| CAC | ACA | GCC | CAT | GCC | AGC | CGA | CCT | GGA | GCC | AAG | CTT | AAC | ATC | GAA | GGA | GAG | CTT | CCA | GCA | 5460 |
| A | V | G | L | L | V | Q | F | A | F | R | E | T | R | E | P | V | K | E | V | 1840 |
| GCT | GTT | GGC | TTA | GTC | CAG | TTC | GCT | TTC | AGA | GAG | ACC | CGA | GAA | CCA | GTC | AAG | GAA | GTC | | 5520 |
| T | H | P | S | P | L | S | W | I | K | G | L | K | W | G | E | Y | V | G | S | 1860 |
| ACT | CAT | CCG | AGC | CCT | TTG | TCA | TGG | ATA | AAA | GGC | TTG | AAG | TGG | GGA | GAG | TAC | GTA | GGT | TCC | 5580 |
| P | S | A | P | V | P | V | C | F | S | Q | P | H | G | E | R | F | G | S | | 1880 |
| CCC | AGT | GCT | CCA | GTA | CCT | GTG | GTC | TTC | AGC | CAG | CCC | CAT | GGA | GAA | AGA | TTT | GGT | TCC | | 5640 |
| L | Q | A | L | P | T | R | A | I | C | G | L | S | R | N | F | C | L | M | | 1900 |
| CTG | CAG | GCA | CTG | CCC | ACC | AGA | GCC | ATC | TGT | GGT | TTA | TCA | CGA | AAC | TTC | TGT | CTT | ATG | | 5700 |
| T | Y | N | K | E | Q | G | V | R | S | M | N | T | N | I | Q | W | S | A | | 1920 |
| ACC | TAC | AAC | AAG | GAG | CAA | GGT | GTG | AGA | AGC | ATG | AAC | ACC | AAT | ATT | CAG | TGG | TCT | GCT | | 5760 |
| I | L | S | W | G | Y | A | D | N | I | L | R | L | K | S | K | Q | S | E | P | 1940 |
| ATC | CTA | AGC | TGG | GGA | TAT | GCT | GAC | AAC | ATC | TTA | CGG | TTG | AAA | AGT | AAG | CAG | AGT | GAG | CCA | 5820 |
| P | I | N | F | I | Q | S | Q | Q | H | Q | V | T | S | C | A | W | V | P | | 1960 |
| CCA | ATC | AAC | TTC | ATT | CAG | AGT | CAG | CAG | CAC | CAG | GTA | ACC | AGT | TGT | GCC | TGG | GTG | CCT | | 5880 |
| D | S | C | Q | L | F | T | G | S | K | C | G | V | I | T | A | Y | T | N | R | 1980 |
| GAC | AGT | TGT | CAG | CTC | TTC | ACT | GGG | AGC | AAG | TGT | GGT | GTC | ATC | ACA | GCC | TAT | ACC | AAC | AGG | 5940 |

FIG.4K

| | | | | | | | | | | | | | | | | | | | | |
|---|---|---|---|---|---|---|---|---|---|---|---|---|---|---|---|---|---|---|---|---|
| L | T | S | S | T | P | S | E | I | E | M | E | S | Q | M | H | L | Y | G | H | 2000 |
| CTC | ACC | AGC | AGC | ACG | CCC | TCA | GAA | ATT | GAA | ATG | GAG | AGT | CAG | ATG | CAT | CTC | TAT | GGA | CAC | 6000 |
| T | E | E | I | T | G | L | C | V | C | K | P | Y | S | V | M | I | S | V | S | 2020 |
| ACA | GAG | GAG | ATC | ACC | GGC | TTA | TGT | GTC | TGC | AAG | CCG | TAC | AGC | GTG | ATG | ATA | AGC | GTG | AGC | 6060 |
| R | D | G | T | C | I | V | W | D | L | N | R | L | C | Y | Q | V | Q | S | L | A | 2040 |
| AGA | GAC | GGG | ACC | TGC | ATA | GTA | TGG | GAC | CTG | AAC | AGG | CTG | TGC | TAT | CAA | GTA | CAA | AGT | TTG | GCT | 6120 |
| G | H | K | S | P | V | T | A | S | E | T | S | G | D | I | A | T | 2060 |
| GGA | CAC | AAA | AGC | CCT | GTG | ACG | GCT | AGC | GAA | ACG | TCA | GGT | GAC | ATT | GCT | ACT | 6180 |
| V | C | D | S | A | G | G | G | S | D | L | R | L | W | T | V | N | G | D | L | 2080 |
| GTC | TGT | GAC | TCA | GCT | GGC | GGG | GGT | AGT | GAC | CTG | AGA | CTC | TGG | ACC | GTG | AAT | GGG | GAC | CTC | 6240 |
| V | G | H | V | H | C | R | E | I | I | C | S | V | A | F | S | N | Q | P | E | 2100 |
| GTT | GGA | CAT | GTC | CAC | TGC | AGA | GAG | ATC | ATT | TGT | TCT | GTA | GCT | TTC | TCC | AAC | CAG | CCT | GAG | 6300 |
| G | V | S | I | N | V | I | A | G | L | E | N | G | I | V | R | L | W | S | 2120 |
| GGA | GTC | TCC | ATC | AAC | GTC | ATT | GCT | GGG | TTA | GAA | AAT | GGC | ATT | GTA | AGG | CTA | TGG | AGC | 6360 |
| T | W | D | L | K | P | V | R | E | I | T | F | P | K | S | N | K | P | I | 2140 |
| ACA | TGG | GAC | TTG | AAG | CCT | GTG | AGA | GAG | ATT | ACA | TTT | CCC | AAA | TCA | AAT | AAG | CCC | ATC | ATA | 6420 |
| S | L | T | F | S | C | D | G | H | H | L | Y | T | A | N | S | E | G | T | V | 2160 |
| AGC | CTG | ACA | TTC | TCC | TGT | GAT | GGC | CAC | CAT | TTG | TAC | ACT | GCC | AAC | AGT | GAG | GGG | ACA | GTG | 6480 |

FIG. 4L

|   | | | | | | | | | | | | | | 2180 |
|---|---|---|---|---|---|---|---|---|---|---|---|---|---|---|
| I | A | W | C | R | K | D | Q | Q | R | V | K | L | P | M | F | Y | S | F | L |
| ATC | GCA | TGG | TGC | CGG | AAG | GAC | CAG | CAG | CGT | GTG | AAG | CTG | CCC | ATG | TTC | TAC | TCT | TTC | CTC | 6540 |

|   |   |   |   |   | 2186 |
|---|---|---|---|---|---|
| S | S | Y | A | A | G | * |
| AGC | AGC | TAC | GCA | GCA | GGA | TGA | 6558 |

AGAGAAGGAGTGTCCCCACAGGACATAAGCACCGCTCTGCGGAGCCTGGCTCCACCAACTGCAGAAGCAGATGACTGAGC

AGATATCCAGGAAAGACAACACACGTGCCTCTGTGCGGCTTCCCCAGCCTCCGTGGGCCTGAGAGTAAAGCCCTGCCC

TCATTCCATAATGGCGTGGAAGGCTGGGTCTGCACACACTAGCCAATTAAAGTCAGAATCTTGATGCTTTTTCCCAAAA 6830

GGTTAGGCTGAATCAAAGATCAGGCTCGTGCC

FIG.4M

```
GCGGCCGCGT CGACGCGGGCG GCGGCAGCGG CGTCGGCTCG GGGTTCTCCG GGAGAGGGGG         60

AGTGCGCGGC GGCCGCAGCT GCCACAAACC AGGTGAAGCT TTGTTCTAAG AATATTTGTT        120

TCATCTAGTT TATGAGTCCA AATGATATAG ACTGTAAATG TCACAGCAGT GGTGAAAGAC        180

TGCTCGGTC ATG AGC ACC GAC AGT AAC TCA CTG GCA CGT GAA TTT CTG           228
          Met Ser Thr Asp Ser Asn Ser Leu Ala Arg Glu Phe Leu
           1               5                  10

ACC GAT GTC AAC CGG CTT TGC AAT GCA GTG GTC CAG AGG GTG GAG GCC        276
Thr Asp Val Asn Arg Leu Cys Asn Ala Val Val Gln Arg Val Glu Ala
         15                  20                  25

AGG GAA GAA GAG GAG GAG ACG CAC ATG GCA ACC CTT GGA CAG TAC            324
Arg Glu Glu Glu Glu Glu Thr His Met Ala Thr Leu Gly Gln Tyr
 30                  35                  40                 45

CTT GTC CAT GGT CGA GGA TTT CTA TTA CTT TTA CTT ACC AAG CTA AAT TCT ATA   372
Leu Val His Gly Arg Gly Phe Leu Leu Leu Leu Thr Lys Leu Asn Ser Ile
          50                  55                  60

ATT GAT CAG GCA TTG ACA TGT AGA GAA GAA CTC CTG ACT CTT CTT CTG          420
Ile Asp Gln Ala Leu Thr Cys Arg Glu Glu Leu Leu Thr Leu Leu Leu
         65                  70                  75
```

FIG.7A

```
TCT CTC CTT CCA CTG GTA TGG AAG ATA CCT GTC CAA GAA GAA AAG GCA      468
Ser Leu Pro Leu Val Trp Lys Ile Pro Val Gln Glu Glu Lys Ala
         80                      85                      90

ACA GAT TTT AAC CTA CCG CTC TCA GCA GAT ATA ATC CTG ACC AAA GAA      516
Thr Asp Phe Asn Leu Pro Leu Ser Ala Asp Ile Ile Leu Thr Lys Glu
             95                     100                     105

AAG AAC TCA AGT TCA CAA AGA TCC ACT CAG GAA AAA TTA CAT TTA GAA      564
Lys Asn Ser Ser Ser Gln Arg Ser Thr Gln Glu Lys Leu His Leu Glu
110                     115                     120                     125

GGA AGT GCC CTG TCT AGT CAG GTT TCT GCA AAA GTA AAT GTT TTT CGA      612
Gly Ser Ala Leu Ser Ser Gln Val Ser Ala Lys Val Asn Val Phe Arg
                 130                     135                     140

AAA AGC AGA CGA CAG CGT AAA ATT ACC CAT CGC TAT TCT GTA AGA GAT      660
Lys Ser Arg Arg Gln Arg Lys Ile Thr His Arg Tyr Ser Val Arg Asp
                     145                     150                     155

GCA AGA AAG ACA CAG CTC TCC ACC TCA GAT TCA GAA GCC AAT TCA GAT      708
Ala Arg Lys Thr Gln Leu Ser Thr Ser Asp Ser Glu Ala Asn Ser Asp
                     160                     165                     170

GAA AAA GGC ATA GCA ATG AAT AAG CAT AGA AGG CCC CAT CTG CTG CAT      756
Glu Lys Gly Ile Ala Met Asn Lys His Arg Arg Pro His Leu Leu His
             175                     180                     185
```

FIG. 7B

```
CAT TTT TTA ACA TCG TTT CCT AAA CAA GAC CAC CCC AAA GCT AAA CTT    804
His Phe Leu Thr Ser Phe Pro Lys Gln Asp His Pro Lys Ala Lys Leu
190                 195                 200                 205

GAC CGC TTA GCA ACC AAA GAA CAG ACT CCT CCA GAT GCT ATG GCT TTG    852
Asp Arg Leu Ala Thr Lys Glu Gln Thr Pro Pro Asp Ala Met Ala Leu
        210                 215                 220

GAA AAT TCC AGA GAG ATT ATT CCA AGA CAG GGG TCA AAC ACT GAC ATT    900
Glu Asn Ser Arg Glu Ile Ile Pro Arg Gln Gly Ser Asn Thr Asp Ile
            225                 230                 235

TTA AGT GAG CCA GCT GCC TTG TCT GTT ATC AGT AAC ATG AAC AAT TCT    948
Leu Ser Glu Pro Ala Ala Leu Ser Val Ile Ser Asn Met Asn Asn Ser
                240                 245                 250

CCA TTT GAC TTA TGT CAT GTT ACC TTG TTG TCT TTA GAA AAA GTT TGT    996
Pro Phe Asp Leu Cys His Val Thr Leu Leu Ser Leu Glu Lys Val Cys
    255                 260                 265

AAG TTT GAC GTT ACC TTG AAT CAT AAT TCT CCT TTA GCA GCC AGT GTA    1044
Lys Phe Asp Val Thr Leu Asn His Asn Ser Pro Leu Ala Ala Ser Val
270                 275                 280                 285

GTG CCC ACA CTA ACT GAA TTC CTA GCA GGC TTT GGG GAC TGC TGC AGT    1092
Val Pro Thr Leu Thr Glu Phe Leu Ala Gly Phe Gly Asp Cys Cys Ser
        290                 295                 300
```

FIG.7C

```
CTG AGC GAC AAC TTG GAG AGT CGA GTA GTT TCT GCA GGT TGG ACC GAA    1140
Leu Ser Asp Asn Leu Glu Ser Arg Val Val Ser Ala Gly Trp Thr Glu
            305                 310                 315

GAA CCG GTG GCT TTG ATT CAA AGG CTC TTT CGA ACA GTG TTG CAT        1188
Glu Pro Val Ala Leu Ile Gln Arg Leu Phe Arg Thr Val Leu His
        320                 325                 330

CTT CTG TCA GTA GAT GTT AGT ACT GCA GAG ATG ATG CCA GAA AAT CTT    1236
Leu Leu Ser Val Asp Val Ser Thr Ala Glu Met Met Pro Glu Asn Leu
        335                 340                 345

AGG AAA AAT TTA ACT GAA TTG CTT AGA GCA GCT TTA AAA ATT AGA ATA    1284
Arg Lys Asn Leu Thr Glu Leu Leu Arg Ala Ala Leu Lys Ile Arg Ile
350                 355                 360                 365

TGC CTA GAA AAG CAG CCT GAC CCT TTT GCA CCA AGA CAA AAG AAA ACA    1332
Cys Leu Glu Lys Gln Pro Asp Pro Phe Ala Pro Arg Gln Lys Lys Thr
        370                 375                 380

CTG CAG GAG GTT CAG GAA GAT TTT GTG TTT TCA AAG TAT CGT CAT AGA    1380
Leu Gln Glu Val Gln Glu Asp Phe Val Phe Ser Lys Tyr Arg His Arg
        385                 390                 395

GCC CTT CTT TTA CCT GAG CTT TTG GAA GGA GTT CTT CAG ATT CTG ATC    1428
Ala Leu Leu Leu Pro Glu Leu Leu Glu Gly Val Leu Gln Ile Leu Ile
400                 405                 410
```

FIG.7D

```
TGT TGT CTT CAA AGT GCA GCT TCA AAT CCC TTC TAC TTC AGT CAA GCC    1476
Cys Cys Leu Gln Ser Ala Ala Ser Asn Pro Phe Tyr Phe Ser Gln Ala
415                     420                     425

ATG GAT TTG GTT CAA GAA TTC ATT CAG CAT CAT GGA TTT AAT TTA TTT    1524
Met Asp Leu Val Gln Glu Phe Ile Gln His His Gly Phe Asn Leu Phe
430                     435                     440             445

GAA ACA GCA GTT CTT CAA ATG GAA TGG CTG GTT TTA AGA GAT GGA GTT    1572
Glu Thr Ala Val Leu Gln Met Glu Trp Leu Val Leu Arg Asp Gly Val
        450                     455                     460

CCT CCC GAG GCC TCA GAG CAT TTG AAA AAA GCC CTA ATA AAT AGT GTG ATG    1620
Pro Pro Glu Ala Ser Glu His Leu Lys Lys Ala Leu Ile Asn Ser Val Met
            465                     470                     475

AAA ATA ATG AGC ACT GTC AAA AAA GTG AAA TCA GAG CAA CTT CAT CAT    1668
Lys Ile Met Ser Thr Val Lys Lys Val Lys Ser Glu Gln Leu His His
    480                     485                     490

TCG ATG TGT ACA AGA AAA AGG CAC AGA CGA TGT GAA TAT TCT CAT TTT    1716
Ser Met Cys Thr Arg Lys Arg His Arg Arg Cys Glu Tyr Ser His Phe
495                     500                     505

ATG CAT CAT CAC CGA GAT CTC TCA GGT CTT CTG TCG GCT TTT AAA    1764
Met His His His Arg Asp Leu Ser Gly Leu Leu Ser Ala Phe Lys
510                     515                     520         525
```

FIG.7E

```
AAC CAG GTT TCC AAA AAC CCA TTT GAA GAG ACT GCA GAT GGA GAT GTT    1812
Asn Gln Val Ser Lys Asn Pro Phe Glu Glu Thr Ala Asp Gly Asp Val
            530                 535                 540

TAT TAT CCT GAG CGG TGC TGT ATT GCA GTG TGT GCC CAT CAG TGC        1860
Tyr Tyr Pro Glu Arg Cys Cys Ile Ala Val Cys Ala His Gln Cys
            545                 550                 555

TTG CGC TTA CTA CAG CAG GCT TCC TTG AGC AGC ACT TGT GTC CAG ATC    1908
Leu Arg Leu Leu Gln Gln Ala Ser Leu Ser Ser Thr Cys Val Gln Ile
            560                 565                 570

CTA TCG GGT GTT CAT AAC ATT GGA ATA TGC TGT TGT CYS ATG GAT CCC AAA 1956
Leu Ser Gly Val His Asn Ile Gly Ile Cys Cys Cys Met Asp Pro Lys
            575                 580                 585

TCT GTA ATC ATT CCT TTG CTC CAT GCT TTT AAA TTG CCA GCA CTG AAA    2004
Ser Val Ile Ile Pro Leu Leu His Ala Phe Lys Leu Pro Ala Leu Lys
            590                 595                 600        605

AAT TTT CAG CAG CAT ATA TTG AAT ATC CTT AAC AAA CTT ATT TTG GAT    2052
Asn Phe Gln Gln His Ile Leu Asn Ile Leu Asn Lys Leu Ile Leu Asp
            610                 615                 620

CAG TTA GGA GCA GAG ATA TCA CCA AAA ATT AAA AAA GCA GCT TGT        2100
Gln Leu Gly Gly Ala Glu Ile Ser Pro Lys Ile Lys Lys Ala Ala Cys
            625                 630                 635
```

FIG.7F

```
AAT ATT TGT ACT GTT GAC TCT GAC CAA CTA GCC CAA TTA GAA GAG ACA    2148
Asn Ile Cys Thr Val Asp Ser Asp Gln Leu Ala Gln Leu Glu Glu Thr
            640                     645                     650

CTG CAG GGA AAC TTA TGT GAT GCT GAA CTC TCC TCA AGT TTA TCC AGT    2196
Leu Gln Gly Asn Leu Cys Asp Ala Glu Leu Ser Ser Ser Leu Ser Ser
            655                     660                     665

CCT TCT TAC AGA TTT CAA GGG ATC CTG CCC AGC CTG GGA TCT GAA GAT    2244
Pro Ser Tyr Arg Phe Gln Gly Ile Leu Pro Ser Gly Ser Glu Asp
            670                     675                     680                 685

TTG TTG TGG AAA TGG GAT GCT TTA AAG GCT TAT CAG AAC TTT GTT TTT    2292
Leu Leu Trp Lys Trp Asp Ala Leu Lys Ala Tyr Gln Asn Phe Val Phe
            690                     695                     700

GAA GAA GAC AGA TTA CAT AGT ATA CAG AAT ATT GCA AAT CAC ATT TGC AAT    2340
Glu Glu Asp Arg Leu His Ser Ile Gln Lys Ile Ala Asn His Ile Cys Asn
            705                     710                     715

TTA ATC CAG AAA GGC AAT ATA GTT CAG TGG AAA TTA TAT AAT TAC    2388
Leu Ile Gln Lys Gly Asn Ile Val Gln Trp Lys Leu Tyr Asn Tyr
            720                     725                     730

ATA TTT AAT CCT GTG CTC CAA AGA GGA GTT GAA TTA GCA CAT CAT TGT    2436
Ile Phe Asn Pro Val Leu Gln Arg Gly Val Glu Leu Ala His His Cys
            735                     740                     745
```

FIG. 7G

```
CAA CAC CTA AGC GTT ACT TCA GCT CAA AGT CAT GTA TGT AGC CAT CAT    2484
Gln His Leu Ser Val Thr Ser Ala Gln Ser His Val Cys Ser His His
750                 755                 760                 765

AAC CAG TGC TTG CCT CAG GAC GTG CTT CAG ATT TAT GTA AAA ACT CTG    2532
Asn Gln Cys Leu Pro Gln Asp Val Leu Gln Ile Tyr Val Lys Thr Leu
        770                 775                 780

CCT ATC CTG CTT AAA TCC AGG GTA ATA AGA GAT TTG TTT TTG AGT TGT    2580
Pro Ile Leu Leu Lys Ser Arg Val Ile Arg Asp Leu Phe Leu Ser Cys
    785                 790                 795

AAT GGA GTA AGT CAA ATA ATC GAA TTA AAT TGC TTA AAT GGT ATT CGA    2628
Asn Gly Val Ser Gln Ile Ile Glu Leu Asn Cys Leu Asn Gly Ile Arg
800                 805                 810

AGT CAT TCT CTA AAA GCA TTT GAA ACT CTG ATA ATC AGC CTA GGG GAG    2676
Ser His Ser Leu Lys Ala Phe Glu Thr Leu Ile Ile Ser Leu Gly Glu
        815                 820                 825

CAA CAG AAA GAT GCC TCA GTT CCA GAT ATT GAT GGG ATA GAC ATT GAA    2724
Gln Gln Lys Asp Ala Ser Val Pro Asp Ile Asp Gly Ile Asp Ile Glu
    830                 835                 840                 845

CAG AAG GAG TTG TCC TCT GTA CAT GTG GGT ACT TCT TTT CAT CAT CAG    2772
Gln Lys Glu Leu Ser Ser Val His Val Gly Thr Ser Phe His His Gln
850                 855                 860
```

FIG.7H

```
CAA GCT TAT TCA GAT TCT CCT CAG AGT CTC AGC AAA TTT TAT GCT GGC    2820
Gln Ala Tyr Ser Asp Ser Pro Gln Ser Leu Ser Lys Phe Tyr Ala Gly
            865                 870                 875

CTC AAA GAA GCT TAT CCA AAG AGA CGG AAG ACT GTT AAC CAA GAT GTT    2868
Leu Lys Glu Ala Tyr Pro Lys Arg Arg Lys Thr Val Asn Gln Asp Val
        880                 885                 890

CAT ATC AAC ACA ATA AAC CTA TTC CTC TGT GTG GCT TTT TTA TGC GTA    2916
His Ile Asn Thr Ile Asn Leu Phe Leu Cys Val Ala Phe Leu Cys Val
            895                 900                 905

AGT AAA GAA GCA GAG TCT GAC AGG GAG TCG GCC AAT GAC TCA GAA GAT    2964
Ser Lys Glu Ala Glu Ser Asp Arg Glu Ser Ala Asn Asp Ser Glu Asp
        910                 915                 920             925

ACT TCT GGC TAT GAC AGC ACA GCC AGC GAG CCT TTA AGT CAT ATG CTG    3012
Thr Ser Gly Tyr Asp Ser Thr Ala Ser Glu Pro Leu Ser His Met Leu
            930                 935                 940

CCA TGT ATA TCT CTC GAG AGC CTT GTC TTG CCT TCT CCT GAA CAT ATG    3060
Pro Cys Ile Ser Leu Glu Ser Leu Val Leu Pro Ser Pro Glu His Met
        945                 950                 955

CAC CAA GCA GCA GAC ATT TGG TCT ATG TGT CGT TGG ATC TAC ATG TTG    3108
His Gln Ala Ala Asp Ile Trp Ser Met Cys Arg Trp Ile Tyr Met Leu
            960                 965                 970
```

FIG. 71

```
AGT TCA GTG TTC CAG AAA CAG TTT TAT AGG CTT GGT GGT TTC CGA GTA    3156
Ser Ser Val Phe Gln Lys Gln Phe Tyr Arg Leu Gly Gly Phe Arg Val
975                 980                 985

TGC CAT AAG TTA ATA TTT ATG ATA ATA CAG AAA CTG TTC AGA AGT CAC    3204
Cys His Lys Leu Ile Phe Met Ile Ile Gln Lys Leu Phe Arg Ser His
990                 995                 1000                1005

AAA GAG GAG CAA GGA AAA AAG GAG GGA GAT ACA AGT GTA AAT GAA AAC    3252
Lys Glu Glu Gln Gly Lys Lys Glu Gly Asp Thr Ser Val Asn Glu Asn
        1010                1015                1020

CAG GAT TTA AAC AGA ATT TCT CAA CCT AAG AGA ACT ATG AAG GAA GAT    3300
Gln Asp Leu Asn Arg Ile Ser Gln Pro Lys Arg Thr Met Lys Glu Asp
1025                1030                1035

TTA TTA TCT TTG GCT ATA AAA AGT GAC CCC ATA CCA TCA GAA CTA GGT    3348
Leu Leu Ser Leu Ala Ile Lys Ser Asp Pro Ile Pro Ser Glu Leu Gly
        1040                1045                1050

AGT CTA AAA AAG AGT GCT GAC AGT TTA GAT AGT TTA GGT AAA TTA CAG CAT    3396
Ser Leu Lys Lys Ser Ala Asp Ser Leu Asp Ser Leu Gly Lys Leu Gln His
1055                1060                1065

ATT TCT TCC ATA AAT GTG GAA GAA GTT TCA GCT ACT GAA GCC GCT CCC    3444
Ile Ser Ser Ile Asn Val Glu Glu Val Ser Ala Thr Glu Ala Ala Pro
1070                1075                1080                1085
```

FIG.7J

```
GAG GAA GCA AAG CTA TTT ACA AGT CAA GAA AGT GAG ACC TCA CTT CAA      3492
Glu Glu Ala Lys Leu Phe Thr Ser Gln Glu Ser Glu Thr Ser Leu Gln
                    1090                    1095                1100

AGT ATA CGA CTT TTG GAA GCC CTT CTG GCC ATT TGT CTT CAT GGT GCC      3540
Ser Ile Arg Leu Leu Glu Ala Leu Leu Ala Ile Cys Leu His Gly Ala
                    1105                    1110                1115

AGA ACT AGT CAA CAG AAG ATG GAA TTG GAG TTA CCT AAT CAG AAC TTG      3588
Arg Thr Ser Gln Gln Lys Met Glu Leu Glu Leu Pro Asn Gln Asn Leu
                    1120                    1125                1130

TCT GTG GAA AGT ATA TTA TTT GAA ATG AGG GAC CAT CTT TCC CAG TCA      3636
Ser Val Glu Ser Ile Leu Phe Glu Met Arg Asp His Leu Ser Gln Ser
            1135                    1140                    1145

AAG GTG ATT GAA ACA CAA CTA GCA AAG CCG TTA TTT GAT GCC CTG CTT      3684
Lys Val Ile Glu Thr Gln Leu Ala Lys Pro Leu Phe Asp Ala Leu Leu
1150                    1155                    1160              1165

CGA GTT GCC CTC GGG AAT TAT TCA GCA GAT TTT GAA CAT AAT GAT GCT      3732
Arg Val Ala Leu Gly Asn Tyr Ser Ala Asp Phe Glu His Asn Asp Ala
                    1170                    1175                1180

ATG ACT GAG AAG AGT CAT CAA TCT GCA GAA GAA TTG TCA TCC CAG CCT      3780
Met Thr Glu Lys Ser His Gln Ser Ala Glu Glu Leu Ser Ser Gln Pro
                    1185                    1190                1195
```

FIG.7K

```
GGT GAT TTT TCA GAA GAA GCT GAG GAT TCT CAG TGT TGT AGT TTT AAA    3828
Gly Asp Phe Ser Glu Glu Ala Glu Asp Ser Gln Cys Cys Ser Phe Lys
            1200                    1205                    1210

CTT TTA GTT GAA GAA GGT TAC GAA GCA GAT AGT GAA AGC AAT CCT        3876
Leu Leu Val Glu Glu Gly Tyr Glu Ala Asp Ser Glu Ser Asn Pro
            1215                    1220                    1225

GAA GAT GGC GAA ACC CAG GAT GAT GGG GTA GAC TTA AAG TCT GAA ACA    3924
Glu Asp Gly Glu Thr Gln Asp Asp Gly Val Asp Leu Lys Ser Glu Thr
1230                    1235                    1240            1245

GAA GGT TTC AGT GCA TCA AGC AGT CCA AAT GAC TTA CTC GAA AAC CTC    3972
Glu Gly Phe Ser Ala Ser Ser Ser Pro Asn Asp Leu Leu Glu Asn Leu
                1250                    1255                1260

ACT CAA GGG GAA ATA ATT TAT CCT GAG ATT TGT ATG CTG GAA TTA AAT    4020
Thr Gln Gly Glu Ile Ile Tyr Pro Glu Ile Cys Met Leu Glu Leu Asn
            1265                    1270                    1275

TTG CTT TCT GCT AGT AAA GCC AAA CTT GAT GTG CTT GCC CAT GTA TTT    4068
Leu Leu Ser Ala Ser Lys Ala Lys Leu Asp Val Leu Ala His Val Phe
            1280                    1285                    1290

GAG AGT TTT TTG AAA ATT ATT AGG CAG AAA GAA AAG AAT GTT TTT CTG    4116
Glu Ser Phe Leu Lys Ile Ile Arg Gln Lys Glu Lys Asn Val Phe Leu
            1295                    1300                    1305
```

FIG.7L

```
CTC ATG CAA CAG GGA ACT GTG AAA AAT CTT TTA GGA GGG TTC TTG AGT    4164
Leu Met Gln Gln Gly Thr Val Lys Asn Leu Leu Gly Gly Phe Leu Ser
1310                         1315                        1320                        1325

ATT TTA ACA CAG GAT GAT TCT GAT TTT CAA GCA TGC CAG AGA GTA TTG    4212
Ile Leu Thr Gln Asp Asp Ser Asp Phe Gln Ala Cys Gln Arg Val Leu
        1330                        1335                        1340

GTG GAT CTT TTG GTA TCT TTG ATG AGT TCA AGA ACA TGT TCA GAA GAG    4260
Val Asp Leu Leu Val Ser Leu Met Ser Ser Arg Thr Cys Ser Glu Glu
            1345                        1350                        1355

CTA ACC CTT CTT TTG AGA ATA TTT CTG GAG AAA TCT CCT TGT ACA AAA    4308
Leu Thr Leu Leu Leu Arg Ile Phe Leu Glu Lys Ser Pro Cys Thr Lys
                1360                        1365                        1370

ATT CTT CTT CTG GGT ATT CTG AAA ATT ATT GAA AGT GAT ACT ACT ATG    4356
Ile Leu Leu Leu Gly Ile Leu Lys Ile Ile Glu Ser Asp Thr Thr Met
1375                        1380                        1385

AGC CCT TCA CAG TAT CTA ACC TTC CCT TTA CTG CAC GCT CCA AAT TTA    4404
Ser Pro Ser Gln Tyr Leu Thr Phe Pro Leu Leu His Ala Pro Asn Leu
        1390                        1395                        1400                        1405

AGC AAC GGT GTT TCA CAA AAG TAT CCT GGG ATT TTA AAC AGT AAG        4452
Ser Asn Gly Val Ser Ser Gln Lys Tyr Pro Gly Ile Leu Asn Ser Lys
            1410                        1415                        1420
```

FIG. 7M

GCC ATG GGT TTA TTG AGA AGA GCA CGA GTT TCA CGG AGC AAG AAA GAG          4500
Ala Met Gly Leu Leu Arg Arg Ala Arg Val Ser Arg Ser Lys Lys Glu
1425                               1430                          1435

GCT GAT AGA GAG AGT TTT CCC CAT CGG CTG CTT TCA TCT TGG CAC ATA          4548
Ala Asp Arg Glu Ser Phe Pro His Arg Leu Leu Ser Ser Trp His Ile
1440                              1445                           1450

GCC CCA GTC CAC CTG CCG TTG CTG GGG CAA AAC TGC TGG CCA CAC CTA          4596
Ala Pro Val His Leu Pro Leu Leu Gly Gln Asn Cys Trp Pro His Leu
1455                              1460                           1465

TCA GAA GGT TTC AGT GTT TCC CTG TGG TTT AAT GTG GAG TGT ATC CAT          4644
Ser Glu Gly Phe Ser Val Ser Leu Trp Phe Asn Val Glu Cys Ile His
1470                              1475                           1480                1485

GAA GCT GAG AGT ACT ACA GAA AAA GGA AAG AAG ATA AAG AAA AGA AAC          4692
Glu Ala Glu Ser Thr Thr Glu Lys Gly Lys Lys Ile Lys Lys Arg Asn
1485                              1490                           1495                1500

AAA TCA TTA ATT TTA CCA GAT AGC AGT TTT GAT GGT ACA GAG AGC GAC          4740
Lys Ser Leu Ile Leu Pro Asp Ser Ser Phe Asp Gly Thr Glu Ser Asp
1505                              1510                           1515

AGA CCA GAA GGT GCA GAG TAC ATA AAT CCT GGT GAA AGA CTC ATA GAA          4788
Arg Pro Glu Gly Ala Glu Tyr Ile Asn Pro Gly Glu Arg Leu Ile Glu
1520                              1525                           1530

FIG. 7N

```
GAA GGA TGT ATT CAT ATA ATT TCA CTG GGA TCC AAA GCG TTG ATG ATC    4836
Glu Gly Cys Ile His Ile Ile Ser Leu Gly Ser Lys Ala Leu Met Ile
             1535                    1540                    1545

CAA GTG TGG GCT GAT CCC CAC AAT GCC ACT CTT ATC TTT CGT GTG TGC    4884
Gln Val Trp Ala Asp Pro His Asn Ala Thr Leu Ile Phe Arg Val Cys
1550                    1555                    1560          1565

ATG GAT TCA AAT GAT GAC ATG AAA GCT GTT TTA CTA GCA CAG GTT GAA    4932
Met Asp Ser Asn Asp Asp Met Lys Ala Val Leu Leu Ala Gln Val Glu
        1570                    1575                         1580

TCA CAG GAG AAT ATT TTC CTC CCA AGC AAA TGG CAA CAT TTA GTA CTC    4980
Ser Gln Glu Asn Ile Phe Leu Pro Ser Lys Trp Gln His Leu Val Leu
             1585                    1590                    1595

ACC TAC TTA CAG CAG CCC CAA GGG AAA AGG AGG ATT CAT GGG AAA ATC    5028
Thr Tyr Leu Gln Gln Pro Gln Gly Lys Arg Arg Ile His Gly Lys Ile
1600                    1605                    1610

TCC ATA TGG GTC TCT GGA CAG AGG AAG CCT GAT GTT ACT TTG GAT TTT    5076
Ser Ile Trp Val Ser Gly Gln Arg Lys Pro Asp Val Thr Leu Asp Phe
        1615                    1620                    1625

ATG CTT CCA AGA AAA ACA AGT TTG TCA TCT GAT AGC AAT AAA ACA TTT    5124
Met Leu Pro Arg Lys Thr Ser Leu Ser Ser Asp Ser Asn Lys Thr Phe
             1630                    1635                    1640          1645
```

FIG.70

```
TGC ATG ATT GGC CAT TGT TTA TCA TCC CAA GAA GAG TTT TTG CAG TTG    5172
Cys Met Ile Gly His Cys Leu Ser Ser Gln Glu Glu Phe Leu Gln Leu
                 1650                    1655                1660

GCT GGA AAA TGG GAC CTG GGA AAT TTG CTT CTC TTC AAC GGA GCT AAG    5220
Ala Gly Lys Trp Asp Leu Gly Asn Leu Leu Leu Phe Asn Gly Ala Lys
                 1665                    1670                1675

GTT GGT TCA CAA GAG GCC TTT TAT CTG TAT GCT TGT GGA CCC AAC CAT    5268
Val Gly Ser Gln Glu Ala Phe Tyr Leu Tyr Ala Cys Gly Pro Asn His
                 1680                    1685                1690

ACA TCT GTA ATG CCA TGT AAG TAT GGC AAG CCA GTC AAT GAC TAC TCC    5316
Thr Ser Val Met Pro Cys Lys Tyr Gly Lys Pro Val Asn Asp Tyr Ser
                 1695                    1700                1705

AAA TAT ATT AAT AAA GAA ATT TTG CGA TGT GAA CAA ATC AGA GAA CTT    5364
Lys Tyr Ile Asn Lys Glu Ile Leu Arg Cys Glu Gln Ile Arg Glu Leu
                 1710                    1715                1725

TTT ATG ACC AAG AAA GAT GTG GAT ATT GGT CTC TTA ATT GAA AGT CTT    5412
Phe Met Thr Lys Lys Asp Val Asp Ile Gly Leu Leu Ile Glu Ser Leu
                 1730                    1735                1740

TCA GTT GTT TAT ACA ACT TAC TGT CCT GCT CAG TAT ACC ATC TAT GAA    5460
Ser Val Val Tyr Thr Thr Tyr Cys Pro Ala Gln Tyr Thr Ile Tyr Glu
                 1745                    1750                1755
```

FIG.7P

```
CCA GTG ATT AGA CTT AAA GGT CAA ATG AAA ACC CAA CTC TCT CAA AGA         5508
Pro Val Ile Arg Leu Lys Gly Gln Met Lys Thr Gln Leu Ser Gln Arg
        1760                    1765                    1770

CCC TTC AGC TCA AAA GAA GTT CAG AGC ATC TTA GAA CCT CAT CAT CAT         5556
Pro Phe Ser Ser Lys Glu Val Gln Ser Ile Leu Glu Pro His His His
        1775                    1780                    1785

CTA AAG AAT CTC CAA CCT ACT GAA TAT AAA ACT ATT CAA GGC ATT CTG         5604
Leu Lys Asn Leu Gln Pro Thr Glu Tyr Lys Thr Ile Gln Gly Ile Leu
        1790                    1795                    1800        1805

CAC GAA ATT GGT GGA ACT GGC ATA TTT GTT TTT CTC TTT GCC AGG GTT         5652
His Glu Ile Gly Gly Thr Gly Ile Phe Val Phe Leu Phe Ala Arg Val
        1810                    1815                    1820

GTT GAA CTC AGT AGC TGT GAA GAA ACT CAA GCA TTA GCA CTG CGA GTT         5700
Val Glu Leu Ser Ser Cys Glu Glu Thr Gln Ala Leu Ala Leu Arg Val
        1825                    1830                    1835

ATA CTC TCA TTA ATT AAA TAC AAC CAA CAA AGA GTA CAT GAA TTA GAA         5748
Ile Leu Ser Leu Ile Lys Tyr Asn Gln Gln Arg Val His Glu Leu Glu
        1840                    1845                    1850

AAT TGT AAT GGA CTT TCT ATG ATT CAT CAG GTG TTG ATC AAA CAA AAA         5796
Asn Cys Asn Gly Leu Ser Met Ile His Gln Val Leu Ile Lys Gln Lys
        1855                    1860                    1865
```

FIG. 7Q

```
TGC ATT GTT GGG TTT TAC ATT TTG AAG ACC CTT CTT GAA GGA TGC TGT    5844
Cys Ile Val Gly Phe Tyr Ile Leu Lys Thr Leu Leu Glu Gly Cys Cys
1870                     1875                    1880              1885

GGT GAA GAT ATT ATT TAT ATG AAT GAG GAG TTT AAG TTG GAT            5892
Gly Glu Asp Ile Ile Tyr Met Asn Glu Glu Phe Lys Leu Asp
          1890                    1895                   1900

GTA GAC TCT AAT GCT ATA ATC CAA GAT GTT AAG CTG TTA GAG GAA CTA    5940
Val Asp Ser Asn Ala Ile Ile Gln Asp Val Lys Leu Leu Glu Glu Leu
          1905                    1910                   1915

TTG CTT GAC TGG AAG ATA TGG AGT AAA GCA GAG CAA GGT GTT TGG GAA    5988
Leu Leu Asp Trp Lys Ile Trp Ser Lys Ala Glu Gln Gly Val Trp Glu
          1920                    1925                   1930

ACT TTG CTA GCA GCT CTA GAA GTC CTC ATC AGA GCA GAT CAC CAC CAG    6036
Thr Leu Leu Ala Ala Leu Glu Val Leu Ile Arg Ala Asp His His Gln
          1935                    1940                   1945

CAG ATG TTT AAT ATT AAG CAG TTA TTG AAA GCT CAA GTG GTT CAT CAC    6084
Gln Met Phe Asn Ile Lys Gln Leu Leu Lys Ala Gln Val Val His His
          1950                    1955                   1960       1965

TTT CTA CTG ACT TGT CAG GTT TTG CAG GAA TAC AAA GAG GGG CAA CTC    6132
Phe Leu Thr Cys Gln Val Leu Gln Glu Tyr Lys Glu Gly Gln Leu
          1970                    1975                   1980
```

FIG.7R

```
ACA CCC ATG CCC CGA GAG GTT TGT AGA TCA TTT GTG AAA ATT ATA GCA    6180
Thr Pro Met Pro Arg Glu Val Cys Arg Ser Phe Val Lys Ile Ile Ala
           1985                    1990                    1995

GAA GTC CTT GGA TCT CCT CCA GAT TTG GAA TTA TTG ACA ATT ATC TTC    6228
Glu Val Leu Gly Ser Pro Pro Asp Leu Glu Leu Leu Thr Ile Ile Phe
           2000                    2005                    2010

AAT TTC CTT TTA GCA GTT CAC CCT CCT ACT AAT ACT TAC GTT TGT CAC    6276
Asn Phe Leu Leu Ala Val His Pro Pro Thr Asn Thr Tyr Val Cys His
           2015                    2020                    2025

AAT CCC ACG AAC TTC TAC TTT TCT TTG CAC ATA GAT GGC AAG ATC TTT    6324
Asn Pro Thr Asn Phe Tyr Phe Ser Leu His Ile Asp Gly Lys Ile Phe
           2030                    2035                    2040                    2045

CAG GAG AAA GTG CGG TCA ATC ATG TAC CTG AGG CAT TCC AGC AGT GGA    6372
Gln Glu Lys Val Arg Ser Ile Met Tyr Leu Arg His Ser Ser Ser Gly
           2050                    2055                    2060

GGA AGG TCC CTT ATG AGC CCT GGA TTT ATG GTA ATA AGC CCA TCT GGT    6420
Gly Arg Ser Leu Met Ser Pro Gly Phe Met Val Ile Ser Pro Ser Gly
           2065                    2070                    2075

TTT ACT GCT TCA CCA TAT GAA GGA GAG AAT TCC TCT AAT ATT ATT CCA    6468
Phe Thr Ala Ser Pro Tyr Glu Gly Glu Asn Ser Ser Asn Ile Ile Pro
           2080                    2085                    2090
```

FIG.7S

```
CAA CAG ATG GCC GCC CAT ATG CTG CGT TCT AGA AGC CTA CCA GCA TTC    6516
Gln Gln Met Ala Ala His Met Leu Arg Ser Arg Ser Leu Pro Ala Phe
2095                                    2100                2105

CCT ACT TCT TCA CTA CTA ACG CAA TCA CAA AAA CTG ACT GGA AGT TTG    6564
Pro Thr Ser Ser Leu Leu Thr Gln Ser Gln Lys Leu Thr Gly Ser Leu
2110                      2115                          2125

GGT TGT AGT ATC GAC AGG TTA CAA AAT ATT GCA GAT ACT TAT GTT GCC    6612
Gly Cys Ser Ile Asp Arg Leu Gln Asn Ile Ala Asp Thr Tyr Val Ala
        2130                      2135                    2140

ACC CAA TCA AAG CAA AAA AAT TCT TTG GGG AGT TCC GAC ACA CTG AAA    6660
Thr Gln Ser Lys Gln Lys Asn Ser Leu Gly Ser Ser Asp Thr Leu Lys
2145                                2150                      2155

AAA GGC AAA GAG GAC GCA TTC ATC AGT AGC TGT GAG TCT GCA AAA ACT    6708
Lys Gly Lys Glu Asp Ala Phe Ile Ser Ser Cys Glu Ser Ala Lys Thr
             2160                      2165                  2170

GTT TGT GAA ATG GAA GCT GTC CTC TCA GCC CAG GTC TCT GTC AGT GAT    6756
Val Cys Glu Met Glu Ala Val Leu Ser Ala Gln Val Ser Val Ser Asp
2175                            2180                      2185

GTC CCA AAG GGA GTG CTG GGA TTT CCA GTG GTC AAA GCA GAT CAT AAA    6804
Val Pro Lys Gly Val Leu Gly Phe Pro Val Val Lys Ala Asp His Lys
2190                      2195                    2200        2205
```

FIG.7T

```
CAG TTG GGA GCA GAA CCC AGG TCA GAA GAT GAC AGT CCT GGG GAT GAG    6852
Gln Leu Gly Ala Glu Pro Arg Ser Glu Asp Asp Ser Pro Gly Asp Glu
                2210                            2215            2220

TCC TGC CCA CGC CGA CCT GAT TAC CTA AAG GGA TTG GCC TCC TTC CAG    6900
Ser Cys Pro Arg Arg Pro Asp Tyr Leu Lys Gly Leu Ala Ser Phe Gln
                2225                            2230            2235

CGA AGC CAC AGC ACT ATT GCA AGC CTT GGG CTA GCT TTT CCT TCA CAG    6948
Arg Ser His Ser Thr Ile Ala Ser Leu Gly Leu Ala Phe Pro Ser Gln
                2240                            2245            2250

AAC GGA TCT GCA GCT GTT GGC CGT TGG CCA AGT CTT GTT GAT AGA AAC    6996
Asn Gly Ser Ala Ala Val Gly Arg Trp Pro Ser Leu Val Asp Arg Asn
                2255                            2260            2265

ACT GAT GAT TGG GAA AAC TTT GCC TAT TCT CTT GGT TAT GAG CCA AAT    7044
Thr Asp Asp Trp Glu Asn Phe Ala Tyr Ser Leu Gly Tyr Glu Pro Asn
                2270                            2275            2280    2285

TAC AAC CGA ACT GCA AGT GCT CAC AGT GTA ACT GAA GAC TGT TTG GTA    7092
Tyr Asn Arg Thr Ala Ser Ala His Ser Val Thr Glu Asp Cys Leu Val
                2285                            2290    2295        2300

CCT ATA TGC TGT GGA TTA TAT GAA CTC CTA AGT GGG GTT CTT CTT ATC    7140
Pro Ile Cys Cys Gly Leu Tyr Glu Leu Leu Ser Gly Val Leu Leu Ile
                2305                            2310            2315
```

FIG.7U

```
CTG CCT GAT GTT TTG CTT GAA GAT GTG ATG GAC AAG CTT ATT CAA GCA      7188
Leu Pro Asp Val Leu Leu Glu Asp Val Met Asp Lys Leu Ile Gln Ala
            2320                      2325                  2330

GAT ACA CTT TTG GTC CTC GTT AAC CAC CCA TCA CCA ATA CAA CAA          7236
Asp Thr Leu Leu Val Leu Val Asn His Pro Ser Pro Ile Gln Gln
            2335                      2340                  2345

GGT GTT ATT AAA CTA TTA GAT GCA TAT TTT GCT AGA GCA TCT AAG GAA      7284
Gly Val Ile Lys Leu Leu Asp Ala Tyr Phe Ala Arg Ala Ser Lys Glu
2350                      2355                      2360        2365

CAA AAA GAT AAA TTT CTG AAG AAT CGT GGA TTT TCC TTG CTA GCC AAC      7332
Gln Lys Asp Lys Phe Leu Lys Asn Arg Gly Phe Ser Leu Leu Ala Asn
            2370                      2375                  2380

CAG TTG TAT CTT CAT CGA GGA ACT CAA GAA TTG TTA GAA TGC TTC ATC      7380
Gln Leu Tyr Leu His Arg Gly Thr Gln Glu Leu Leu Glu Cys Phe Ile
            2385                      2390                  2395

GAA ATG TTC TTT GGT CGA CAT ATT GGC CTT GAT GAA TTT GAT CTG          7428
Glu Met Phe Phe Gly Arg His Ile Gly Leu Asp Glu Phe Asp Leu
            2400                      2405                  2410

GAA GAT GTG AGA AAC ATG GGA TTG TTT CAG AAG TGG TCT GTC ATT CCT      7476
Glu Asp Val Arg Asn Met Gly Leu Phe Gln Lys Trp Ser Val Ile Pro
            2415                      2420                  2425
```

FIG.7V

```
ATT CTG GGA CTA ATA GAG ACC TCT CTA TAT GAC AAC ATA CTC TTG CAT     7524
Ile Leu Gly Leu Ile Glu Thr Ser Leu Tyr Asp Asn Ile Leu Leu His
2430                    2435                    2440           2445

AAT GCT CTT TTA CTT CTC CAA ATT TTA AAT TCT TGT TCT AAG GTA         7572
Asn Ala Leu Leu Leu Leu Gln Ile Leu Asn Ser Cys Ser Lys Val
        2450                    2455                    2460

GCA GAT ATG TTG CTG GAT AAT GGT CTA CTC TAT GTG TTA TGT AAT ACA     7620
Ala Asp Met Leu Leu Asp Asn Gly Leu Leu Tyr Val Leu Cys Asn Thr
            2465                    2470                    2475

GTA GCA GCC CTG AAT GGA TTA GAA AAG AAC ATT CCC ATG AGT GAA TAT     7668
Val Ala Ala Leu Asn Gly Leu Glu Lys Asn Ile Pro Met Ser Glu Tyr
2480                    2485                    2490

AAA TTG CTT GCT TGT GAT ATA CAG CAA CTT TTC ATA GCA GTT ACA ATT     7716
Lys Leu Leu Ala Cys Asp Ile Gln Gln Leu Phe Ile Ala Val Thr Ile
        2495                    2500                    2505

CAT GCT TGC AGT TCC TCA GGC TCA CAA TAT TTT AGG GTT ATT GAA GAC     7764
His Ala Cys Ser Ser Ser Gly Ser Gln Tyr Phe Arg Val Ile Glu Asp
            2510                    2515                    2520                    2525

CTT ATT GTA ATG CTT GGA TAT CTT CAA AAT AGC AAA AAC AAG AGG ACA     7812
Leu Ile Val Met Leu Gly Tyr Leu Gln Asn Ser Lys Asn Lys Arg Thr
2530                    2535                    2540
```

FIG. 7W

```
CAA AAT ATG GCT GTT GCA CTA CAG CTT AGA GTT CTC CAG GCT GCT ATG    7860
Gln Asn Met Ala Val Ala Leu Gln Leu Arg Val Leu Gln Ala Ala Met
                2545                    2550                2555

GAA TTT ATA AGG ACC ACC GCA AAT CAT GAC TCT GAA AAC CTC ACA GAT    7908
Glu Phe Ile Arg Thr Thr Ala Asn His Asp Ser Glu Asn Leu Thr Asp
                2560                    2565                2570

TCA CTC CAG TCA CCT TCT GCT CCC CAT CAT GCA GTA GTT CAA AAG CGG    7956
Ser Leu Gln Ser Pro Ser Ala Pro His His Ala Val Val Gln Lys Arg
                2575                    2580                2585

AAA AGC ATT GCT GGT CCT CGA AAA TTT CCC CTT GCT CAA ACT GAA TCG    8004
Lys Ser Ile Ala Gly Pro Arg Lys Phe Pro Leu Ala Gln Thr Glu Ser
                2590                    2595                2600    2605

CTT CTG ATG AAA ATG CGT TCA GTG GCA AAT GAT GAG CTT CAT GTG ATG    8052
Leu Leu Met Lys Met Arg Ser Val Ala Asn Asp Glu Leu His Val Met
                2610                    2615                2620

ATG CAA CGG AGA ATG AGC CAA ATG GAG AAC CCT AGC CAA GCA ACT GAA ACG    8100
Met Gln Arg Arg Met Ser Gln Met Glu Asn Pro Ser Gln Ala Thr Glu Thr
                2625                    2630                2635

GAA CTT GCG CAG AGA CTA CAG AGG CTC ACT GTT TTA GCA GTC AAC AGG    8148
Glu Leu Ala Gln Arg Leu Gln Arg Leu Thr Val Leu Ala Val Asn Arg
                2640                    2645                2650
```

FIG.7X

```
ATT ATT TAT CAA GAA TTT AAT TCA GAC ATT ATT GAC ATT TTG AGA ACT         8196
Ile Ile Tyr Gln Glu Phe Asn Ser Asp Ile Ile Asp Ile Leu Arg Thr
2655                          2660                     2665

CCA GAA AAT GTA ACT CAA AGC AAG ACC TCA GTT TTC CAG ACC GAA ATT         8244
Pro Glu Asn Val Thr Gln Ser Lys Thr Ser Val Phe Gln Thr Glu Ile
2670                          2675                     2680           2685

TCT GAG GAA AAT ATT CAT CAT GAA CAG TCT TCT GTT TTC AAT CCA TTT         8292
Ser Glu Glu Asn Ile His His Glu Gln Ser Ser Val Phe Asn Pro Phe
          2690                          2695                     2700

CAG AAA GAA ATT TTT ACA TAT CTG GTA GAA GGA TTC AAA GTA TCT ATT         8340
Gln Lys Glu Ile Phe Thr Tyr Leu Val Glu Gly Phe Lys Val Ser Ile
2705                          2710                     2715

GGT TCA AGT AAA GCC AGT GGT TCC AAG CAG CAA TGG ACT AAA ATT CTG         8388
Gly Ser Ser Lys Ala Ser Gly Ser Lys Gln Gln Trp Thr Lys Ile Leu
          2720                          2725                     2730

TGG TCT TGT AAG GAG ACC TTC CGA ATG CAG CTT GGG AGA CTA CTA GTG         8436
Trp Ser Cys Lys Glu Thr Phe Arg Met Gln Leu Gly Arg Leu Leu Val
2735                          2740                     2745

CAT ATT TTG TCG CCA GCC CAC GCT GCA CAA GAG AGA AAG CAA ATT TTT         8484
His Ile Leu Ser Pro Ala His Ala Ala Gln Glu Arg Lys Gln Ile Phe
          2750                          2755                     2760           2765
```

FIG.7Y

```
GAA ATA GTT CAT GAA CCA AAT CAT CAG GAA ATA CTA CGA GAC TGT CTC      8532
Glu Ile Val His Glu Pro Asn His Gln Glu Ile Leu Arg Asp Cys Leu
                    2770                             2775                   2780

AGC CCA TCC CTA CAA CAT GGA GCC AAG TTA GTT TTG TAT TTG TCA GAG      8580
Ser Pro Ser Leu Gln His Gly Ala Lys Leu Val Leu Tyr Leu Ser Glu
           2785                              2790                        2795

TTG ATA CAT AAT CAC CAA GGT GAA TTG ACT GAA GAA GAG CTA GGC ACA      8628
Leu Ile His Asn His Gln Gly Glu Leu Thr Glu Glu Glu Leu Gly Thr
                2800                             2805                   2810

GCA GAA CTG CTT ATG AAT GCT TTG AAG TTA TGT GGT CAC AAG TGC ATC      8676
Ala Glu Leu Leu Met Asn Ala Leu Lys Leu Cys Gly His Lys Cys Ile
           2815                              2820                        2825

CCT CCC AGT GCA TCA ACA AAA GCA GAC CTT ATT AAA ATG ATC AAA GAG      8724
Pro Pro Ser Ala Ser Thr Lys Ala Asp Leu Ile Lys Met Ile Lys Glu
                2830                             2835                   2840                   2845

GAA CAA AAG AAA TAT GAA ACT GAA GAA GGA GTG AAT AAA GCT GCT TGG      8772
Glu Gln Lys Lys Tyr Glu Thr Glu Glu Gly Val Asn Lys Ala Ala Trp
           2850                              2855                        2860

CAG AAA ACA GTT AAC AAT AAT CAA AGT CTC TTT CAG CGT CTG GAT          8820
Gln Lys Thr Val Asn Asn Asn Gln Ser Leu Phe Gln Arg Leu Asp
                2865                             2870                   2875
```

FIG. 7Z

```
TCA AAA TCA AAG GAT ATA TCT AAA ATA GCT GCA GAT ATC ACC CAG GCA    8868
Ser Lys Ser Lys Asp Ile Ser Lys Ile Ala Ala Asp Ile Thr Gln Ala
        2880                    2885                    2890

GTG TCT CTC TCC CAA GGA AAT GAG AGA AAA AAG GTG ATC CAG CAT ATT    8916
Val Ser Leu Ser Gln Gly Asn Glu Arg Lys Lys Val Ile Gln His Ile
        2895                    2900                    2905

AGA GGA ATG TAT AAA GTA GAT TTG AGT GCC AGC AGA CAT TGG CAG GAA    8964
Arg Gly Met Tyr Lys Val Asp Leu Ser Ala Ser Arg His Trp Gln Glu
    2910                    2915                    2920        2925

CTT ATT CAG CAG CTG ACA CAT GAT AGA GCA TGG TAT GAC CCC ATC        9012
Leu Ile Gln Gln Leu Thr His Asp Arg Ala Trp Tyr Asp Pro Ile
            2930                    2935                    2940

TAC TAT CCA ACC TCA TGG CAG TTG GAT CCA ACA GAA GGG CCA AAT CGA    9060
Tyr Tyr Pro Thr Ser Trp Gln Leu Asp Pro Thr Glu Gly Pro Asn Arg
        2945                    2950                    2955

GAG AGG CGT TTA CAG AGA CGT TAT TTA ACT ATT CCA AAT AAG TAT        9108
Glu Arg Arg Arg Leu Gln Arg Cys Tyr Leu Thr Ile Pro Asn Lys Tyr
        2960                    2965                    2970

CTC CTT AGG GAT AGA CAG AAA TCA GAA GAT GTT GTC AAA CCA CCA CTC    9156
Leu Leu Arg Asp Arg Gln Lys Ser Glu Asp Val Val Lys Pro Pro Leu
        2975                    2980                    2985
```

FIG.7A1

```
TCT TAC CTG TTT GAA GAC AAA ACT CAT TCT TCT TTC TCT TCT ACT GTC        9204
Ser Tyr Leu Phe Glu Asp Lys Thr His Ser Ser Phe Ser Ser Thr Val
2990                    2995                    3000            3005

AAA GAC AAA GCT GCA AGT GAA TCT ATA AGA GTG AAT CGA AGA TGC ATC        9252
Lys Asp Lys Ala Ala Ser Glu Ser Ile Arg Val Asn Arg Arg Cys Ile
        3010                    3015                    3020

AGT GTT GCA CCA TCT AGA GAG ACA GCT GGT GAA TTG TTA CTA GGT AAA        9300
Ser Val Ala Pro Ser Arg Glu Thr Ala Gly Glu Leu Leu Leu Gly Lys
3025                    3030                    3035

TGT GGA ATG TAT TTT GTG GAA GAT AAT GCT TCT GAT ACA GTT GAA AGT        9348
Cys Gly Met Tyr Phe Val Glu Asp Asn Ala Ser Asp Thr Val Glu Ser
        3040                    3045                    3050

TCG AGC CTT CAG GGA GAG TTG GAA CCA GCA TCA TTT TCC TGG ACA TAT        9396
Ser Ser Leu Gln Gly Glu Leu Glu Pro Ala Ser Phe Ser Trp Thr Tyr
3055                    3060                    3065

GAA GAA ATT AAA GAA GTT CAC AAG CGT TGG TGG CAA TTG AGA GAT AAT        9444
Glu Glu Ile Lys Glu Val His Lys Arg Trp Trp Gln Leu Arg Asp Asn
        3070                    3075                    3080   3085

GCT GTA GAA ATC TTT CTA ACA AAT GGC AGA ACA CTC CTG TTG GCA TTT        9492
Ala Val Glu Ile Phe Leu Thr Asn Gly Arg Thr Leu Leu Leu Ala Phe
3090                    3095                    3100
```

FIG.7B1

```
GAT AAC ACC AAG GTT CGT GAT GAT GTA TAC CAC AAT ATA CTC ACA AAT       9540
Asp Asn Thr Lys Val Arg Asp Asp Val Tyr His Asn Ile Leu Thr Asn
3105                              3110                    3115

AAC CTC CCT AAT CTT CTG GAA TAT GGT AAC ATC ACC GCT CTG ACA AAT       9588
Asn Leu Pro Asn Leu Leu Glu Tyr Gly Asn Ile Thr Ala Leu Thr Asn
        3120                    3125                    3130

TTA TGG TAT ACT GGG CAA ATT ACT AAT TTT GAA TAT TTG ACT CAC TTA       9636
Leu Trp Tyr Thr Gly Gln Ile Thr Asn Phe Glu Tyr Leu Thr His Leu
3135                    3140                    3145

AAC AAA CAT GCT GGC CGA TCC TTC AAT GAT CTC ATG CAG TAT CCT GTG       9684
Asn Lys His Ala Gly Arg Ser Phe Asn Asp Leu Met Gln Tyr Pro Val
        3150                    3155                    3160                    3165

TTC CCA TTT ATA CTT GCT GAC TAC GTT AGT GAG ACA CTT GAC CTC AAT       9732
Phe Pro Phe Ile Leu Ala Asp Tyr Val Ser Glu Thr Leu Asp Leu Asn
                3170                    3175                    3180

GAT CTG TTG ATA TAC AGA AAT CTC TCT AAA CCT ATA GCT GTT CAG TAT       9780
Asp Leu Leu Ile Tyr Arg Asn Leu Ser Lys Pro Ile Ala Val Gln Tyr
            3185                    3190                    3195

AAA GAA AAA GAA GAT CGT TAT GTG GAC ACA TAC AAG TAC TTG GAG GAA       9828
Lys Glu Lys Glu Asp Arg Tyr Val Asp Thr Tyr Lys Tyr Leu Glu Glu
                    3200                    3205                    3210
```

FIG.7C1

```
GAG TAC CGC AAA GGA GCC AGA GAA GAT GAC CCC ATG CCT CCC GTG CAG      9876
Glu Tyr Arg Lys Gly Ala Arg Glu Asp Asp Pro Met Pro Pro Val Gln
3215                         3220                    3225

CCC TAT CAC TAT GGC TCC CAC TAT TCC AAT AGC GGC ACT GTG CTT CAC      9924
Pro Tyr His Tyr Gly Ser His Tyr Ser Asn Ser Gly Thr Val Leu His
3230                    3235                    3240           3245

TTC CTG GTC AGG ATG CCT CCT TTC ACT AAA ATG TTT TTA GCC TAT CAA      9972
Phe Leu Val Arg Met Pro Pro Phe Thr Lys Met Phe Leu Ala Tyr Gln
          3250                    3255                    3260

GAT CAA AGT TTT GAC ATT CCA GAC AGA ACT TTT CAT TCT ACA AAT ACA     10020
Asp Gln Ser Phe Asp Ile Pro Asp Arg Thr Phe His Ser Thr Asn Thr
     3265                    3270                    3275

ACT TGG CGA CTC TCA TCT TTT GAA TCT ATG ACT GAT GTG AAA GAA CTT     10068
Thr Trp Arg Leu Ser Ser Phe Glu Ser Met Thr Asp Val Lys Glu Leu
               3280                    3285                    3290

ATC CCA GAG TTT TTC TAT CTT CCA GAG TTC CTA GTT AAC CGT GAA GGT     10116
Ile Pro Glu Phe Phe Tyr Leu Pro Glu Phe Leu Val Asn Arg Glu Gly
3295                    3300                    3305

TTT GAT TTT GGT GTG CGT CAG AAT GGT GAA CGG GTT AAT CAC GTC AAC     10164
Phe Asp Phe Gly Val Arg Gln Asn Gly Glu Arg Val Asn His Val Asn
3310                    3315                    3320           3325
```

FIG.7D1

```
CTT CCC CCT TGG GCG CGT AAT GAT CCT CGT CTT TTT ATC CTC ATC CAT    10212
Leu Pro Pro Trp Ala Arg Asn Asp Pro Arg Leu Phe Ile Leu Ile His
                3330                            3335            3340

CGG CAG GCT CTA GAG TCT GAC TAC GTG TCG CAG AAC ATC TGT CAG TGG    10260
Arg Gln Ala Leu Glu Ser Asp Tyr Val Ser Gln Asn Ile Cys Gln Trp
                3345                3350                3355

ATT GAC TTG GTG TTT GGG TAT AAG CAA AAG GGG AAG GCT TCT GTT CAA    10308
Ile Asp Leu Val Phe Gly Tyr Lys Gln Lys Gly Lys Ala Ser Val Gln
        3360                3365                3370

GCG ATC AAT GTT TTT CAT CCT GCT ACA TAT TTT GGA ATG GAT GTC TCT    10356
Ala Ile Asn Val Phe His Pro Ala Thr Tyr Phe Gly Met Asp Val Ser
    3375                3380                3385

GCA GTT GAA GAT CCA GTT CAG AGA CGA GCG CTA GAA ACC ATG ATA AAA    10404
Ala Val Glu Asp Pro Val Gln Arg Arg Ala Leu Glu Thr Met Ile Lys
            3390                3395                3400        3405

ACC TAC GGG CAG ACT CCC CGT CAG CTG TTC CAC ATG GCC CAT GTG AGC    10452
Thr Tyr Gly Gln Thr Pro Arg Gln Leu Phe His Met Ala His Val Ser
                        3410                3415            3420

AGA CCT GGA GCC AAG CTC AAT ATT GAA GGA GAG CTT CCA GCT GCT GTG    10500
Arg Pro Gly Ala Lys Leu Asn Ile Glu Gly Glu Leu Pro Ala Ala Val
            3425                3430                3435
```

FIG.7E1

```
GGG TTG CTA GTG CAG TTT GCT TTC AGG GAG ACC CGA GAA CAG GTC AAA      10548
Gly Leu Leu Val Gln Phe Ala Phe Arg Glu Thr Arg Glu Gln Val Lys
             3440                3445                3450

GAA ATC ACC TAT CCG AGT CCT TTG TCA TGG ATA AAA GGC TTG AAA TGG      10596
Glu Ile Thr Tyr Pro Ser Pro Leu Ser Trp Ile Lys Gly Leu Lys Trp
             3455                3460                3465

GGG GAA TAC GTG GGT TCC CCC AGT GCT CCA GTA CCT GTG GTC TGC TTC      10644
Gly Glu Tyr Val Gly Ser Pro Ser Ala Pro Val Pro Val Val Cys Phe
3470                3475                3480                3485

AGC CAG CCC CAC GGA GAA AGA TTT GGC TCT CTC CAG GCT CTG CCC ACC      10692
Ser Gln Pro His Gly Glu Arg Phe Gly Ser Leu Gln Ala Leu Pro Thr
             3490                3495                3500

AGA GCA ATC TGT GGT TTG TCA CGG AAT TTC TGT CTT GTG ATG ACA TAT      10740
Arg Ala Ile Cys Gly Leu Ser Arg Asn Phe Cys Leu Val Met Thr Tyr
             3505                3510                3515

AGC AAG GAA CAA GGT GTG AGA AGC ATG AAC AGT ACG GAC ATT CAG TGG      10788
Ser Lys Glu Gln Gly Val Arg Ser Met Asn Ser Thr Asp Ile Gln Trp
             3520                3525                3530

TCA GCC ATC CTG AGC TGG GGA TAT GCT GAT AAT ATT TTA AGG TTG AAG      10836
Ser Ala Ile Leu Ser Trp Gly Tyr Ala Asp Asn Ile Leu Arg Leu Lys
             3535                3540                3545
```

FIG.7F1

```
AGT AAA CAA AGT GAG CCT CCA GTA AAC TTT ATT CAA AGT TCA CAA CAG         10884
Ser Lys Gln Ser Glu Pro Pro Val Asn Phe Ile Gln Ser Ser Gln Gln
3550                      3555                  3560              3565

TAC CAG GTG ACT AGT TGT GCT TGG GTG CCT GAC AGT TGC CAG CTG TTT         10932
Tyr Gln Val Thr Ser Cys Ala Trp Val Pro Asp Ser Cys Gln Leu Phe
              3570                  3575                  3580

ACT GGA AGC AAA TGC GGT GTC ATC ACA GCC TAC ACA AAC AGA TTT ACA         10980
Thr Gly Ser Lys Cys Gly Val Ile Thr Ala Tyr Thr Asn Arg Phe Thr
        3585                  3590                  3595

AGC AGC ACG CCA TCA GAA ATA GAA ATG GAG ACT CAA ATA CAT CTC TAT         11028
Ser Ser Thr Pro Ser Glu Ile Glu Met Glu Thr Gln Ile His Leu Tyr
                3600                  3605                  3610

GGT CAC ACA GAA GAG ATA ACC AGC TTA TTT GTT TGC AAA CCA TAC AGT         11076
Gly His Thr Glu Glu Ile Thr Ser Leu Phe Val Cys Lys Pro Tyr Ser
          3615                  3620                  3625

ATA CTG ATA AGT GTG AGC AGA GAC GGA ACC TGC ATC ATA TGG GAT TTA         11124
Ile Leu Ile Ser Val Ser Arg Asp Gly Thr Cys Ile Ile Trp Asp Leu
3630                  3635                  3640              3645

AAC AGG TTA TGC TAT GTA CAA AGT CTG GCG GGA CAC AAA AGC CCT GTC         11172
Asn Arg Leu Cys Tyr Val Gln Ser Leu Ala Gly His Lys Ser Pro Val
              3650                  3655                  3660
```

FIG.7G1

```
ACA GCT GTC TCT GCC AGT GAA ACC TCA GGT GAT ATT GCT ACT GTG TGT    11220
Thr Ala Val Ser Ala Ser Glu Thr Ser Gly Asp Ile Ala Thr Val Cys
                3665                        3670                3675

GAT TCA GCT GGC GGA GGC AGT GAC CTC AGA CTC TGG ACG GTG AAC GGG    11268
Asp Ser Ala Gly Gly Gly Ser Asp Leu Arg Leu Trp Thr Val Asn Gly
                3680                        3685                3690

GAT CTC GTT GGA CAT GTC CAC TGC AGG GAG ATC TGT TCC GTG GCT        11316
Asp Leu Val Gly His Val His Cys Arg Glu Ile Cys Ser Val Ala
            3695                        3700                3705

TTC TCC AAC CAG CCT GAG GGA GTA TCT ATC AAT GTA ATC GCT GGG GGA    11364
Phe Ser Asn Gln Pro Glu Gly Val Ser Ile Asn Val Ile Ala Gly Gly
3710                        3715                        3720       3725

TTA GAA AAT GGA ATT GTT AGG TTA TGG AGC ACA TGG GAC TTA AAG CCT    11412
Leu Glu Asn Gly Ile Val Arg Leu Trp Ser Thr Trp Asp Leu Lys Pro
                3725                        3730           3735    3740

GTG AGA GAA ATT ACA TTT CCC AAA TCA AAT AAG CCC ATC ATC AGC CTT    11460
Val Arg Glu Ile Thr Phe Pro Lys Ser Asn Lys Pro Ile Ile Ser Leu
                3745                        3750                3755

ACA TTT TCT TGT GAT GGC CAC CAT TTG TNC ACA GCA AAC AGT GAT GGG    11508
Thr Phe Ser Cys Asp Gly His His Leu Xaa Thr Ala Asn Ser Asp Gly
                3760                        3765                3770
```

FIG.7H1

```
ACC GTG ATT GCC TGG TGT CGG AAG GAC CAG CAC CGC TTG AAA CAG CCA                         11556
Thr Val Ile Ala Trp Cys Arg Lys Asp Gln His Arg Leu Lys Gln Pro
     3775                      3780                     3785

ATG TTC TAT TCC TTC CTT AGC AGC TAT GCA GCC GGG TGA ATGCGAATGA                          11605
Met Phe Tyr Ser Phe Leu Ser Ser Tyr Ala Ala Gly  *
3790                     3795                3800

ACTTCATGTT CTCCAAAGCA CTTTAACTCC AAACTAGATT TGTTGACTTC ACCAGTTTTA                        11665
GGAGGTTGAA CCTAAAGAAA TGGATGACTG GACAAACCAT CCAAATAATG ATAAAGTCTA                        11725
TTCATCTGCA CAAAATTCTG AAGAGTCACA TGATCCTAAG AGGAAAGTTC TGTTCTATTT                        11785
TAGTGATAAT CTGGAAGATT GTGTCAATAT GCACTAGCCA ACAAGTTTTA AGCCTCGCAT                        11845
GGTACATTAA AATGATATTC TTAAAATTTT TTCCCACCAA GGTATTCCAA AGAAAATATT                        11905
AAGGTCTCCC CTTTTTCTAT GATTCCAAAA GGACCAGTAG AATTTAAATT GGTTGGTTGA                        11965
TNGTTTATAT AAAACACACT AAAATTATAT TTTAAAAGTT TANTGCCNTG AAATACTCCT                        12025
CCCACCACAC ACACATGCTC CAAAAGAGGA AAGAAAAAAA GATAATTTTT AGGACTTGAT                        12085
AATTGCTTTC TTTGAGAAGC AAATTATTCA GTAGGTGCCT CTGTACCAAA TATTTTATGG                        12145
AATATCTAAA TACTAAAATA AACTATGAAT GAATCTCAAA TTTTTTGACA GCCACAAACA AGAATACAGG            12205
TGCTTTCTTA GCTCAAAGGA GAACCAGAAT TTCTGTTTCT TCATAAAAAT TTTACTTAAA ATCTGTAACG            12265
TATCTTGGAT TTCAGACACA ACTATCCTTA GTTGAGTCAC TGAGGTTTAA ACACAATGGT AAGTCTTAAA            12325
CTAGATATTG ACTATCCTTA TACAGAGCAT TGAATCTGTA CCAATTTGCA ATAGAAAGCC TTCAGTATGC            12385
GTCTGCTATT TACAGAGCAT TGAATCTGTA CCAATTTGCA ATAGAAAGCC TTCAGTATGC                        12385
AAGAAGTTTG CATGGGTATT AAGAACACAG CCTAAATAAG GCATTTGATC TAATCTGCAG                        12445
GAAGAATTTT CTTCCCCAAA ACAGAATTAT AAAAGCTTAC TTTAAACAGG AGGCAGAATA                        12505
ATTCTTTTAG GAAACCATTT CATTCTGTTT CTACTAACCT ATACCATCTG A                                 12565
                                                                                        12616
```

FIG. 711

```
GCGGCCGCGT CGACGCGGCG GCGGCAGCGG CGTCGGCTCG GGGTTCTCCG GGAGAGGGGG        60

AGTGCGCGGC GGCCGCAGCT GCCACAAACC AGGTGAAGCT TTGTTCTAAG AATATTTGTT       120

TCATCTAGTT TATGAGTCCA AATGATATAG ACTGTAAATG TCACAGCAGT GGTGAAAGAC       180

TGCTCGGTC ATG AGC ACC GAC AGT AAC TCA CTG GCA CGT GAA TTT CTG          228
           Met Ser Thr Asp Ser Asn Ser Leu Ala Arg Glu Phe Leu
            1               5                      10

ACC GAT GTC AAC CGG CTT TGC AAT GCA GTG GTC CAG AGG GTG GAG GCC        276
Thr Asp Val Asn Arg Leu Cys Asn Ala Val Val Gln Arg Val Glu Ala
           15                  20                  25

AGG GAA GAA GAG GAG ACG CAC ATG GCA ACC CTT GGA CAG TAC                324
Arg Glu Glu Glu Glu Thr His Met Ala Thr Leu Gly Gln Tyr
 30                  35                  40              45

CTT GTC CAT GGT CGA GGA TTT CTA TTA CTT ACC AAG CTA AAT TCT ATA        372
Leu Val His Gly Arg Gly Phe Leu Leu Leu Thr Lys Leu Asn Ser Ile
             50                  55                  60

ATT GAT CAG GCA TTG ACA TGT AGA GAA CTC CTG ACT CTT CTT CTG            420
Ile Asp Gln Ala Leu Thr Cys Arg Glu Leu Leu Thr Leu Leu Leu
 65                  70                  75
```

FIG.8A

```
TCT CTC CTT CCA CTG GTA TGG AAG ATA CCT GTC CAA GAA GAA AAG GCA          468
Ser Leu Leu Pro Leu Val Trp Lys Ile Pro Val Gln Glu Glu Lys Ala
             80                       85                    90

ACA GAT TTT AAC CTA CCG CTC TCA GCA GAT ATA ATC CTG ACC AAA GAA          516
Thr Asp Phe Asn Leu Pro Leu Ser Ala Asp Ile Ile Leu Thr Lys Glu
         95                      100                     105

AAG AAC TCA AGT TCA CAA AGA TCC ACT CAG GAA AAA TTA CAT TTA GAA          564
Lys Asn Ser Ser Ser Gln Arg Ser Thr Gln Glu Lys Leu His Leu Glu
     110                     115                     120         125

GGA AGT GCC CTG TCT AGT CAG GTT TCT GCA AAA GTA AAT GTT TTT CGA          612
Gly Ser Ala Leu Ser Ser Gln Val Ser Ala Lys Val Asn Val Phe Arg
                     130                     135                 140

AAA AGC AGA CGA CAG CGT AAA ATT ACC CAT CGC TAT TCT GTA AGA GAT          660
Lys Ser Arg Arg Gln Arg Lys Ile Thr His Arg Tyr Ser Val Arg Asp
                 145                     150                     155

GCA AGA AAG ACA CAG CTC TCC ACC TCA GAT TCA GAA GCC AAT TCA GAT          708
Ala Arg Lys Thr Gln Leu Ser Thr Ser Asp Ser Glu Ala Asn Ser Asp
             160                     165                     170

GAA AAA GGC ATA GCA ATG AAT AAG CAT AGA AGG CCC CAT CTG CTG CAT          756
Glu Lys Gly Ile Ala Met Asn Lys His Arg Arg Pro His Leu Leu His
         175                     180                     185
```

FIG. 8B

| | |
|---|---|
| CAT TTT TTA ACA TCG TTT CCT AAA CAA GAC CAC CCC AAA GCT AAA CTT<br>His Phe Leu Thr Ser Phe Pro Lys Gln Asp His Pro Lys Ala Lys Leu<br>190                        195                      200                   205 | 804 |
| GAC CGC TTA GCA ACC AAA GAA CAG ACT CCT CCA GAT GCT ATG GCT TTG<br>Asp Arg Leu Ala Thr Lys Glu Gln Thr Pro Pro Asp Ala Met Ala Leu<br>210                        215                                220 | 852 |
| GAA AAT TCC AGA GAG ATT ATT CCA AGA CAG GGG TCA AAC ACT GAC ATT<br>Glu Asn Ser Arg Glu Ile Ile Pro Arg Gln Gly Ser Asn Thr Asp Ile<br>225                        230                      235 | 900 |
| TTA AGT GAG CCA GCT GCC TTG TCT GTT ATC AGT AAC ATG AAC AAT TCT<br>Leu Ser Glu Pro Ala Ala Leu Ser Val Ile Ser Asn Met Asn Asn Ser<br>240                        245                                250 | 948 |
| CCA TTT GAC TTA TGT CAT GTT TTG TTA TCT TTA GAA AAA GTT TGT<br>Pro Phe Asp Leu Cys His Val Leu Leu Ser Leu Glu Lys Val Cys<br>255                        260                      265 | 996 |
| AAG TTT GAC GTT ACC TTG AAT CAT AAT TCT CCT TTA GCA GCC AGT GTA<br>Lys Phe Asp Val Thr Leu Asn His Asn Ser Pro Leu Ala Ala Ser Val<br>270                        275                                280                      285 | 1044 |
| GTG CCC ACA CTA ACT GAA TTC CTA GCA GGC TTT GGG GAC TGC TGC AGT<br>Val Pro Thr Leu Thr Glu Phe Leu Ala Gly Phe Gly Asp Cys Cys Ser<br>290                        295                                300 | 1092 |

FIG.8C

```
CTG AGC GAC AAC TTG GAG AGT CGA GTA GTT TCT GCA GGT TGG ACC GAA      1140
Leu Ser Asp Asn Leu Glu Ser Arg Val Val Ser Ala Gly Trp Thr Glu
                305                 310                 315

GAA CCG GTG GCT TTG ATT CAA AGG ATG CTC TTT CGA ACA GTG TTG CAT      1188
Glu Pro Val Ala Leu Ile Gln Arg Met Leu Phe Arg Thr Val Leu His
            320                 325                 330

CTT CTG TCA GTA GAT GTT AGT ACT GCA GAG ATG ATG CCA GAA AAT CTT      1236
Leu Leu Ser Val Asp Val Ser Thr Ala Glu Met Met Pro Glu Asn Leu
        335                 340                 345

AGG AAA AAT TTA ACT GAA TTG CTT AGA GCA GCT GCA CTT AAA ATT AGA ATA  1284
Arg Lys Asn Leu Thr Glu Leu Leu Arg Ala Ala Ala Leu Lys Ile Arg Ile
    350                 355                 360                 365

TGC CTA GAA AAG CAG CCT GAC CCT TTT GCA CCA AGA CAA AAG AAA ACA      1332
Cys Leu Glu Lys Gln Pro Asp Pro Phe Ala Pro Arg Gln Lys Lys Thr
                370                 375                 380

CTG CAG GAG GTT CAG GAA GAT TTT GTG TTT TCA AAG TAT CGT CAT AGA      1380
Leu Gln Glu Val Gln Glu Asp Phe Val Phe Ser Lys Tyr Arg His Arg
            385                 390                 395

GCC CTT CTT TTA CCT GAG CTT TTG GAA GGA GTT CTT CAG ATT CTG ATC      1428
Ala Leu Leu Leu Pro Glu Leu Leu Glu Gly Val Leu Gln Ile Leu Ile
        400                 405                 410
```

FIG. 8D

```
TGT TGT CTT CAA AGT GCA GCT TCA AAT CCC TTC TAC TTC AGT CAA GCC    1476
Cys Cys Leu Gln Ser Ala Ala Ser Asn Pro Phe Tyr Phe Ser Gln Ala
415                 420                 425

ATG GAT TTG GTT CAA GAA TTC ATT CAG CAT CAT GGA TTT AAT TTA TTT    1524
Met Asp Leu Val Gln Glu Phe Ile Gln His His Gly Phe Asn Leu Phe
430                 435                 440                 445

GAA ACA GCA GTT CTT CAA ATG GAA TGG CTG GTT TTA AGA GAT GGA GTT    1572
Glu Thr Ala Val Leu Gln Met Glu Trp Leu Val Leu Arg Asp Gly Val
450                 455                 460

CCT CCC GAG GCC TCA GAG CAT TTG AAA GCC CTA ATA AAT AGT GTG ATG    1620
Pro Pro Glu Ala Ser Glu His Leu Lys Ala Leu Ile Asn Ser Val Met
465                 470                 475

AAA ATA ATG AGC ACT GTC AAA AAA GTG AAA TCA GAG CAA CTT CAT CAT    1668
Lys Ile Met Ser Thr Val Lys Lys Val Lys Ser Glu Gln Leu His His
480                 485                 490

TCG ATG TGT ACA AGA AAA AGG CAC AGA CGA TGT GAA TAT TCT CAT TTT    1716
Ser Met Cys Thr Arg Lys Arg His Arg Arg Cys Glu Tyr Ser His Phe
495                 500                 505

ATG CAT CAT CAC CGA GAT CTC TCA GGT CTT CTG GTT TCG GCT TTT AAA    1764
Met His His His Arg Asp Leu Ser Gly Leu Leu Val Ser Ala Phe Lys
510                 515                 520                 525
```

FIG.8E

```
AAC CAG GTT TCC AAA AAC CCA TTT GAA GAG ACT GCA GAT GGA GAT GTT   1812
Asn Gln Val Ser Lys Asn Pro Phe Glu Glu Thr Ala Asp Gly Asp Val
                530                     535                 540

TAT TAT CCT GAG CGG TGC TGT ATT GCA GTG TGT GCC CAT CAG TGC       1860
Tyr Tyr Pro Glu Arg Cys Cys Ile Ala Val Cys Ala His Gln Cys
            545                     550                 555

TTG CGC TTA CTA CAG CAG GCT TCC TTG AGC ACT TGT GTC CAG ATC       1908
Leu Arg Leu Leu Gln Gln Ala Ser Leu Ser Ser Thr Cys Val Gln Ile
            560                     565                 570

CTA TCG GGT GTT CAT AAC ATT GGA ATA TGC TGT TGT ATG GAT CCC AAA   1956
Leu Ser Gly Val His Asn Ile Gly Ile Cys Cys Cys Met Asp Pro Lys
            575                     580                 585

TCT GTA ATC ATT CCT TTG CTC CAT GCT TTT AAA TTG CCA GCA CTG AAA   2004
Ser Val Ile Ile Pro Leu Leu His Ala Phe Lys Leu Pro Ala Leu Lys
            590                     595                 600          605

AAT TTT CAG CAG CAT ATA TTG AAT ATC CTT AAC AAA CTT ATT TTG GAT   2052
Asn Phe Gln Gln His Ile Leu Asn Ile Leu Asn Lys Leu Ile Leu Asp
            610                     615                 620

CAG TTA GGA GGA GCA GAG ATA TCA CCA AAA ATT AAA AAA GCA GCT TGT   2100
Gln Leu Gly Gly Ala Glu Ile Ser Pro Lys Ile Lys Lys Ala Ala Cys
            625                     630                 635
```

FIG.8F

```
AAT ATT TGT ACT GTT GAC TCT GAC CAA CTA GCC CAA TTA GAA GAG ACA      2148
Asn Ile Cys Thr Val Asp Ser Asp Gln Leu Ala Gln Leu Glu Glu Thr
            640                 645                 650

CTG CAG GGA AAC TTA TGT GAT GCT GAA CTC TCC TCA AGT TTA TCC AGT      2196
Leu Gln Gly Asn Leu Cys Asp Ala Glu Leu Ser Ser Ser Leu Ser Ser
        655                 660                 665

CCT TCT TAC AGA TTT CAA GGG ATC CTG CCC AGC CTG CCT GAA GAT          2244
Pro Ser Tyr Arg Phe Gln Gly Ile Leu Pro Ser Leu Pro Ser Glu Asp
    670                 675                 680                 685

TTG TTG TGG AAA TGG GAT GCT TTA AAG GCT TAT CAG AAC TTT GTT TTT      2292
Leu Leu Trp Lys Trp Asp Ala Leu Lys Ala Tyr Gln Asn Phe Val Phe
                690                 695                 700

GAA GAC AGA AGA TTA CAT AGT ATA CAG ATT GCA AAT CAC ATT TGC AAT      2340
Glu Glu Asp Arg Leu His Ser Ile Gln Ile Ala Asn His Ile Cys Asn
            705                 710                 715

TTA ATC CAG AAA GGC AAT ATA GTT GTT CAG TGG AAA TTA TAT AAT TAC      2388
Leu Ile Gln Lys Gly Asn Ile Val Val Gln Trp Lys Leu Tyr Asn Tyr
        720                 725                 730

ATA TTT AAT CCT GTG CTC CAA AGA GGA GTT GAA TTA GCA CAT CAT TGT      2436
Ile Phe Asn Pro Val Leu Gln Arg Gly Val Glu Leu Ala His His Cys
    735                 740                 745
```

FIG.8G

```
CAA CAC CTA AGC GTT ACT TCA GCT CAA AGT CAT GTA TGT AGC CAT CAT    2484
Gln His Leu Ser Val Thr Ser Ala Gln Ser His Val Cys Ser His His
750                 755                 760                 765

AAC CAG TGC TTG CCT CAG GAC GTG CTT CAG ATT TAT GTA AAA ACT CTG    2532
Asn Gln Cys Leu Pro Gln Asp Val Leu Gln Ile Tyr Val Lys Thr Leu
        770                 775                 780

CCT ATC CTG CTT AAA TCC AGG GTA ATA AGA GAT TTG TTT TTG AGT TGT    2580
Pro Ile Leu Leu Lys Ser Arg Val Ile Arg Asp Leu Phe Leu Ser Cys
                785                 790                 795

AAT GGA GTA AGT CAA ATA ATC GAA TTA AAT TGC TTA AAT GGT ATT CGA    2628
Asn Gly Val Ser Gln Ile Ile Glu Leu Asn Cys Leu Asn Gly Ile Arg
        800                 805                 810

AGT CAT TCT CTA AAA GCA TTT GAA ACT CTG ATA ATC AGC CTA GGG GAG    2676
Ser His Ser Leu Lys Ala Phe Glu Thr Leu Ile Ile Ser Leu Gly Glu
                815                 820                 825

CAA CAG AAA GAT GCC TCA GTT CCA GAT ATT GAT GGG ATA GAC ATT GAA    2724
Gln Gln Lys Asp Ala Ser Val Pro Asp Ile Asp Gly Ile Asp Ile Glu
        830                 835                 840                 845

CAG AAG GAG TTG TCC TCT GTA CAT GTG GGT ACT TCT TTT CAT CAT CAG    2772
Gln Lys Glu Leu Ser Ser Val His Val Gly Thr Ser Phe His His Gln
                850                 855                 860
```

FIG.8H

```
CAA GCT TAT TCA GAT TCT CCT CAG AGT CTC AGC AAA TTT TAT GCT GGC    2820
Gln Ala Tyr Ser Asp Ser Pro Gln Ser Leu Ser Lys Phe Tyr Ala Gly
865                         870                 875

CTC AAA GAA GCT TAT CCA AAG AGA CGG AAG ACT GTT AAC CAA GAT GTT    2868
Leu Lys Glu Ala Tyr Pro Lys Arg Arg Lys Thr Val Asn Gln Asp Val
    880                     885                 890

CAT ATC AAC ACA ATA AAC CTA TTC CTC TGT GTG GCT TTA TGC GTA        2916
His Ile Asn Thr Ile Asn Leu Phe Leu Cys Val Ala Phe Leu Cys Val
895                         900                 905

AGT AAA GAA GCA GAG TCT GAC AGG GAG TCG GCC AAT GAC TCA GAA GAT    2964
Ser Lys Glu Ala Glu Ser Asp Arg Glu Ser Ala Asn Asp Ser Glu Asp
910                         915                 920             925

ACT TCT GGC TAT GAC AGC ACA AGC GAG CTT GTC TTG CCT TCT CCT GAA CAT ATG CTG    3012
Thr Ser Gly Tyr Asp Ser Thr Ala Ser Glu Leu Val Leu Pro Ser Pro Glu His Met Leu
                930                 935                 940

CCA TGT ATA TCT CTC GAG AGC CTT GTC TTG CCT TCT CCT GAA CAT ATG    3060
Pro Cys Ile Ser Leu Glu Ser Leu Val Leu Pro Ser Pro Glu His Met
    945                 950                 955

CAC CAA GCA GCA GAC ATT TGG TCT ATG TGT CGT TGG ATC TAC ATG TTG    3108
His Gln Ala Ala Asp Ile Trp Ser Met Cys Arg Trp Ile Tyr Met Leu
960                 965                 970

FIG. 81
```

```
AGT TCA GTG TTC CAG AAA CAG TTT TAT AGG CTT GGT GGT TTC CGA GTA     3156
Ser Ser Val Phe Gln Lys Gln Phe Tyr Arg Leu Gly Gly Phe Arg Val
            975                 980                 985

TGC CAT AAG TTA ATA TTT ATG ATA ATA CAG AAA CTG TTC AGA AGT CAC     3204
Cys His Lys Leu Ile Phe Met Ile Ile Gln Lys Leu Phe Arg Ser His
            990                 995                 1000       1005

AAA GAG GAG CAA GGA AAA AAG GAG GGA GAT ACA AGT GTA AAT GAA AAC     3252
Lys Glu Glu Gln Gly Lys Lys Glu Gly Asp Thr Ser Val Asn Glu Asn
            1010                1015                1020

CAG GAT TTA AAC AGA ATT TCT CAA CCT AAG AGA ACT ATG AAG GAA GAT     3300
Gln Asp Leu Asn Arg Ile Ser Gln Pro Lys Arg Thr Met Lys Glu Asp
            1025                1030                1035

TTA TTA TCT TTG GCT ATA AAA AGT GAC CCC ATA CCA TCA GAA CTA GGT     3348
Leu Leu Ser Leu Ala Ile Lys Ser Asp Pro Ile Pro Ser Glu Leu Gly
            1040                1045                1050

AGT CTA AAA AAG AGT GCT GAC AGT TTA GGT AAA TTA GAG TTA CAG CAT     3396
Ser Leu Lys Lys Ser Ala Asp Ser Leu Gly Lys Leu Glu Leu Gln His
            1055                1060                1065

ATT TCT TCC ATA AAT GTG GAA GAA GTT TCA GCT ACT GAA GCC GCT CCC     3444
Ile Ser Ser Ile Asn Val Glu Glu Val Ser Ala Thr Glu Ala Ala Pro
            1070                1075                1080       1085
```

FIG. 8J

```
GAG GAA GCA AAG CTA TTT ACA AGT CAA GAA AGT GAG ACC TCA CTT CAA    3492
Glu Glu Ala Lys Leu Phe Thr Ser Gln Glu Ser Glu Thr Ser Leu Gln
                1090                    1095                1100

AGT ATA CGA CTT TTG GAA GCC CTT CTG GCC ATT TGT CTT CAT GGT GCC    3540
Ser Ile Arg Leu Leu Glu Ala Leu Leu Ala Ile Cys Leu His Gly Ala
                1105                    1110                1115

AGA ACT AGT CAA CAG AAG ATG GAA TTG GAG TTA CCT AAT CAG AAC TTG    3588
Arg Thr Ser Gln Gln Lys Met Glu Leu Glu Leu Pro Asn Gln Asn Leu
                1120                    1125                1130

TCT GTG GAA AGT ATA TTA TTT GAA ATG AGG GAC CAT CTT TCC CAG TCA    3636
Ser Val Glu Ser Ile Leu Phe Glu Met Arg Asp His Leu Ser Gln Ser
                1135                    1140                1145

AAG GTG ATT GAA ACA CAA CTA GCA AAG CCG TTA TTT GAT GCC CTG CTT    3684
Lys Val Ile Glu Thr Gln Leu Ala Lys Pro Leu Phe Asp Ala Leu Leu
                1150                    1155                1165

CGA GTT GCC CTC GGG AAT TAT TCA GCA GAT TTT GAA CAT AAT GAT GCT    3732
Arg Val Ala Leu Gly Asn Tyr Ser Ala Asp Phe Glu His Asn Asp Ala
                1170                    1175                1180

ATG ACT GAG AAG AGT CAT CAA TCT GCA GAA GAA TTG TCA TCC CAG CCT    3780
Met Thr Glu Lys Ser His Gln Ser Ala Glu Glu Leu Ser Ser Gln Pro
                1185                    1190                1195
```

FIG.8K

```
GGT GAT TTT TCA GAA GAA GCT GAG GAT TCT CAG TGT TGT AGT TTT AAA        3828
Gly Asp Phe Ser Glu Glu Ala Glu Asp Ser Gln Cys Cys Ser Phe Lys
            1200                    1205                    1210

CTT TTA GTT GAA GAA GGT TAC GAA GCA GAT AGT GAA AGC AAT CCT            3876
Leu Leu Val Glu Glu Gly Tyr Glu Ala Asp Ser Glu Ser Asn Pro
    1215                    1220                    1225

GAA GAT GGC GAA ACC CAG GAT GGG GTA GAC TTA AAG TCT GAA ACA            3924
Glu Asp Gly Glu Thr Gln Asp Gly Val Asp Leu Lys Ser Glu Thr
            1230                    1235                    1240                1245

GAA GGT TTC AGT GCA TCA AGT CCA AAT GAC TTA GAA AAC CTC                3972
Glu Gly Phe Ser Ala Ser Ser Pro Asn Asp Leu Glu Asn Leu
    1250                    1255                    1260

ACT CAA GGG GAA ATA ATT TAT CCT GAG ATT TGT ATG CTG GAA TTA AAT        4020
Thr Gln Gly Glu Ile Ile Tyr Pro Glu Ile Cys Met Leu Glu Leu Asn
            1265                    1270                    1275

TTG CTT TCT GCT AGT AAA GCC AAA CTT GAT GTG CTT GCC CAT GTA TTT        4068
Leu Leu Ser Ala Ser Lys Ala Lys Leu Asp Val Leu Ala His Val Phe
    1280                    1285                    1290

GAG AGT TTT TTG AAA ATT ATT AGG CAG AAA GAA AAG AAT GTT TTT CTG        4116
Glu Ser Phe Leu Lys Ile Ile Arg Gln Lys Glu Lys Asn Val Phe Leu
            1295                    1300                    1305
```

FIG.8L

CTC ATG CAA CAG GGA ACT GTG AAA AAT CTT TTA GGA GGG TTC TTG AGT    4164
Leu Met Gln Gln Gly Thr Val Lys Asn Leu Leu Gly Gly Phe Leu Ser
1310                              1320                        1325

ATT TTA ACA CAG GAT GAT TCT GAT TTT CAA GCA TGC CAG AGA GTA TTG    4212
Ile Leu Thr Gln Asp Asp Ser Asp Phe Gln Ala Cys Gln Arg Val Leu
       1330                              1335                 1340

GTG GAT CTT TTG GTA TCT TTG ATG AGT TCA AGA ACA TGT TCA GAA GAG    4260
Val Asp Leu Leu Val Ser Leu Met Ser Ser Arg Thr Cys Ser Glu Glu
           1345                              1350                 1355

CTA ACC CTT CTT TTG AGA ATA TTT CTG GAG AAA TCT CCT TGT ACA AAA    4308
Leu Thr Leu Leu Leu Arg Ile Phe Leu Glu Lys Ser Pro Cys Thr Lys
               1360                              1365             1370

ATT CTT CTT CTG GGT ATT CTG AAA ATT ATT GAA AGT GAT ACT ACT ATG    4356
Ile Leu Leu Leu Gly Ile Leu Lys Ile Ile Glu Ser Asp Thr Thr Met
1375                              1380                        1385

AGC CCT TCA CAG TAT CTA ACC TTC CCT TTA CTG CAC GCT CCA AAT TTA    4404
Ser Pro Ser Gln Tyr Leu Thr Phe Pro Leu Leu His Ala Pro Asn Leu
       1390                              1395                 1400                 1405

AGC AAC GGT GTT TCA TCA CAA AAG TAT CCT GGG ATT TTA AAC AGT AAG    4452
Ser Asn Gly Val Ser Ser Gln Lys Tyr Pro Gly Ile Leu Asn Ser Lys
           1410                              1415                 1420

FIG.8M

```
GCC ATG GGT TTA TTG AGA AGA GCA CGA GTT TCA CGG AGC AAG AAA GAG      4500
Ala Met Gly Leu Leu Arg Arg Ala Arg Val Ser Arg Ser Lys Lys Glu
             1425                    1430                   1435

GCT GAT AGA GAG AGT TTT CCC CAT CGG CTG CTT TCA TCT TGG CAC ATA      4548
Ala Asp Arg Glu Ser Phe Pro His Arg Leu Leu Ser Ser Trp His Ile
             1440                    1445                   1450

GCC CCA GTC CAC CTG CCG TTG CTG GGG CAA AAC TGC TGG CCA CAC CTA      4596
Ala Pro Val His Leu Pro Leu Leu Gly Gln Asn Cys Trp Pro His Leu
             1455                    1460                   1465

TCA GAA GGT TTC AGT GTT TCC CTG TGG TTT AAT GTG GAG TGT ATC CAT      4644
Ser Glu Gly Phe Ser Val Ser Leu Trp Phe Asn Val Glu Cys Ile His
             1470                    1475                   1480    1485

GAA GCT GAG AGT ACT ACA GAA AAA GGA AAG ATA AAG AAA AGA AAC          4692
Glu Ala Glu Ser Thr Thr Glu Lys Gly Lys Ile Lys Lys Arg Asn
             1490                    1495                   1500

AAA TCA TTA ATT TTA CCA GAT AGC AGT TTT GAT GGT ACA GAG AGC GAC      4740
Lys Ser Leu Ile Leu Pro Asp Ser Ser Phe Asp Gly Thr Glu Ser Asp
             1505                    1510                   1515

AGA CCA GAA GGT GCA GAG TAC ATA AAT CCT GGT GAA AGA CTC ATA GAA      4788
Arg Pro Glu Gly Ala Glu Tyr Ile Asn Pro Gly Glu Arg Leu Ile Glu
             1520                    1525                   1530
```

FIG.8N

```
GAA GGA TGT ATT CAT ATA ATT TCA CTG GGA TCC AAA GCG TTG ATG ATC      4836
Glu Gly Cys Ile His Ile Ile Ser Leu Gly Ser Lys Ala Leu Met Ile
1535                          1540                         1545

CAA GTG TGG GCT GAT CCC CAC AAT GCC ACT CTT ATC TTT CGT GTG TGC      4884
Gln Val Trp Ala Asp Pro His Asn Ala Thr Leu Ile Phe Arg Val Cys
1550                          1555                         1560            1565

ATG GAT TCA AAT GAT GAC ATG AAA GCT GTT TTA CTA GCA CAG GTT GAA      4932
Met Asp Ser Asn Asp Asp Met Lys Ala Val Leu Leu Ala Gln Val Glu
          1570                         1575                         1580

TCA CAG GAG AAT ATT TTC CTC CCA AGC AAA TGG CAA CAT TTA GTA CTC      4980
Ser Gln Glu Asn Ile Phe Leu Pro Ser Lys Trp Gln His Leu Val Leu
                1585                         1590                         1595

ACC TAC TTA CAG CAG CCC CAA GGG AAA AGG AGG ATT CAT GGG AAA ATC      5028
Thr Tyr Leu Gln Gln Pro Gln Gly Lys Arg Arg Ile His Gly Lys Ile
          1600                         1605                         1610

TCC ATA TGG GTC TCT GGA CAG AGG AAG CCT GAT GTT ACT TTG GAT TTT      5076
Ser Ile Trp Val Ser Gly Gln Arg Lys Pro Asp Val Thr Leu Asp Phe
          1615                         1620                         1625

ATG CTT CCA AGA AAA ACA AGT TTG TCA TCT GAT AGC AAT AAA ACA TTT      5124
Met Leu Pro Arg Lys Thr Ser Leu Ser Ser Asp Ser Asn Lys Thr Phe
1630                          1635                         1640            1645
```

FIG.80

FIG.8P

```
TGC ATG ATT GGC CAT TGT TTA TCA TCC CAA GAA GAG TTT TTG CAG TTG      5172
Cys Met Ile Gly His Cys Leu Ser Ser Gln Glu Glu Phe Leu Gln Leu
             1650                    1655                   1660

GCT GGA AAA TGG GAC CTG GGA AAT TTG CTT CTC TTC AAC GGA GCT AAG      5220
Ala Gly Lys Trp Asp Leu Gly Asn Leu Leu Leu Phe Asn Gly Ala Lys
             1665                    1670                   1675

GTT GGT TCA CAA GAG GCC TTT TAT CTG TAT GCT TGT GGA CCC AAC CAT      5268
Val Gly Ser Gln Glu Ala Phe Tyr Leu Tyr Ala Cys Gly Pro Asn His
             1680                    1685                   1690

ACA TCT GTA ATG CCA TGT AAG TAT GGC AAG CCA GTC AAT GAC TAC TCC      5316
Thr Ser Val Met Pro Cys Lys Tyr Gly Lys Pro Val Asn Asp Tyr Ser
             1695                    1700                   1705

AAA TAT ATT AAT AAA GAA ATT TTG CGA TGT GAA CAA ATC AGA GAA CTT      5364
Lys Tyr Ile Asn Lys Glu Ile Leu Arg Cys Glu Gln Ile Arg Glu Leu
1710              1715                    1720                   1725

TTT ATG ACC AAG AAA GAT GTG GAT ATT GGT CTC TTA ATT GAA AGT CTT      5412
Phe Met Thr Lys Lys Asp Val Asp Ile Gly Leu Leu Ile Glu Ser Leu
             1730                    1735                   1740

TCA GTT TAT ACA ACT TAC TGT CCT GCT CAG TAT ACC ATC TAT GAA          5460
Ser Val Tyr Thr Thr Tyr Cys Pro Ala Gln Tyr Thr Ile Tyr Glu
             1745                    1750                   1755
```

```
CCA GTG ATT AGA CTT AAA GGT CAA ATG AAA ACC CAA CTC TCT CAA AGA    5508
Pro Val Ile Arg Leu Lys Gly Gln Met Lys Thr Gln Leu Ser Gln Arg
        1760             1765             1770

CCC TTC AGC TCA AAA GAA GTT CAG AGC ATC TTA TTA GAA CCT CAT CAT    5556
Pro Phe Ser Ser Lys Glu Val Gln Ser Ile Leu Leu Glu Pro His His
        1775             1780             1785

CTA AAA AAT CTC CAA CCT ACT GAA TAT AAA ACT ATT CAA GGC ATT CTG    5604
Leu Lys Asn Leu Gln Pro Thr Glu Tyr Lys Thr Ile Gln Gly Ile Leu
1790             1795             1800             1805

CAC GAA ATT GGT GGA ACT GGC ATA TTT GTT TTT CTC TTT GCC AGG GTT    5652
His Glu Ile Gly Gly Thr Gly Ile Phe Val Phe Leu Phe Ala Arg Val
        1810             1815             1820

GTT GAA CTC AGT AGC TGT GAA GAA ACT CAA GCA TTA GCA CTG CGA GTT    5700
Val Glu Leu Ser Ser Cys Glu Glu Thr Gln Ala Leu Ala Leu Arg Val
        1825             1830             1835

ATA CTC TCA TTA ATT AAA TAC AAC CAA AGA GTA CAT GAA TTA GAA        5748
Ile Leu Ser Leu Ile Lys Tyr Asn Gln Arg Val His Glu Leu Glu
        1840             1845             1850

AAT TGT AAT GGA CTT TCT ATG ATT CAT CAG TTG ATC AAA CAA AAA        5796
Asn Cys Asn Gly Leu Ser Met Ile His Gln Leu Ile Lys Gln Lys
        1855             1860             1865
```

FIG. 8Q

```
TGC ATT GTT GGG TTT TAC ATT TTG AAG ACC CTT CTT GAA GGA TGC TGT    5844
Cys Ile Val Gly Phe Tyr Ile Leu Lys Thr Leu Leu Glu Gly Cys Cys
1870                    1875                    1880                    1885

GGT GAA GAT ATT ATT TAT ATG AAT GAG AAT GGA GAG TTT AAG TTG GAT    5892
Gly Glu Asp Ile Ile Tyr Met Asn Glu Asn Gly Glu Phe Lys Leu Asp
1890                    1895                    1900

GTA GAC TCT AAT GCT ATA ATC CAA GAT GTT AAG CTG TTA GAG GAA CTA    5940
Val Asp Ser Asn Ala Ile Ile Gln Asp Val Lys Leu Leu Glu Glu Leu
1905                    1910                    1915

TTG CTT GAC TGG AAG ATA TGG AGT AAA GCA GAG CAA GGT GTT TGG GAA    5988
Leu Leu Asp Trp Lys Ile Trp Ser Lys Ala Glu Gln Gly Val Trp Glu
1920                    1925                    1930

ACT TTG CTA GCA GCT CTA GAA GTC CTC ATC AGA GCA GAT CAC CAC CAG    6036
Thr Leu Leu Ala Ala Leu Glu Val Leu Ile Arg Ala Asp His His Gln
1935                    1940                    1945

CAG ATG TTT AAT ATT AAG CAG TTA TTG AAA GCT CAA GTG GTT CAT CAC    6084
Gln Met Phe Asn Ile Lys Gln Leu Leu Lys Ala Gln Val Val His His
1950                    1955                    1960                    1965

TTT CTA CTG ACT TGT CAG GTT TTG CAG GAA TAC AAA GAG GGG CAA CTC    6132
Phe Leu Leu Thr Cys Gln Val Leu Gln Glu Tyr Lys Glu Gly Gln Leu
1970                    1975                    1980
```

FIG.8R

```
ACA CCC ATG CCC CGA GAG GTT TGT AGA TCA TTT GTG AAA ATT ATA GCA    6180
Thr Pro Met Pro Arg Glu Val Cys Arg Ser Phe Val Lys Ile Ile Ala
              1985                    1990                  1995

GAA GTC CTT GGA TCT CCT CCA GAT TTG GAA TTA TTG ACA ATT ATC TTC    6228
Glu Val Leu Gly Ser Pro Pro Asp Leu Glu Leu Leu Thr Ile Ile Phe
         2000                    2005                    2010

AAT TTC CTT TTA GCA GTT CAC CCT CCT ACT AAT ACT TAC GTT TGT CAC    6276
Asn Phe Leu Leu Ala Val His Pro Pro Thr Asn Thr Tyr Val Cys His
    2015                    2020                    2025

AAT CCC ACG AAC TTC TAC TTT TCT TTG CAC ATA ATC ATG ATC TTT        6324
Asn Pro Thr Asn Phe Tyr Phe Ser Leu His Ile Asp Gly Lys Ile Phe
2030                    2035                    2040          2045

CAG GAG AAA GTG CGG TCA ATC ATG TAC CTG AGG CAT TCC AGC AGT GGA    6372
Gln Glu Lys Val Arg Ser Ile Met Tyr Leu Arg His Ser Ser Ser Gly
              2050                    2055                  2060

GGA AGG TCC CTT ATG AGC CCT GGA TTT ATG GTA ATA AGC CCA TCT GGT    6420
Gly Arg Ser Leu Met Ser Pro Gly Phe Met Val Ile Ser Pro Ser Gly
         2065                    2070                    2075

TTT ACT GCT TCA CCA TAT GAA GGA GAG AAT TCC TCT AAT ATT ATT CCA    6468
Phe Thr Ala Ser Pro Tyr Glu Gly Glu Asn Ser Ser Asn Ile Ile Pro
    2080                    2085                    2090
```

FIG.8S

```
CAA CAG ATG GCC GCC CAT ATG CTG CGT TCT AGA AGC CTA CCA GCA TTC    6516
Gln Gln Met Ala Ala His Met Leu Arg Ser Arg Ser Leu Pro Ala Phe
                2095                                    2105

CCT ACT TCT TCA CTA CTA ACG CAA TCA CAA AAA CTG ACT GGA AGT TTG    6564
Pro Thr Ser Ser Leu Leu Thr Gln Ser Gln Lys Leu Thr Gly Ser Leu
        2110                        2115                    2125

GGT TGT AGT ATC GAC AGG TTA CAA AAT ATT GCA GAT ACT TAT GTT GCC    6612
Gly Cys Ser Ile Asp Arg Leu Gln Asn Ile Ala Asp Thr Tyr Val Ala
                2130                            2135            2140

ACC CAA TCA AAG AAA CAA AAT TCT TTG GGG AGT TCC GAC ACA CTG AAA    6660
Thr Gln Ser Lys Lys Gln Asn Ser Leu Gly Ser Ser Asp Thr Leu Lys
            2145                        2150                2155

AAA GGC AAA GAG GAC GCA TTC ATC AGT AGC TGT GAG TCT GCA AAA ACT    6708
Lys Gly Lys Glu Asp Ala Phe Ile Ser Ser Cys Glu Ser Ala Lys Thr
        2160                        2165                    2170

GTT TGT GAA ATG GAA GCT GTC CTC TCA GCC CAG GTC TCT GTC AGT GAT    6756
Val Cys Glu Met Glu Ala Val Leu Ser Ala Gln Val Ser Val Ser Asp
                2175                        2180                2185

GTC CCA AAG GGA GTG CTG GGA TTT CCA GTG GTC AAA GCA GAT CAT AAA    6804
Val Pro Lys Gly Val Leu Gly Phe Pro Val Val Lys Ala Asp His Lys
            2190                        2195                2200        2205
```

FIG.8T

```
CAG TTG GGA GCA GAA CCC AGG TCA GAA GAT GAC AGT CCT GGG GAT GAG     6852
Gln Leu Gly Ala Glu Pro Arg Ser Glu Asp Asp Ser Pro Gly Asp Glu
                    2210                2215                2220

TCC TGC CCA CGC CGA CCT GAT TAC CTA AAG GGA TTG GCC TCC TTC CAG     6900
Ser Cys Pro Arg Arg Pro Asp Tyr Leu Lys Gly Leu Ala Ser Phe Gln
            2225                2230                2235

CGA AGC CAC AGC ACT ATT GCA AGC CTT GGG CTA GCT TTT CCT TCA CAG     6948
Arg Ser His Ser Thr Ile Ala Ser Leu Gly Leu Ala Phe Pro Ser Gln
                2240                2245                2250

AAC TCT GCA GCT GTT GGC CGT TGG CCA AGT CTT GTT GAT AGA AAC         6996
Asn Ser Ala Ala Val Gly Arg Trp Pro Ser Leu Val Asp Arg Asn
        2255                2260                2265

ACT GAT GAT TGG GAA AAC TTT GCC TAT TCT CTT GGT TAT GAG CCA AAT     7044
Thr Asp Asp Trp Glu Asn Phe Ala Tyr Ser Leu Gly Tyr Glu Pro Asn
2270                2275                2280                2285

TAC AAC CGA ACT GCA AGT GCT CAC AGT GTA ACT GAA GAC TGT TTG GTA     7092
Tyr Asn Arg Thr Ala Ser Ala His Ser Val Thr Glu Asp Cys Leu Val
            2290                2295                2300

CCT ATA TGC TGT GGA TTA TAT GAA CTC CTA AGT GGG GTT CTT CTT ATC     7140
Pro Ile Cys Cys Gly Leu Tyr Glu Leu Leu Ser Gly Val Leu Leu Ile
        2305                2310                2315
```

FIG.8U

```
CTG CCT GAT GTT TTG CTT GAA GAT GTG ATG GAC AAG CTT ATT CAA GCA        7188
Leu Pro Asp Val Leu Leu Glu Asp Val Met Asp Lys Leu Ile Gln Ala
                2320                    2325                2330

GAT ACA CTT TTG GTC CTC GTT AAC CAC CCA TCA CCA GCT ATA CAA CAA        7236
Asp Thr Leu Leu Val Leu Val Asn His Pro Ser Pro Ala Ile Gln Gln
    2335                    2340                    2345

GGT GTT ATT AAA CTA TTA GAT GCA TAT TTT GCT AGA GCA TCT AAG GAA        7284
Gly Val Ile Lys Leu Leu Asp Ala Tyr Phe Ala Arg Ala Ser Lys Glu
2350                    2355                    2360           2365

CAA AAA GAT AAA TTT CTG AAG AAT CGT GGA TTT TCC TTG CTA GCC AAC        7332
Gln Lys Asp Lys Phe Leu Lys Asn Arg Gly Phe Ser Leu Leu Ala Asn
        2370                    2375                    2380

CAG TTG TAT CTT CAT CGA GGA ACT CAA GAA TTG TTA GAA TGC TTC ATC        7380
Gln Leu Tyr Leu His Arg Gly Thr Gln Glu Leu Leu Glu Cys Phe Ile
            2385                    2390                  2395

GAA ATG TTC TTT GGT CGA CAT ATT GGC CTT GAT GAA GAA TTT GAT CTG        7428
Glu Met Phe Phe Gly Arg His Ile Gly Leu Asp Glu Glu Phe Asp Leu
                2400                    2405                2410

GAA GAT GTG AGA AAC ATG GGA TTG TTT CAG AAG TGG TCT GTC ATT CCT        7476
Glu Asp Val Arg Asn Met Gly Leu Phe Gln Lys Trp Ser Val Ile Pro
    2415                    2420                    2425
```

FIG.8V

```
ATT CTG GGA CTA ATA GAG ACC TCT CTA TAT GAC AAC ATA CTC TTG CAT    7524
Ile Leu Gly Leu Ile Glu Thr Ser Leu Tyr Asp Asn Ile Leu Leu His
2430                         2435                    2440                    2445

AAT GCT CTT TTA CTT CTT CCC CAT CAT GCA GTA GTT CAA AAG CGG AAA    7572
Asn Ala Leu Leu Leu Leu Pro His His Ala Val Val Gln Lys Arg Lys
           2450                    2455                    2460

AGC ATT GCT GGT CCT CGA AAA TTT CCC CTT GCT CAA ACT GAA TCG CTT    7620
Ser Ile Ala Gly Pro Arg Lys Phe Pro Leu Ala Gln Thr Glu Ser Leu
2465                         2470                    2475

CTG ATG AAA ATG CGT TCA GTG GCA AAT GAT GAG CTT CAT GTG ATG ATG    7668
Leu Met Lys Met Arg Ser Val Ala Asn Asp Glu Leu His Val Met Met
           2480                    2485                    2490

CAA CGG AGA ATG AGC CAA GAG AAC CCT AGC CAA GCA ACT GAA ACG GAA    7716
Gln Arg Arg Met Ser Gln Glu Asn Pro Ser Gln Ala Thr Glu Thr Glu
2495                         2500                    2505

CTT GCG CAG AGA CTA CAG AGG CTC ACT GTT TTA GCA GTC AAC AGG ATT    7764
Leu Ala Gln Arg Leu Gln Arg Leu Thr Val Leu Ala Val Asn Arg Ile
           2510                    2515                    2520                    2525

ATT TAT CAA GAA TTT AAT TCA GAC ATT ATT GAC ATT TTG AGA ACT CCA    7812
Ile Tyr Gln Glu Phe Asn Ser Asp Ile Ile Asp Ile Leu Arg Thr Pro
2530                         2535                    2540
```

FIG. 8W

```
GAA AAT GTA ACT CAA AGC AAG ACC TCA GTT TTC CAG ACC GAA ATT TCT         7860
Glu Asn Val Thr Gln Ser Lys Thr Ser Val Phe Gln Thr Glu Ile Ser
                2545                2550                2555

GAG GAA AAT ATT CAT CAT CAG CAG TCT GTT TTC AAT CCA TTT CAG             7908
Glu Glu Asn Ile His His Gln Gln Ser Ser Val Phe Asn Pro Phe Gln
            2560                2565                2570

AAA GAA ATT TTT ACA TAT CTG GTA GAA GGA TTC AAA GTA TCT ATT GGT         7956
Lys Glu Ile Phe Thr Tyr Leu Val Glu Gly Phe Lys Val Ser Ile Gly
                2575                2580                2585

TCA AGT AAA GCC AGT GGT TCC AAG CAG CAA TGG ACT AAA ATT CTG TGG         8004
Ser Ser Lys Ala Ser Gly Ser Lys Gln Gln Trp Thr Lys Ile Leu Trp
            2590                2595                2600            2605

TCT TGT AAG GAG ACC TTC CGA ATG CAG CTT GGG AGA CTA CTA GTG CAT         8052
Ser Cys Lys Glu Thr Phe Arg Met Gln Leu Gly Arg Leu Leu Val His
                2610                2615                2620

ATT TTG TCG CCA CAC GCT GCA CAA GAG AGA AAG CAA ATT TTT GAA             8100
Ile Leu Ser Pro Ala His Ala Ala Gln Glu Arg Lys Gln Ile Phe Glu
            2625                2630                2635

ATA GTT CAT GAA CCA AAT CAT CAG GAA ATA CTA CGA GAC TGT CTC AGC         8148
Ile Val His Glu Pro Asn His Gln Glu Ile Leu Arg Asp Cys Leu Ser
                2640                2645                2650
```

FIG.8X

```
CCA TCC CTA CAA CAT GGA GCC AAG TTA GTT TTG TAT TTG TCA GAG TTG    8196
Pro Ser Leu Gln His Gly Ala Lys Leu Val Leu Tyr Leu Ser Glu Leu
2655                2660                2665

ATA CAT AAT CAC CAA GGT GAA TTG ACT GAA GAG CTA GGC ACA GCA        8244
Ile His Asn His Gln Gly Glu Leu Thr Glu Glu Leu Gly Thr Ala
2670                2675                2680          2685

GAA CTG CTT ATG AAT GCT TTG AAG TTA TGT GGT CAC AAG TGC ATC CCT    8292
Glu Leu Leu Met Asn Ala Leu Lys Leu Cys Gly His Lys Cys Ile Pro
       2690                2695                2700

CCC AGT GCA TCA ACA AAA GCA GAC CTT ATT AAA ATG ATC AAA GAG GAA    8340
Pro Ser Ala Ser Thr Lys Ala Asp Leu Ile Lys Met Ile Lys Glu Glu
2705                2710                2715

CAA AAG AAA TAT GAA ACT GAA GAA GGA GTG AAT AAA GCT GCT TGG CAG    8388
Gln Lys Lys Tyr Glu Thr Glu Glu Gly Val Asn Lys Ala Ala Trp Gln
             2720                2725                2730

AAA ACA GTT AAC AAT AAT CAA CAA AGT CTC TTT CAG CGT CTG GAT TCA    8436
Lys Thr Val Asn Asn Asn Gln Gln Ser Leu Phe Gln Arg Leu Asp Ser
2735                2740                2745

AAA TCA AAG GAT ATA TCT AAA ATA GCT GCA GAT ATC ACC CAG GCA GTG    8484
Lys Ser Lys Asp Ile Ser Lys Ile Ala Ala Asp Ile Thr Gln Ala Val
2750                2755                2760          2765
```

FIG. 8Y

```
TCT CTC TCC CAA GGA AAT GAG AGA AAA AAG GTG ATC CAG CAT ATT AGA    8532
Ser Leu Ser Gln Gly Asn Glu Arg Lys Val Ile Gln His Ile Arg
                2770                2775                2780

GGA ATG TAT AAA GTA GAT TTG AGT GCC AGC AGA CAT TGG CAG GAA CTT    8580
Gly Met Tyr Lys Val Asp Leu Ser Ala Ser Arg His Trp Gln Glu Leu
                2785                2790                2795

ATT CAG CAG CTG ACA CAT GAT AGA GCA GTA TGG TAT GAC CCC ATC TAC    8628
Ile Gln Gln Leu Thr His Asp Arg Ala Val Trp Tyr Asp Pro Ile Tyr
                2800                2805                2810

TAT CCA ACC TCA TGG CAG TTG GAT CCA ACA GAA GGG CCA AAT CGA GAG    8676
Tyr Pro Thr Ser Trp Gln Leu Asp Pro Thr Glu Gly Pro Asn Arg Glu
                2815                2820                2825

AGG AGA CGT TTA CAG AGA TGT TAT TTA ACT ATT CCA AAT AAG TAT CTC    8724
Arg Arg Arg Leu Gln Arg Cys Tyr Leu Thr Ile Pro Asn Lys Tyr Leu
                2830                2835                2840                2845

CTT AGG GAT AGA CAG AAA TCA GAA GAT GTT GTC AAA CCA CCA CTC TCT    8772
Leu Arg Asp Arg Gln Lys Ser Glu Asp Val Val Lys Pro Pro Leu Ser
                2850                2855                2860

TAC CTG TTT GAA GAC AAA ACT CAT TCT TCT TTC TCT ACT GTC AAA        8820
Tyr Leu Phe Glu Asp Lys Thr His Ser Ser Phe Ser Thr Val Lys
                2865                2870                2875
```

FIG.8Z

```
GAC AAA GCT GCA AGT GAA TCT ATA AGA GTG AAT CGA AGA TGC ATC AGT    8868
Asp Lys Ala Ala Ser Glu Ser Ile Arg Val Asn Arg Arg Cys Ile Ser
                2880                2885                2890

GTT GCA CCA TCT AGA GAG ACA GCT GGT GAA TTG TTA CTA GGT AAA TGT    8916
Val Ala Pro Ser Arg Glu Thr Ala Gly Glu Leu Leu Leu Gly Lys Cys
        2895                2900                2905

GGA ATG TAT TTT GTG GAA GAT AAT GCT TCT GAT ACA GTT GAA AGT TCG    8964
Gly Met Tyr Phe Val Glu Asp Asn Ala Ser Asp Thr Val Glu Ser Ser
    2910                2915                2920              2925

AGC CTT CAG GGA GAG TTG GAA CCA GCA TCA TTT TCC TGG ACA TAT GAA    9012
Ser Leu Gln Gly Glu Leu Glu Pro Ala Ser Phe Ser Trp Thr Tyr Glu
                2930                2935                2940

GAA ATT AAA GAA GTT CAC AAG CGT TGG TGG CAA TTG AGA GAT AAT GCT    9060
Glu Ile Lys Glu Val His Lys Arg Trp Trp Gln Leu Arg Asp Asn Ala
        2945                2950                2955

GTA GAA ATC TTT CTA ACA AAT GGC AGA ACA CTC CTG TTG GCA TTT GAT    9108
Val Glu Ile Phe Leu Thr Asn Gly Arg Thr Leu Leu Leu Ala Phe Asp
    2960                2965                2970

AAC ACC AAG GTT CGT GAT GAT GTA TAC CAC AAT ATA CTC ACA AAT AAC    9156
Asn Thr Lys Val Arg Asp Asp Val Tyr His Asn Ile Leu Thr Asn Asn
                2975                2980                2985
```

FIG.8A1

```
CTC CCT AAT CTT CTG GAA TAT GGT AAC ATC ACC GCT CTG ACA AAT TTA    9204
Leu Pro Asn Leu Leu Glu Tyr Gly Asn Ile Thr Ala Leu Thr Asn Leu
         2990                    2995                 3000      3005

TGG TAT ACT GGG CAA ATT ACT AAT TTT GAA TAT TTG ACT CAC TTA AAC    9252
Trp Tyr Thr Gly Gln Ile Thr Asn Phe Glu Tyr Leu Thr His Leu Asn
         3010                    3015                 3020

AAA CAT GCT GGC CGA TCC TTC AAT GAT CTC ATG CAG TAT CCT GTG TTC    9300
Lys His Ala Gly Arg Ser Phe Asn Asp Leu Met Gln Tyr Pro Val Phe
         3025                    3030                 3035

CCA TTT ATA CTT GCT GAC TAC GTT AGT GAG ACA CTT GAC CTC AAT GAT    9348
Pro Phe Ile Leu Ala Asp Tyr Val Ser Glu Thr Leu Asp Leu Asn Asp
         3040                    3045                 3050

CTG TTG ATA TAC AGA AAT CTC TCT AAA CCT ATA GCT GTT CAG TAT AAA    9396
Leu Leu Ile Tyr Arg Asn Leu Ser Lys Pro Ile Ala Val Gln Tyr Lys
         3055                    3060                 3065

GAA AAA GAT CGT GTG GAC ACA TAC AAG TAC TTG GAG GAA GAG            9444
Glu Lys Asp Arg Val Asp Thr Tyr Lys Tyr Leu Glu Glu Glu
         3070                    3075                 3080    3085

TAC CGC AAA GGA GCC AGA GAA GAT GAC CCC ATG CCT CCC GTG CAG CCC    9492
Tyr Arg Lys Gly Ala Arg Glu Asp Asp Pro Met Pro Pro Val Gln Pro
         3090                    3095                 3100
```

FIG.8B1

```
TAT CAC TAT GGC TCC CAC TAT TCC AAT AGC GGC ACT GTG CTT CAC TTC    9540
Tyr His Tyr Gly Ser His Tyr Ser Asn Ser Gly Thr Val Leu His Phe
            3105                  3110                  3115

CTG GTC AGG ATG CCT CCT TTC ACT AAA ATG TTT TTA GCC TAT CAA GAT    9588
Leu Val Arg Met Pro Pro Phe Thr Lys Met Phe Leu Ala Tyr Gln Asp
            3120                  3125                  3130

CAA AGT TTT GAC ATT CCA GAC AGA ACT TTT CAT TCT ACA AAT ACA ACT    9636
Gln Ser Phe Asp Ile Pro Asp Arg Thr Phe His Ser Thr Asn Thr Thr
            3135                  3140                  3145

TGG CGA CTC TCA TCT TTT GAA TCT ATG ACT GAT GTG AAA GAA CTT ATC    9684
Trp Arg Leu Ser Ser Phe Glu Ser Met Thr Asp Val Lys Glu Leu Ile
3150                  3155                  3160                  3165

CCA GAG TTT TTC TAT CTT CCA GAG TTC CTA GTT AAC CGT GAA GGT TTT    9732
Pro Glu Phe Phe Tyr Leu Pro Glu Phe Leu Val Asn Arg Glu Gly Phe
            3170                  3175                  3180

GAT TTT GGT GTG CGT CAG AAT GGT GAA CGG GTT AAT CAC GTC AAC CTT    9780
Asp Phe Gly Val Arg Gln Asn Gly Glu Arg Val Asn His Val Asn Leu
            3185                  3190                  3195

CCC CCT TGG GCG CGT AAT GAT CCT CGT CTT TTT ATC CTC ATC CAT CGG    9828
Pro Pro Trp Ala Arg Asn Asp Pro Arg Leu Phe Ile Leu Ile His Arg
            3200                  3205                  3210
```

FIG.8C1

```
CAG GCT CTA GAG TCT GAC TAC GTG TCG CAG AAC ATC TGT CAG TGG ATT    9876
Gln Ala Leu Glu Ser Asp Tyr Val Ser Gln Asn Ile Cys Gln Trp Ile
        3215                    3220                    3225

GAC TTG GTG TTT GGG TAT AAG CAA AAG GGG AAG GCT TCT GTT CAA GCG    9924
Asp Leu Val Phe Gly Tyr Lys Gln Lys Gly Lys Ala Ser Val Gln Ala
        3230                    3235                    3240    3245

ATC AAT GTT TTT CAT CCT GCT ACA TAT TTT GGA ATG GAT GTC TCT GCA    9972
Ile Asn Val Phe His Pro Ala Thr Tyr Phe Gly Met Asp Val Ser Ala
        3250                    3255                    3260

GTT GAA GAT CCA GTT CAG AGA CGA GCG CTA GAA ACC ATG ATA AAA ACC   10020
Val Glu Asp Pro Val Gln Arg Arg Ala Leu Glu Thr Met Ile Lys Thr
        3265                    3270                    3275

TAC GGG CAG ACT CCC CGT CAG CTG TTC CAC ATG GCC CAT GTG AGC AGA   10068
Tyr Gly Gln Thr Pro Arg Gln Leu Phe His Met Ala His Val Ser Arg
        3280                    3285                    3290

CCT GGA GCC AAG CTC AAT ATT GAA GGA GAG CTT CCA GCT GCT GTG GGG   10116
Pro Gly Ala Lys Leu Asn Ile Glu Gly Glu Leu Pro Ala Ala Val Gly
        3295                    3300                    3305

TTG CTA GTG CAG TTT GCT TTC AGG GAG ACC CGA GAA CAG GTC AAA GAA   10164
Leu Leu Val Gln Phe Ala Phe Arg Glu Thr Arg Glu Gln Val Lys Glu
        3310                    3315                    3320    3325
```

FIG.8D1

```
ATC ACC TAT CCG AGT CCT TTG TCA TGG ATA AAA GGC TTG AAA TGG GGG    10212
Ile Thr Tyr Pro Ser Pro Leu Ser Trp Ile Lys Gly Leu Lys Trp Gly
                3330                    3335                3340

GAA TAC GTG GGT TCC CCC AGT GCT CCA GTA CCT GTG GTC TGC TTC AGC    10260
Glu Tyr Val Gly Ser Pro Ser Ala Pro Val Pro Val Val Cys Phe Ser
                3345                    3350                3355

CAG CCC CAC GGA GAA AGA TTT GGC TCT CTC CAG GCT CTG CCC ACC AGA    10308
Gln Pro His Gly Glu Arg Phe Gly Ser Leu Gln Ala Leu Pro Thr Arg
                3360                    3365                3370

GCA ATC TGT GGT TTG TCA CGG AAT TTC TGT CTT GTG ATG ACA TAT AGC    10356
Ala Ile Cys Gly Leu Ser Arg Asn Phe Cys Leu Val Met Thr Tyr Ser
                3375                    3380                3385

AAG GAA CAA GGT GTG AGA AGC ATG AAC AGT ACG GAC ATT CAG TGG TCA    10404
Lys Glu Gln Gly Val Arg Ser Met Asn Ser Thr Asp Ile Gln Trp Ser
                3390                    3395                3400                3405

GCC ATC CTG AGC TGG GGA TAT GCT GAT AAT ATT TTA AGG TTG AAG AGT    10452
Ala Ile Leu Ser Trp Gly Tyr Ala Asp Asn Ile Leu Arg Leu Lys Ser
                3410                    3415                3420

AAA CAA AGT GAG CCT CCA GTA AAC TTT ATT CAA AGT TCA CAA CAG TAC    10500
Lys Gln Ser Glu Pro Pro Val Asn Phe Ile Gln Ser Ser Gln Gln Tyr
                3425                    3430                3435
```

FIG.8E1

```
CAG GTG ACT AGT TGT GCT TGG GTG CCT GAC AGT TGC CAG CTG TTT ACT    10548
Gln Val Thr Ser Cys Ala Trp Val Pro Asp Ser Cys Gln Leu Phe Thr
              3440                          3445                3450

GGA AGC AAA TGC GGT GTC ATC ACA GCC TAC ACA AAC AGA TTT ACA AGC    10596
Gly Ser Lys Cys Gly Val Ile Thr Ala Tyr Thr Asn Arg Phe Thr Ser
              3455                          3460                3465

AGC ACG CCA TCA GAA ATA GAA ATG GAG ACT CAA ATA CAT CTC TAT GGT    10644
Ser Thr Pro Ser Glu Ile Glu Met Glu Thr Gln Ile His Leu Tyr Gly
3470                          3475                3480          3485

CAC ACA GAA GAG ATA ACC AGC TTA TTT GTT TGC AAA CCA TAC AGT ATA    10692
His Thr Glu Glu Ile Thr Ser Leu Phe Val Cys Lys Pro Tyr Ser Ile
              3490                          3495                3500

CTG ATA AGT GTG AGC AGA GAC GGA ACC TGC ATC ATA TGG GAT TTA AAC    10740
Leu Ile Ser Val Ser Arg Asp Gly Thr Cys Ile Ile Trp Asp Leu Asn
              3505                          3510                3515

AGG TTA TGC TAT GTA CAA AGT CTG GCG GGA CAC AAA AGC CCT GTC ACA    10788
Arg Leu Cys Tyr Val Gln Ser Leu Ala Gly His Lys Ser Pro Val Thr
              3520                          3525                3530

GCT GTC TCT GCC AGT GAA ACC TCA GGT GAT ATT GCT ACT GTG TGT GAT    10836
Ala Val Ser Ala Ser Glu Thr Ser Gly Asp Ile Ala Thr Val Cys Asp
              3535                          3540                3545
```

FIG.8F1

```
TCA GCT GGC GGA GGC AGT GAC CTC AGA CTC TGG ACG GTG AAC GGG GAT        10884
Ser Ala Gly Gly Gly Ser Asp Leu Arg Leu Trp Thr Val Asn Gly Asp
3550                          3555                  3560           3565

CTC GTT GGA CAT GTC CAC TGC AGG GAG ATC ATC TGT TCC GTG GCT TTC        10932
Leu Val Gly His Val His Cys Arg Glu Ile Ile Cys Ser Val Ala Phe
                3570                      3575              3580

TCC AAC CAG CCT GAG GGA GTA TCT ATC AAT GTA ATC GCT GGG GGA TTA        10980
Ser Asn Gln Pro Glu Gly Val Ser Ile Asn Val Ile Ala Gly Gly Leu
            3585                      3590              3595

GAA AAT GGA ATT GTT AGG TTA TGG AGC ACA TGG GAC TTA AAG CCT GTG        11028
Glu Asn Gly Ile Val Arg Leu Trp Ser Thr Trp Asp Leu Lys Pro Val
        3600                      3605              3610

AGA GAA ATT ACA TTT CCC AAA TCA AAT AAG CCC ATC ATC AGC CTT ACA        11076
Arg Glu Ile Thr Phe Pro Lys Ser Asn Lys Pro Ile Ile Ser Leu Thr
    3615                      3620              3625

TTT TCT TGT GAT GGC CAC CAT TTG TAC ACA GCA AAC AGT GAT GGG ACC        11124
Phe Ser Cys Asp Gly His His Leu Tyr Thr Ala Asn Ser Asp Gly Thr
3630                      3635              3640              3645

GTG ATT GCC TGG TGT CGG AAG GAC CAG CAC CGC TTG AAA CAG CCA ATG        11172
Val Ile Ala Trp Cys Arg Lys Asp Gln His Arg Leu Lys Gln Pro Met
                      3650              3655              3660
```

FIG. 8G1

```
TTC TAT TCC TTC CTT AGC AGC TAT GCA GCC GGG TGA ATGGAATGA                    11218
Phe Tyr Ser Phe Leu Ser Ser Tyr Ala Ala Gly  *
3665                                    3670

ACTTCATGTT CTCCAAAGCA CTTTAACTCC AAACTAGATT TGTTGACTTC ACCAGTTTTA            11278

GGAGGTTGAA CCTAAAGAAA TGGATGACTG GACAAACCAT CCAAATAATG ATAAAGTCTA            11338

TTCATCTGCA CAAAATTCTG AAGAGTCACA TGATCCTAAG AGGAAAGTTC TGTTCTATTT            11398

TAGTGATAAT CTGGAAGATT GTGTCAATAT GCACTAGCCA ACAAGTTTTA AGCCTCGCAT            11458

GGTACATTAA AATGATATTC TTAAAAATTT TTCCCACCAA GGTATTCCAA AGAAAATATT           11518

AAGGTCTCCC CTTTTTCTAT GATTCCAAAA GGACCAGTAG AATTTAAATT GGTTGGTTGA            11578

TGTTTATATA AAACACACTA AAATTATATT TTAAAAGTTT ATGCCTGAAA TACTCCTCCC            11638

ACCACACACA CATGCTCCAA AAGAGGAAAG AAAAAAAGAT AATTTTTAGG ACTTGATAAT            11698

TGCTTTCTTT GAGAAGCAAA TTATTCAGTA GGTGCCTCTG TACCAAATAT TTTATGGAAT           11758

ATCTAAATAC TAAAATAAAC TATGAATGAA TCTCAAAATT AGGCAGTTTT TGCCAGTTGC            11818

TTTCTTAGCT CAAAGGAGAA CCAGAATTTT TTTGACAGCC ACAAACAAGA ATACAGGTAT           11878

CTTGGATTTC AGACACATTC TGTTTCTTCA TAAAAATTTT ACTTAAAAATC TGTAACGCTA           11938
```

FIG.8H1

```
GATATTGACT ATCCTTAGTT GAGTCACTGA GGTTTAAACA CAATGGTAAG TCTTAAAGTC    11998

TGCTATTTAC AGAGCATTGA ATCTGTACCA ATTTGCAATA GAAAGCCTTC AGTATGCAAG    12058

AAGTTTGCAT GGGTATTAAG AACACAGCCT AAATAAGGCA TTTGATTAAT CTGCAGGAAG    12118

AATTTCTTC  CCCAAAACAG AATTATAAAA GCTTACTTTA AACAGGAGGC AGAATAATTC    12178

TTTTAGGAAA CCATTTCATT CTGTTTCTAC TAACCTATAC CATCTGA                  12225
```

FIG. 8I1

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
        (A) LENGTH: 6830 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Coding Sequence
        (B) LOCATION: 1...6558
        (D) OTHER INFORMATION:

(xi) SEQUENCE DESCRIPTION: SEQ ID NO:1:

```
GCA CGA GGG GAA ATC TCC ATA TGG GTC TCT GGG CAG AGG AAG ACT GAT      48
Ala Arg Gly Glu Ile Ser Ile Trp Val Ser Gly Gln Arg Lys Thr Asp
 1               5                  10                  15

GTC ATC TTG GAT TTT GTG CTC CCA AGA AAA ACA AGC TTA TCA TCA GAC      96
Val Ile Leu Asp Phe Val Leu Pro Arg Lys Thr Ser Leu Ser Ser Asp
                20                  25                  30

AGC AAT AAA ACA TTT TGC ATG ATT GGT CAT TGC TTA ACA TCC CAA GAA     144
Ser Asn Lys Thr Phe Cys Met Ile Gly His Cys Leu Thr Ser Gln Glu
            35                  40                  45

GAG TCT CTG CAA TTA GCT GGA AAA TGG GAC CTG GGG AAC TTG CTC CTC     192
Glu Ser Leu Gln Leu Ala Gly Lys Trp Asp Leu Gly Asn Leu Leu Leu
        50                  55                  60

TTC AAT GGA GCT AAA ATT GGC TCA CAA GAG GCC TTT TTC CTG TAT GCT     240
Phe Asn Gly Ala Lys Ile Gly Ser Gln Glu Ala Phe Phe Leu Tyr Ala
65                  70                  75                  80

TGT GGA CCC AAC TAC ACA TCC ATC ATG CCG TGT AAA TAT GGA CAG CCA     288
Cys Gly Pro Asn Tyr Thr Ser Ile Met Pro Cys Lys Tyr Gly Gln Pro
                85                  90                  95

GTC ATT GAC TAC TCC AAA TAC ATT AAT AAA GAC ATT TTG AGA TGT GAT     336
Val Ile Asp Tyr Ser Lys Tyr Ile Asn Lys Asp Ile Leu Arg Cys Asp
                100                 105                 110

GAA ATC AGA GAC CTT TTT ATG ACC AAG AAA GAA GTG GAT GTT GGT CTC     384
Glu Ile Arg Asp Leu Phe Met Thr Lys Lys Glu Val Asp Val Gly Leu
            115                 120                 125

TTA ATT GAA AGT CTT TCA GTT GTT TAT ACA ACT TGC TGT CCT GCT CAG     432
Leu Ile Glu Ser Leu Ser Val Val Tyr Thr Thr Cys Cys Pro Ala Gln
        130                 135                 140

TAC ACC ATC TAT GAA CCA GTG ATT CGA CTC AAG GGC CAA GTG AAA ACT     480
Tyr Thr Ile Tyr Glu Pro Val Ile Arg Leu Lys Gly Gln Val Lys Thr
145                 150                 155                 160

CAG CCC TCT CAA AGA CCC TTC AGC TCA AAG GAA GCC CAG AGC ATC TTG     528
Gln Pro Ser Gln Arg Pro Phe Ser Ser Lys Glu Ala Gln Ser Ile Leu
                165                 170                 175

CTA GAA CCT TCT CAA CTC AAA GGC CTC CAA CCT ACG GAA TGT AAA GCC     576
Leu Glu Pro Ser Gln Leu Lys Gly Leu Gln Pro Thr Glu Cys Lys Ala
                180                 185                 190

ATC CAG GGC ATT CTG CAT GAG ATT GGT GGG GCT GGA ACA TTT GTT TTT     624
Ile Gln Gly Ile Leu His Glu Ile Gly Gly Ala Gly Thr Phe Val Phe
```

-continued

|  |  |  |  |
|---|---|---|---|
| | 195 | 200 | 205 |

```
CTC TTT GCT AGG GTT GTT GAA CTT AGT AGC TGT GAA GAA ACT CAA GCA    672
Leu Phe Ala Arg Val Val Glu Leu Ser Ser Cys Glu Glu Thr Gln Ala
    210                 215                 220

TTA GCA CTG CGG GTT ATA CTG TCT TTA ATT AAG TAC AGC CAA CAG AGA    720
Leu Ala Leu Arg Val Ile Leu Ser Leu Ile Lys Tyr Ser Gln Gln Arg
225                 230                 235                 240

ACA CAG GAA CTG GAA AAT TGT AAT GGA CTC TCT ATG ATT CAC CAA GTG    768
Thr Gln Glu Leu Glu Asn Cys Asn Gly Leu Ser Met Ile His Gln Val
                245                 250                 255

TTG GTC AAA CAG AAA TGC ATT GTT GGC TTT CAC ATT TTG AAG ACC CTT    816
Leu Val Lys Gln Lys Cys Ile Val Gly Phe His Ile Leu Lys Thr Leu
            260                 265                 270

CTT GAA GGT TGC TGC GGT GAA GAA GTT ATC CAC GTC AGT GAG CAT GGA    864
Leu Glu Gly Cys Cys Gly Glu Glu Val Ile His Val Ser Glu His Gly
        275                 280                 285

GAG TTC AAG CTG GAT GTT GAG TCT CAT GCT ATA ATC CAA GAT GTT AAG    912
Glu Phe Lys Leu Asp Val Glu Ser His Ala Ile Ile Gln Asp Val Lys
    290                 295                 300

CTG CTG CAG GAA CTG TTA CTT GAC TGG AAG ATA TGG AAT AAG GCA GAG    960
Leu Leu Gln Glu Leu Leu Leu Asp Trp Lys Ile Trp Asn Lys Ala Glu
305                 310                 315                 320

CAA GGT GTG TGG GAG ACT CTG CTA GCA GCT TTG GAA GTC CTC ATC CGG   1008
Gln Gly Val Trp Glu Thr Leu Leu Ala Ala Leu Glu Val Leu Ile Arg
                325                 330                 335

GTA GAG CAC CAC CAG CAG CAG TTT AAT ATT AAG CAG TTG CTG AAC GCC   1056
Val Glu His His Gln Gln Gln Phe Asn Ile Lys Gln Leu Leu Asn Ala
            340                 345                 350

CAC GTG GTT CAC CAC TTC CTA CTG ACC TGT CAG GTT TTA CAG GAA CAC   1104
His Val Val His His Phe Leu Leu Thr Cys Gln Val Leu Gln Glu His
        355                 360                 365

AGA GAG GGG CAG CTT ACA TCT ATG CCC CGA GAA GTT TGT AGA TCA TTT   1152
Arg Glu Gly Gln Leu Thr Ser Met Pro Arg Glu Val Cys Arg Ser Phe
    370                 375                 380

GTG AAA ATC ATT GCA GAA GTC CTT GGT TCT CCT CCA GAC TTG GAA TTA   1200
Val Lys Ile Ile Ala Glu Val Leu Gly Ser Pro Pro Asp Leu Glu Leu
385                 390                 395                 400

TTG ACA GTT ATT TTC AAT TTC CTG TTA GCT GTA CAC CCT CCT ACT AAT   1248
Leu Thr Val Ile Phe Asn Phe Leu Leu Ala Val His Pro Pro Thr Asn
                405                 410                 415

ACT TAT GTT TGT CAC AAT CCC ACA AAC TTC TAC TTC TCT TTG CAC ATA   1296
Thr Tyr Val Cys His Asn Pro Thr Asn Phe Tyr Phe Ser Leu His Ile
            420                 425                 430

GAT GGC AAG ATC TTT CAG GAG AAA GTG CAG TCA CTC GCG TAC CTG AGG   1344
Asp Gly Lys Ile Phe Gln Glu Lys Val Gln Ser Leu Ala Tyr Leu Arg
        435                 440                 445

CAT TCT AGC AGC GGA GGG CAA GCC TTT CCC AGC CCT GGA TTC CTG GTA   1392
His Ser Ser Ser Gly Gly Gln Ala Phe Pro Ser Pro Gly Phe Leu Val
    450                 455                 460

ATA AGC CCA TCT GCC TTT ACT GCA GCT CCT CCT GAA GGA ACC AGT TCT   1440
Ile Ser Pro Ser Ala Phe Thr Ala Ala Pro Pro Glu Gly Thr Ser Ser
465                 470                 475                 480

TCC AAT ATT GTT CCA CAG CGG ATG GCT GCT CAG ATG GTT CGA TCT AGA   1488
Ser Asn Ile Val Pro Gln Arg Met Ala Ala Gln Met Val Arg Ser Arg
                485                 490                 495

AGT CTA CCA GCA TTT CCT ACT TAT TTA CCA CTA ATA CGA GCA CAA AAA   1536
Ser Leu Pro Ala Phe Pro Thr Tyr Leu Pro Leu Ile Arg Ala Gln Lys
            500                 505                 510

CTG GCT GCA AGT TTG GGT TTT AGT GTT GAC AAG TTA CAA AAT ATT GCA   1584
Leu Ala Ala Ser Leu Gly Phe Ser Val Asp Lys Leu Gln Asn Ile Ala
```

```
                515                 520                 525
GAT GCC AAC CCA GAG AAA CAG AAT CTT TTA GGA AGA CCC TAC GCA CTG    1632
Asp Ala Asn Pro Glu Lys Gln Asn Leu Leu Gly Arg Pro Tyr Ala Leu
            530                 535                 540

AAA ACA AGC AAA GAG GAA GCA TTC ATC AGC AGC TGT GAG TCT GCA AAG    1680
Lys Thr Ser Lys Glu Glu Ala Phe Ile Ser Ser Cys Glu Ser Ala Lys
545                 550                 555                 560

ACT GTT TGT GAA ATG GAG GCT CTT CTT GGA GCC CAC GCC TCT GCC AAT    1728
Thr Val Cys Glu Met Glu Ala Leu Leu Gly Ala His Ala Ser Ala Asn
                565                 570                 575

GGG GTT TCC AGA GGA TCA CCG AGG TTC CCC AGG GCC AGA GTA GAT CAC    1776
Gly Val Ser Arg Gly Ser Pro Arg Phe Pro Arg Ala Arg Val Asp His
            580                 585                 590

AAA GAT GTG GGA ACA GAG CCC AGA TCA GAT GAT GAC AGT CCT GGG GAT    1824
Lys Asp Val Gly Thr Glu Pro Arg Ser Asp Asp Asp Ser Pro Gly Asp
595                 600                 605

GAG TCT TAC CCA CGT CGG CCT GAC AAC CTC AAG GGA CTG GCC TCA TTC    1872
Glu Ser Tyr Pro Arg Arg Pro Asp Asn Leu Lys Gly Leu Ala Ser Phe
            610                 615                 620

CAG CGA AGC CAA AGC ACT GTC GCA AGC CTT GGG CTG GCG TTT CCC TCT    1920
Gln Arg Ser Gln Ser Thr Val Ala Ser Leu Gly Leu Ala Phe Pro Ser
625                 630                 635                 640

CAG AAT GGA TCT GCA GTT GCT AGC AGG TGG CCA AGT CTT GTT GAT AGG    1968
Gln Asn Gly Ser Ala Val Ala Ser Arg Trp Pro Ser Leu Val Asp Arg
                645                 650                 655

AAT GCT GAT GAC TGG GAG AAC TTT ACC TTT TCT CCT GCT TAT GAG GCA    2016
Asn Ala Asp Asp Trp Glu Asn Phe Thr Phe Ser Pro Ala Tyr Glu Ala
            660                 665                 670

AGC TAC AAC CGA GCC ACA AGC ACC CAC AGT GTC ATT GAA GAC TGT CTG    2064
Ser Tyr Asn Arg Ala Thr Ser Thr His Ser Val Ile Glu Asp Cys Leu
675                 680                 685

ATA CCT ATC TGC TGT GGA TTA TAT GAA CTC TTA AGT GGG GTT CTT CTT    2112
Ile Pro Ile Cys Cys Gly Leu Tyr Glu Leu Leu Ser Gly Val Leu Leu
            690                 695                 700

GTC CTG CCT GAT GCT ATG CTT GAA GAT GTG ATG GAC AGG ATT ATT CAA    2160
Val Leu Pro Asp Ala Met Leu Glu Asp Val Met Asp Arg Ile Ile Gln
705                 710                 715                 720

GCA GAT ATT CTT CTA GTC CTT GTT AAC CAC CCA TCA CCT GCT ATC CAG    2208
Ala Asp Ile Leu Leu Val Leu Val Asn His Pro Ser Pro Ala Ile Gln
                725                 730                 735

CAA GGA GTA ATT AAA CTG TTA CAT GCA TAC ATT AAT AGA GCA TCA AAG    2256
Gln Gly Val Ile Lys Leu Leu His Ala Tyr Ile Asn Arg Ala Ser Lys
            740                 745                 750

GAG CAA AAG GAC AAG TTT CTG AAG AAC CGT GGC TTT TCC TTA TTA GCC    2304
Glu Gln Lys Asp Lys Phe Leu Lys Asn Arg Gly Phe Ser Leu Leu Ala
755                 760                 765

AAC CAG TTG TAT CTT CAT AGG GGA ACT CAG GAG TTG TTG GAG TGC TTT    2352
Asn Gln Leu Tyr Leu His Arg Gly Thr Gln Glu Leu Leu Glu Cys Phe
                770                 775                 780

GTT GAA ATG TTC TTT GGT CGA CCG ATT GGC CTG GAT GAA GAA TTT GAT    2400
Val Glu Met Phe Phe Gly Arg Pro Ile Gly Leu Asp Glu Glu Phe Asp
785                 790                 795                 800

CTG GAG GAA GTG AAG CAC ATG GAA CTG TTC CAG AAG TGG TCT GTC ATT    2448
Leu Glu Glu Val Lys His Met Glu Leu Phe Gln Lys Trp Ser Val Ile
            805                 810                 815

CCC GTT CTC GGA CTA ATA GAG ACC TCT CTC TAT GAC AAT GTC CTC TTG    2496
Pro Val Leu Gly Leu Ile Glu Thr Ser Leu Tyr Asp Asn Val Leu Leu
            820                 825                 830

CAC AAT GCT CTT TTA CTT CTT CTG CAA GTT TTA AAC TCT TGT TCC AAG    2544
His Asn Ala Leu Leu Leu Leu Leu Gln Val Leu Asn Ser Cys Ser Lys
```

```
                835              840              845
GTA GCA GAC ATG CTA CTG GAC AAT GGT CTA CTC TAT GTA TTA TGT AAT      2592
Val Ala Asp Met Leu Leu Asp Asn Gly Leu Leu Tyr Val Leu Cys Asn
        850              855              860

ACA GTA GCA GCC CTG AAT GGA TTA GAA AAG AAC ATT CCT GTG AAC GAA      2640
Thr Val Ala Ala Leu Asn Gly Leu Glu Lys Asn Ile Pro Val Asn Glu
865              870              875              880

TAC AAA TTG CTC GCA TGT GAT ATA CAG CAG CTT TTC ATA GCA GTT ACA      2688
Tyr Lys Leu Leu Ala Cys Asp Ile Gln Gln Leu Phe Ile Ala Val Thr
                885              890              895

ATT CAT GCT TGC AGT TCC TCA GGC ACA CAG TAT TTT AGA GTG ATT GAA      2736
Ile His Ala Cys Ser Ser Ser Gly Thr Gln Tyr Phe Arg Val Ile Glu
        900              905              910

GAC CTT ATT GTA CTT CTT GGA TAT CTT CAT AAT AGC AAA AAC AAG AGG      2784
Asp Leu Ile Val Leu Leu Gly Tyr Leu His Asn Ser Lys Asn Lys Arg
        915              920              925

ACA CAA AAT ATG GCT TTG GCC CTG CAG CTT AGA GTT CTC CAG GCT GCT      2832
Thr Gln Asn Met Ala Leu Ala Leu Gln Leu Arg Val Leu Gln Ala Ala
        930              935              940

TTG GAA TTT ATA AGG AGC ACA GCC AAT CAT GAC TCT GAA AGT CCA GTG      2880
Leu Glu Phe Ile Arg Ser Thr Ala Asn His Asp Ser Glu Ser Pro Val
945              950              955              960

CAC TCG CCT TCT GCC CAC CGC CAT TCA GTG CCT CCG AAG CGG AGA AGC      2928
His Ser Pro Ser Ala His Arg His Ser Val Pro Pro Lys Arg Arg Ser
                965              970              975

ATT GCT GGT TCT CGC AAA TTC CCT CTG GCT CAG ACA GAG TCT CTG CTG      2976
Ile Ala Gly Ser Arg Lys Phe Pro Leu Ala Gln Thr Glu Ser Leu Leu
        980              985              990

ATG AAG ATG CGC TCA GTG GCC AGC GAT GAG CTA CAC TCT ATG ATG CAG      3024
Met Lys Met Arg Ser Val Ala Ser Asp Glu Leu His Ser Met Met Gln
        995              1000             1005

AGG AGG ATG AGC CAA GAG CAC CCC AGC CAG GCC TCG GAG GCA GAG CTC      3072
Arg Arg Met Ser Gln Glu His Pro Ser Gln Ala Ser Glu Ala Glu Leu
        1010             1015             1020

GCT CAG AGG CTG CAG AGG CTC ACC ATC TTA GCT GTG AAC AGG ATT ATT      3120
Ala Gln Arg Leu Gln Arg Leu Thr Ile Leu Ala Val Asn Arg Ile Ile
1025             1030             1035             1040

TAC CAA GAG TTG AAT TCA GAT ATT ATT GAC ATT TTG AGA ACT CCA GAA      3168
Tyr Gln Glu Leu Asn Ser Asp Ile Ile Asp Ile Leu Arg Thr Pro Glu
        1045             1050             1055

AAT ACA TCC CAA AGC AAG ACC TCA GTT TCT CAG ACT GAA ATT TCT GAA      3216
Asn Thr Ser Gln Ser Lys Thr Ser Val Ser Gln Thr Glu Ile Ser Glu
        1060             1065             1070

GAA GAC ATG CAT CAT GAG CAA CCT TCT GTA TAT AAT CCA TTT CAA AAA      3264
Glu Asp Met His His Glu Gln Pro Ser Val Tyr Asn Pro Phe Gln Lys
        1075             1080             1085

GAA ATG TTA ACC TAT CTG TTG GAT GGC TTC AAA GTG TGT ATT GGT TCA      3312
Glu Met Leu Thr Tyr Leu Leu Asp Gly Phe Lys Val Cys Ile Gly Ser
        1090             1095             1100

AGT AAA ACT AGC GTT TCT AAG CAG CAG TGG ACT AAA ATC CTG GGG TCT      3360
Ser Lys Thr Ser Val Ser Lys Gln Gln Trp Thr Lys Ile Leu Gly Ser
1105             1110             1115             1120

TGT AAA GAA ACC CTC CGA GAC CAG CTT GGA AGA TTG CTA GCG CAT ATT      3408
Cys Lys Glu Thr Leu Arg Asp Gln Leu Gly Arg Leu Leu Ala His Ile
                1125             1130             1135

TTG TCT CCA ACC CAC ACT GTA CAA GAA CGG AAG CAG ATA CTT GAG ATA      3456
Leu Ser Pro Thr His Thr Val Gln Glu Arg Lys Gln Ile Leu Glu Ile
        1140             1145             1150

GTT CAT GAA CCA GCT CAC CAG GAT ATA CTT CGT GAC TGT CTT AGC CCC      3504
Val His Glu Pro Ala His Gln Asp Ile Leu Arg Asp Cys Leu Ser Pro
```

-continued

```
             1155              1160              1165
TCC CCA CAA CAT GGA GCC AAG TTG GTT TTG TAT TTG TCA GAG TTG ATA    3552
Ser Pro Gln His Gly Ala Lys Leu Val Leu Tyr Leu Ser Glu Leu Ile
        1170              1175              1180

CAT AAT CAT CAG GAT GAG TTA AGT GAA GAA GAA ATG GAC ACA GCA GAA    3600
His Asn His Gln Asp Glu Leu Ser Glu Glu Glu Met Asp Thr Ala Glu
1185              1190              1195              1200

CTG CTT ATG AAT GCT CTA AAG TTA TGT GGC CAC AAG TGC ATC CCG CCC    3648
Leu Leu Met Asn Ala Leu Lys Leu Cys Gly His Lys Cys Ile Pro Pro
            1205              1210              1215

AGT GCC CCT TCC AAA CCA GAG CTC ATT AAG ATC ATC AGA GAG GAG CAA    3696
Ser Ala Pro Ser Lys Pro Glu Leu Ile Lys Ile Ile Arg Glu Glu Gln
        1220              1225              1230

AAG AAG TAT GAA AGT GAA GAG AGT GTG AGC AAA GGC TCA TGG CAG AAA    3744
Lys Lys Tyr Glu Ser Glu Glu Ser Val Ser Lys Gly Ser Trp Gln Lys
        1235              1240              1245

ACG GTG AAC AAC AAC CAG CAA AGT CTC TTC CAG AGG CTC GAT TTC AAA    3792
Thr Val Asn Asn Asn Gln Gln Ser Leu Phe Gln Arg Leu Asp Phe Lys
        1250              1255              1260

TCC AAG GAT ATA TCT AAA ATC GCT GCA GAC ATC ACC CAG GCT GTA TCA    3840
Ser Lys Asp Ile Ser Lys Ile Ala Ala Asp Ile Thr Gln Ala Val Ser
1265              1270              1275              1280

CTC TCC CAA GGC ATT GAA AGG AAG AAG GTG ATC CAG CAC ATC AGA GGG    3888
Leu Ser Gln Gly Ile Glu Arg Lys Lys Val Ile Gln His Ile Arg Gly
            1285              1290              1295

ATG TAC AAA GTT GAC CTG AGT GCC AGC AGG CAC TGG CAG GAA TGC ATC    3936
Met Tyr Lys Val Asp Leu Ser Ala Ser Arg His Trp Gln Glu Cys Ile
            1300              1305              1310

CAG CAG CTG ACA CAT GAC AGA GCA GTC TGG TAT GAC CCA ATC TAC TAT    3984
Gln Gln Leu Thr His Asp Arg Ala Val Trp Tyr Asp Pro Ile Tyr Tyr
        1315              1320              1325

CCA ACT TCA TGG CAG TTG GAT CCA ACA GAA GGG CCA AAC CGA GAG AGG    4032
Pro Thr Ser Trp Gln Leu Asp Pro Thr Glu Gly Pro Asn Arg Glu Arg
        1330              1335              1340

AGA CGT TTG CAG AGA TGC TAT CTA ACT ATT CCC AAT AAG TAC CTC CTG    4080
Arg Arg Leu Gln Arg Cys Tyr Leu Thr Ile Pro Asn Lys Tyr Leu Leu
1345              1350              1355              1360

AGG GAC AGA CAG AAG TCA GAA GGT GTG CTC AGG CCC CCA CTC TCT TAC    4128
Arg Asp Arg Gln Lys Ser Glu Gly Val Leu Arg Pro Pro Leu Ser Tyr
            1365              1370              1375

CTT TTT GAA GAT AAA ACT CAT TCT TCC TTC TCC TCT ACT GTC AAA GAC    4176
Leu Phe Glu Asp Lys Thr His Ser Ser Phe Ser Ser Thr Val Lys Asp
            1380              1385              1390

AAA GCT GCA AGT GAA TCC ATC AGA GTG AAT CGA AGA TGT ATC AGT GTT    4224
Lys Ala Ala Ser Glu Ser Ile Arg Val Asn Arg Arg Cys Ile Ser Val
        1395              1400              1405

GCA CCA TCT AGA GAG ACA GCT GGG GAA TTG TTG TTA GGT AAA TGT GGG    4272
Ala Pro Ser Arg Glu Thr Ala Gly Glu Leu Leu Leu Gly Lys Cys Gly
        1410              1415              1420

ATG TAC TTT GTG GAA GAC AAT GCC TCT GAC GCA GTT GAA AGC TCG AGC    4320
Met Tyr Phe Val Glu Asp Asn Ala Ser Asp Ala Val Glu Ser Ser Ser
1425              1430              1435              1440

CTC CAA GGG GAG TTA GAG CCG GCA TCA TTT TCT TGG ACA TAT GAG GAA    4368
Leu Gln Gly Glu Leu Glu Pro Ala Ser Phe Ser Trp Thr Tyr Glu Glu
            1445              1450              1455

ATT AAA GAA GTT CAC AGG CGC TGG TGG CAA CTA AGA GAT AAT GCT GTA    4416
Ile Lys Glu Val His Arg Arg Trp Trp Gln Leu Arg Asp Asn Ala Val
            1460              1465              1470

GAA ATC TTT TTA ACA AAT GGC AGA ACA CTC CTA TTA GCA TTT GAC AAT    4464
Glu Ile Phe Leu Thr Asn Gly Arg Thr Leu Leu Leu Ala Phe Asp Asn
```

-continued

```
          1475                1480                1485

AAC AAG GTT CGT GAT GAC GTG TAC CAG AGC ATC CTC ACA AAT AAC CTC      4512
Asn Lys Val Arg Asp Asp Val Tyr Gln Ser Ile Leu Thr Asn Asn Leu
    1490                1495                1500

CCA AAT CTT CTG GAG TAC GGC AAC ATC ACC GCT CTG ACA AAC CTG TGG      4560
Pro Asn Leu Leu Glu Tyr Gly Asn Ile Thr Ala Leu Thr Asn Leu Trp
1505                1510                1515                1520

TAT TCT GGA CAA ATT ACC AAT TTT GAA TAT TTG ACT CAT TTA AAC AAG      4608
Tyr Ser Gly Gln Ile Thr Asn Phe Glu Tyr Leu Thr His Leu Asn Lys
            1525                1530                1535

CAT GCG GGC CGG TCC TTC AAT GAT CTC ATG CAG TAC CCG GTG TTC CCC      4656
His Ala Gly Arg Ser Phe Asn Asp Leu Met Gln Tyr Pro Val Phe Pro
        1540                1545                1550

TTC ATC CTT TCT GAC TAT GTT AGT GAG ACT CTT GAC CTC AAT GAT CCA      4704
Phe Ile Leu Ser Asp Tyr Val Ser Glu Thr Leu Asp Leu Asn Asp Pro
    1555                1560                1565

TCT ATC TAC AGA AAC CTA TCT AAG CCT ATA GCT GTG CAG TAT AAA GAA      4752
Ser Ile Tyr Arg Asn Leu Ser Lys Pro Ile Ala Val Gln Tyr Lys Glu
    1570                1575                1580

AAA GAA GAC CGT TAC GTT GAC ACA TAC AAG TAC TTG GAG GAG GAG TAT      4800
Lys Glu Asp Arg Tyr Val Asp Thr Tyr Lys Tyr Leu Glu Glu Glu Tyr
1585                1590                1595                1600

CGC AAG GGA GCT CGA GAG GAT GAC CCC ATG CCT CCT GTG CAA CCC TAC      4848
Arg Lys Gly Ala Arg Glu Asp Asp Pro Met Pro Pro Val Gln Pro Tyr
            1605                1610                1615

CAC TAT GGC TCC CAC TAC TCC AAC AGC GGC ACC GTG CTC CAC TTC CTG      4896
His Tyr Gly Ser His Tyr Ser Asn Ser Gly Thr Val Leu His Phe Leu
        1620                1625                1630

GTC AGG ATG CCG CCT TTC ACT AAA ATG TTT CTA GCC TAT CAA GAT CAG      4944
Val Arg Met Pro Pro Phe Thr Lys Met Phe Leu Ala Tyr Gln Asp Gln
    1635                1640                1645

AGT TTC GAC ATT CCA GAC CGA ACA TTT CAT TCT ACA AAC ACA ACT TGG      4992
Ser Phe Asp Ile Pro Asp Arg Thr Phe His Ser Thr Asn Thr Thr Trp
        1650                1655                1660

CGC CTC TCC TCC TTT GAG TCC ATG ACT GAT GTG AAG GAG CTG ATT CCA      5040
Arg Leu Ser Ser Phe Glu Ser Met Thr Asp Val Lys Glu Leu Ile Pro
1665                1670                1675                1680

GAG TTT TTC TAT CTT CCT GAG TTC TTA GTG AAC CGT GAA GGC TTT GAC      5088
Glu Phe Phe Tyr Leu Pro Glu Phe Leu Val Asn Arg Glu Gly Phe Asp
            1685                1690                1695

TTC GGT GTT CGT CAG AAT GGA GAG CGG GTT AAC CAC GTC AAT CTT CCT      5136
Phe Gly Val Arg Gln Asn Gly Glu Arg Val Asn His Val Asn Leu Pro
        1700                1705                1710

CCC TGG GCA CGC AAC GAT CCT CGG CTG TTC ATC CTT ATT CAC CGG CAA      5184
Pro Trp Ala Arg Asn Asp Pro Arg Leu Phe Ile Leu Ile His Arg Gln
    1715                1720                1725

GCA CTA GAG TCT GAC CAT GTG TCC CAG AAC ATC TGT CAC TGG ATC GAC      5232
Ala Leu Glu Ser Asp His Val Ser Gln Asn Ile Cys His Trp Ile Asp
        1730                1735                1740

TTA GTG TTT GGC TAC AAG CAA AAG GGG AAG GCG TCT GTT CAA GCC ATC      5280
Leu Val Phe Gly Tyr Lys Gln Lys Gly Lys Ala Ser Val Gln Ala Ile
1745                1750                1755                1760

AAT GTC TTC CAC CCT GCT ACA TAT TTT GGA ATG GAT GTC TCT GCA GTT      5328
Asn Val Phe His Pro Ala Thr Tyr Phe Gly Met Asp Val Ser Ala Val
            1765                1770                1775

GAA GAT CCA GTG CAG AGA CGG GCT TTA GAA ACC ATG ATA AAA ACC TAC      5376
Glu Asp Pro Val Gln Arg Arg Ala Leu Glu Thr Met Ile Lys Thr Tyr
        1780                1785                1790

GGG CAG ACC CCA CGT CAG TTG TTC CAC ACA GCC CAT GCC AGC CGA CCT      5424
Gly Gln Thr Pro Arg Gln Leu Phe His Thr Ala His Ala Ser Arg Pro
```

-continued

```
            1795                1800                1805
GGA GCC AAG CTT AAC ATC GAA GGA GAG CTT CCA GCA GCT GTT GGC TTG         5472
Gly Ala Lys Leu Asn Ile Glu Gly Glu Leu Pro Ala Ala Val Gly Leu
         1810                1815                1820

TTA GTC CAG TTC GCT TTC AGA GAG ACC CGA GAA CCA GTC AAG GAA GTC         5520
Leu Val Gln Phe Ala Phe Arg Glu Thr Arg Glu Pro Val Lys Glu Val
1825                1830                1835                1840

ACT CAT CCG AGC CCT TTG TCA TGG ATA AAA GGC TTG AAG TGG GGG GAG         5568
Thr His Pro Ser Pro Leu Ser Trp Ile Lys Gly Leu Lys Trp Gly Glu
              1845                1850                1855

TAC GTA GGT TCC CCC AGT GCT CCA GTA CCT GTG GTC TGC TTC AGC CAG         5616
Tyr Val Gly Ser Pro Ser Ala Pro Val Pro Val Val Cys Phe Ser Gln
         1860                1865                1870

CCC CAT GGA GAA AGA TTT GGT TCC CTG CAG GCA CTG CCC ACC AGA GCC         5664
Pro His Gly Glu Arg Phe Gly Ser Leu Gln Ala Leu Pro Thr Arg Ala
         1875                1880                1885

ATC TGT GGT TTA TCA CGA AAC TTC TGT CTT CTG ATG ACC TAC AAC AAG         5712
Ile Cys Gly Leu Ser Arg Asn Phe Cys Leu Leu Met Thr Tyr Asn Lys
         1890                1895                1900

GAG CAA GGT GTG AGA AGC ATG AAC AAC ACC AAT ATT CAG TGG TCT GCT         5760
Glu Gln Gly Val Arg Ser Met Asn Asn Thr Asn Ile Gln Trp Ser Ala
1905                1910                1915                1920

ATC CTA AGC TGG GGA TAT GCT GAC AAC ATC TTA CGG TTG AAA AGT AAG         5808
Ile Leu Ser Trp Gly Tyr Ala Asp Asn Ile Leu Arg Leu Lys Ser Lys
              1925                1930                1935

CAG AGT GAG CCA CCA ATC AAC TTC ATT CAG AGT TCA CAG CAG CAC CAG         5856
Gln Ser Glu Pro Pro Ile Asn Phe Ile Gln Ser Ser Gln Gln His Gln
         1940                1945                1950

GTA ACC AGT TGT GCC TGG GTG CCT GAC AGT TGT CAG CTC TTC ACT GGG         5904
Val Thr Ser Cys Ala Trp Val Pro Asp Ser Cys Gln Leu Phe Thr Gly
         1955                1960                1965

AGC AAG TGT GGT GTC ATC ACA GCC TAT ACC AAC AGG CTC ACC AGC AGC         5952
Ser Lys Cys Gly Val Ile Thr Ala Tyr Thr Asn Arg Leu Thr Ser Ser
         1970                1975                1980

ACG CCC TCA GAA ATT GAA ATG GAG AGT CAG ATG CAT CTC TAT GGA CAC         6000
Thr Pro Ser Glu Ile Glu Met Glu Ser Gln Met His Leu Tyr Gly His
1985                1990                1995                2000

ACA GAG GAG ATC ACC GGC TTA TGT GTC TGC AAG CCG TAC AGC GTG ATG         6048
Thr Glu Glu Ile Thr Gly Leu Cys Val Cys Lys Pro Tyr Ser Val Met
              2005                2010                2015

ATA AGC GTG AGC AGA GAC GGG ACC TGC ATA GTA TGG GAC CTG AAC AGG         6096
Ile Ser Val Ser Arg Asp Gly Thr Cys Ile Val Trp Asp Leu Asn Arg
              2020                2025                2030

CTG TGC TAT GTA CAA AGT TTG GCT GGA CAC AAA AGC CCT GTG ACG GCT         6144
Leu Cys Tyr Val Gln Ser Leu Ala Gly His Lys Ser Pro Val Thr Ala
              2035                2040                2045

GTC TCT GCC AGT GAA ACG TCA GGT GAC ATT GCT ACT GTG TGT GAC TCA         6192
Val Ser Ala Ser Glu Thr Ser Gly Asp Ile Ala Thr Val Cys Asp Ser
         2050                2055                2060

GCT GGC GGG GGC AGT GAC CTG AGA CTC TGG ACC GTG AAT GGG GAC CTC         6240
Ala Gly Gly Gly Ser Asp Leu Arg Leu Trp Thr Val Asn Gly Asp Leu
2065                2070                2075                2080

GTT GGA CAT GTC CAC TGC AGA GAG ATC ATT TGT TCT GTA GCT TTC TCC         6288
Val Gly His Val His Cys Arg Glu Ile Ile Cys Ser Val Ala Phe Ser
              2085                2090                2095

AAC CAG CCT GAG GGA GTC TCC ATC AAC GTC ATT GCT GGG GGA TTA GAA         6336
Asn Gln Pro Glu Gly Val Ser Ile Asn Val Ile Ala Gly Gly Leu Glu
              2100                2105                2110

AAT GGC ATT GTA AGG CTA TGG AGC ACA TGG GAC TTG AAG CCT GTG AGA         6384
Asn Gly Ile Val Arg Leu Trp Ser Thr Trp Asp Leu Lys Pro Val Arg
```

```
                        2115                2120                2125

GAG ATT ACA TTT CCC AAA TCA AAT AAG CCC ATC ATA AGC CTG ACA TTC       6432
Glu Ile Thr Phe Pro Lys Ser Asn Lys Pro Ile Ile Ser Leu Thr Phe
        2130                2135                2140

TCC TGT GAT GGC CAC CAT TTG TAC ACT GCC AAC AGT GAG GGG ACA GTG       6480
Ser Cys Asp Gly His His Leu Tyr Thr Ala Asn Ser Glu Gly Thr Val
2145                2150                2155                2160

ATC GCA TGG TGC CGG AAG GAC CAG CAG CGT GTG AAG CTG CCC ATG TTC       6528
Ile Ala Trp Cys Arg Lys Asp Gln Gln Arg Val Lys Leu Pro Met Phe
                2165                2170                2175

TAC TCT TTC CTC AGC AGC TAC GCA GCT GGA TGAAGAGAAG GAGTGTCCCC ACA     6581
Tyr Ser Phe Leu Ser Ser Tyr Ala Ala Gly
            2180                2185

GGACATAAGC ACCGCTCTGC GAGCCTGGCT CCACCAACTG CAGAAGCAGA TGACTGAGCA     6641

GATATCCAGG AAAGACAACA CACGTGCCTC TGTGCGCGCT TCCCCAGCCT CCGTGGGCCT     6701

GAGAGTAAAG CCCTGCCCTC ATTCCATAAT GGCGTGGAAG GCTGGGTCTG CACACACTAG     6761

CCAATTAAAG TCAGAATCTT GATGCTTTTT CCCAAAAGGT TAGGCTGAAT CAAAGATCAG     6821

GCTCGTGCC                                                              6830
```

(2) INFORMATION FOR SEQ ID NO:2:

(i) SEQUENCE CHARACTERISTICS:
        (A) LENGTH: 2186 amino acids
        (B) TYPE: amino acid
        (C) TOPOLOGY: unknown (ii) MOLECULE TYPE: protein (v) FRAGMENT TYPE: internal (xi) SEQUENCE DESCRIPTION: SEQ ID NO:2:

```
Ala Arg Gly Glu Ile Ser Ile Trp Val Ser Gly Gln Arg Lys Thr Asp
1               5                   10                  15

Val Ile Leu Asp Phe Val Leu Pro Arg Lys Thr Ser Leu Ser Ser Asp
                20                  25                  30

Ser Asn Lys Thr Phe Cys Met Ile Gly His Cys Leu Thr Ser Gln Glu
            35                  40                  45

Glu Ser Leu Gln Leu Ala Gly Lys Trp Asp Leu Gly Asn Leu Leu Leu
50                  55                  60

Phe Asn Gly Ala Lys Ile Gly Ser Gln Glu Ala Phe Phe Leu Tyr Ala
65                  70                  75                  80

Cys Gly Pro Asn Tyr Thr Ser Ile Met Pro Cys Lys Tyr Gly Gln Pro
                85                  90                  95

Val Ile Asp Tyr Ser Lys Tyr Ile Asn Lys Asp Ile Leu Arg Cys Asp
                100                 105                 110

Glu Ile Arg Asp Leu Phe Met Thr Lys Lys Glu Val Asp Val Gly Leu
            115                 120                 125

Leu Ile Glu Ser Leu Ser Val Val Tyr Thr Thr Cys Cys Pro Ala Gln
130                 135                 140

Tyr Thr Ile Tyr Glu Pro Val Ile Arg Leu Lys Gly Gln Val Lys Thr
145                 150                 155                 160

Gln Pro Ser Gln Arg Pro Phe Ser Ser Lys Glu Ala Gln Ser Ile Leu
                165                 170                 175

Leu Glu Pro Ser Gln Leu Lys Gly Leu Gln Pro Thr Glu Cys Lys Ala
                180                 185                 190

Ile Gln Gly Ile Leu His Glu Ile Gly Gly Ala Gly Thr Phe Val Phe
            195                 200                 205
```

-continued

```
Leu Phe Ala Arg Val Val Glu Leu Ser Ser Cys Glu Glu Thr Gln Ala
    210                 215                 220
Leu Ala Leu Arg Val Ile Leu Ser Leu Ile Lys Tyr Ser Gln Gln Arg
225                 230                 235                 240
Thr Gln Glu Leu Glu Asn Cys Asn Gly Leu Ser Met Ile His Gln Val
                245                 250                 255
Leu Val Lys Gln Lys Cys Ile Val Gly Phe His Ile Leu Lys Thr Leu
                260                 265                 270
Leu Glu Gly Cys Cys Gly Glu Val Ile His Val Ser Glu His Gly
            275                 280                 285
Glu Phe Lys Leu Asp Val Glu Ser His Ala Ile Ile Gln Asp Val Lys
        290                 295                 300
Leu Leu Gln Glu Leu Leu Leu Asp Trp Lys Ile Trp Asn Lys Ala Glu
305                 310                 315                 320
Gln Gly Val Trp Glu Thr Leu Leu Ala Ala Leu Glu Val Leu Ile Arg
                325                 330                 335
Val Glu His His Gln Gln Gln Phe Asn Ile Lys Gln Leu Leu Asn Ala
                340                 345                 350
His Val Val His His Phe Leu Leu Thr Cys Gln Val Leu Gln Glu His
            355                 360                 365
Arg Glu Gly Gln Leu Thr Ser Met Pro Arg Glu Val Cys Arg Ser Phe
370                 375                 380
Val Lys Ile Ile Ala Glu Val Leu Gly Ser Pro Pro Asp Leu Glu Leu
385                 390                 395                 400
Leu Thr Val Ile Phe Asn Phe Leu Leu Ala Val His Pro Pro Thr Asn
                405                 410                 415
Thr Tyr Val Cys His Asn Pro Thr Asn Phe Tyr Phe Ser Leu His Ile
                420                 425                 430
Asp Gly Lys Ile Phe Gln Glu Lys Val Gln Ser Leu Ala Tyr Leu Arg
            435                 440                 445
His Ser Ser Gly Gly Gln Ala Phe Pro Ser Pro Gly Phe Leu Val
        450                 455                 460
Ile Ser Pro Ser Ala Phe Thr Ala Ala Pro Pro Glu Gly Thr Ser Ser
465                 470                 475                 480
Ser Asn Ile Val Pro Gln Arg Met Ala Ala Gln Met Val Arg Ser Arg
                485                 490                 495
Ser Leu Pro Ala Phe Pro Thr Tyr Leu Pro Leu Ile Arg Ala Gln Lys
            500                 505                 510
Leu Ala Ala Ser Leu Gly Phe Ser Val Asp Lys Leu Gln Asn Ile Ala
        515                 520                 525
Asp Ala Asn Pro Glu Lys Gln Asn Leu Leu Gly Arg Pro Tyr Ala Leu
    530                 535                 540
Lys Thr Ser Lys Glu Glu Ala Phe Ile Ser Ser Cys Glu Ser Ala Lys
545                 550                 555                 560
Thr Val Cys Glu Met Glu Ala Leu Leu Gly Ala His Ala Ser Ala Asn
                565                 570                 575
Gly Val Ser Arg Gly Ser Pro Arg Phe Pro Arg Ala Arg Val Asp His
                580                 585                 590
Lys Asp Val Gly Thr Glu Pro Arg Ser Asp Asp Ser Pro Gly Asp
            595                 600                 605
Glu Ser Tyr Pro Arg Arg Pro Asp Asn Leu Lys Gly Leu Ala Ser Phe
        610                 615                 620
Gln Arg Ser Gln Ser Thr Val Ala Ser Leu Gly Leu Ala Phe Pro Ser
```

```
                625                 630                 635                 640
Gln Asn Gly Ser Ala Val Ala Ser Arg Trp Pro Ser Leu Val Asp Arg
                645                 650                 655

Asn Ala Asp Asp Trp Glu Asn Phe Thr Phe Ser Pro Ala Tyr Glu Ala
                660                 665                 670

Ser Tyr Asn Arg Ala Thr Ser Thr His Ser Val Ile Glu Asp Cys Leu
                675                 680                 685

Ile Pro Ile Cys Cys Gly Leu Tyr Glu Leu Leu Ser Gly Val Leu Leu
                690                 695                 700

Val Leu Pro Asp Ala Met Leu Glu Asp Val Met Asp Arg Ile Ile Gln
705                 710                 715                 720

Ala Asp Ile Leu Leu Val Leu Val Asn His Pro Ser Pro Ala Ile Gln
                725                 730                 735

Gln Gly Val Ile Lys Leu Leu His Ala Tyr Ile Asn Arg Ala Ser Lys
                740                 745                 750

Glu Gln Lys Asp Lys Phe Leu Lys Asn Arg Gly Phe Ser Leu Leu Ala
                755                 760                 765

Asn Gln Leu Tyr Leu His Arg Gly Thr Gln Glu Leu Leu Glu Cys Phe
                770                 775                 780

Val Glu Met Phe Phe Gly Arg Pro Ile Gly Leu Asp Glu Glu Phe Asp
785                 790                 795                 800

Leu Glu Glu Val Lys His Met Glu Leu Phe Gln Lys Trp Ser Val Ile
                805                 810                 815

Pro Val Leu Gly Leu Ile Glu Thr Ser Leu Tyr Asp Asn Val Leu Leu
                820                 825                 830

His Asn Ala Leu Leu Leu Leu Gln Val Leu Asn Ser Cys Ser Lys
835                 840                 845

Val Ala Asp Met Leu Leu Asp Asn Gly Leu Leu Tyr Val Leu Cys Asn
850                 855                 860

Thr Val Ala Ala Leu Asn Gly Leu Glu Lys Asn Ile Pro Val Asn Glu
865                 870                 875                 880

Tyr Lys Leu Leu Ala Cys Asp Ile Gln Gln Leu Phe Ile Ala Val Thr
                885                 890                 895

Ile His Ala Cys Ser Ser Ser Gly Thr Gln Tyr Phe Arg Val Ile Glu
                900                 905                 910

Asp Leu Ile Val Leu Leu Gly Tyr Leu His Asn Ser Lys Asn Lys Arg
                915                 920                 925

Thr Gln Asn Met Ala Leu Ala Leu Gln Leu Arg Val Leu Gln Ala Ala
                930                 935                 940

Leu Glu Phe Ile Arg Ser Thr Ala Asn His Asp Ser Glu Ser Pro Val
945                 950                 955                 960

His Ser Pro Ser Ala His Arg His Ser Val Pro Pro Lys Arg Arg Ser
                965                 970                 975

Ile Ala Gly Ser Arg Lys Phe Pro Leu Ala Gln Thr Glu Ser Leu Leu
                980                 985                 990

Met Lys Met Arg Ser Val Ala Ser Asp Glu Leu His Ser Met Met Gln
                995                 1000                1005

Arg Arg Met Ser Gln Glu His Pro Ser Gln Ala Ser Glu Ala Glu Leu
        1010                1015                1020

Ala Gln Arg Leu Gln Arg Leu Thr Ile Leu Ala Val Asn Arg Ile Ile
025                 1030                1035                1040

Tyr Gln Glu Leu Asn Ser Asp Ile Ile Asp Ile Leu Arg Thr Pro Glu
                1045                1050                1055
```

-continued

```
Asn Thr Ser Gln Ser Lys Thr Ser Val Ser Gln Thr Glu Ile Ser Glu
            1060                1065                1070
Glu Asp Met His His Glu Gln Pro Ser Val Tyr Asn Pro Phe Gln Lys
        1075                1080                1085
Glu Met Leu Thr Tyr Leu Leu Asp Gly Phe Lys Val Cys Ile Gly Ser
        1090                1095                1100
Ser Lys Thr Ser Val Ser Lys Gln Gln Trp Thr Lys Ile Leu Gly Ser
1105                1110                1115                1120
Cys Lys Glu Thr Leu Arg Asp Gln Leu Gly Arg Leu Leu Ala His Ile
            1125                1130                1135
Leu Ser Pro Thr His Thr Val Gln Glu Arg Lys Gln Ile Leu Glu Ile
            1140                1145                1150
Val His Glu Pro Ala His Gln Asp Ile Leu Arg Asp Cys Leu Ser Pro
        1155                1160                1165
Ser Pro Gln His Gly Ala Lys Leu Val Leu Tyr Leu Ser Glu Leu Ile
        1170                1175                1180
His Asn His Gln Asp Glu Leu Ser Glu Glu Met Asp Thr Ala Glu
1185                1190                1195                1200
Leu Leu Met Asn Ala Leu Lys Leu Cys Gly His Lys Cys Ile Pro Pro
            1205                1210                1215
Ser Ala Pro Ser Lys Pro Glu Leu Ile Lys Ile Arg Glu Glu Gln
            1220                1225                1230
Lys Lys Tyr Glu Ser Glu Glu Ser Val Ser Lys Gly Ser Trp Gln Lys
            1235                1240                1245
Thr Val Asn Asn Gln Gln Ser Leu Phe Gln Arg Leu Asp Phe Lys
            1250                1255                1260
Ser Lys Asp Ile Ser Lys Ile Ala Ala Asp Ile Thr Gln Ala Val Ser
1265                1270                1275                1280
Leu Ser Gln Gly Ile Glu Arg Lys Lys Val Ile Gln His Ile Arg Gly
            1285                1290                1295
Met Tyr Lys Val Asp Leu Ser Ala Ser Arg His Trp Gln Glu Cys Ile
            1300                1305                1310
Gln Gln Leu Thr His Asp Arg Ala Val Trp Tyr Asp Pro Ile Tyr Tyr
            1315                1320                1325
Pro Thr Ser Trp Gln Leu Asp Pro Thr Glu Gly Pro Asn Arg Glu Arg
        1330                1335                1340
Arg Arg Leu Gln Arg Cys Tyr Leu Thr Ile Pro Asn Lys Tyr Leu Leu
1345                1350                1355                1360
Arg Asp Arg Gln Lys Ser Glu Gly Val Leu Arg Pro Pro Leu Ser Tyr
            1365                1370                1375
Leu Phe Glu Asp Lys Thr His Ser Ser Phe Ser Ser Thr Val Lys Asp
            1380                1385                1390
Lys Ala Ala Ser Glu Ser Ile Arg Val Asn Arg Arg Cys Ile Ser Val
            1395                1400                1405
Ala Pro Ser Arg Glu Thr Ala Gly Glu Leu Leu Leu Gly Lys Cys Gly
            1410                1415                1420
Met Tyr Phe Val Glu Asp Asn Ala Ser Asp Ala Val Glu Ser Ser Ser
1425                1430                1435                1440
Leu Gln Gly Glu Leu Glu Pro Ala Ser Phe Ser Trp Thr Tyr Glu Glu
            1445                1450                1455
Ile Lys Glu Val His Arg Arg Trp Trp Gln Leu Arg Asp Asn Ala Val
            1460                1465                1470
Glu Ile Phe Leu Thr Asn Gly Arg Thr Leu Leu Leu Ala Phe Asp Asn
            1475                1480                1485
```

-continued

Asn Lys Val Arg Asp Asp Val Tyr Gln Ser Ile Leu Thr Asn Asn Leu
        1490                1495                1500

Pro Asn Leu Leu Glu Tyr Gly Asn Ile Thr Ala Leu Thr Asn Leu Trp
1505                1510                1515                1520

Tyr Ser Gly Gln Ile Thr Asn Phe Glu Tyr Leu Thr His Leu Asn Lys
            1525                1530                1535

His Ala Gly Arg Ser Phe Asn Asp Leu Met Gln Tyr Pro Val Phe Pro
        1540                1545                1550

Phe Ile Leu Ser Asp Tyr Val Ser Glu Thr Leu Asp Leu Asn Asp Pro
        1555                1560                1565

Ser Ile Tyr Arg Asn Leu Ser Lys Pro Ile Ala Val Gln Tyr Lys Glu
        1570                1575                1580

Lys Glu Asp Arg Tyr Val Asp Thr Tyr Lys Tyr Leu Glu Glu Glu Tyr
1585                1590                1595                1600

Arg Lys Gly Ala Arg Glu Asp Asp Pro Met Pro Pro Val Gln Pro Tyr
            1605                1610                1615

His Tyr Gly Ser His Tyr Ser Asn Ser Gly Thr Val Leu His Phe Leu
        1620                1625                1630

Val Arg Met Pro Pro Phe Thr Lys Met Phe Leu Ala Tyr Gln Asp Gln
        1635                1640                1645

Ser Phe Asp Ile Pro Asp Arg Thr Phe His Ser Thr Asn Thr Thr Trp
        1650                1655                1660

Arg Leu Ser Ser Phe Glu Ser Met Thr Asp Val Lys Glu Leu Ile Pro
1665                1670                1675                1680

Glu Phe Phe Tyr Leu Pro Glu Phe Leu Val Asn Arg Glu Gly Phe Asp
            1685                1690                1695

Phe Gly Val Arg Gln Asn Gly Glu Arg Val Asn His Val Asn Leu Pro
        1700                1705                1710

Pro Trp Ala Arg Asn Asp Pro Arg Leu Phe Ile Leu Ile His Arg Gln
        1715                1720                1725

Ala Leu Glu Ser Asp His Val Ser Gln Asn Ile Cys His Trp Ile Asp
        1730                1735                1740

Leu Val Phe Gly Tyr Lys Gln Lys Gly Lys Ala Ser Val Gln Ala Ile
1745                1750                1755                1760

Asn Val Phe His Pro Ala Thr Tyr Phe Gly Met Asp Val Ser Ala Val
            1765                1770                1775

Glu Asp Pro Val Gln Arg Arg Ala Leu Glu Thr Met Ile Lys Thr Tyr
        1780                1785                1790

Gly Gln Thr Pro Arg Gln Leu Phe His Thr Ala His Ala Ser Arg Pro
        1795                1800                1805

Gly Ala Lys Leu Asn Ile Glu Gly Glu Leu Pro Ala Ala Val Gly Leu
        1810                1815                1820

Leu Val Gln Phe Ala Phe Arg Glu Thr Arg Glu Pro Val Lys Glu Val
1825                1830                1835                1840

Thr His Pro Ser Pro Leu Ser Trp Ile Lys Gly Leu Lys Trp Gly Glu
            1845                1850                1855

Tyr Val Gly Ser Pro Ser Ala Pro Val Pro Val Val Cys Phe Ser Gln
            1860                1865                1870

Pro His Gly Glu Arg Phe Gly Ser Leu Gln Ala Leu Pro Thr Arg Ala
        1875                1880                1885

Ile Cys Gly Leu Ser Arg Asn Phe Cys Leu Leu Met Thr Tyr Asn Lys
        1890                1895                1900

Glu Gln Gly Val Arg Ser Met Asn Asn Thr Asn Ile Gln Trp Ser Ala

-continued

```
                1905                1910                1915                1920
    Ile Leu Ser Trp Gly Tyr Ala Asp Asn Ile Leu Arg Leu Lys Ser Lys
                    1925                1930                1935
    Gln Ser Glu Pro Pro Ile Asn Phe Ile Gln Ser Ser Gln Gln His Gln
                    1940                1945                1950
    Val Thr Ser Cys Ala Trp Val Pro Asp Ser Cys Gln Leu Phe Thr Gly
                    1955                1960                1965
    Ser Lys Cys Gly Val Ile Thr Ala Tyr Thr Asn Arg Leu Thr Ser Ser
                    1970                1975                1980
    Thr Pro Ser Glu Ile Glu Met Glu Ser Gln Met His Leu Tyr Gly His
    1985                1990                1995                2000
    Thr Glu Glu Ile Thr Gly Leu Cys Val Cys Lys Pro Tyr Ser Val Met
                    2005                2010                2015
    Ile Ser Val Ser Arg Asp Gly Thr Cys Ile Val Trp Asp Leu Asn Arg
                    2020                2025                2030
    Leu Cys Tyr Val Gln Ser Leu Ala Gly His Lys Ser Pro Val Thr Ala
                    2035                2040                2045
    Val Ser Ala Ser Glu Thr Ser Gly Asp Ile Ala Thr Val Cys Asp Ser
                    2050                2055                2060
    Ala Gly Gly Gly Ser Asp Leu Arg Leu Trp Thr Val Asn Gly Asp Leu
    2065                2070                2075                2080
    Val Gly His Val His Cys Arg Glu Ile Ile Cys Ser Val Ala Phe Ser
                    2085                2090                2095
    Asn Gln Pro Glu Gly Val Ser Ile Asn Val Ile Ala Gly Gly Leu Glu
                    2100                2105                2110
    Asn Gly Ile Val Arg Leu Trp Ser Thr Trp Asp Leu Lys Pro Val Arg
                    2115                2120                2125
    Glu Ile Thr Phe Pro Lys Ser Asn Lys Pro Ile Ile Ser Leu Thr Phe
                    2130                2135                2140
    Ser Cys Asp Gly His His Leu Tyr Thr Ala Asn Ser Glu Gly Thr Val
    2145                2150                2155                2160
    Ile Ala Trp Cys Arg Lys Asp Gln Gln Arg Val Lys Leu Pro Met Phe
                    2165                2170                2175
    Tyr Ser Phe Leu Ser Ser Tyr Ala Ala Gly
                    2180                2185
```

(2) INFORMATION FOR SEQ ID NO:3:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

TTAAAGTAAG C                                                  11

(2) INFORMATION FOR SEQ ID NO:4:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

TTTAGCTGCT G                                                                 11

(2) INFORMATION FOR SEQ ID NO:5:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

TTAAAGTAAG G                                                                 11

(2) INFORMATION FOR SEQ ID NO:6:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

TGCAGGCTTG T                                                                 11

(2) INFORMATION FOR SEQ ID NO:7:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

TCCAACTGGT AATA                                                              14

(2) INFORMATION FOR SEQ ID NO:8:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

GAGTGAGGTA ACA                                                               13

(2) INFORMATION FOR SEQ ID NO:9:

(i) SEQUENCE CHARACTERISTICS:
        (A) LENGTH: 12616 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 190..11592

(xi) SEQUENCE DESCRIPTION: SEQ ID NO:9:

```
                                                                -continued

GCGGCCGCGT CGACGCGGCG GCGGCAGCGG CGTCGGCTCG GGGTTCTCCG GGAGAGGGGG          60

AGTGCGCGGC GGCCGCAGCT GCCACAAACC AGGTGAAGCT TTGTTCTAAG AATATTTGTT         120

TCATCTAGTT TATGAGTCCA AATGATATAG ACTGTAAATG TCACAGCAGT GGTGAAAGAC         180

TGCTCGGTC ATG AGC ACC GAC AGT AAC TCA CTG GCA CGT GAA TTT CTG            228
          Met Ser Thr Asp Ser Asn Ser Leu Ala Arg Glu Phe Leu
            1               5                  10

ACC GAT GTC AAC CGG CTT TGC AAT GCA GTG GTC CAG AGG GTG GAG GCC          276
Thr Asp Val Asn Arg Leu Cys Asn Ala Val Val Gln Arg Val Glu Ala
    15                  20                  25

AGG GAG GAA GAA GAG GAG GAG ACG CAC ATG GCA ACC CTT GGA CAG TAC          324
Arg Glu Glu Glu Glu Glu Glu Thr His Met Ala Thr Leu Gly Gln Tyr
 30                  35                  40                  45

CTT GTC CAT GGT CGA GGA TTT CTA TTA CTT ACC AAG CTA AAT TCT ATA          372
Leu Val His Gly Arg Gly Phe Leu Leu Leu Thr Lys Leu Asn Ser Ile
                50                  55                  60

ATT GAT CAG GCA TTG ACA TGT AGA GAA GAA CTC CTG ACT CTT CTT CTG          420
Ile Asp Gln Ala Leu Thr Cys Arg Glu Glu Leu Leu Thr Leu Leu Leu
        65                  70                  75

TCT CTC CTT CCA CTG GTA TGG AAG ATA CCT GTC CAA GAA GAA AAG GCA          468
Ser Leu Leu Pro Leu Val Trp Lys Ile Pro Val Gln Glu Glu Lys Ala
            80                  85                  90

ACA GAT TTT AAC CTA CCG CTC TCA GCA GAT ATA ATC CTG ACC AAA GAA          516
Thr Asp Phe Asn Leu Pro Leu Ser Ala Asp Ile Ile Leu Thr Lys Glu
        95                  100                 105

AAG AAC TCA AGT TCA CAA AGA TCC ACT CAG GAA AAA TTA CAT TTA GAA          564
Lys Asn Ser Ser Ser Gln Arg Ser Thr Gln Glu Lys Leu His Leu Glu
110                 115                 120                 125

GGA AGT GCC CTG TCT AGT CAG GTT TCT GCA AAA GTA AAT GTT TTT CGA          612
Gly Ser Ala Leu Ser Ser Gln Val Ser Ala Lys Val Asn Val Phe Arg
                130                 135                 140

AAA AGC AGA CGA CAG CGT AAA ATT ACC CAT CGC TAT TCT GTA AGA GAT          660
Lys Ser Arg Arg Gln Arg Lys Ile Thr His Arg Tyr Ser Val Arg Asp
                145                 150                 155

GCA AGA AAG ACA CAG CTC TCC ACC TCA GAT TCA GAA GCC AAT TCA GAT          708
Ala Arg Lys Thr Gln Leu Ser Thr Ser Asp Ser Glu Ala Asn Ser Asp
        160                 165                 170

GAA AAA GGC ATA GCA ATG AAT AAG CAT AGA AGG CCC CAT CTG CTG CAT          756
Glu Lys Gly Ile Ala Met Asn Lys His Arg Arg Pro His Leu Leu His
    175                 180                 185

CAT TTT TTA ACA TCG TTT CCT AAA CAA GAC CAC CCC AAA GCT AAA CTT          804
His Phe Leu Thr Ser Phe Pro Lys Gln Asp His Pro Lys Ala Lys Leu
190                 195                 200                 205

GAC CGC TTA GCA ACC AAA GAA CAG ACT CCT CCA GAT GCT ATG GCT TTG          852
Asp Arg Leu Ala Thr Lys Glu Gln Thr Pro Pro Asp Ala Met Ala Leu
                210                 215                 220

GAA AAT TCC AGA GAG ATT ATT CCA AGA CAG GGG TCA AAC ACT GAC ATT          900
Glu Asn Ser Arg Glu Ile Ile Pro Arg Gln Gly Ser Asn Thr Asp Ile
                225                 230                 235

TTA AGT GAG CCA GCT GCC TTG TCT GTT ATC AGT AAC ATG AAC AAT TCT          948
Leu Ser Glu Pro Ala Ala Leu Ser Val Ile Ser Asn Met Asn Asn Ser
                240                 245                 250

CCA TTT GAC TTA TGT CAT GTT TTG TTA TCT TTA TTA GAA AAA GTT TGT          996
Pro Phe Asp Leu Cys His Val Leu Leu Ser Leu Leu Glu Lys Val Cys
        255                 260                 265

AAG TTT GAC GTT ACC TTG AAT CAT AAT TCT CCT TTA GCA GCC AGT GTA         1044
Lys Phe Asp Val Thr Leu Asn His Asn Ser Pro Leu Ala Ala Ser Val
270                 275                 280                 285

GTG CCC ACA CTA ACT GAA TTC CTA GCA GGC TTT GGG GAC TGC TGC AGT         1092
Val Pro Thr Leu Thr Glu Phe Leu Ala Gly Phe Gly Asp Cys Cys Ser
```

```
                              290                         295                         300
CTG AGC GAC AAC TTG GAG AGT CGA GTA GTT TCT GCA GGT TGG ACC GAA                1140
Leu Ser Asp Asn Leu Glu Ser Arg Val Val Ser Ala Gly Trp Thr Glu
                305                         310                         315

GAA CCG GTG GCT TTG ATT CAA AGG ATG CTC TTT CGA ACA GTG TTG CAT                1188
Glu Pro Val Ala Leu Ile Gln Arg Met Leu Phe Arg Thr Val Leu His
            320                         325                         330

CTT CTG TCA GTA GAT GTT AGT ACT GCA GAG ATG ATG CCA GAA AAT CTT                1236
Leu Leu Ser Val Asp Val Ser Thr Ala Glu Met Met Pro Glu Asn Leu
        335                         340                         345

AGG AAA AAT TTA ACT GAA TTG CTT AGA GCA GCT TTA AAA ATT AGA ATA                1284
Arg Lys Asn Leu Thr Glu Leu Leu Arg Ala Ala Leu Lys Ile Arg Ile
350                         355                         360                         365

TGC CTA GAA AAG CAG CCT GAC CCT TTT GCA CCA AGA CAA AAG AAA ACA                1332
Cys Leu Glu Lys Gln Pro Asp Pro Phe Ala Pro Arg Gln Lys Lys Thr
                370                         375                         380

CTG CAG GAG GTT CAG GAA GAT TTT GTG TTT TCA AAG TAT CGT CAT AGA                1380
Leu Gln Glu Val Gln Glu Asp Phe Val Phe Ser Lys Tyr Arg His Arg
            385                         390                         395

GCC CTT CTT TTA CCT GAG CTT TTG GAA GGA GTT CTT CAG ATT CTG ATC                1428
Ala Leu Leu Leu Pro Glu Leu Leu Glu Gly Val Leu Gln Ile Leu Ile
        400                         405                         410

TGT TGT CTT CAA AGT GCA GCT TCA AAT CCC TTC TAC TTC AGT CAA GCC                1476
Cys Cys Leu Gln Ser Ala Ala Ser Asn Pro Phe Tyr Phe Ser Gln Ala
    415                         420                         425

ATG GAT TTG GTT CAA GAA TTC ATT CAG CAT CAT GGA TTT AAT TTA TTT                1524
Met Asp Leu Val Gln Glu Phe Ile Gln His His Gly Phe Asn Leu Phe
430                         435                         440                         445

GAA ACA GCA GTT CTT CAA ATG GAA TGG CTG GTT TTA AGA GAT GGA GTT                1572
Glu Thr Ala Val Leu Gln Met Glu Trp Leu Val Leu Arg Asp Gly Val
                450                         455                         460

CCT CCC GAG GCC TCA GAG CAT TTG AAA GCC CTA ATA AAT AGT GTG ATG                1620
Pro Pro Glu Ala Ser Glu His Leu Lys Ala Leu Ile Asn Ser Val Met
            465                         470                         475

AAA ATA ATG AGC ACT GTC AAA AAA GTG AAA TCA GAG CAA CTT CAT CAT                1668
Lys Ile Met Ser Thr Val Lys Lys Val Lys Ser Glu Gln Leu His His
        480                         485                         490

TCG ATG TGT ACA AGA AAA AGG CAC AGA CGA TGT GAA TAT TCT CAT TTT                1716
Ser Met Cys Thr Arg Lys Arg His Arg Arg Cys Glu Tyr Ser His Phe
    495                         500                         505

ATG CAT CAT CAC CGA GAT CTC TCA GGT CTT CTG GTT TCG GCT TTT AAA                1764
Met His His His Arg Asp Leu Ser Gly Leu Leu Val Ser Ala Phe Lys
510                         515                         520                         525

AAC CAG GTT TCC AAA AAC CCA TTT GAA GAG ACT GCA GAT GGA GAT GTT                1812
Asn Gln Val Ser Lys Asn Pro Phe Glu Glu Thr Ala Asp Gly Asp Val
                530                         535                         540

TAT TAT CCT GAG CGG TGC TGT TGC ATT GCA GTG TGT GCC CAT CAG TGC                1860
Tyr Tyr Pro Glu Arg Cys Cys Cys Ile Ala Val Cys Ala His Gln Cys
            545                         550                         555

TTG CGC TTA CTA CAG CAG GCT TCC TTG AGC AGC ACT TGT GTC CAG ATC                1908
Leu Arg Leu Leu Gln Gln Ala Ser Leu Ser Ser Thr Cys Val Gln Ile
        560                         565                         570

CTA TCG GGT GTT CAT AAC ATT GGA ATA TGC TGT TGT ATG GAT CCC AAA                1956
Leu Ser Gly Val His Asn Ile Gly Ile Cys Cys Cys Met Asp Pro Lys
    575                         580                         585

TCT GTA ATC ATT CCT TTG CTC CAT GCT TTT AAA TTG CCA GCA CTG AAA                2004
Ser Val Ile Ile Pro Leu Leu His Ala Phe Lys Leu Pro Ala Leu Lys
590                         595                         600                         605

AAT TTT CAG CAG CAT ATA TTG AAT ATC CTT AAC AAA CTT ATT TTG GAT                2052
Asn Phe Gln Gln His Ile Leu Asn Ile Leu Asn Lys Leu Ile Leu Asp
```

-continued

|     |     |     | 610 |     |     |     | 615 |     |     |     | 620 |     |     |     |      |
| --- | --- | --- | --- | --- | --- | --- | --- | --- | --- | --- | --- | --- | --- | --- | ---- |
| CAG | TTA | GGA | GGA | GCA | GAG | ATA | TCA | CCA | AAA | ATT | AAA | AAA | GCA | GCT | TGT  | 2100 |
| Gln | Leu | Gly | Gly | Ala | Glu | Ile | Ser | Pro | Lys | Ile | Lys | Lys | Ala | Ala | Cys  |
|     |     |     | 625 |     |     |     | 630 |     |     |     | 635 |     |     |     |      |
| AAT | ATT | TGT | ACT | GTT | GAC | TCT | GAC | CAA | CTA | GCC | CAA | TTA | GAA | GAG | ACA  | 2148 |
| Asn | Ile | Cys | Thr | Val | Asp | Ser | Asp | Gln | Leu | Ala | Gln | Leu | Glu | Glu | Thr  |
|     |     |     | 640 |     |     |     | 645 |     |     |     | 650 |     |     |     |      |
| CTG | CAG | GGA | AAC | TTA | TGT | GAT | GCT | GAA | CTC | TCC | TCA | AGT | TTA | TCC | AGT  | 2196 |
| Leu | Gln | Gly | Asn | Leu | Cys | Asp | Ala | Glu | Leu | Ser | Ser | Ser | Leu | Ser | Ser  |
|     | 655 |     |     |     | 660 |     |     |     | 665 |     |     |     |     |     |      |
| CCT | TCT | TAC | AGA | TTT | CAA | GGG | ATC | CTG | CCC | AGC | AGT | GGA | TCT | GAA | GAT  | 2244 |
| Pro | Ser | Tyr | Arg | Phe | Gln | Gly | Ile | Leu | Pro | Ser | Ser | Gly | Ser | Glu | Asp  |
| 670 |     |     |     | 675 |     |     |     | 680 |     |     |     |     |     |     | 685  |
| TTG | TTG | TGG | AAA | TGG | GAT | GCT | TTA | AAG | GCT | TAT | CAG | AAC | TTT | GTT | TTT  | 2292 |
| Leu | Leu | Trp | Lys | Trp | Asp | Ala | Leu | Lys | Ala | Tyr | Gln | Asn | Phe | Val | Phe  |
|     |     |     | 690 |     |     |     | 695 |     |     |     | 700 |     |     |     |      |
| GAA | GAA | GAC | AGA | TTA | CAT | AGT | ATA | CAG | ATT | GCA | AAT | CAC | ATT | TGC | AAT  | 2340 |
| Glu | Glu | Asp | Arg | Leu | His | Ser | Ile | Gln | Ile | Ala | Asn | His | Ile | Cys | Asn  |
|     |     |     | 705 |     |     |     | 710 |     |     |     | 715 |     |     |     |      |
| TTA | ATC | CAG | AAA | GGC | AAT | ATA | GTT | GTT | CAG | TGG | AAA | TTA | TAT | AAT | TAC  | 2388 |
| Leu | Ile | Gln | Lys | Gly | Asn | Ile | Val | Val | Gln | Trp | Lys | Leu | Tyr | Asn | Tyr  |
|     |     |     | 720 |     |     |     | 725 |     |     |     | 730 |     |     |     |      |
| ATA | TTT | AAT | CCT | GTG | CTC | CAA | AGA | GGA | GTT | GAA | TTA | GCA | CAT | CAT | TGT  | 2436 |
| Ile | Phe | Asn | Pro | Val | Leu | Gln | Arg | Gly | Val | Glu | Leu | Ala | His | His | Cys  |
|     | 735 |     |     |     | 740 |     |     |     | 745 |     |     |     |     |     |      |
| CAA | CAC | CTA | AGC | GTT | ACT | TCA | GCT | CAA | AGT | CAT | GTA | TGT | AGC | CAT | CAT  | 2484 |
| Gln | His | Leu | Ser | Val | Thr | Ser | Ala | Gln | Ser | His | Val | Cys | Ser | His | His  |
| 750 |     |     |     | 755 |     |     |     | 760 |     |     |     |     |     |     | 765  |
| AAC | CAG | TGC | TTG | CCT | CAG | GAC | GTG | CTT | CAG | ATT | TAT | GTA | AAA | ACT | CTG  | 2532 |
| Asn | Gln | Cys | Leu | Pro | Gln | Asp | Val | Leu | Gln | Ile | Tyr | Val | Lys | Thr | Leu  |
|     |     |     | 770 |     |     |     | 775 |     |     |     | 780 |     |     |     |      |
| CCT | ATC | CTG | CTT | AAA | TCC | AGG | GTA | ATA | AGA | GAT | TTG | TTT | TTG | AGT | TGT  | 2580 |
| Pro | Ile | Leu | Leu | Lys | Ser | Arg | Val | Ile | Arg | Asp | Leu | Phe | Leu | Ser | Cys  |
|     |     |     | 785 |     |     |     | 790 |     |     |     | 795 |     |     |     |      |
| AAT | GGA | GTA | AGT | CAA | ATA | ATC | GAA | TTA | AAT | TGC | TTA | AAT | GGT | ATT | CGA  | 2628 |
| Asn | Gly | Val | Ser | Gln | Ile | Ile | Glu | Leu | Asn | Cys | Leu | Asn | Gly | Ile | Arg  |
|     |     |     | 800 |     |     |     | 805 |     |     |     | 810 |     |     |     |      |
| AGT | CAT | TCT | CTA | AAA | GCA | TTT | GAA | ACT | CTG | ATA | ATC | AGC | CTA | GGG | GAG  | 2676 |
| Ser | His | Ser | Leu | Lys | Ala | Phe | Glu | Thr | Leu | Ile | Ile | Ser | Leu | Gly | Glu  |
|     | 815 |     |     |     | 820 |     |     |     | 825 |     |     |     |     |     |      |
| CAA | CAG | AAA | GAT | GCC | TCA | GTT | CCA | GAT | ATT | GAT | GGG | ATA | GAC | ATT | GAA  | 2724 |
| Gln | Gln | Lys | Asp | Ala | Ser | Val | Pro | Asp | Ile | Asp | Gly | Ile | Asp | Ile | Glu  |
| 830 |     |     |     | 835 |     |     |     | 840 |     |     |     |     |     |     | 845  |
| CAG | AAG | GAG | TTG | TCC | TCT | GTA | CAT | GTG | GGT | ACT | TCT | TTT | CAT | CAT | CAG  | 2772 |
| Gln | Lys | Glu | Leu | Ser | Ser | Val | His | Val | Gly | Thr | Ser | Phe | His | His | Gln  |
|     |     |     | 850 |     |     |     | 855 |     |     |     | 860 |     |     |     |      |
| CAA | GCT | TAT | TCA | GAT | TCT | CCT | CAG | AGT | CTC | AGC | AAA | TTT | TAT | GCT | GGC  | 2820 |
| Gln | Ala | Tyr | Ser | Asp | Ser | Pro | Gln | Ser | Leu | Ser | Lys | Phe | Tyr | Ala | Gly  |
|     |     |     | 865 |     |     |     | 870 |     |     |     | 875 |     |     |     |      |
| CTC | AAA | GAA | GCT | TAT | CCA | AAG | AGA | CGG | AAG | ACT | GTT | AAC | CAA | GAT | GTT  | 2868 |
| Leu | Lys | Glu | Ala | Tyr | Pro | Lys | Arg | Arg | Lys | Thr | Val | Asn | Gln | Asp | Val  |
|     |     |     | 880 |     |     |     | 885 |     |     |     | 890 |     |     |     |      |
| CAT | ATC | AAC | ACA | ATA | AAC | CTA | TTC | CTC | TGT | GTG | GCT | TTT | TTA | TGC | GTA  | 2916 |
| His | Ile | Asn | Thr | Ile | Asn | Leu | Phe | Leu | Cys | Val | Ala | Phe | Leu | Cys | Val  |
|     |     |     | 895 |     |     |     | 900 |     |     |     | 905 |     |     |     |      |
| AGT | AAA | GAA | GCA | GAG | TCT | GAC | AGG | GAG | TCG | GCC | AAT | GAC | TCA | GAA | GAT  | 2964 |
| Ser | Lys | Glu | Ala | Glu | Ser | Asp | Arg | Glu | Ser | Ala | Asn | Asp | Ser | Glu | Asp  |
| 910 |     |     |     | 915 |     |     |     | 920 |     |     |     |     |     |     | 925  |
| ACT | TCT | GGC | TAT | GAC | AGC | ACA | GCC | AGC | GAG | CCT | TTA | AGT | CAT | ATG | CTG  | 3012 |
| Thr | Ser | Gly | Tyr | Asp | Ser | Thr | Ala | Ser | Glu | Pro | Leu | Ser | His | Met | Leu  |

-continued

```
                  930              935             940
CCA TGT ATA TCT CTC GAG AGC CTT GTC TTG CCT TCT CCT GAA CAT ATG    3060
Pro Cys Ile Ser Leu Glu Ser Leu Val Leu Pro Ser Pro Glu His Met
            945             950             955

CAC CAA GCA GCA GAC ATT TGG TCT ATG TGT CGT TGG ATC TAC ATG TTG    3108
His Gln Ala Ala Asp Ile Trp Ser Met Cys Arg Trp Ile Tyr Met Leu
            960             965             970

AGT TCA GTG TTC CAG AAA CAG TTT TAT AGG CTT GGT GGT TTC CGA GTA    3156
Ser Ser Val Phe Gln Lys Gln Phe Tyr Arg Leu Gly Gly Phe Arg Val
            975             980             985

TGC CAT AAG TTA ATA TTT ATG ATA ATA CAG AAA CTG TTC AGA AGT CAC    3204
Cys His Lys Leu Ile Phe Met Ile Ile Gln Lys Leu Phe Arg Ser His
990             995             1000            1005

AAA GAG GAG CAA GGA AAA AAG GAG GGA GAT ACA AGT GTA AAT GAA AAC    3252
Lys Glu Glu Gln Gly Lys Lys Glu Gly Asp Thr Ser Val Asn Glu Asn
            1010            1015            1020

CAG GAT TTA AAC AGA ATT TCT CAA CCT AAG AGA ACT ATG AAG GAA GAT    3300
Gln Asp Leu Asn Arg Ile Ser Gln Pro Lys Arg Thr Met Lys Glu Asp
            1025            1030            1035

TTA TTA TCT TTG GCT ATA AAA AGT GAC CCC ATA CCA TCA GAA CTA GGT    3348
Leu Leu Ser Leu Ala Ile Lys Ser Asp Pro Ile Pro Ser Glu Leu Gly
            1040            1045            1050

AGT CTA AAA AAG AGT GCT GAC AGT TTA GGT AAA TTA GAG TTA CAG CAT    3396
Ser Leu Lys Lys Ser Ala Asp Ser Leu Gly Lys Leu Glu Leu Gln His
            1055            1060            1065

ATT TCT TCC ATA AAT GTG GAA GAA GTT TCA GCT ACT GAA GCC GCT CCC    3444
Ile Ser Ser Ile Asn Val Glu Glu Val Ser Ala Thr Glu Ala Ala Pro
1070            1075            1080            1085

GAG GAA GCA AAG CTA TTT ACA AGT CAA GAA AGT GAG ACC TCA CTT CAA    3492
Glu Glu Ala Lys Leu Phe Thr Ser Gln Glu Ser Glu Thr Ser Leu Gln
            1090            1095            1100

AGT ATA CGA CTT TTG GAA GCC CTT CTG GCC ATT TGT CTT CAT GGT GCC    3540
Ser Ile Arg Leu Leu Glu Ala Leu Leu Ala Ile Cys Leu His Gly Ala
            1105            1110            1115

AGA ACT AGT CAA CAG AAG ATG GAA TTG GAG TTA CCT AAT CAG AAC TTG    3588
Arg Thr Ser Gln Gln Lys Met Glu Leu Glu Leu Pro Asn Gln Asn Leu
            1120            1125            1130

TCT GTG GAA AGT ATA TTA TTT GAA ATG AGG GAC CAT CTT TCC CAG TCA    3636
Ser Val Glu Ser Ile Leu Phe Glu Met Arg Asp His Leu Ser Gln Ser
            1135            1140            1145

AAG GTG ATT GAA ACA CAA CTA GCA AAG CCG TTA TTT GAT GCC CTG CTT    3684
Lys Val Ile Glu Thr Gln Leu Ala Lys Pro Leu Phe Asp Ala Leu Leu
1150            1155            1160            1165

CGA GTT GCC CTC GGG AAT TAT TCA GCA GAT TTT GAA CAT AAT GAT GCT    3732
Arg Val Ala Leu Gly Asn Tyr Ser Ala Asp Phe Glu His Asn Asp Ala
            1170            1175            1180

ATG ACT GAG AAG AGT CAT CAA TCT GCA GAA GAA TTG TCA TCC CAG CCT    3780
Met Thr Glu Lys Ser His Gln Ser Ala Glu Glu Leu Ser Ser Gln Pro
            1185            1190            1195

GGT GAT TTT TCA GAA GAA GCT GAG GAT TCT CAG TGT TGT AGT TTT AAA    3828
Gly Asp Phe Ser Glu Glu Ala Glu Asp Ser Gln Cys Cys Ser Phe Lys
            1200            1205            1210

CTT TTA GTT GAA GAA GAA GGT TAC GAA GCA GAT AGT GAA AGC AAT CCT    3876
Leu Leu Val Glu Glu Glu Gly Tyr Glu Ala Asp Ser Glu Ser Asn Pro
            1215            1220            1225

GAA GAT GGC GAA ACC CAG GAT GAT GGG GTA GAC TTA AAG TCT GAA ACA    3924
Glu Asp Gly Glu Thr Gln Asp Asp Gly Val Asp Leu Lys Ser Glu Thr
1230            1235            1240            1245

GAA GGT TTC AGT GCA TCA AGC AGT CCA AAT GAC TTA CTC GAA AAC CTC    3972
Glu Gly Phe Ser Ala Ser Ser Ser Pro Asn Asp Leu Leu Glu Asn Leu
```

|         |         |         |         |         |         |         |         |         |         |         |         |         |         |         |         |      |
|---------|---------|---------|---------|---------|---------|---------|---------|---------|---------|---------|---------|---------|---------|---------|---------|------|
|         |         |         |         | 1250    |         |         |         |         | 1255    |         |         |         |         | 1260    |         |      |
| ACT     | CAA     | GGG     | GAA     | ATA     | ATT     | TAT     | CCT     | GAG     | ATT     | TGT     | ATG     | CTG     | GAA     | TTA     | AAT     | 4020 |
| Thr     | Gln     | Gly     | Glu     | Ile     | Ile     | Tyr     | Pro     | Glu     | Ile     | Cys     | Met     | Leu     | Glu     | Leu     | Asn     |      |
|         |         |         |         | 1265    |         |         |         |         | 1270    |         |         |         |         | 1275    |         |      |
| TTG     | CTT     | TCT     | GCT     | AGT     | AAA     | GCC     | AAA     | CTT     | GAT     | GTG     | CTT     | GCC     | CAT     | GTA     | TTT     | 4068 |
| Leu     | Leu     | Ser     | Ala     | Ser     | Lys     | Ala     | Lys     | Leu     | Asp     | Val     | Leu     | Ala     | His     | Val     | Phe     |      |
|         |         |         | 1280    |         |         |         |         | 1285    |         |         |         |         | 1290    |         |         |      |
| GAG     | AGT     | TTT     | TTG     | AAA     | ATT     | ATT     | AGG     | CAG     | AAA     | GAA     | AAG     | AAT     | GTT     | TTT     | CTG     | 4116 |
| Glu     | Ser     | Phe     | Leu     | Lys     | Ile     | Ile     | Arg     | Gln     | Lys     | Glu     | Lys     | Asn     | Val     | Phe     | Leu     |      |
|         | 1295    |         |         |         |         | 1300    |         |         |         |         | 1305    |         |         |         |         |      |
| CTC     | ATG     | CAA     | CAG     | GGA     | ACT     | GTG     | AAA     | AAT     | CTT     | TTA     | GGA     | GGG     | TTC     | TTG     | AGT     | 4164 |
| Leu     | Met     | Gln     | Gln     | Gly     | Thr     | Val     | Lys     | Asn     | Leu     | Leu     | Gly     | Gly     | Phe     | Leu     | Ser     |      |
| 1310    |         |         |         |         | 1315    |         |         |         |         | 1320    |         |         |         |         | 1325    |      |
| ATT     | TTA     | ACA     | CAG     | GAT     | GAT     | TCT     | GAT     | TTT     | CAA     | GCA     | TGC     | CAG     | AGA     | GTA     | TTG     | 4212 |
| Ile     | Leu     | Thr     | Gln     | Asp     | Asp     | Ser     | Asp     | Phe     | Gln     | Ala     | Cys     | Gln     | Arg     | Val     | Leu     |      |
|         |         |         | 1330    |         |         |         |         | 1335    |         |         |         |         | 1340    |         |         |      |
| GTG     | GAT     | CTT     | TTG     | GTA     | TCT     | TTG     | ATG     | AGT     | TCA     | AGA     | ACA     | TGT     | TCA     | GAA     | GAG     | 4260 |
| Val     | Asp     | Leu     | Leu     | Val     | Ser     | Leu     | Met     | Ser     | Ser     | Arg     | Thr     | Cys     | Ser     | Glu     | Glu     |      |
|         |         |         | 1345    |         |         |         |         | 1350    |         |         |         |         | 1355    |         |         |      |
| CTA     | ACC     | CTT     | CTT     | TTG     | AGA     | ATA     | TTT     | CTG     | GAG     | AAA     | TCT     | CCT     | TGT     | ACA     | AAA     | 4308 |
| Leu     | Thr     | Leu     | Leu     | Leu     | Arg     | Ile     | Phe     | Leu     | Glu     | Lys     | Ser     | Pro     | Cys     | Thr     | Lys     |      |
|         |         | 1360    |         |         |         |         | 1365    |         |         |         |         | 1370    |         |         |         |      |
| ATT     | CTT     | CTT     | CTG     | GGT     | ATT     | CTG     | AAA     | ATT     | ATT     | GAA     | AGT     | GAT     | ACT     | ACT     | ATG     | 4356 |
| Ile     | Leu     | Leu     | Leu     | Gly     | Ile     | Leu     | Lys     | Ile     | Ile     | Glu     | Ser     | Asp     | Thr     | Thr     | Met     |      |
|         | 1375    |         |         |         |         | 1380    |         |         |         |         | 1385    |         |         |         |         |      |
| AGC     | CCT     | TCA     | CAG     | TAT     | CTA     | ACC     | TTC     | CCT     | TTA     | CTG     | CAC     | GCT     | CCA     | AAT     | TTA     | 4404 |
| Ser     | Pro     | Ser     | Gln     | Tyr     | Leu     | Thr     | Phe     | Pro     | Leu     | Leu     | His     | Ala     | Pro     | Asn     | Leu     |      |
| 1390    |         |         |         |         | 1395    |         |         |         |         | 1400    |         |         |         |         | 1405    |      |
| AGC     | AAC     | GGT     | GTT     | TCA     | TCA     | CAA     | AAG     | TAT     | CCT     | GGG     | ATT     | TTA     | AAC     | AGT     | AAG     | 4452 |
| Ser     | Asn     | Gly     | Val     | Ser     | Ser     | Gln     | Lys     | Tyr     | Pro     | Gly     | Ile     | Leu     | Asn     | Ser     | Lys     |      |
|         |         |         | 1410    |         |         |         |         | 1415    |         |         |         |         | 1420    |         |         |      |
| GCC     | ATG     | GGT     | TTA     | TTG     | AGA     | AGA     | GCA     | CGA     | GTT     | TCA     | CGG     | AGC     | AAG     | AAA     | GAG     | 4500 |
| Ala     | Met     | Gly     | Leu     | Leu     | Arg     | Arg     | Ala     | Arg     | Val     | Ser     | Arg     | Ser     | Lys     | Lys     | Glu     |      |
|         |         |         | 1425    |         |         |         |         | 1430    |         |         |         |         | 1435    |         |         |      |
| GCT     | GAT     | AGA     | GAG     | AGT     | TTT     | CCC     | CAT     | CGG     | CTG     | CTT     | TCA     | TCT     | TGG     | CAC     | ATA     | 4548 |
| Ala     | Asp     | Arg     | Glu     | Ser     | Phe     | Pro     | His     | Arg     | Leu     | Leu     | Ser     | Ser     | Trp     | His     | Ile     |      |
|         |         |         | 1440    |         |         |         |         | 1445    |         |         |         |         | 1450    |         |         |      |
| GCC     | CCA     | GTC     | CAC     | CTG     | CCG     | TTG     | CTG     | GGG     | CAA     | AAC     | TGC     | TGG     | CCA     | CAC     | CTA     | 4596 |
| Ala     | Pro     | Val     | His     | Leu     | Pro     | Leu     | Leu     | Gly     | Gln     | Asn     | Cys     | Trp     | Pro     | His     | Leu     |      |
|         | 1455    |         |         |         |         | 1460    |         |         |         |         | 1465    |         |         |         |         |      |
| TCA     | GAA     | GGT     | TTC     | AGT     | GTT     | TCC     | CTG     | TGG     | TTT     | AAT     | GTG     | GAG     | TGT     | ATC     | CAT     | 4644 |
| Ser     | Glu     | Gly     | Phe     | Ser     | Val     | Ser     | Leu     | Trp     | Phe     | Asn     | Val     | Glu     | Cys     | Ile     | His     |      |
| 1470    |         |         |         |         | 1475    |         |         |         |         | 1480    |         |         |         |         | 1485    |      |
| GAA     | GCT     | GAG     | AGT     | ACT     | ACA     | GAA     | AAA     | GGA     | AAG     | AAG     | ATA     | AAG     | AAA     | AGA     | AAC     | 4692 |
| Glu     | Ala     | Glu     | Ser     | Thr     | Thr     | Glu     | Lys     | Gly     | Lys     | Lys     | Ile     | Lys     | Lys     | Arg     | Asn     |      |
|         |         |         | 1490    |         |         |         |         | 1495    |         |         |         |         | 1500    |         |         |      |
| AAA     | TCA     | TTA     | ATT     | TTA     | CCA     | GAT     | AGC     | AGT     | TTT     | GAT     | GGT     | ACA     | GAG     | AGC     | GAC     | 4740 |
| Lys     | Ser     | Leu     | Ile     | Leu     | Pro     | Asp     | Ser     | Ser     | Phe     | Asp     | Gly     | Thr     | Glu     | Ser     | Asp     |      |
|         |         |         | 1505    |         |         |         |         | 1510    |         |         |         |         | 1515    |         |         |      |
| AGA     | CCA     | GAA     | GGT     | GCA     | GAG     | TAC     | ATA     | AAT     | CCT     | GGT     | GAA     | AGA     | CTC     | ATA     | GAA     | 4788 |
| Arg     | Pro     | Glu     | Gly     | Ala     | Glu     | Tyr     | Ile     | Asn     | Pro     | Gly     | Glu     | Arg     | Leu     | Ile     | Glu     |      |
|         |         |         | 1520    |         |         |         |         | 1525    |         |         |         |         | 1530    |         |         |      |
| GAA     | GGA     | TGT     | ATT     | CAT     | ATA     | ATT     | TCA     | CTG     | GGA     | TCC     | AAA     | GCG     | TTG     | ATG     | ATC     | 4836 |
| Glu     | Gly     | Cys     | Ile     | His     | Ile     | Ile     | Ser     | Leu     | Gly     | Ser     | Lys     | Ala     | Leu     | Met     | Ile     |      |
|         |         |         | 1535    |         |         |         |         | 1540    |         |         |         |         | 1545    |         |         |      |
| CAA     | GTG     | TGG     | GCT     | GAT     | CCC     | CAC     | AAT     | GCC     | ACT     | CTT     | ATC     | TTT     | CGT     | GTG     | TGC     | 4884 |
| Gln     | Val     | Trp     | Ala     | Asp     | Pro     | His     | Asn     | Ala     | Thr     | Leu     | Ile     | Phe     | Arg     | Val     | Cys     |      |
| 1550    |         |         |         |         | 1555    |         |         |         |         | 1560    |         |         |         |         | 1565    |      |
| ATG     | GAT     | TCA     | AAT     | GAT     | GAC     | ATG     | AAA     | GCT     | GTT     | TTA     | CTA     | GCA     | CAG     | GTT     | GAA     | 4932 |
| Met     | Asp     | Ser     | Asn     | Asp     | Asp     | Met     | Lys     | Ala     | Val     | Leu     | Leu     | Ala     | Gln     | Val     | Glu     |      |

-continued

|  | 1570 | | | | 1575 | | | | 1580 | | | | | |
|---|---|---|---|---|---|---|---|---|---|---|---|---|---|---|
| TCA | CAG | GAG | AAT | ATT | TTC | CTC | CCA | AGC | AAA | TGG | CAA | CAT | TTA GTA CTC | 4980 |
| Ser | Gln | Glu | Asn | Ile | Phe | Leu | Pro | Ser | Lys | Trp | Gln | His | Leu Val Leu | |
| | | | | 1585 | | | | 1590 | | | | 1595 | | |

| ACC | TAC | TTA | CAG | CAG | CCC | CAA | GGG | AAA | AGG | AGG | ATT | CAT | GGG AAA ATC | 5028 |
| Thr | Tyr | Leu | Gln | Gln | Pro | Gln | Gly | Lys | Arg | Arg | Ile | His | Gly Lys Ile | |
| | | | 1600 | | | | 1605 | | | | 1610 | | | |

| TCC | ATA | TGG | GTC | TCT | GGA | CAG | AGG | AAG | CCT | GAT | GTT | ACT | TTG GAT TTT | 5076 |
| Ser | Ile | Trp | Val | Ser | Gly | Gln | Arg | Lys | Pro | Asp | Val | Thr | Leu Asp Phe | |
| | 1615 | | | | 1620 | | | | 1625 | | | | | |

| ATG | CTT | CCA | AGA | AAA | ACA | AGT | TTG | TCA | TCT | GAT | AGC | AAT | AAA ACA TTT | 5124 |
| Met | Leu | Pro | Arg | Lys | Thr | Ser | Leu | Ser | Ser | Asp | Ser | Asn | Lys Thr Phe | |
| 1630 | | | | 1635 | | | | 1640 | | | | 1645 | | |

| TGC | ATG | ATT | GGC | CAT | TGT | TTA | TCA | TCC | CAA | GAA | GAG | TTT | TTG CAG TTG | 5172 |
| Cys | Met | Ile | Gly | His | Cys | Leu | Ser | Ser | Gln | Glu | Glu | Phe | Leu Gln Leu | |
| | | | 1650 | | | | 1655 | | | | 1660 | | | |

| GCT | GGA | AAA | TGG | GAC | CTG | GGA | AAT | TTG | CTT | CTC | TTC | AAC | GGA GCT AAG | 5220 |
| Ala | Gly | Lys | Trp | Asp | Leu | Gly | Asn | Leu | Leu | Leu | Phe | Asn | Gly Ala Lys | |
| | | 1665 | | | | 1670 | | | | 1675 | | | | |

| GTT | GGT | TCA | CAA | GAG | GCC | TTT | TAT | CTG | TAT | GCT | TGT | GGA | CCC AAC CAT | 5268 |
| Val | Gly | Ser | Gln | Glu | Ala | Phe | Tyr | Leu | Tyr | Ala | Cys | Gly | Pro Asn His | |
| | 1680 | | | | 1685 | | | | 1690 | | | | | |

| ACA | TCT | GTA | ATG | CCA | TGT | AAG | TAT | GGC | AAG | CCA | GTC | AAT | GAC TAC TCC | 5316 |
| Thr | Ser | Val | Met | Pro | Cys | Lys | Tyr | Gly | Lys | Pro | Val | Asn | Asp Tyr Ser | |
| 1695 | | | | 1700 | | | | 1705 | | | | | | |

| AAA | TAT | ATT | AAT | AAA | GAA | ATT | TTG | CGA | TGT | GAA | CAA | ATC | AGA GAA CTT | 5364 |
| Lys | Tyr | Ile | Asn | Lys | Glu | Ile | Leu | Arg | Cys | Glu | Gln | Ile | Arg Glu Leu | |
| 1710 | | | | 1715 | | | | 1720 | | | | 1725 | | |

| TTT | ATG | ACC | AAG | AAA | GAT | GTG | GAT | ATT | GGT | CTC | TTA | ATT | GAA AGT CTT | 5412 |
| Phe | Met | Thr | Lys | Lys | Asp | Val | Asp | Ile | Gly | Leu | Leu | Ile | Glu Ser Leu | |
| | | | 1730 | | | | 1735 | | | | 1740 | | | |

| TCA | GTT | GTT | TAT | ACA | ACT | TAC | TGT | CCT | GCT | CAG | TAT | ACC | ATC TAT GAA | 5460 |
| Ser | Val | Val | Tyr | Thr | Thr | Tyr | Cys | Pro | Ala | Gln | Tyr | Thr | Ile Tyr Glu | |
| | | | | 1745 | | | | 1750 | | | | 1755 | | |

| CCA | GTG | ATT | AGA | CTT | AAA | GGT | CAA | ATG | AAA | ACC | CAA | CTC | TCT CAA AGA | 5508 |
| Pro | Val | Ile | Arg | Leu | Lys | Gly | Gln | Met | Lys | Thr | Gln | Leu | Ser Gln Arg | |
| | | 1760 | | | | 1765 | | | | 1770 | | | | |

| CCC | TTC | AGC | TCA | AAA | GAA | GTT | CAG | AGC | ATC | TTA | TTA | GAA | CCT CAT CAT | 5556 |
| Pro | Phe | Ser | Ser | Lys | Glu | Val | Gln | Ser | Ile | Leu | Leu | Glu | Pro His His | |
| 1775 | | | | 1780 | | | | 1785 | | | | | | |

| CTA | AAA | AAT | CTC | CAA | CCT | ACT | GAA | TAT | AAA | ACT | ATT | CAA | GGC ATT CTG | 5604 |
| Leu | Lys | Asn | Leu | Gln | Pro | Thr | Glu | Tyr | Lys | Thr | Ile | Gln | Gly Ile Leu | |
| 1790 | | | | 1795 | | | | 1800 | | | | 1805 | | |

| CAC | GAA | ATT | GGT | GGA | ACT | GGC | ATA | TTT | GTT | TTT | CTC | TTT | GCC AGG GTT | 5652 |
| His | Glu | Ile | Gly | Gly | Thr | Gly | Ile | Phe | Val | Phe | Leu | Phe | Ala Arg Val | |
| | | | 1810 | | | | 1815 | | | | 1820 | | | |

| GTT | GAA | CTC | AGT | AGC | TGT | GAA | GAA | ACT | CAA | GCA | TTA | GCA | CTG CGA GTT | 5700 |
| Val | Glu | Leu | Ser | Ser | Cys | Glu | Glu | Thr | Gln | Ala | Leu | Ala | Leu Arg Val | |
| | | | 1825 | | | | 1830 | | | | 1835 | | | |

| ATA | CTC | TCA | TTA | ATT | AAA | TAC | AAC | CAA | CAA | AGA | GTA | CAT | GAA TTA GAA | 5748 |
| Ile | Leu | Ser | Leu | Ile | Lys | Tyr | Asn | Gln | Gln | Arg | Val | His | Glu Leu Glu | |
| | | 1840 | | | | 1845 | | | | 1850 | | | | |

| AAT | TGT | AAT | GGA | CTT | TCT | ATG | ATT | CAT | CAG | GTG | TTG | ATC | AAA CAA AAA | 5796 |
| Asn | Cys | Asn | Gly | Leu | Ser | Met | Ile | His | Gln | Val | Leu | Ile | Lys Gln Lys | |
| | 1855 | | | | 1860 | | | | 1865 | | | | | |

| TGC | ATT | GTT | GGG | TTT | TAC | ATT | TTG | AAG | ACC | CTT | CTT | GAA | GGA TGC TGT | 5844 |
| Cys | Ile | Val | Gly | Phe | Tyr | Ile | Leu | Lys | Thr | Leu | Leu | Glu | Gly Cys Cys | |
| 1870 | | | | 1875 | | | | 1880 | | | | 1885 | | |

| GGT | GAA | GAT | ATT | ATT | TAT | ATG | AAT | GAG | AAT | GGA | GAG | TTT | AAG TTG GAT | 5892 |
| Gly | Glu | Asp | Ile | Ile | Tyr | Met | Asn | Glu | Asn | Gly | Glu | Phe | Lys Leu Asp | |

-continued

```
                    1890                1895                 1900
GTA GAC TCT AAT GCT ATA ATC CAA GAT GTT AAG CTG TTA GAG GAA CTA        5940
Val Asp Ser Asn Ala Ile Ile Gln Asp Val Lys Leu Leu Glu Glu Leu
            1905                1910                1915

TTG CTT GAC TGG AAG ATA TGG AGT AAA GCA GAG CAA GGT GTT TGG GAA        5988
Leu Leu Asp Trp Lys Ile Trp Ser Lys Ala Glu Gln Gly Val Trp Glu
        1920                1925                1930

ACT TTG CTA GCA GCT CTA GAA GTC CTC ATC AGA GCA GAT CAC CAC CAG        6036
Thr Leu Leu Ala Ala Leu Glu Val Leu Ile Arg Ala Asp His His Gln
    1935                1940                1945

CAG ATG TTT AAT ATT AAG CAG TTA TTG AAA GCT CAA GTG GTT CAT CAC        6084
Gln Met Phe Asn Ile Lys Gln Leu Leu Lys Ala Gln Val Val His His
1950                1955                1960                1965

TTT CTA CTG ACT TGT CAG GTT TTG CAG GAA TAC AAA GAG GGG CAA CTC        6132
Phe Leu Leu Thr Cys Gln Val Leu Gln Glu Tyr Lys Glu Gly Gln Leu
                1970                1975                1980

ACA CCC ATG CCC CGA GAG GTT TGT AGA TCA TTT GTG AAA ATT ATA GCA        6180
Thr Pro Met Pro Arg Glu Val Cys Arg Ser Phe Val Lys Ile Ile Ala
            1985                1990                1995

GAA GTC CTT GGA TCT CCT CCA GAT TTG GAA TTA TTG ACA ATT ATC TTC        6228
Glu Val Leu Gly Ser Pro Pro Asp Leu Glu Leu Leu Thr Ile Ile Phe
        2000                2005                2010

AAT TTC CTT TTA GCA GTT CAC CCT CCT ACT AAT ACT TAC GTT TGT CAC        6276
Asn Phe Leu Leu Ala Val His Pro Pro Thr Asn Thr Tyr Val Cys His
    2015                2020                2025

AAT CCC ACG AAC TTC TAC TTT TCT TTG CAC ATA GAT GGC AAG ATC TTT        6324
Asn Pro Thr Asn Phe Tyr Phe Ser Leu His Ile Asp Gly Lys Ile Phe
2030                2035                2040                2045

CAG GAG AAA GTG CGG TCA ATC ATG TAC CTG AGG CAT TCC AGC AGT GGA        6372
Gln Glu Lys Val Arg Ser Ile Met Tyr Leu Arg His Ser Ser Ser Gly
                2050                2055                2060

GGA AGG TCC CTT ATG AGC CCT GGA TTT ATG GTA ATA AGC CCA TCT GGT        6420
Gly Arg Ser Leu Met Ser Pro Gly Phe Met Val Ile Ser Pro Ser Gly
            2065                2070                2075

TTT ACT GCT TCA CCA TAT GAA GGA GAG AAT TCC TCT AAT ATT ATT CCA        6468
Phe Thr Ala Ser Pro Tyr Glu Gly Glu Asn Ser Ser Asn Ile Ile Pro
        2080                2085                2090

CAA CAG ATG GCC GCC CAT ATG CTG CGT TCT AGA AGC CTA CCA GCA TTC        6516
Gln Gln Met Ala Ala His Met Leu Arg Ser Arg Ser Leu Pro Ala Phe
    2095                2100                2105

CCT ACT TCT TCA CTA CTA ACG CAA TCA CAA AAA CTG ACT GGA AGT TTG        6564
Pro Thr Ser Ser Leu Leu Thr Gln Ser Gln Lys Leu Thr Gly Ser Leu
2110                2115                2120                2125

GGT TGT AGT ATC GAC AGG TTA CAA AAT ATT GCA GAT ACT TAT GTT GCC        6612
Gly Cys Ser Ile Asp Arg Leu Gln Asn Ile Ala Asp Thr Tyr Val Ala
                2130                2135                2140

ACC CAA TCA AAG AAA CAA AAT TCT TTG GGG AGT TCC GAC ACA CTG AAA        6660
Thr Gln Ser Lys Lys Gln Asn Ser Leu Gly Ser Ser Asp Thr Leu Lys
            2145                2150                2155

AAA GGC AAA GAG GAC GCA TTC ATC AGT AGC TGT GAG TCT GCA AAA ACT        6708
Lys Gly Lys Glu Asp Ala Phe Ile Ser Ser Cys Glu Ser Ala Lys Thr
        2160                2165                2170

GTT TGT GAA ATG GAA GCT GTC CTC TCA GCC CAG GTC TCT GTC AGT GAT        6756
Val Cys Glu Met Glu Ala Val Leu Ser Ala Gln Val Ser Val Ser Asp
    2175                2180                2185

GTC CCA AAG GGA GTG CTG GGA TTT CCA GTG GTC AAA GCA GAT CAT AAA        6804
Val Pro Lys Gly Val Leu Gly Phe Pro Val Val Lys Ala Asp His Lys
2190                2195                2200                2205

CAG TTG GGA GCA GAA CCC AGG TCA GAA GAT GAC AGT CCT GGG GAT GAG        6852
Gln Leu Gly Ala Glu Pro Arg Ser Glu Asp Asp Ser Pro Gly Asp Glu
```

```
                     2210              2215              2220
TCC TGC CCA CGC CGA CCT GAT TAC CTA AAG GGA TTG GCC TCC TTC CAG       6900
Ser Cys Pro Arg Arg Pro Asp Tyr Leu Lys Gly Leu Ala Ser Phe Gln
            2225              2230              2235

CGA AGC CAC AGC ACT ATT GCA AGC CTT GGG CTA GCT TTT CCT TCA CAG       6948
Arg Ser His Ser Thr Ile Ala Ser Leu Gly Leu Ala Phe Pro Ser Gln
            2240              2245              2250

AAC GGA TCT GCA GCT GTT GGC CGT TGG CCA AGT CTT GTT GAT AGA AAC       6996
Asn Gly Ser Ala Ala Val Gly Arg Trp Pro Ser Leu Val Asp Arg Asn
            2255              2260              2265

ACT GAT GAT TGG GAA AAC TTT GCC TAT TCT CTT GGT TAT GAG CCA AAT       7044
Thr Asp Asp Trp Glu Asn Phe Ala Tyr Ser Leu Gly Tyr Glu Pro Asn
2270              2275              2280              2285

TAC AAC CGA ACT GCA AGT GCT CAC AGT GTA ACT GAA GAC TGT TTG GTA       7092
Tyr Asn Arg Thr Ala Ser Ala His Ser Val Thr Glu Asp Cys Leu Val
            2290              2295              2300

CCT ATA TGC TGT GGA TTA TAT GAA CTC CTA AGT GGG GTT CTT CTT ATC       7140
Pro Ile Cys Cys Gly Leu Tyr Glu Leu Leu Ser Gly Val Leu Leu Ile
            2305              2310              2315

CTG CCT GAT GTT TTG CTT GAA GAT GTG ATG GAC AAG CTT ATT CAA GCA       7188
Leu Pro Asp Val Leu Leu Glu Asp Val Met Asp Lys Leu Ile Gln Ala
            2320              2325              2330

GAT ACA CTT TTG GTC CTC GTT AAC CAC CCA TCA CCA GCT ATA CAA CAA       7236
Asp Thr Leu Leu Val Leu Val Asn His Pro Ser Pro Ala Ile Gln Gln
            2335              2340              2345

GGT GTT ATT AAA CTA TTA GAT GCA TAT TTT GCT AGA GCA TCT AAG GAA       7284
Gly Val Ile Lys Leu Leu Asp Ala Tyr Phe Ala Arg Ala Ser Lys Glu
2350              2355              2360              2365

CAA AAA GAT AAA TTT CTG AAG AAT CGT GGA TTT TCC TTG CTA GCC AAC       7332
Gln Lys Asp Lys Phe Leu Lys Asn Arg Gly Phe Ser Leu Leu Ala Asn
            2370              2375              2380

CAG TTG TAT CTT CAT CGA GGA ACT CAA GAA TTG TTA GAA TGC TTC ATC       7380
Gln Leu Tyr Leu His Arg Gly Thr Gln Glu Leu Leu Glu Cys Phe Ile
            2385              2390              2395

GAA ATG TTC TTT GGT CGA CAT ATT GGC CTT GAT GAA GAA TTT GAT CTG       7428
Glu Met Phe Phe Gly Arg His Ile Gly Leu Asp Glu Glu Phe Asp Leu
            2400              2405              2410

GAA GAT GTG AGA AAC ATG GGA TTG TTT CAG AAG TGG TCT GTC ATT CCT       7476
Glu Asp Val Arg Asn Met Gly Leu Phe Gln Lys Trp Ser Val Ile Pro
            2415              2420              2425

ATT CTG GGA CTA ATA GAG ACC TCT CTA TAT GAC AAC ATA CTC TTG CAT       7524
Ile Leu Gly Leu Ile Glu Thr Ser Leu Tyr Asp Asn Ile Leu Leu His
2430              2435              2440              2445

AAT GCT CTT TTA CTT CTT CTC CAA ATT TTA AAT TCT TGT TCT AAG GTA       7572
Asn Ala Leu Leu Leu Leu Leu Gln Ile Leu Asn Ser Cys Ser Lys Val
            2450              2455              2460

GCA GAT ATG TTG CTG GAT AAT GGT CTA CTC TAT GTG TTA TGT AAT ACA       7620
Ala Asp Met Leu Leu Asp Asn Gly Leu Leu Tyr Val Leu Cys Asn Thr
            2465              2470              2475

GTA GCA GCC CTG AAT GGA TTA GAA AAG AAC ATT CCC ATG AGT GAA TAT       7668
Val Ala Ala Leu Asn Gly Leu Glu Lys Asn Ile Pro Met Ser Glu Tyr
            2480              2485              2490

AAA TTG CTT GCT TGT GAT ATA CAG CAA CTT TTC ATA GCA GTT ACA ATT       7716
Lys Leu Leu Ala Cys Asp Ile Gln Gln Leu Phe Ile Ala Val Thr Ile
            2495              2500              2505

CAT GCT TGC AGT TCC TCA GGC TCA CAA TAT TTT AGG GTT ATT GAA GAC       7764
His Ala Cys Ser Ser Ser Gly Ser Gln Tyr Phe Arg Val Ile Glu Asp
2510              2515              2520              2525

CTT ATT GTA ATG CTT GGA TAT CTT CAA AAT AGC AAA AAC AAG AGG ACA       7812
Leu Ile Val Met Leu Gly Tyr Leu Gln Asn Ser Lys Asn Lys Arg Thr
```

-continued

|  |  |  |  |
|---|---|---|---|
| 2530 | 2535 | 2540 | |

| CAA AAT ATG GCT GTT GCA CTA CAG CTT AGA GTT CTC CAG GCT GCT ATG | 7860 |
| Gln Asn Met Ala Val Ala Leu Gln Leu Arg Val Leu Gln Ala Ala Met | |
| 2545 2550 2555 | |

| GAA TTT ATA AGG ACC ACC GCA AAT CAT GAC TCT GAA AAC CTC ACA GAT | 7908 |
| Glu Phe Ile Arg Thr Thr Ala Asn His Asp Ser Glu Asn Leu Thr Asp | |
| 2560 2565 2570 | |

| TCA CTC CAG TCA CCT TCT GCT CCC CAT CAT GCA GTA GTT CAA AAG CGG | 7956 |
| Ser Leu Gln Ser Pro Ser Ala Pro His His Ala Val Val Gln Lys Arg | |
| 2575 2580 2585 | |

| AAA AGC ATT GCT GGT CCT CGA AAA TTT CCC CTT GCT CAA ACT GAA TCG | 8004 |
| Lys Ser Ile Ala Gly Pro Arg Lys Phe Pro Leu Ala Gln Thr Glu Ser | |
| 2590 2595 2600 2605 | |

| CTT CTG ATG AAA ATG CGT TCA GTG GCA AAT GAT GAG CTT CAT GTG ATG | 8052 |
| Leu Leu Met Lys Met Arg Ser Val Ala Asn Asp Glu Leu His Val Met | |
| 2610 2615 2620 | |

| ATG CAA CGG AGA ATG AGC CAA GAG AAC CCT AGC CAA GCA ACT GAA ACG | 8100 |
| Met Gln Arg Arg Met Ser Gln Glu Asn Pro Ser Gln Ala Thr Glu Thr | |
| 2625 2630 2635 | |

| GAA CTT GCG CAG AGA CTA CAG AGG CTC ACT GTT TTA GCA GTC AAC AGG | 8148 |
| Glu Leu Ala Gln Arg Leu Gln Arg Leu Thr Val Leu Ala Val Asn Arg | |
| 2640 2645 2650 | |

| ATT ATT TAT CAA GAA TTT AAT TCA GAC ATT ATT GAC ATT TTG AGA ACT | 8196 |
| Ile Ile Tyr Gln Glu Phe Asn Ser Asp Ile Ile Asp Ile Leu Arg Thr | |
| 2655 2660 2665 | |

| CCA GAA AAT GTA ACT CAA AGC AAG ACC TCA GTT TTC CAG ACC GAA ATT | 8244 |
| Pro Glu Asn Val Thr Gln Ser Lys Thr Ser Val Phe Gln Thr Glu Ile | |
| 2670 2675 2680 2685 | |

| TCT GAG GAA AAT ATT CAT CAT GAA CAG TCT TCT GTT TTC AAT CCA TTT | 8292 |
| Ser Glu Glu Asn Ile His His Glu Gln Ser Ser Val Phe Asn Pro Phe | |
| 2690 2695 2700 | |

| CAG AAA GAA ATT TTT ACA TAT CTG GTA GAA GGA TTC AAA GTA TCT ATT | 8340 |
| Gln Lys Glu Ile Phe Thr Tyr Leu Val Glu Gly Phe Lys Val Ser Ile | |
| 2705 2710 2715 | |

| GGT TCA AGT AAA GCC AGT GGT TCC AAG CAG CAA TGG ACT AAA ATT CTG | 8388 |
| Gly Ser Ser Lys Ala Ser Gly Ser Lys Gln Gln Trp Thr Lys Ile Leu | |
| 2720 2725 2730 | |

| TGG TCT TGT AAG GAG ACC TTC CGA ATG CAG CTT GGG AGA CTA CTA GTG | 8436 |
| Trp Ser Cys Lys Glu Thr Phe Arg Met Gln Leu Gly Arg Leu Leu Val | |
| 2735 2740 2745 | |

| CAT ATT TTG TCG CCA GCC CAC GCT GCA CAA GAG AGA AAG CAA ATT TTT | 8484 |
| His Ile Leu Ser Pro Ala His Ala Ala Gln Glu Arg Lys Gln Ile Phe | |
| 2750 2755 2760 2765 | |

| GAA ATA GTT CAT GAA CCA AAT CAT CAG GAA ATA CTA CGA GAC TGT CTC | 8532 |
| Glu Ile Val His Glu Pro Asn His Gln Glu Ile Leu Arg Asp Cys Leu | |
| 2770 2775 2780 | |

| AGC CCA TCC CTA CAA CAT GGA GCC AAG TTA GTT TTG TAT TTG TCA GAG | 8580 |
| Ser Pro Ser Leu Gln His Gly Ala Lys Leu Val Leu Tyr Leu Ser Glu | |
| 2785 2790 2795 | |

| TTG ATA CAT AAT CAC CAA GGT GAA TTG ACT GAA GAA GAG CTA GGC ACA | 8628 |
| Leu Ile His Asn His Gln Gly Glu Leu Thr Glu Glu Glu Leu Gly Thr | |
| 2800 2805 2810 | |

| GCA GAA CTG CTT ATG AAT GCT TTG AAG TTA TGT GGT CAC AAG TGC ATC | 8676 |
| Ala Glu Leu Leu Met Asn Ala Leu Lys Leu Cys Gly His Lys Cys Ile | |
| 2815 2820 2825 | |

| CCT CCC AGT GCA TCA ACA AAA GCA GAC CTT ATT AAA ATG ATC AAA GAG | 8724 |
| Pro Pro Ser Ala Ser Thr Lys Ala Asp Leu Ile Lys Met Ile Lys Glu | |
| 2830 2835 2840 2845 | |

| GAA CAA AAG AAA TAT GAA ACT GAA GAA GGA GTG AAT AAA GCT GCT TGG | 8772 |
| Glu Gln Lys Lys Tyr Glu Thr Glu Glu Gly Val Asn Lys Ala Ala Trp | |

-continued

```
                2850            2855            2860
CAG AAA ACA GTT AAC AAT AAT CAA CAA AGT CTC TTT CAG CGT CTG GAT       8820
Gln Lys Thr Val Asn Asn Asn Gln Gln Ser Leu Phe Gln Arg Leu Asp
            2865            2870            2875

TCA AAA TCA AAG GAT ATA TCT AAA ATA GCT GCA GAT ATC ACC CAG GCA       8868
Ser Lys Ser Lys Asp Ile Ser Lys Ile Ala Ala Asp Ile Thr Gln Ala
        2880            2885            2890

GTG TCT CTC TCC CAA GGA AAT GAG AGA AAA AAG GTG ATC CAG CAT ATT       8916
Val Ser Leu Ser Gln Gly Asn Glu Arg Lys Lys Val Ile Gln His Ile
        2895            2900            2905

AGA GGA ATG TAT AAA GTA GAT TTG AGT GCC AGC AGA CAT TGG CAG GAA       8964
Arg Gly Met Tyr Lys Val Asp Leu Ser Ala Ser Arg His Trp Gln Glu
2910            2915            2920            2925

CTT ATT CAG CAG CTG ACA CAT GAT AGA GCA GTA TGG TAT GAC CCC ATC       9012
Leu Ile Gln Gln Leu Thr His Asp Arg Ala Val Trp Tyr Asp Pro Ile
            2930            2935            2940

TAC TAT CCA ACC TCA TGG CAG TTG GAT CCA ACA GAA GGG CCA AAT CGA       9060
Tyr Tyr Pro Thr Ser Trp Gln Leu Asp Pro Thr Glu Gly Pro Asn Arg
        2945            2950            2955

GAG AGG AGA CGT TTA CAG AGA TGT TAT TTA ACT ATT CCA AAT AAG TAT       9108
Glu Arg Arg Arg Leu Gln Arg Cys Tyr Leu Thr Ile Pro Asn Lys Tyr
        2960            2965            2970

CTC CTT AGG GAT AGA CAG AAA TCA GAA GAT GTT GTC AAA CCA CCA CTC       9156
Leu Leu Arg Asp Arg Gln Lys Ser Glu Asp Val Val Lys Pro Pro Leu
2975            2980            2985

TCT TAC CTG TTT GAA GAC AAA ACT CAT TCT TCT TTC TCT TCT ACT GTC       9204
Ser Tyr Leu Phe Glu Asp Lys Thr His Ser Ser Phe Ser Ser Thr Val
2990            2995            3000            3005

AAA GAC AAA GCT GCA AGT GAA TCT ATA AGA GTG AAT CGA AGA TGC ATC       9252
Lys Asp Lys Ala Ala Ser Glu Ser Ile Arg Val Asn Arg Arg Cys Ile
            3010            3015            3020

AGT GTT GCA CCA TCT AGA GAG ACA GCT GGT GAA TTG TTA CTA GGT AAA       9300
Ser Val Ala Pro Ser Arg Glu Thr Ala Gly Glu Leu Leu Leu Gly Lys
        3025            3030            3035

TGT GGA ATG TAT TTT GTG GAA GAT AAT GCT TCT GAT ACA GTT GAA AGT       9348
Cys Gly Met Tyr Phe Val Glu Asp Asn Ala Ser Asp Thr Val Glu Ser
        3040            3045            3050

TCG AGC CTT CAG GGA GAG TTG GAA CCA GCA TCA TTT TCC TGG ACA TAT       9396
Ser Ser Leu Gln Gly Glu Leu Glu Pro Ala Ser Phe Ser Trp Thr Tyr
        3055            3060            3065

GAA GAA ATT AAA GAA GTT CAC AAG CGT TGG TGG CAA TTG AGA GAT AAT       9444
Glu Glu Ile Lys Glu Val His Lys Arg Trp Trp Gln Leu Arg Asp Asn
3070            3075            3080            3085

GCT GTA GAA ATC TTT CTA ACA AAT GGC AGA ACA CTC CTG TTG GCA TTT       9492
Ala Val Glu Ile Phe Leu Thr Asn Gly Arg Thr Leu Leu Leu Ala Phe
            3090            3095            3100

GAT AAC ACC AAG GTT CGT GAT GAT GTA TAC CAC AAT ATA CTC ACA AAT       9540
Asp Asn Thr Lys Val Arg Asp Asp Val Tyr His Asn Ile Leu Thr Asn
        3105            3110            3115

AAC CTC CCT AAT CTT CTG GAA TAT GGT AAC ATC ACC GCT CTG ACA AAT       9588
Asn Leu Pro Asn Leu Leu Glu Tyr Gly Asn Ile Thr Ala Leu Thr Asn
        3120            3125            3130

TTA TGG TAT ACT GGG CAA ATT ACT AAT TTT GAA TAT TTG ACT CAC TTA       9636
Leu Trp Tyr Thr Gly Gln Ile Thr Asn Phe Glu Tyr Leu Thr His Leu
        3135            3140            3145

AAC AAA CAT GCT GGC CGA TCC TTC AAT GAT CTC ATG CAG TAT CCT GTG       9684
Asn Lys His Ala Gly Arg Ser Phe Asn Asp Leu Met Gln Tyr Pro Val
3150            3155            3160            3165

TTC CCA TTT ATA CTT GCT GAC TAC GTT AGT GAG ACA CTT GAC CTC AAT       9732
Phe Pro Phe Ile Leu Ala Asp Tyr Val Ser Glu Thr Leu Asp Leu Asn
```

```
                    3170                3175                3180
GAT CTG TTG ATA TAC AGA AAT CTC TCT AAA CCT ATA GCT GTT CAG TAT        9780
Asp Leu Leu Ile Tyr Arg Asn Leu Ser Lys Pro Ile Ala Val Gln Tyr
                3185                3190                3195

AAA GAA AAA GAA GAT CGT TAT GTG GAC ACA TAC AAG TAC TTG GAG GAA        9828
Lys Glu Lys Glu Asp Arg Tyr Val Asp Thr Tyr Lys Tyr Leu Glu Glu
            3200                3205                3210

GAG TAC CGC AAA GGA GCC AGA GAA GAT GAC CCC ATG CCT CCC GTG CAG        9876
Glu Tyr Arg Lys Gly Ala Arg Glu Asp Asp Pro Met Pro Pro Val Gln
        3215                3220                3225

CCC TAT CAC TAT GGC TCC CAC TAT TCC AAT AGC GGC ACT GTG CTT CAC        9924
Pro Tyr His Tyr Gly Ser His Tyr Ser Asn Ser Gly Thr Val Leu His
3230                3235                3240                3245

TTC CTG GTC AGG ATG CCT CCT TTC ACT AAA ATG TTT TTA GCC TAT CAA        9972
Phe Leu Val Arg Met Pro Pro Phe Thr Lys Met Phe Leu Ala Tyr Gln
            3250                3255                3260

GAT CAA AGT TTT GAC ATT CCA GAC AGA ACT TTT CAT TCT ACA AAT ACA       10020
Asp Gln Ser Phe Asp Ile Pro Asp Arg Thr Phe His Ser Thr Asn Thr
        3265                3270                3275

ACT TGG CGA CTC TCA TCT TTT GAA TCT ATG ACT GAT GTG AAA GAA CTT       10068
Thr Trp Arg Leu Ser Ser Phe Glu Ser Met Thr Asp Val Lys Glu Leu
    3280                3285                3290

ATC CCA GAG TTT TTC TAT CTT CCA GAG TTC CTA GTT AAC CGT GAA GGT       10116
Ile Pro Glu Phe Phe Tyr Leu Pro Glu Phe Leu Val Asn Arg Glu Gly
            3295                3300                3305

TTT GAT TTT GGT GTG CGT CAG AAT GGT GAA CGG GTT AAT CAC GTC AAC       10164
Phe Asp Phe Gly Val Arg Gln Asn Gly Glu Arg Val Asn His Val Asn
3310                3315                3320                3325

CTT CCC CCT TGG GCG CGT AAT GAT CCT CGT CTT TTT ATC CTC ATC CAT       10212
Leu Pro Pro Trp Ala Arg Asn Asp Pro Arg Leu Phe Ile Leu Ile His
            3330                3335                3340

CGG CAG GCT CTA GAG TCT GAC TAC GTG TCG CAG AAC ATC TGT CAG TGG       10260
Arg Gln Ala Leu Glu Ser Asp Tyr Val Ser Gln Asn Ile Cys Gln Trp
        3345                3350                3355

ATT GAC TTG GTG TTT GGG TAT AAG CAA AAG GGG AAG GCT TCT GTT CAA       10308
Ile Asp Leu Val Phe Gly Tyr Lys Gln Lys Gly Lys Ala Ser Val Gln
    3360                3365                3370

GCG ATC AAT GTT TTT CAT CCT GCT ACA TAT TTT GGA ATG GAT GTC TCT       10356
Ala Ile Asn Val Phe His Pro Ala Thr Tyr Phe Gly Met Asp Val Ser
3375                3380                3385

GCA GTT GAA GAT CCA GTT CAG AGA CGA GCG CTA GAA ACC ATG ATA AAA       10404
Ala Val Glu Asp Pro Val Gln Arg Arg Ala Leu Glu Thr Met Ile Lys
3390                3395                3400                3405

ACC TAC GGG CAG ACT CCC CGT CAG CTG TTC CAC ATG GCC CAT GTG AGC       10452
Thr Tyr Gly Gln Thr Pro Arg Gln Leu Phe His Met Ala His Val Ser
            3410                3415                3420

AGA CCT GGA GCC AAG CTC AAT ATT GAA GGA GAG CTT CCA GCT GCT GTG       10500
Arg Pro Gly Ala Lys Leu Asn Ile Glu Gly Glu Leu Pro Ala Ala Val
        3425                3430                3435

GGG TTG CTA GTG CAG TTT GCT TTC AGG GAG ACC CGA GAA CAG GTC AAA       10548
Gly Leu Leu Val Gln Phe Ala Phe Arg Glu Thr Arg Glu Gln Val Lys
    3440                3445                3450

GAA ATC ACC TAT CCG AGT CCT TTG TCA TGG ATA AAA GGC TTG AAA TGG       10596
Glu Ile Thr Tyr Pro Ser Pro Leu Ser Trp Ile Lys Gly Leu Lys Trp
3455                3460                3465

GGG GAA TAC GTG GGT TCC CCC AGT GCT CCA GTA CCT GTG GTC TGC TTC       10644
Gly Glu Tyr Val Gly Ser Pro Ser Ala Pro Val Pro Val Val Cys Phe
3470                3475                3480                3485

AGC CAG CCC CAC GGA GAA AGA TTT GGC TCT CTC CAG GCT CTG CCC ACC       10692
Ser Gln Pro His Gly Glu Arg Phe Gly Ser Leu Gln Ala Leu Pro Thr
```

-continued

| | | | | | | | | | | | | | | | |
|---|---|---|---|---|---|---|---|---|---|---|---|---|---|---|---|
| | | | 3490 | | | | 3495 | | | | 3500 | | | | |
| AGA | GCA | ATC | TGT | GGT | TTG | TCA | CGG | AAT | TTC | TGT | CTT | GTG | ATG | ACA | TAT | 10740 |
| Arg | Ala | Ile | Cys | Gly | Leu | Ser | Arg | Asn | Phe | Cys | Leu | Val | Met | Thr | Tyr |
| | | | 3505 | | | | 3510 | | | | 3515 | | | | |

```
AGA GCA ATC TGT GGT TTG TCA CGG AAT TTC TGT CTT GTG ATG ACA TAT    10740
Arg Ala Ile Cys Gly Leu Ser Arg Asn Phe Cys Leu Val Met Thr Tyr
            3505            3510            3515

AGC AAG GAA CAA GGT GTG AGA AGC ATG AAC AGT ACG GAC ATT CAG TGG    10788
Ser Lys Glu Gln Gly Val Arg Ser Met Asn Ser Thr Asp Ile Gln Trp
            3520            3525            3530

TCA GCC ATC CTG AGC TGG GGA TAT GCT GAT AAT ATT TTA AGG TTG AAG    10836
Ser Ala Ile Leu Ser Trp Gly Tyr Ala Asp Asn Ile Leu Arg Leu Lys
            3535            3540            3545

AGT AAA CAA AGT GAG CCT CCA GTA AAC TTT ATT CAA AGT TCA CAA CAG    10884
Ser Lys Gln Ser Glu Pro Pro Val Asn Phe Ile Gln Ser Ser Gln Gln
3550            3555            3560            3565

TAC CAG GTG ACT AGT TGT GCT TGG GTG CCT GAC AGT TGC CAG CTG TTT    10932
Tyr Gln Val Thr Ser Cys Ala Trp Val Pro Asp Ser Cys Gln Leu Phe
            3570            3575            3580

ACT GGA AGC AAA TGC GGT GTC ATC ACA GCC TAC ACA AAC AGA TTT ACA    10980
Thr Gly Ser Lys Cys Gly Val Ile Thr Ala Tyr Thr Asn Arg Phe Thr
            3585            3590            3595

AGC AGC ACG CCA TCA GAA ATA GAA ATG GAG ACT CAA ATA CAT CTC TAT    11028
Ser Ser Thr Pro Ser Glu Ile Glu Met Glu Thr Gln Ile His Leu Tyr
            3600            3605            3610

GGT CAC ACA GAA GAG ATA ACC AGC TTA TTT GTT TGC AAA CCA TAC AGT    11076
Gly His Thr Glu Glu Ile Thr Ser Leu Phe Val Cys Lys Pro Tyr Ser
            3615            3620            3625

ATA CTG ATA AGT GTG AGC AGA GAC GGA ACC TGC ATC ATA TGG GAT TTA    11124
Ile Leu Ile Ser Val Ser Arg Asp Gly Thr Cys Ile Ile Trp Asp Leu
3630            3635            3640            3645

AAC AGG TTA TGC TAT GTA CAA AGT CTG GCG GGA CAC AAA AGC CCT GTC    11172
Asn Arg Leu Cys Tyr Val Gln Ser Leu Ala Gly His Lys Ser Pro Val
            3650            3655            3660

ACA GCT GTC TCT GCC AGT GAA ACC TCA GGT GAT ATT GCT ACT GTG TGT    11220
Thr Ala Val Ser Ala Ser Glu Thr Ser Gly Asp Ile Ala Thr Val Cys
            3665            3670            3675

GAT TCA GCT GGC GGA GGC AGT GAC CTC AGA CTC TGG ACG GTG AAC GGG    11268
Asp Ser Ala Gly Gly Gly Ser Asp Leu Arg Leu Trp Thr Val Asn Gly
            3680            3685            3690

GAT CTC GTT GGA CAT GTC CAC TGC AGG GAG ATC ATC TGT TCC GTG GCT    11316
Asp Leu Val Gly His Val His Cys Arg Glu Ile Ile Cys Ser Val Ala
            3695            3700            3705

TTC TCC AAC CAG CCT GAG GGA GTA TCT ATC AAT GTA ATC GCT GGG GGA    11364
Phe Ser Asn Gln Pro Glu Gly Val Ser Ile Asn Val Ile Ala Gly Gly
3710            3715            3720            3725

TTA GAA AAT GGA ATT GTT AGG TTA TGG AGC ACA TGG GAC TTA AAG CCT    11412
Leu Glu Asn Gly Ile Val Arg Leu Trp Ser Thr Trp Asp Leu Lys Pro
            3730            3735            3740

GTG AGA GAA ATT ACA TTT CCC AAA TCA AAT AAG CCC ATC ATC AGC CTT    11460
Val Arg Glu Ile Thr Phe Pro Lys Ser Asn Lys Pro Ile Ile Ser Leu
            3745            3750            3755

ACA TTT TCT TGT GAT GGC CAC CAT TTG TAC ACA GCA AAC AGT GAT GGG    11508
Thr Phe Ser Cys Asp Gly His His Leu Tyr Thr Ala Asn Ser Asp Gly
            3760            3765            3770

ACC GTG ATT GCC TGG TGT CGG AAG GAC CAG CAC CGC TTG AAA CAG CCA    11556
Thr Val Ile Ala Trp Cys Arg Lys Asp Gln His Arg Leu Lys Gln Pro
            3775            3780            3785

ATG TTC TAT TCC TTC CTT AGC AGC TAT GCA GCC GGG TGAATGCGAA         11602
Met Phe Tyr Ser Phe Leu Ser Ser Tyr Ala Ala Gly
3790            3795            3800

TGAACTTCAT GTTCTCCAAA GCACTTTAAC TCCAAACTAG ATTTGTTGAC TTCACCAGTT  11662
```

-continued

```
TTAGGAGGTT GAACCTAAAG AAATGGATGA CTGGACAAAC CATCCAAATA ATGATAAAGT    11722

CTATTCATCT GCACAAAATT CTGAAGAGTC ACATGATCCT AAGAGGAAAG TTCTGTTCTA    11782

TTTTAGTGAT AATCTGGAAG ATTGTGTCAA TATGCACTAG CCAACAAGTT TTAAGCCTCG    11842

CATGGTACAT TAAAATGATA TTCTTAAAAT TTTTTCCCAC CAAGGTATTC CAAAGAAAAT    11902

ATTAAGGTCT CCCCTTTTTC TATGATTCCA AAAGGACCAG TAGAATTTAA ATTGGTTGGT    11962

TGATNGTTTA TATAAAACAC ACTAAAATTA TATTTTAAAA GTTTANTGCCN TGAAATACT    12022

CCTCCCACCA CACACACATG CTCCAAAAGA GGAAAGAAAA AAAGATAATTT TTAGGACTT    12082

GATAATTGCT TTCTTTGAGA AGCAAATTAT TCAGTAGGTG CCTCTGTACCA AATATTTTA    12142

TGGAATATCT AAATACTAAA ATAAACTATG AATGAATCTC AAAATTAGGCA GTTTTTGCC    12202

TGCTTTCTTA GCTCAAAGGA GAACCAGAAT TTTTTTGACA GCCACAAACA AGAATACAGG    12262

AGTTATCTTG GATTTCAGAC ACATTCTGTT TCTTCATAAA AATTTTACTT AAAATCTGTA    12322

ACGCTAGATA TTGACTATCC TTAGTTGAGT CACTGAGGTT TAAACACAAT GGTAAGTCTT    12382

AAAGTCTGCT ATTTACAGAG CATTGAATCT GTACCAATTT GCAATAGAAA GCCTTCAGTA    12442

TGCAAGAAGT TTGCATGGGT ATTAAGAACA CAGCCTAAAT AAGGCATTTG ATCTAATCTG    12502

CAGGAAGAAT TTTCTTCCCC AAAACAGAAT TATAAAAGCT TACTTAAAAC AGGAGGCAGA    12562

ATAATTCTTT TAGGAAACCA TTTCATTCTG TTTCTACTAA CCTATACCAT CTGA          12616
```

(2) INFORMATION FOR SEQ ID NO:10:

(i) SEQUENCE CHARACTERISTICS:
        (A) LENGTH: 3801 amino acids
        (B) TYPE: amino acid
        (D) TOPOLOGY: unknown (ii) MOLECULE TYPE: protein (xi) SEQUENCE DESCRIPTION: SEQ ID NO:10:

```
Met Ser Thr Asp Ser Asn Ser Leu Ala Arg Glu Phe Leu Thr Asp Val
  1               5                  10                  15

Asn Arg Leu Cys Asn Ala Val Val Gln Arg Val Glu Ala Arg Glu Glu
             20                  25                  30

Glu Glu Glu Glu Thr His Met Ala Thr Leu Gly Gln Tyr Leu Val His
         35                  40                  45

Gly Arg Gly Phe Leu Leu Leu Thr Lys Leu Asn Ser Ile Ile Asp Gln
     50                  55                  60

Ala Leu Thr Cys Arg Glu Glu Leu Leu Thr Leu Leu Leu Ser Leu Leu
 65                  70                  75                  80

Pro Leu Val Trp Lys Ile Pro Val Gln Glu Glu Lys Ala Thr Asp Phe
                 85                  90                  95

Asn Leu Pro Leu Ser Ala Asp Ile Ile Leu Thr Lys Glu Lys Asn Ser
            100                 105                 110

Ser Ser Gln Arg Ser Thr Gln Glu Lys Leu His Leu Glu Gly Ser Ala
        115                 120                 125

Leu Ser Ser Gln Val Ser Ala Lys Val Asn Val Phe Arg Lys Ser Arg
    130                 135                 140

Arg Gln Arg Lys Ile Thr His Arg Tyr Ser Val Arg Asp Ala Arg Lys
145                 150                 155                 160

Thr Gln Leu Ser Thr Ser Asp Ser Glu Ala Asn Ser Asp Glu Lys Gly
                165                 170                 175

Ile Ala Met Asn Lys His Arg Arg Pro His Leu Leu His Phe Leu
            180                 185                 190
```

```
Thr Ser Phe Pro Lys Gln Asp His Pro Lys Ala Lys Leu Asp Arg Leu
        195                 200                 205

Ala Thr Lys Glu Gln Thr Pro Pro Asp Ala Met Ala Leu Glu Asn Ser
210                 215                 220

Arg Glu Ile Ile Pro Arg Gln Gly Ser Asn Thr Asp Ile Leu Ser Glu
225                 230                 235                 240

Pro Ala Ala Leu Ser Val Ile Ser Asn Met Asn Asn Ser Pro Phe Asp
                245                 250                 255

Leu Cys His Val Leu Leu Ser Leu Leu Glu Lys Val Cys Lys Phe Asp
            260                 265                 270

Val Thr Leu Asn His Asn Ser Pro Leu Ala Ala Ser Val Val Pro Thr
        275                 280                 285

Leu Thr Glu Phe Leu Ala Gly Phe Gly Asp Cys Cys Ser Leu Ser Asp
    290                 295                 300

Asn Leu Glu Ser Arg Val Val Ser Ala Gly Trp Thr Glu Glu Pro Val
305                 310                 315                 320

Ala Leu Ile Gln Arg Met Leu Phe Arg Thr Val Leu His Leu Leu Ser
                325                 330                 335

Val Asp Val Ser Thr Ala Glu Met Met Pro Glu Asn Leu Arg Lys Asn
            340                 345                 350

Leu Thr Glu Leu Leu Arg Ala Ala Leu Lys Ile Arg Ile Cys Leu Glu
        355                 360                 365

Lys Gln Pro Asp Pro Phe Ala Pro Arg Gln Lys Lys Thr Leu Gln Glu
    370                 375                 380

Val Gln Glu Asp Phe Val Phe Ser Lys Tyr Arg His Arg Ala Leu Leu
385                 390                 395                 400

Leu Pro Glu Leu Leu Glu Gly Val Leu Gln Ile Leu Ile Cys Cys Leu
                405                 410                 415

Gln Ser Ala Ala Ser Asn Pro Phe Tyr Phe Ser Gln Ala Met Asp Leu
            420                 425                 430

Val Gln Glu Phe Ile Gln His His Gly Phe Asn Leu Phe Glu Thr Ala
        435                 440                 445

Val Leu Gln Met Glu Trp Leu Val Leu Arg Asp Gly Val Pro Pro Glu
    450                 455                 460

Ala Ser Glu His Leu Lys Ala Leu Ile Asn Ser Val Met Lys Ile Met
465                 470                 475                 480

Ser Thr Val Lys Lys Val Lys Ser Glu Gln Leu His His Ser Met Cys
                485                 490                 495

Thr Arg Lys Arg His Arg Arg Cys Glu Tyr Ser His Phe Met His His
            500                 505                 510

His Arg Asp Leu Ser Gly Leu Leu Val Ser Ala Phe Lys Asn Gln Val
        515                 520                 525

Ser Lys Asn Pro Phe Glu Glu Thr Ala Asp Gly Asp Val Tyr Tyr Pro
    530                 535                 540

Glu Arg Cys Cys Cys Ile Ala Val Cys Ala His Gln Cys Leu Arg Leu
545                 550                 555                 560

Leu Gln Gln Ala Ser Leu Ser Ser Thr Cys Val Gln Ile Leu Ser Gly
                565                 570                 575

Val His Asn Ile Gly Ile Cys Cys Met Asp Pro Lys Ser Val Ile
            580                 585                 590

Ile Pro Leu Leu His Ala Phe Lys Leu Pro Ala Leu Lys Asn Phe Gln
        595                 600                 605

Gln His Ile Leu Asn Ile Leu Asn Lys Leu Ile Leu Asp Gln Leu Gly
    610                 615                 620
```

```
Gly Ala Glu Ile Ser Pro Lys Ile Lys Lys Ala Ala Cys Asn Ile Cys
625                 630                 635                 640

Thr Val Asp Ser Asp Gln Leu Ala Gln Leu Glu Glu Thr Leu Gln Gly
                645                 650                 655

Asn Leu Cys Asp Ala Glu Leu Ser Ser Ser Leu Ser Ser Pro Ser Tyr
                660                 665                 670

Arg Phe Gln Gly Ile Leu Pro Ser Ser Gly Ser Glu Asp Leu Leu Trp
                675                 680                 685

Lys Trp Asp Ala Leu Lys Ala Tyr Gln Asn Phe Val Phe Glu Glu Asp
690                 695                 700

Arg Leu His Ser Ile Gln Ile Ala Asn His Ile Cys Asn Leu Ile Gln
705                 710                 715                 720

Lys Gly Asn Ile Val Val Gln Trp Lys Leu Tyr Asn Tyr Ile Phe Asn
                725                 730                 735

Pro Val Leu Gln Arg Gly Val Glu Leu Ala His His Cys Gln His Leu
                740                 745                 750

Ser Val Thr Ser Ala Gln Ser His Val Cys Ser His His Asn Gln Cys
                755                 760                 765

Leu Pro Gln Asp Val Leu Gln Ile Tyr Val Lys Thr Leu Pro Ile Leu
770                 775                 780

Leu Lys Ser Arg Val Ile Arg Asp Leu Phe Leu Ser Cys Asn Gly Val
785                 790                 795                 800

Ser Gln Ile Ile Glu Leu Asn Cys Leu Asn Gly Ile Arg Ser His Ser
                805                 810                 815

Leu Lys Ala Phe Glu Thr Leu Ile Ile Ser Leu Gly Glu Gln Gln Lys
                820                 825                 830

Asp Ala Ser Val Pro Asp Ile Asp Gly Ile Asp Ile Glu Gln Lys Glu
                835                 840                 845

Leu Ser Ser Val His Val Gly Thr Ser Phe His His Gln Gln Ala Tyr
850                 855                 860

Ser Asp Ser Pro Gln Ser Leu Ser Lys Phe Tyr Ala Gly Leu Lys Glu
865                 870                 875                 880

Ala Tyr Pro Lys Arg Arg Lys Thr Val Asn Gln Asp Val His Ile Asn
                885                 890                 895

Thr Ile Asn Leu Phe Leu Cys Val Ala Phe Leu Cys Val Ser Lys Glu
                900                 905                 910

Ala Glu Ser Asp Arg Glu Ser Ala Asn Asp Ser Glu Asp Thr Ser Gly
                915                 920                 925

Tyr Asp Ser Thr Ala Ser Glu Pro Leu Ser His Met Leu Pro Cys Ile
930                 935                 940

Ser Leu Glu Ser Leu Val Leu Pro Ser Pro Glu His Met His Gln Ala
945                 950                 955                 960

Ala Asp Ile Trp Ser Met Cys Arg Trp Ile Tyr Met Leu Ser Ser Val
                965                 970                 975

Phe Gln Lys Gln Phe Tyr Arg Leu Gly Gly Phe Arg Val Cys His Lys
                980                 985                 990

Leu Ile Phe Met Ile Ile Gln Lys Leu Phe Arg Ser His Lys Glu Glu
                995                 1000                1005

Gln Gly Lys Lys Glu Gly Asp Thr Ser Val Asn Glu Asn Gln Asp Leu
                1010                1015                1020

Asn Arg Ile Ser Gln Pro Lys Arg Thr Met Lys Glu Asp Leu Leu Ser
1025                1030                1035                1040

Leu Ala Ile Lys Ser Asp Pro Ile Pro Ser Glu Leu Gly Ser Leu Lys
```

```
                    1045                1050                1055
Lys Ser Ala Asp Ser Leu Gly Lys Leu Glu Leu Gln His Ile Ser Ser
                1060                1065                1070

Ile Asn Val Glu Glu Val Ser Ala Thr Glu Ala Ala Pro Glu Glu Ala
            1075                1080                1085

Lys Leu Phe Thr Ser Gln Glu Ser Glu Thr Ser Leu Gln Ser Ile Arg
        1090                1095                1100

Leu Leu Glu Ala Leu Leu Ala Ile Cys Leu His Gly Ala Arg Thr Ser
1105                1110                1115                1120

Gln Gln Lys Met Glu Leu Glu Leu Pro Asn Gln Asn Leu Ser Val Glu
                1125                1130                1135

Ser Ile Leu Phe Glu Met Arg Asp His Leu Ser Gln Ser Lys Val Ile
            1140                1145                1150

Glu Thr Gln Leu Ala Lys Pro Leu Phe Asp Ala Leu Leu Arg Val Ala
        1155                1160                1165

Leu Gly Asn Tyr Ser Ala Asp Phe Glu His Asn Asp Ala Met Thr Glu
1170                1175                1180

Lys Ser His Gln Ser Ala Glu Glu Leu Ser Ser Gln Pro Gly Asp Phe
1185                1190                1195                1200

Ser Glu Glu Ala Glu Asp Ser Gln Cys Cys Ser Phe Lys Leu Leu Val
            1205                1210                1215

Glu Glu Glu Gly Tyr Glu Ala Asp Ser Glu Ser Asn Pro Glu Asp Gly
        1220                1225                1230

Glu Thr Gln Asp Asp Gly Val Asp Leu Lys Ser Glu Thr Glu Gly Phe
    1235                1240                1245

Ser Ala Ser Ser Ser Pro Asn Asp Leu Leu Glu Asn Leu Thr Gln Gly
1250                1255                1260

Glu Ile Ile Tyr Pro Glu Ile Cys Met Leu Glu Leu Asn Leu Leu Ser
1265                1270                1275                1280

Ala Ser Lys Ala Lys Leu Asp Val Leu Ala His Val Phe Glu Ser Phe
            1285                1290                1295

Leu Lys Ile Ile Arg Gln Lys Glu Lys Asn Val Phe Leu Leu Met Gln
        1300                1305                1310

Gln Gly Thr Val Lys Asn Leu Leu Gly Gly Phe Leu Ser Ile Leu Thr
    1315                1320                1325

Gln Asp Asp Ser Asp Phe Gln Ala Cys Gln Arg Val Leu Val Asp Leu
1330                1335                1340

Leu Val Ser Leu Met Ser Ser Arg Thr Cys Ser Glu Glu Leu Thr Leu
1345                1350                1355                1360

Leu Leu Arg Ile Phe Leu Glu Lys Ser Pro Cys Thr Lys Ile Leu Leu
            1365                1370                1375

Leu Gly Ile Leu Lys Ile Ile Glu Ser Asp Thr Thr Met Ser Pro Ser
        1380                1385                1390

Gln Tyr Leu Thr Phe Pro Leu Leu His Ala Pro Asn Leu Ser Asn Gly
    1395                1400                1405

Val Ser Ser Gln Lys Tyr Pro Gly Ile Leu Asn Ser Lys Ala Met Gly
1410                1415                1420

Leu Leu Arg Arg Ala Arg Val Ser Arg Ser Lys Lys Glu Ala Asp Arg
1425                1430                1435                1440

Glu Ser Phe Pro His Arg Leu Leu Ser Ser Trp His Ile Ala Pro Val
            1445                1450                1455

His Leu Pro Leu Leu Gly Gln Asn Cys Trp Pro His Leu Ser Glu Gly
        1460                1465                1470
```

-continued

```
Phe Ser Val Ser Leu Trp Phe Asn Val Glu Cys Ile His Glu Ala Glu
    1475                1480                1485

Ser Thr Thr Glu Lys Gly Lys Lys Ile Lys Arg Asn Lys Ser Leu
    1490                1495                1500

Ile Leu Pro Asp Ser Ser Phe Asp Gly Thr Glu Ser Asp Arg Pro Glu
1505                1510                1515                1520

Gly Ala Glu Tyr Ile Asn Pro Gly Glu Arg Leu Ile Glu Gly Cys
                1525                1530                1535

Ile His Ile Ile Ser Leu Gly Ser Lys Ala Leu Met Ile Gln Val Trp
                1540                1545                1550

Ala Asp Pro His Asn Ala Thr Leu Ile Phe Arg Val Cys Met Asp Ser
                1555                1560                1565

Asn Asp Asp Met Lys Ala Val Leu Leu Ala Gln Val Glu Ser Gln Glu
    1570                1575                1580

Asn Ile Phe Leu Pro Ser Lys Trp Gln His Leu Val Leu Thr Tyr Leu
1585                1590                1595                1600

Gln Gln Pro Gln Gly Lys Arg Arg Ile His Gly Lys Ile Ser Ile Trp
                1605                1610                1615

Val Ser Gly Gln Arg Lys Pro Asp Val Thr Leu Asp Phe Met Leu Pro
                1620                1625                1630

Arg Lys Thr Ser Leu Ser Ser Asp Ser Asn Lys Thr Phe Cys Met Ile
    1635                1640                1645

Gly His Cys Leu Ser Ser Gln Glu Glu Phe Leu Gln Leu Ala Gly Lys
    1650                1655                1660

Trp Asp Leu Gly Asn Leu Leu Leu Phe Asn Gly Ala Lys Val Gly Ser
1665                1670                1675                1680

Gln Glu Ala Phe Tyr Leu Tyr Ala Cys Gly Pro Asn His Thr Ser Val
                1685                1690                1695

Met Pro Cys Lys Tyr Gly Lys Pro Val Asn Asp Tyr Ser Lys Tyr Ile
                1700                1705                1710

Asn Lys Glu Ile Leu Arg Cys Glu Gln Ile Arg Glu Leu Phe Met Thr
    1715                1720                1725

Lys Lys Asp Val Asp Ile Gly Leu Leu Ile Glu Ser Leu Ser Val Val
    1730                1735                1740

Tyr Thr Thr Tyr Cys Pro Ala Gln Tyr Thr Ile Tyr Glu Pro Val Ile
1745                1750                1755                1760

Arg Leu Lys Gly Gln Met Lys Thr Gln Leu Ser Gln Arg Pro Phe Ser
                1765                1770                1775

Ser Lys Glu Val Gln Ser Ile Leu Leu Glu Pro His His Leu Lys Asn
                1780                1785                1790

Leu Gln Pro Thr Glu Tyr Lys Thr Ile Gln Gly Ile Leu His Glu Ile
                1795                1800                1805

Gly Gly Thr Gly Ile Phe Val Phe Leu Phe Ala Arg Val Val Glu Leu
    1810                1815                1820

Ser Ser Cys Glu Glu Thr Gln Ala Leu Ala Leu Arg Val Ile Leu Ser
1825                1830                1835                1840

Leu Ile Lys Tyr Asn Gln Gln Arg Val His Glu Leu Glu Asn Cys Asn
                1845                1850                1855

Gly Leu Ser Met Ile His Gln Val Leu Ile Lys Gln Lys Cys Ile Val
                1860                1865                1870

Gly Phe Tyr Ile Leu Lys Thr Leu Leu Glu Gly Cys Cys Gly Glu Asp
                1875                1880                1885

Ile Ile Tyr Met Asn Glu Asn Gly Glu Phe Lys Leu Asp Val Asp Ser
    1890                1895                1900
```

-continued

Asn Ala Ile Ile Gln Asp Val Lys Leu Leu Glu Glu Leu Leu Leu Asp
1905                1910                1915                1920

Trp Lys Ile Trp Ser Lys Ala Glu Gln Gly Val Trp Glu Thr Leu Leu
               1925                1930                1935

Ala Ala Leu Glu Val Leu Ile Arg Ala Asp His His Gln Gln Met Phe
           1940                1945                1950

Asn Ile Lys Gln Leu Leu Lys Ala Gln Val Val His His Phe Leu Leu
       1955                1960                1965

Thr Cys Gln Val Leu Gln Glu Tyr Lys Glu Gly Gln Leu Thr Pro Met
   1970                1975                1980

Pro Arg Glu Val Cys Arg Ser Phe Val Lys Ile Ile Ala Glu Val Leu
1985                1990                1995                2000

Gly Ser Pro Pro Asp Leu Glu Leu Leu Thr Ile Ile Phe Asn Phe Leu
               2005                2010                2015

Leu Ala Val His Pro Pro Thr Asn Thr Tyr Val Cys His Asn Pro Thr
           2020                2025                2030

Asn Phe Tyr Phe Ser Leu His Ile Asp Gly Lys Ile Phe Gln Glu Lys
       2035                2040                2045

Val Arg Ser Ile Met Tyr Leu Arg His Ser Ser Ser Gly Gly Arg Ser
   2050                2055                2060

Leu Met Ser Pro Gly Phe Met Val Ile Ser Pro Ser Gly Phe Thr Ala
2065                2070                2075                2080

Ser Pro Tyr Glu Gly Glu Asn Ser Ser Asn Ile Ile Pro Gln Gln Met
               2085                2090                2095

Ala Ala His Met Leu Arg Ser Arg Ser Leu Pro Ala Phe Pro Thr Ser
           2100                2105                2110

Ser Leu Leu Thr Gln Ser Gln Lys Leu Thr Gly Ser Leu Gly Cys Ser
       2115                2120                2125

Ile Asp Arg Leu Gln Asn Ile Ala Asp Thr Tyr Val Ala Thr Gln Ser
   2130                2135                2140

Lys Lys Gln Asn Ser Leu Gly Ser Ser Asp Thr Leu Lys Lys Gly Lys
2145                2150                2155                2160

Glu Asp Ala Phe Ile Ser Ser Cys Glu Ser Ala Lys Thr Val Cys Glu
               2165                2170                2175

Met Glu Ala Val Leu Ser Ala Gln Val Ser Val Ser Asp Val Pro Lys
           2180                2185                2190

Gly Val Leu Gly Phe Pro Val Val Lys Ala Asp His Lys Gln Leu Gly
       2195                2200                2205

Ala Glu Pro Arg Ser Glu Asp Asp Ser Pro Gly Asp Glu Ser Cys Pro
   2210                2215                2220

Arg Arg Pro Asp Tyr Leu Lys Gly Leu Ala Ser Phe Gln Arg Ser His
2225                2230                2235                2240

Ser Thr Ile Ala Ser Leu Gly Leu Ala Phe Pro Ser Gln Asn Gly Ser
               2245                2250                2255

Ala Ala Val Gly Arg Trp Pro Ser Leu Val Asp Arg Asn Thr Asp Asp
           2260                2265                2270

Trp Glu Asn Phe Ala Tyr Ser Leu Gly Tyr Glu Pro Asn Tyr Asn Arg
       2275                2280                2285

Thr Ala Ser Ala His Ser Val Thr Glu Asp Cys Leu Val Pro Ile Cys
   2290                2295                2300

Cys Gly Leu Tyr Glu Leu Leu Ser Gly Val Leu Leu Ile Leu Pro Asp
2305                2310                2315                2320

Val Leu Leu Glu Asp Val Met Asp Lys Leu Ile Gln Ala Asp Thr Leu

-continued

```
                2325                2330                2335
Leu Val Leu Val Asn His Pro Ser Pro Ala Ile Gln Gln Gly Val Ile
                2340                2345                2350
Lys Leu Leu Asp Ala Tyr Phe Ala Arg Ala Ser Lys Glu Gln Lys Asp
                2355                2360                2365
Lys Phe Leu Lys Asn Arg Gly Phe Ser Leu Leu Ala Asn Gln Leu Tyr
                2370                2375                2380
Leu His Arg Gly Thr Gln Glu Leu Leu Glu Cys Phe Ile Glu Met Phe
2385                2390                2395                2400
Phe Gly Arg His Ile Gly Leu Asp Glu Glu Phe Asp Leu Glu Asp Val
                2405                2410                2415
Arg Asn Met Gly Leu Phe Gln Lys Trp Ser Val Ile Pro Ile Leu Gly
                2420                2425                2430
Leu Ile Glu Thr Ser Leu Tyr Asp Asn Ile Leu Leu His Asn Ala Leu
                2435                2440                2445
Leu Leu Leu Leu Gln Ile Leu Asn Ser Cys Ser Lys Val Ala Asp Met
                2450                2455                2460
Leu Leu Asp Asn Gly Leu Leu Tyr Val Leu Cys Asn Thr Val Ala Ala
2465                2470                2475                2480
Leu Asn Gly Leu Glu Lys Asn Ile Pro Met Ser Glu Tyr Lys Leu Leu
                2485                2490                2495
Ala Cys Asp Ile Gln Gln Leu Phe Ile Ala Val Thr Ile His Ala Cys
                2500                2505                2510
Ser Ser Ser Gly Ser Gln Tyr Phe Arg Val Ile Glu Asp Leu Ile Val
                2515                2520                2525
Met Leu Gly Tyr Leu Gln Asn Ser Lys Asn Lys Arg Thr Gln Asn Met
                2530                2535                2540
Ala Val Ala Leu Gln Leu Arg Val Leu Gln Ala Ala Met Glu Phe Ile
2545                2550                2555                2560
Arg Thr Thr Ala Asn His Asp Ser Glu Asn Leu Thr Asp Ser Leu Gln
                2565                2570                2575
Ser Pro Ser Ala Pro His His Ala Val Val Gln Lys Arg Lys Ser Ile
                2580                2585                2590
Ala Gly Pro Arg Lys Phe Pro Leu Ala Gln Thr Glu Ser Leu Leu Met
                2595                2600                2605
Lys Met Arg Ser Val Ala Asn Asp Glu Leu His Val Met Met Gln Arg
2610                2615                2620
Arg Met Ser Gln Glu Asn Pro Ser Gln Ala Thr Glu Thr Glu Leu Ala
2625                2630                2635                2640
Gln Arg Leu Gln Arg Leu Thr Val Leu Ala Val Asn Arg Ile Ile Tyr
                2645                2650                2655
Gln Glu Phe Asn Ser Asp Ile Ile Asp Ile Leu Arg Thr Pro Glu Asn
                2660                2665                2670
Val Thr Gln Ser Lys Thr Ser Val Phe Gln Thr Glu Ile Ser Glu Glu
                2675                2680                2685
Asn Ile His His Glu Gln Ser Ser Val Phe Asn Pro Phe Gln Lys Glu
                2690                2695                2700
Ile Phe Thr Tyr Leu Val Glu Gly Phe Lys Val Ser Ile Gly Ser Ser
2705                2710                2715                2720
Lys Ala Ser Gly Ser Lys Gln Gln Trp Thr Lys Ile Leu Trp Ser Cys
                2725                2730                2735
Lys Glu Thr Phe Arg Met Gln Leu Gly Arg Leu Leu Val His Ile Leu
                2740                2745                2750
```

-continued

```
Ser Pro Ala His Ala Ala Gln Glu Arg Lys Gln Ile Phe Glu Ile Val
            2755                2760                2765

His Glu Pro Asn His Gln Glu Ile Leu Arg Asp Cys Leu Ser Pro Ser
        2770                2775                2780

Leu Gln His Gly Ala Lys Leu Val Leu Tyr Leu Ser Glu Leu Ile His
2785                2790                2795                2800

Asn His Gln Gly Glu Leu Thr Glu Glu Leu Gly Thr Ala Glu Leu
            2805                2810                2815

Leu Met Asn Ala Leu Lys Leu Cys Gly His Lys Cys Ile Pro Pro Ser
        2820                2825                2830

Ala Ser Thr Lys Ala Asp Leu Ile Lys Met Ile Lys Glu Glu Gln Lys
            2835                2840                2845

Lys Tyr Glu Thr Glu Glu Gly Val Asn Lys Ala Ala Trp Gln Lys Thr
        2850                2855                2860

Val Asn Asn Gln Gln Ser Leu Phe Gln Arg Leu Asp Ser Lys Ser
2865                2870                2875                2880

Lys Asp Ile Ser Lys Ile Ala Ala Asp Ile Thr Gln Ala Val Ser Leu
            2885                2890                2895

Ser Gln Gly Asn Glu Arg Lys Lys Val Ile Gln His Ile Arg Gly Met
        2900                2905                2910

Tyr Lys Val Asp Leu Ser Ala Ser Arg His Trp Gln Glu Leu Ile Gln
            2915                2920                2925

Gln Leu Thr His Asp Arg Ala Val Trp Tyr Asp Pro Ile Tyr Tyr Pro
2930                2935                2940

Thr Ser Trp Gln Leu Asp Pro Thr Glu Gly Pro Asn Arg Glu Arg Arg
2945                2950                2955                2960

Arg Leu Gln Arg Cys Tyr Leu Thr Ile Pro Asn Lys Tyr Leu Leu Arg
            2965                2970                2975

Asp Arg Gln Lys Ser Glu Asp Val Val Lys Pro Pro Leu Ser Tyr Leu
            2980                2985                2990

Phe Glu Asp Lys Thr His Ser Ser Phe Ser Ser Thr Val Lys Asp Lys
            2995                3000                3005

Ala Ala Ser Glu Ser Ile Arg Val Asn Arg Arg Cys Ile Ser Val Ala
        3010                3015                3020

Pro Ser Arg Glu Thr Ala Gly Glu Leu Leu Gly Lys Cys Gly Met
3025                3030                3035                3040

Tyr Phe Val Glu Asp Asn Ala Ser Asp Thr Val Glu Ser Ser Ser Leu
            3045                3050                3055

Gln Gly Glu Leu Glu Pro Ala Ser Phe Ser Trp Thr Tyr Glu Glu Ile
            3060                3065                3070

Lys Glu Val His Lys Arg Trp Trp Gln Leu Arg Asp Asn Ala Val Glu
        3075                3080                3085

Ile Phe Leu Thr Asn Gly Arg Thr Leu Leu Ala Phe Asp Asn Thr
3090                3095                3100

Lys Val Arg Asp Asp Val Tyr His Asn Ile Leu Thr Asn Asn Leu Pro
3105                3110                3115                3120

Asn Leu Leu Glu Tyr Gly Asn Ile Thr Ala Leu Thr Asn Leu Trp Tyr
            3125                3130                3135

Thr Gly Gln Ile Thr Asn Phe Glu Tyr Leu Thr His Leu Asn Lys His
            3140                3145                3150

Ala Gly Arg Ser Phe Asn Asp Leu Met Gln Tyr Pro Val Phe Pro Phe
            3155                3160                3165

Ile Leu Ala Asp Tyr Val Ser Glu Thr Leu Asp Leu Asn Asp Leu Leu
        3170                3175                3180
```

-continued

Ile Tyr Arg Asn Leu Ser Lys Pro Ile Ala Val Gln Tyr Lys Glu Lys
3185              3190              3195              3200

Glu Asp Arg Tyr Val Asp Thr Tyr Lys Tyr Leu Glu Glu Tyr Arg
          3205              3210              3215

Lys Gly Ala Arg Glu Asp Asp Pro Met Pro Pro Val Gln Pro Tyr His
          3220              3225              3230

Tyr Gly Ser His Tyr Ser Asn Ser Gly Thr Val Leu His Phe Leu Val
          3235              3240              3245

Arg Met Pro Pro Phe Thr Lys Met Phe Leu Ala Tyr Gln Asp Gln Ser
3250              3255              3260

Phe Asp Ile Pro Asp Arg Thr Phe His Ser Thr Asn Thr Thr Trp Arg
3265              3270              3275              3280

Leu Ser Ser Phe Glu Ser Met Thr Asp Val Lys Glu Leu Ile Pro Glu
          3285              3290              3295

Phe Phe Tyr Leu Pro Glu Phe Leu Val Asn Arg Glu Gly Phe Asp Phe
          3300              3305              3310

Gly Val Arg Gln Asn Gly Glu Arg Val Asn His Val Asn Leu Pro Pro
          3315              3320              3325

Trp Ala Arg Asn Asp Pro Arg Leu Phe Ile Leu Ile His Arg Gln Ala
3330              3335              3340

Leu Glu Ser Asp Tyr Val Ser Gln Asn Ile Cys Gln Trp Ile Asp Leu
3345              3350              3355              3360

Val Phe Gly Tyr Lys Gln Lys Gly Lys Ala Ser Val Gln Ala Ile Asn
          3365              3370              3375

Val Phe His Pro Ala Thr Tyr Phe Gly Met Asp Val Ser Ala Val Glu
          3380              3385              3390

Asp Pro Val Gln Arg Arg Ala Leu Glu Thr Met Ile Lys Thr Tyr Gly
          3395              3400              3405

Gln Thr Pro Arg Gln Leu Phe His Met Ala His Val Ser Arg Pro Gly
          3410              3415              3420

Ala Lys Leu Asn Ile Glu Gly Glu Leu Pro Ala Ala Val Gly Leu Leu
3425              3430              3435              3440

Val Gln Phe Ala Phe Arg Glu Thr Arg Glu Gln Val Lys Glu Ile Thr
          3445              3450              3455

Tyr Pro Ser Pro Leu Ser Trp Ile Lys Gly Leu Lys Trp Gly Glu Tyr
          3460              3465              3470

Val Gly Ser Pro Ser Ala Pro Val Pro Val Val Cys Phe Ser Gln Pro
          3475              3480              3485

His Gly Glu Arg Phe Gly Ser Leu Gln Ala Leu Pro Thr Arg Ala Ile
          3490              3495              3500

Cys Gly Leu Ser Arg Asn Phe Cys Leu Val Met Thr Tyr Ser Lys Glu
3505              3510              3515              3520

Gln Gly Val Arg Ser Met Asn Ser Thr Asp Ile Gln Trp Ser Ala Ile
          3525              3530              3535

Leu Ser Trp Gly Tyr Ala Asp Asn Ile Leu Arg Leu Lys Ser Lys Gln
          3540              3545              3550

Ser Glu Pro Pro Val Asn Phe Ile Gln Ser Ser Gln Gln Tyr Gln Val
          3555              3560              3565

Thr Ser Cys Ala Trp Val Pro Asp Ser Cys Gln Leu Phe Thr Gly Ser
          3570              3575              3580

Lys Cys Gly Val Ile Thr Ala Tyr Thr Asn Arg Phe Thr Ser Ser Thr
3585              3590              3595              3600

Pro Ser Glu Ile Glu Met Glu Thr Gln Ile His Leu Tyr Gly His Thr

-continued

```
                 3605                    3610                    3615
Glu Glu Ile Thr Ser Leu Phe Val Cys Lys Pro Tyr Ser Ile Leu Ile
             3620                    3625                    3630

Ser Val Ser Arg Asp Gly Thr Cys Ile Ile Trp Asp Leu Asn Arg Leu
             3635                    3640                    3645

Cys Tyr Val Gln Ser Leu Ala Gly His Lys Ser Pro Val Thr Ala Val
 3650                    3655                    3660

Ser Ala Ser Glu Thr Ser Gly Asp Ile Ala Thr Val Cys Asp Ser Ala
3665                    3670                    3675                    3680

Gly Gly Gly Ser Asp Leu Arg Leu Trp Thr Val Asn Gly Asp Leu Val
             3685                    3690                    3695

Gly His Val His Cys Arg Glu Ile Ile Cys Ser Val Ala Phe Ser Asn
             3700                    3705                    3710

Gln Pro Glu Gly Val Ser Ile Asn Val Ile Ala Gly Gly Leu Glu Asn
             3715                    3720                    3725

Gly Ile Val Arg Leu Trp Ser Thr Trp Asp Leu Lys Pro Val Arg Glu
 3730                    3735                    3740

Ile Thr Phe Pro Lys Ser Asn Lys Pro Ile Ile Ser Leu Thr Phe Ser
3745                    3750                    3755                    3760

Cys Asp Gly His His Leu Tyr Thr Ala Asn Ser Asp Gly Thr Val Ile
             3765                    3770                    3775

Ala Trp Cys Arg Lys Asp Gln His Arg Leu Lys Gln Pro Met Phe Tyr
             3780                    3785                    3790

Ser Phe Leu Ser Ser Tyr Ala Ala Gly
             3795                    3800
```

(2) INFORMATION FOR SEQ ID NO:11:

(i) SEQUENCE CHARACTERISTICS:
        (A) LENGTH: 12225 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 190..11208

(xi) SEQUENCE DESCRIPTION: SEQ ID NO:11:

```
GCGGCCGCGT CGACGCGGCG GCGGCAGCGG CGTCGGCTCG GGGTTCTCCG GGAGAGGGGG      60

AGTGCGCGGC GGCCGCAGCT GCCACAAACC AGGTGAAGCT TGTTCTAAG AATATTTGTT      120

TCATCTAGTT TATGAGTCCA AATGATATAG ACTGTAAATG TCACAGCAGT GGTGAAAGAC     180

TGCTCGGTC ATG AGC ACC GAC AGT AAC TCA CTG GCA CGT GAA TTT CTG         228
           Met Ser Thr Asp Ser Asn Ser Leu Ala Arg Glu Phe Leu
            1               5                  10

ACC GAT GTC AAC CGG CTT TGC AAT GCA GTG GTC CAG AGG GTG GAG GCC       276
Thr Asp Val Asn Arg Leu Cys Asn Ala Val Val Gln Arg Val Glu Ala
 15                  20                  25

AGG GAG GAA GAA GAG GAG GAG ACG CAC ATG GCA ACC CTT GGA CAG TAC       324
Arg Glu Glu Glu Glu Glu Thr His Met Ala Thr Leu Gly Gln Tyr
 30                  35                  40                  45

CTT GTC CAT GGT CGA GGA TTT CTA TTA CTT ACC AAG CTA AAT TCT ATA       372
Leu Val His Gly Arg Gly Phe Leu Leu Leu Thr Lys Leu Asn Ser Ile
             50                  55                  60

ATT GAT CAG GCA TTG ACA TGT AGA GAA GAA CTC CTG ACT CTT CTT CTG       420
Ile Asp Gln Ala Leu Thr Cys Arg Glu Glu Leu Leu Thr Leu Leu Leu
 65                  70                  75
```

```
TCT CTC CTT CCA CTG GTA TGG AAG ATA CCT GTC CAA GAA GAA AAG GCA      468
Ser Leu Leu Pro Leu Val Trp Lys Ile Pro Val Gln Glu Glu Lys Ala
         80                  85                  90

ACA GAT TTT AAC CTA CCG CTC TCA GCA GAT ATA ATC CTG ACC AAA GAA      516
Thr Asp Phe Asn Leu Pro Leu Ser Ala Asp Ile Ile Leu Thr Lys Glu
         95                 100                 105

AAG AAC TCA AGT TCA CAA AGA TCC ACT CAG GAA AAA TTA CAT TTA GAA      564
Lys Asn Ser Ser Ser Gln Arg Ser Thr Gln Glu Lys Leu His Leu Glu
110                 115                 120                 125

GGA AGT GCC CTG TCT AGT CAG GTT TCT GCA AAA GTA AAT GTT TTT CGA      612
Gly Ser Ala Leu Ser Ser Gln Val Ser Ala Lys Val Asn Val Phe Arg
                130                 135                 140

AAA AGC AGA CGA CAG CGT AAA ATT ACC CAT CGC TAT TCT GTA AGA GAT      660
Lys Ser Arg Arg Gln Arg Lys Ile Thr His Arg Tyr Ser Val Arg Asp
                145                 150                 155

GCA AGA AAG ACA CAG CTC TCC ACC TCA GAT TCA GAA GCC AAT TCA GAT      708
Ala Arg Lys Thr Gln Leu Ser Thr Ser Asp Ser Glu Ala Asn Ser Asp
                160                 165                 170

GAA AAA GGC ATA GCA ATG AAT AAG CAT AGA AGG CCC CAT CTG CTG CAT      756
Glu Lys Gly Ile Ala Met Asn Lys His Arg Arg Pro His Leu Leu His
175                 180                 185

CAT TTT TTA ACA TCG TTT CCT AAA CAA GAC CAC CCC AAA GCT AAA CTT      804
His Phe Leu Thr Ser Phe Pro Lys Gln Asp His Pro Lys Ala Lys Leu
190                 195                 200                 205

GAC CGC TTA GCA ACC AAA GAA CAG ACT CCT CCA GAT GCT ATG GCT TTG      852
Asp Arg Leu Ala Thr Lys Glu Gln Thr Pro Pro Asp Ala Met Ala Leu
                210                 215                 220

GAA AAT TCC AGA GAG ATT ATT CCA AGA CAG GGG TCA AAC ACT GAC ATT      900
Glu Asn Ser Arg Glu Ile Ile Pro Arg Gln Gly Ser Asn Thr Asp Ile
                225                 230                 235

TTA AGT GAG CCA GCT GCC TTG TCT GTT ATC AGT AAC ATG AAC AAT TCT      948
Leu Ser Glu Pro Ala Ala Leu Ser Val Ile Ser Asn Met Asn Asn Ser
                240                 245                 250

CCA TTT GAC TTA TGT CAT GTT TTG TTA TCT TTA TTA GAA AAA GTT TGT      996
Pro Phe Asp Leu Cys His Val Leu Leu Ser Leu Leu Glu Lys Val Cys
255                 260                 265

AAG TTT GAC GTT ACC TTG AAT CAT AAT TCT CCT TTA GCA GCC AGT GTA     1044
Lys Phe Asp Val Thr Leu Asn His Asn Ser Pro Leu Ala Ala Ser Val
270                 275                 280                 285

GTG CCC ACA CTA ACT GAA TTC CTA GCA GGC TTT GGG GAC TGC TGC AGT     1092
Val Pro Thr Leu Thr Glu Phe Leu Ala Gly Phe Gly Asp Cys Cys Ser
                290                 295                 300

CTG AGC GAC AAC TTG GAG AGT CGA GTA GTT TCT GCA GGT TGG ACC GAA     1140
Leu Ser Asp Asn Leu Glu Ser Arg Val Val Ser Ala Gly Trp Thr Glu
                305                 310                 315

GAA CCG GTG GCT TTG ATT CAA AGG ATG CTC TTT CGA ACA GTG TTG CAT     1188
Glu Pro Val Ala Leu Ile Gln Arg Met Leu Phe Arg Thr Val Leu His
                320                 325                 330

CTT CTG TCA GTA GAT GTT AGT ACT GCA GAG ATG ATG CCA GAA AAT CTT     1236
Leu Leu Ser Val Asp Val Ser Thr Ala Glu Met Met Pro Glu Asn Leu
335                 340                 345

AGG AAA AAT TTA ACT GAA TTG CTT AGA GCA GCT TTA AAA ATT AGA ATA     1284
Arg Lys Asn Leu Thr Glu Leu Leu Arg Ala Ala Leu Lys Ile Arg Ile
350                 355                 360                 365

TGC CTA GAA AAG CAG CCT GAC CCT TTT GCA CCA AGA CAA AAG AAA ACA     1332
Cys Leu Glu Lys Gln Pro Asp Pro Phe Ala Pro Arg Gln Lys Lys Thr
                370                 375                 380

CTG CAG GAG GTT CAG GAA GAT TTT GTG TTT TCA AAG TAT CGT CAT AGA     1380
Leu Gln Glu Val Gln Glu Asp Phe Val Phe Ser Lys Tyr Arg His Arg
                385                 390                 395
```

```
GCC CTT CTT TTA CCT GAG CTT TTG GAA GGA GTT CTT CAG ATT CTG ATC     1428
Ala Leu Leu Leu Pro Glu Leu Leu Glu Gly Val Leu Gln Ile Leu Ile
            400                 405                 410

TGT TGT CTT CAA AGT GCA GCT TCA AAT CCC TTC TAC TTC AGT CAA GCC     1476
Cys Cys Leu Gln Ser Ala Ala Ser Asn Pro Phe Tyr Phe Ser Gln Ala
415                 420                 425

ATG GAT TTG GTT CAA GAA TTC ATT CAG CAT CAT GGA TTT AAT TTA TTT     1524
Met Asp Leu Val Gln Glu Phe Ile Gln His His Gly Phe Asn Leu Phe
430                 435                 440                 445

GAA ACA GCA GTT CTT CAA ATG GAA TGG CTG GTT TTA AGA GAT GGA GTT     1572
Glu Thr Ala Val Leu Gln Met Glu Trp Leu Val Leu Arg Asp Gly Val
                450                 455                 460

CCT CCC GAG GCC TCA GAG CAT TTG AAA GCC CTA ATA AAT AGT GTG ATG     1620
Pro Pro Glu Ala Ser Glu His Leu Lys Ala Leu Ile Asn Ser Val Met
            465                 470                 475

AAA ATA ATG AGC ACT GTC AAA AAA GTG AAA TCA GAG CAA CTT CAT CAT     1668
Lys Ile Met Ser Thr Val Lys Lys Val Lys Ser Glu Gln Leu His His
            480                 485                 490

TCG ATG TGT ACA AGA AAA AGG CAC AGA CGA TGT GAA TAT TCT CAT TTT     1716
Ser Met Cys Thr Arg Lys Arg His Arg Arg Cys Glu Tyr Ser His Phe
495                 500                 505

ATG CAT CAT CAC CGA GAT CTC TCA GGT CTT CTG GTT TCG GCT TTT AAA     1764
Met His His His Arg Asp Leu Ser Gly Leu Leu Val Ser Ala Phe Lys
510                 515                 520                 525

AAC CAG GTT TCC AAA AAC CCA TTT GAA GAG ACT GCA GAT GGA GAT GTT     1812
Asn Gln Val Ser Lys Asn Pro Phe Glu Glu Thr Ala Asp Gly Asp Val
                530                 535                 540

TAT TAT CCT GAG CGG TGC TGT TGC ATT GCA GTG TGT GCC CAT CAG TGC     1860
Tyr Tyr Pro Glu Arg Cys Cys Cys Ile Ala Val Cys Ala His Gln Cys
            545                 550                 555

TTG CGC TTA CTA CAG CAG GCT TCC TTG AGC AGC ACT TGT GTC CAG ATC     1908
Leu Arg Leu Leu Gln Gln Ala Ser Leu Ser Ser Thr Cys Val Gln Ile
            560                 565                 570

CTA TCG GGT GTT CAT AAC ATT GGA ATA GCC TGT TGT ATG GAT CCC AAA     1956
Leu Ser Gly Val His Asn Ile Gly Ile Cys Cys Cys Met Asp Pro Lys
575                 580                 585

TCT GTA ATC ATT CCT TTG CTC CAT GCT TTT AAA TTG CCA GCA CTG AAA     2004
Ser Val Ile Ile Pro Leu Leu His Ala Phe Lys Leu Pro Ala Leu Lys
590                 595                 600                 605

AAT TTT CAG CAG CAT ATA TTG AAT ATC CTT AAC AAA CTT ATT TTG GAT     2052
Asn Phe Gln Gln His Ile Leu Asn Ile Leu Asn Lys Leu Ile Leu Asp
                610                 615                 620

CAG TTA GGA GGA GCA GAG ATA TCA CCA AAA ATT AAA AAA GCA GCT TGT     2100
Gln Leu Gly Gly Ala Glu Ile Ser Pro Lys Ile Lys Lys Ala Ala Cys
            625                 630                 635

AAT ATT TGT ACT GTT GAC TCT GAC CAA CTA GCC CAA TTA GAA GAG ACA     2148
Asn Ile Cys Thr Val Asp Ser Asp Gln Leu Ala Gln Leu Glu Glu Thr
            640                 645                 650

CTG CAG GGA AAC TTA TGT GAT GCT GAA CTC TCC TCA AGT TTA TCC AGT     2196
Leu Gln Gly Asn Leu Cys Asp Ala Glu Leu Ser Ser Ser Leu Ser Ser
655                 660                 665

CCT TCT TAC AGA TTT CAA GGG ATC CTG CCC AGC AGT GGA TCT GAA GAT     2244
Pro Ser Tyr Arg Phe Gln Gly Ile Leu Pro Ser Ser Gly Ser Glu Asp
670                 675                 680                 685

TTG TTG TGG AAA TGG GAT GCT TTA AAG GCT TAT CAG AAC TTT GTT TTT     2292
Leu Leu Trp Lys Trp Asp Ala Leu Lys Ala Tyr Gln Asn Phe Val Phe
                690                 695                 700

GAA GAA GAC AGA TTA CAT AGT ATA CAG ATT GCA AAT CAC ATT TGC AAT     2340
Glu Glu Asp Arg Leu His Ser Ile Gln Ile Ala Asn His Ile Cys Asn
            705                 710                 715
```

-continued

| | |
|---|---|
| TTA ATC CAG AAA GGC AAT ATA GTT GTT CAG TGG AAA TTA TAT AAT TAC<br>Leu Ile Gln Lys Gly Asn Ile Val Val Gln Trp Lys Leu Tyr Asn Tyr<br>           720                725               730 | 2388 |
| ATA TTT AAT CCT GTG CTC CAA AGA GGA GTT GAA TTA GCA CAT CAT TGT<br>Ile Phe Asn Pro Val Leu Gln Arg Gly Val Glu Leu Ala His His Cys<br>735                     740                 745 | 2436 |
| CAA CAC CTA AGC GTT ACT TCA GCT CAA AGT CAT GTA TGT AGC CAT CAT<br>Gln His Leu Ser Val Thr Ser Ala Gln Ser His Val Cys Ser His His<br>750                     755                760               765 | 2484 |
| AAC CAG TGC TTG CCT CAG GAC GTG CTT CAG ATT TAT GTA AAA ACT CTG<br>Asn Gln Cys Leu Pro Gln Asp Val Leu Gln Ile Tyr Val Lys Thr Leu<br>           770                775               780 | 2532 |
| CCT ATC CTG CTT AAA TCC AGG GTA ATA AGA GAT TTG TTT TTG AGT TGT<br>Pro Ile Leu Leu Lys Ser Arg Val Ile Arg Asp Leu Phe Leu Ser Cys<br>785                     790                 795 | 2580 |
| AAT GGA GTA AGT CAA ATA ATC GAA TTA AAT TGC TTA AAT GGT ATT CGA<br>Asn Gly Val Ser Gln Ile Ile Glu Leu Asn Cys Leu Asn Gly Ile Arg<br>800                     805                810 | 2628 |
| AGT CAT TCT CTA AAA GCA TTT GAA ACT CTG ATA ATC AGC CTA GGG GAG<br>Ser His Ser Leu Lys Ala Phe Glu Thr Leu Ile Ile Ser Leu Gly Glu<br>           815                820               825 | 2676 |
| CAA CAG AAA GAT GCC TCA GTT CCA GAT ATT GAT GGG ATA GAC ATT GAA<br>Gln Gln Lys Asp Ala Ser Val Pro Asp Ile Asp Gly Ile Asp Ile Glu<br>830                     835                840               845 | 2724 |
| CAG AAG GAG TTG TCC TCT GTA CAT GTG GGT ACT TCT TTT CAT CAT CAG<br>Gln Lys Glu Leu Ser Ser Val His Val Gly Thr Ser Phe His His Gln<br>           850                855               860 | 2772 |
| CAA GCT TAT TCA GAT TCT CCT CAG AGT CTC AGC AAA TTT TAT GCT GGC<br>Gln Ala Tyr Ser Asp Ser Pro Gln Ser Leu Ser Lys Phe Tyr Ala Gly<br>865                     870                 875 | 2820 |
| CTC AAA GAA GCT TAT CCA AAG AGA CGG AAG ACT GTT AAC CAA GAT GTT<br>Leu Lys Glu Ala Tyr Pro Lys Arg Arg Lys Thr Val Asn Gln Asp Val<br>           880                885               890 | 2868 |
| CAT ATC AAC ACA ATA AAC CTA TTC CTC TGT GTG GCT TTT TTA TGC GTA<br>His Ile Asn Thr Ile Asn Leu Phe Leu Cys Val Ala Phe Leu Cys Val<br>895                     900                 905 | 2916 |
| AGT AAA GAA GCA GAG TCT GAC AGG GAG TCG GCC AAT GAC TCA GAA GAT<br>Ser Lys Glu Ala Glu Ser Asp Arg Glu Ser Ala Asn Asp Ser Glu Asp<br>910                     915                920               925 | 2964 |
| ACT TCT GGC TAT GAC AGC ACA GCC AGC GAG CCT TTA AGT CAT ATG CTG<br>Thr Ser Gly Tyr Asp Ser Thr Ala Ser Glu Pro Leu Ser His Met Leu<br>           930                935               940 | 3012 |
| CCA TGT ATA TCT CTC GAG AGC CTT GTC TTG CCT TCT CCT GAA CAT ATG<br>Pro Cys Ile Ser Leu Glu Ser Leu Val Leu Pro Ser Pro Glu His Met<br>945                     950                 955 | 3060 |
| CAC CAA GCA GCA GAC ATT TGG TCT ATG TGT CGT TGG ATC TAC ATG TTG<br>His Gln Ala Ala Asp Ile Trp Ser Met Cys Arg Trp Ile Tyr Met Leu<br>           960                965               970 | 3108 |
| AGT TCA GTG TTC CAG AAA CAG TTT TAT AGG CTT GGT GGT TTC CGA GTA<br>Ser Ser Val Phe Gln Lys Gln Phe Tyr Arg Leu Gly Gly Phe Arg Val<br>975                     980                 985 | 3156 |
| TGC CAT AAG TTA ATA TTT ATG ATA ATA CAG AAA CTG TTC AGA AGT CAC<br>Cys His Lys Leu Ile Phe Met Ile Ile Gln Lys Leu Phe Arg Ser His<br>990                     995               1000             1005 | 3204 |
| AAA GAG GAG CAA GGA AAA AAG GAG GGA GAT ACA AGT GTA AAT GAA AAC<br>Lys Glu Glu Gln Gly Lys Lys Glu Gly Asp Thr Ser Val Asn Glu Asn<br>           1010               1015               1020 | 3252 |
| CAG GAT TTA AAC AGA ATT TCT CAA CCT AAG AGA ACT ATG AAG GAA GAT<br>Gln Asp Leu Asn Arg Ile Ser Gln Pro Lys Arg Thr Met Lys Glu Asp<br>1025                 1030               1035 | 3300 |

```
TTA TTA TCT TTG GCT ATA AAA AGT GAC CCC ATA CCA TCA GAA CTA GGT    3348
Leu Leu Ser Leu Ala Ile Lys Ser Asp Pro Ile Pro Ser Glu Leu Gly
        1040                1045                1050

AGT CTA AAA AAG AGT GCT GAC AGT TTA GGT AAA TTA GAG TTA CAG CAT    3396
Ser Leu Lys Lys Ser Ala Asp Ser Leu Gly Lys Leu Glu Leu Gln His
        1055                1060                1065

ATT TCT TCC ATA AAT GTG GAA GAA GTT TCA GCT ACT GAA GCC GCT CCC    3444
Ile Ser Ser Ile Asn Val Glu Glu Val Ser Ala Thr Glu Ala Ala Pro
1070                1075                1080                1085

GAG GAA GCA AAG CTA TTT ACA AGT CAA GAA AGT GAG ACC TCA CTT CAA    3492
Glu Glu Ala Lys Leu Phe Thr Ser Gln Glu Ser Glu Thr Ser Leu Gln
                1090                1095                1100

AGT ATA CGA CTT TTG GAA GCC CTT CTG GCC ATT TGT CTT CAT GGT GCC    3540
Ser Ile Arg Leu Leu Glu Ala Leu Leu Ala Ile Cys Leu His Gly Ala
            1105                1110                1115

AGA ACT AGT CAA CAG AAG ATG GAA TTG GAG TTA CCT AAT CAG AAC TTG    3588
Arg Thr Ser Gln Gln Lys Met Glu Leu Glu Leu Pro Asn Gln Asn Leu
        1120                1125                1130

TCT GTG GAA AGT ATA TTA TTT GAA ATG AGG GAC CAT CTT TCC CAG TCA    3636
Ser Val Glu Ser Ile Leu Phe Glu Met Arg Asp His Leu Ser Gln Ser
    1135                1140                1145

AAG GTG ATT GAA ACA CAA CTA GCA AAG CCG TTA TTT GAT GCC CTG CTT    3684
Lys Val Ile Glu Thr Gln Leu Ala Lys Pro Leu Phe Asp Ala Leu Leu
1150                1155                1160                1165

CGA GTT GCC CTC GGG AAT TAT TCA GCA GAT TTT GAA CAT AAT GAT GCT    3732
Arg Val Ala Leu Gly Asn Tyr Ser Ala Asp Phe Glu His Asn Asp Ala
                1170                1175                1180

ATG ACT GAG AAG AGT CAT CAA TCT GCA GAA GAA TTG TCA TCC CAG CCT    3780
Met Thr Glu Lys Ser His Gln Ser Ala Glu Glu Leu Ser Ser Gln Pro
            1185                1190                1195

GGT GAT TTT TCA GAA GAA GCT GAG GAT TCT CAG TGT TGT AGT TTT AAA    3828
Gly Asp Phe Ser Glu Glu Ala Glu Asp Ser Gln Cys Cys Ser Phe Lys
        1200                1205                1210

CTT TTA GTT GAA GAA GAA GGT TAC GAA GCA GAT AGT GAA AGC AAT CCT    3876
Leu Leu Val Glu Glu Glu Gly Tyr Glu Ala Asp Ser Glu Ser Asn Pro
    1215                1220                1225

GAA GAT GGC GAA ACC CAG GAT GAT GGG GTA GAC TTA AAG TCT GAA ACA    3924
Glu Asp Gly Glu Thr Gln Asp Asp Gly Val Asp Leu Lys Ser Glu Thr
1230                1235                1240                1245

GAA GGT TTC AGT GCA TCA AGC AGT CCA AAT GAC TTA CTC GAA AAC CTC    3972
Glu Gly Phe Ser Ala Ser Ser Ser Pro Asn Asp Leu Leu Glu Asn Leu
                1250                1255                1260

ACT CAA GGG GAA ATA ATT TAT CCT GAG ATT TGT ATG CTG GAA TTA AAT    4020
Thr Gln Gly Glu Ile Ile Tyr Pro Glu Ile Cys Met Leu Glu Leu Asn
            1265                1270                1275

TTG CTT TCT GCT AGT AAA GCC AAA CTT GAT GTG CTT GCC CAT GTA TTT    4068
Leu Leu Ser Ala Ser Lys Ala Lys Leu Asp Val Leu Ala His Val Phe
        1280                1285                1290

GAG AGT TTT TTG AAA ATT ATT AGG CAG AAA GAA AAG AAT GTT TTT CTG    4116
Glu Ser Phe Leu Lys Ile Ile Arg Gln Lys Glu Lys Asn Val Phe Leu
    1295                1300                1305

CTC ATG CAA CAG GGA ACT GTG AAA AAT CTT TTA GGA GGG TTC TTG AGT    4164
Leu Met Gln Gln Gly Thr Val Lys Asn Leu Leu Gly Gly Phe Leu Ser
1310                1315                1320                1325

ATT TTA ACA CAG GAT GAT TCT GAT TTT CAA GCA TGC CAG AGA GTA TTG    4212
Ile Leu Thr Gln Asp Asp Ser Asp Phe Gln Ala Cys Gln Arg Val Leu
                1330                1335                1340

GTG GAT CTT TTG GTA TCT TTG ATG AGT TCA AGA ACA TGT TCA GAA GAG    4260
Val Asp Leu Leu Val Ser Leu Met Ser Ser Arg Thr Cys Ser Glu Glu
            1345                1350                1355
```

```
CTA ACC CTT CTT TTG AGA ATA TTT CTG GAG AAA TCT CCT TGT ACA AAA      4308
Leu Thr Leu Leu Leu Arg Ile Phe Leu Glu Lys Ser Pro Cys Thr Lys
1360                    1365                    1370

ATT CTT CTT CTG GGT ATT CTG AAA ATT ATT GAA AGT GAT ACT ACT ATG      4356
Ile Leu Leu Leu Gly Ile Leu Lys Ile Ile Glu Ser Asp Thr Thr Met
        1375                    1380                    1385

AGC CCT TCA CAG TAT CTA ACC TTC CCT TTA CTG CAC GCT CCA AAT TTA      4404
Ser Pro Ser Gln Tyr Leu Thr Phe Pro Leu Leu His Ala Pro Asn Leu
1390                    1395                    1400                    1405

AGC AAC GGT GTT TCA TCA CAA AAG TAT CCT GGG ATT TTA AAC AGT AAG      4452
Ser Asn Gly Val Ser Ser Gln Lys Tyr Pro Gly Ile Leu Asn Ser Lys
        1410                    1415                    1420

GCC ATG GGT TTA TTG AGA AGA GCA CGA GTT TCA CGG AGC AAG AAA GAG      4500
Ala Met Gly Leu Leu Arg Arg Ala Arg Val Ser Arg Ser Lys Lys Glu
1425                    1430                    1435

GCT GAT AGA GAG AGT TTT CCC CAT CGG CTG CTT TCA TCT TGG CAC ATA      4548
Ala Asp Arg Glu Ser Phe Pro His Arg Leu Leu Ser Ser Trp His Ile
        1440                    1445                    1450

GCC CCA GTC CAC CTG CCG TTG CTG GGG CAA AAC TGC TGG CCA CAC CTA      4596
Ala Pro Val His Leu Pro Leu Leu Gly Gln Asn Cys Trp Pro His Leu
1455                    1460                    1465

TCA GAA GGT TTC AGT GTT TCC CTG TGG TTT AAT GTG GAG TGT ATC CAT      4644
Ser Glu Gly Phe Ser Val Ser Leu Trp Phe Asn Val Glu Cys Ile His
1470                    1475                    1480                    1485

GAA GCT GAG AGT ACT ACA GAA AAA GGA AAG AAG ATA AAG AAA AGA AAC      4692
Glu Ala Glu Ser Thr Thr Glu Lys Gly Lys Lys Ile Lys Lys Arg Asn
                1490                    1495                    1500

AAA TCA TTA ATT TTA CCA GAT AGC AGT TTT GAT GGT ACA GAG AGC GAC      4740
Lys Ser Leu Ile Leu Pro Asp Ser Ser Phe Asp Gly Thr Glu Ser Asp
                1505                    1510                    1515

AGA CCA GAA GGT GCA GAG TAC ATA AAT CCT GGT GAA AGA CTC ATA GAA      4788
Arg Pro Glu Gly Ala Glu Tyr Ile Asn Pro Gly Glu Arg Leu Ile Glu
1520                    1525                    1530

GAA GGA TGT ATT CAT ATA ATT TCA CTG GGA TCC AAA GCG TTG ATG ATC      4836
Glu Gly Cys Ile His Ile Ile Ser Leu Gly Ser Lys Ala Leu Met Ile
1535                    1540                    1545

CAA GTG TGG GCT GAT CCC CAC AAT GCC ACT CTT ATC TTT CGT GTG TGC      4884
Gln Val Trp Ala Asp Pro His Asn Ala Thr Leu Ile Phe Arg Val Cys
1550                    1555                    1560                    1565

ATG GAT TCA AAT GAT GAC ATG AAA GCT GTT TTA CTA GCA CAG GTT GAA      4932
Met Asp Ser Asn Asp Asp Met Lys Ala Val Leu Leu Ala Gln Val Glu
                1570                    1575                    1580

TCA CAG GAG AAT ATT TTC CTC CCA AGC AAA TGG CAA CAT TTA GTA CTC      4980
Ser Gln Glu Asn Ile Phe Leu Pro Ser Lys Trp Gln His Leu Val Leu
        1585                    1590                    1595

ACC TAC TTA CAG CAG CCC CAA GGG AAA AGG AGG ATT CAT GGG AAA ATC      5028
Thr Tyr Leu Gln Gln Pro Gln Gly Lys Arg Arg Ile His Gly Lys Ile
        1600                    1605                    1610

TCC ATA TGG GTC TCT GGA CAG AGG AAG CCT GAT GTT ACT TTG GAT TTT      5076
Ser Ile Trp Val Ser Gly Gln Arg Lys Pro Asp Val Thr Leu Asp Phe
1615                    1620                    1625

ATG CTT CCA AGA AAA ACA AGT TTG TCA TCT GAT AGC AAT AAA ACA TTT      5124
Met Leu Pro Arg Lys Thr Ser Leu Ser Ser Asp Ser Asn Lys Thr Phe
1630                    1635                    1640                    1645

TGC ATG ATT GGC CAT TGT TTA TCA TCC CAA GAA GAG TTT TTG CAG TTG      5172
Cys Met Ile Gly His Cys Leu Ser Ser Gln Glu Glu Phe Leu Gln Leu
                1650                    1655                    1660

GCT GGA AAA TGG GAC CTG GGA AAT TTG CTT CTC TTC AAC GGA GCT AAG      5220
Ala Gly Lys Trp Asp Leu Gly Asn Leu Leu Leu Phe Asn Gly Ala Lys
        1665                    1670                    1675
```

```
GTT GGT TCA CAA GAG GCC TTT TAT CTG TAT GCT TGT GGA CCC AAC CAT    5268
Val Gly Ser Gln Glu Ala Phe Tyr Leu Tyr Ala Cys Gly Pro Asn His
        1680             1685             1690

ACA TCT GTA ATG CCA TGT AAG TAT GGC AAG CCA GTC AAT GAC TAC TCC    5316
Thr Ser Val Met Pro Cys Lys Tyr Gly Lys Pro Val Asn Asp Tyr Ser
        1695             1700             1705

AAA TAT ATT AAT AAA GAA ATT TTG CGA TGT GAA CAA ATC AGA GAA CTT    5364
Lys Tyr Ile Asn Lys Glu Ile Leu Arg Cys Glu Gln Ile Arg Glu Leu
1710             1715             1720             1725

TTT ATG ACC AAG AAA GAT GTG GAT ATT GGT CTC TTA ATT GAA AGT CTT    5412
Phe Met Thr Lys Lys Asp Val Asp Ile Gly Leu Leu Ile Glu Ser Leu
            1730             1735             1740

TCA GTT GTT TAT ACA ACT TAC TGT CCT GCT CAG TAT ACC ATC TAT GAA    5460
Ser Val Val Tyr Thr Thr Tyr Cys Pro Ala Gln Tyr Thr Ile Tyr Glu
            1745             1750             1755

CCA GTG ATT AGA CTT AAA GGT CAA ATG AAA ACC CAA CTC TCT CAA AGA    5508
Pro Val Ile Arg Leu Lys Gly Gln Met Lys Thr Gln Leu Ser Gln Arg
            1760             1765             1770

CCC TTC AGC TCA AAA GAA GTT CAG AGC ATC TTA TTA GAA CCT CAT CAT    5556
Pro Phe Ser Ser Lys Glu Val Gln Ser Ile Leu Leu Glu Pro His His
        1775             1780             1785

CTA AAA AAT CTC CAA CCT ACT GAA TAT AAA ACT ATT CAA GGC ATT CTG    5604
Leu Lys Asn Leu Gln Pro Thr Glu Tyr Lys Thr Ile Gln Gly Ile Leu
1790             1795             1800             1805

CAC GAA ATT GGT GGA ACT GGC ATA TTT GTT TTT CTC TTT GCC AGG GTT    5652
His Glu Ile Gly Gly Thr Gly Ile Phe Val Phe Leu Phe Ala Arg Val
            1810             1815             1820

GTT GAA CTC AGT AGC TGT GAA GAA ACT CAA GCA TTA GCA CTG CGA GTT    5700
Val Glu Leu Ser Ser Cys Glu Glu Thr Gln Ala Leu Ala Leu Arg Val
            1825             1830             1835

ATA CTC TCA TTA ATT AAA TAC AAC CAA CAA AGA GTA CAT GAA TTA GAA    5748
Ile Leu Ser Leu Ile Lys Tyr Asn Gln Gln Arg Val His Glu Leu Glu
            1840             1845             1850

AAT TGT AAT GGA CTT TCT ATG ATT CAT CAG GTG TTG ATC AAA CAA AAA    5796
Asn Cys Asn Gly Leu Ser Met Ile His Gln Val Leu Ile Lys Gln Lys
        1855             1860             1865

TGC ATT GTT GGG TTT TAC ATT TTG AAG ACC CTT CTT GAA GGA TGC TGT    5844
Cys Ile Val Gly Phe Tyr Ile Leu Lys Thr Leu Leu Glu Gly Cys Cys
1870             1875             1880             1885

GGT GAA GAT ATT ATT TAT ATG AAT GAG AAT GGA GAG TTT AAG TTG GAT    5892
Gly Glu Asp Ile Ile Tyr Met Asn Glu Asn Gly Glu Phe Lys Leu Asp
            1890             1895             1900

GTA GAC TCT AAT GCT ATA ATC CAA GAT GTT AAG CTG TTA GAG GAA CTA    5940
Val Asp Ser Asn Ala Ile Ile Gln Asp Val Lys Leu Leu Glu Glu Leu
            1905             1910             1915

TTG CTT GAC TGG AAG ATA TGG AGT AAA GCA GAG CAA GGT GTT TGG GAA    5988
Leu Leu Asp Trp Lys Ile Trp Ser Lys Ala Glu Gln Gly Val Trp Glu
            1920             1925             1930

ACT TTG CTA GCA GCT CTA GAA GTC CTC ATC AGA GCA GAT CAC CAC CAG    6036
Thr Leu Leu Ala Ala Leu Glu Val Leu Ile Arg Ala Asp His His Gln
            1935             1940             1945

CAG ATG TTT AAT ATT AAG CAG TTA TTG AAA GCT CAA GTG GTT CAT CAC    6084
Gln Met Phe Asn Ile Lys Gln Leu Leu Lys Ala Gln Val Val His His
1950             1955             1960             1965

TTT CTA CTG ACT TGT CAG GTT TTG CAG GAA TAC AAA GAG GGG CAA CTC    6132
Phe Leu Leu Thr Cys Gln Val Leu Gln Glu Tyr Lys Glu Gly Gln Leu
        1970             1975             1980

ACA CCC ATG CCC CGA GAG GTT TGT AGA TCA TTT GTG AAA ATT ATA GCA    6180
Thr Pro Met Pro Arg Glu Val Cys Arg Ser Phe Val Lys Ile Ile Ala
        1985             1990             1995
```

-continued

```
GAA GTC CTT GGA TCT CCT CCA GAT TTG GAA TTA TTG ACA ATT ATC TTC     6228
Glu Val Leu Gly Ser Pro Pro Asp Leu Glu Leu Leu Thr Ile Ile Phe
        2000            2005            2010

AAT TTC CTT TTA GCA GTT CAC CCT CCT ACT AAT ACT TAC GTT TGT CAC     6276
Asn Phe Leu Leu Ala Val His Pro Pro Thr Asn Thr Tyr Val Cys His
    2015            2020            2025

AAT CCC ACG AAC TTC TAC TTT TCT TTG CAC ATA GAT GGC AAG ATC TTT     6324
Asn Pro Thr Asn Phe Tyr Phe Ser Leu His Ile Asp Gly Lys Ile Phe
2030            2035            2040            2045

CAG GAG AAA GTG CGG TCA ATC ATG TAC CTG AGG CAT TCC AGC AGT GGA     6372
Gln Glu Lys Val Arg Ser Ile Met Tyr Leu Arg His Ser Ser Ser Gly
            2050            2055            2060

GGA AGG TCC CTT ATG AGC CCT GGA TTT ATG GTA ATA AGC CCA TCT GGT     6420
Gly Arg Ser Leu Met Ser Pro Gly Phe Met Val Ile Ser Pro Ser Gly
        2065            2070            2075

TTT ACT GCT TCA CCA TAT GAA GGA GAG AAT TCC TCT AAT ATT ATT CCA     6468
Phe Thr Ala Ser Pro Tyr Glu Gly Glu Asn Ser Ser Asn Ile Ile Pro
    2080            2085            2090

CAA CAG ATG GCC GCC CAT ATG CTG CGT TCT AGA AGC CTA CCA GCA TTC     6516
Gln Gln Met Ala Ala His Met Leu Arg Ser Arg Ser Leu Pro Ala Phe
2095            2100            2105

CCT ACT TCT TCA CTA CTA ACG CAA TCA CAA AAA CTG ACT GGA AGT TTG     6564
Pro Thr Ser Ser Leu Leu Thr Gln Ser Gln Lys Leu Thr Gly Ser Leu
2110            2115            2120            2125

GGT TGT AGT ATC GAC AGG TTA CAA AAT ATT GCA GAT ACT TAT GTT GCC     6612
Gly Cys Ser Ile Asp Arg Leu Gln Asn Ile Ala Asp Thr Tyr Val Ala
            2130            2135            2140

ACC CAA TCA AAG AAA CAA AAT TCT TTG GGG AGT TCC GAC ACA CTG AAA     6660
Thr Gln Ser Lys Lys Gln Asn Ser Leu Gly Ser Ser Asp Thr Leu Lys
        2145            2150            2155

AAA GGC AAA GAG GAC GCA TTC ATC AGT AGC TGT GAG TCT GCA AAA ACT     6708
Lys Gly Lys Glu Asp Ala Phe Ile Ser Ser Cys Glu Ser Ala Lys Thr
    2160            2165            2170

GTT TGT GAA ATG GAA GCT GTC CTC TCA GCC CAG GTC TCT GTC AGT GAT     6756
Val Cys Glu Met Glu Ala Val Leu Ser Ala Gln Val Ser Val Ser Asp
2175            2180            2185

GTC CCA AAG GGA GTG CTG GGA TTT CCA GTG GTC AAA GCA GAT CAT AAA     6804
Val Pro Lys Gly Val Leu Gly Phe Pro Val Val Lys Ala Asp His Lys
2190            2195            2200            2205

CAG TTG GGA GCA GAA CCC AGG TCA GAA GAT GAC AGT CCT GGG GAT GAG     6852
Gln Leu Gly Ala Glu Pro Arg Ser Glu Asp Asp Ser Pro Gly Asp Glu
            2210            2215            2220

TCC TGC CCA CGC CGA CCT GAT TAC CTA AAG GGA TTG GCC TCC TTC CAG     6900
Ser Cys Pro Arg Arg Pro Asp Tyr Leu Lys Gly Leu Ala Ser Phe Gln
        2225            2230            2235

CGA AGC CAC AGC ACT ATT GCA AGC CTT GGG CTA GCT TTT CCT TCA CAG     6948
Arg Ser His Ser Thr Ile Ala Ser Leu Gly Leu Ala Phe Pro Ser Gln
    2240            2245            2250

AAC GGA TCT GCA GCT GTT GGC CGT TGG CCA AGT CTT GTT GAT AGA AAC     6996
Asn Gly Ser Ala Ala Val Gly Arg Trp Pro Ser Leu Val Asp Arg Asn
2255            2260            2265

ACT GAT GAT TGG GAA AAC TTT GCC TAT TCT CTT GGT TAT GAG CCA AAT     7044
Thr Asp Asp Trp Glu Asn Phe Ala Tyr Ser Leu Gly Tyr Glu Pro Asn
2270            2275            2280            2285

TAC AAC CGA ACT GCA AGT GCT CAC AGT GTA ACT GAA GAC TGT TTG GTA     7092
Tyr Asn Arg Thr Ala Ser Ala His Ser Val Thr Glu Asp Cys Leu Val
            2290            2295            2300

CCT ATA TGC TGT GGA TTA TAT GAA CTC CTA AGT GGG GTT CTT CTT ATC     7140
Pro Ile Cys Cys Gly Leu Tyr Glu Leu Leu Ser Gly Val Leu Leu Ile
        2305            2310            2315
```

```
CTG CCT GAT GTT TTG CTT GAA GAT GTG ATG GAC AAG CTT ATT CAA GCA      7188
Leu Pro Asp Val Leu Leu Glu Asp Val Met Asp Lys Leu Ile Gln Ala
2320                2325                2330

GAT ACA CTT TTG GTC CTC GTT AAC CAC CCA TCA CCA GCT ATA CAA CAA      7236
Asp Thr Leu Leu Val Leu Val Asn His Pro Ser Pro Ala Ile Gln Gln
    2335                2340                2345

GGT GTT ATT AAA CTA TTA GAT GCA TAT TTT GCT AGA GCA TCT AAG GAA      7284
Gly Val Ile Lys Leu Leu Asp Ala Tyr Phe Ala Arg Ala Ser Lys Glu
2350                2355                2360                2365

CAA AAA GAT AAA TTT CTG AAG AAT CGT GGA TTT TCC TTG CTA GCC AAC      7332
Gln Lys Asp Lys Phe Leu Lys Asn Arg Gly Phe Ser Leu Leu Ala Asn
            2370                2375                2380

CAG TTG TAT CTT CAT CGA GGA ACT CAA GAA TTG TTA GAA TGC TTC ATC      7380
Gln Leu Tyr Leu His Arg Gly Thr Gln Glu Leu Leu Glu Cys Phe Ile
        2385                2390                2395

GAA ATG TTC TTT GGT CGA CAT ATT GGC CTT GAT GAA GAA TTT GAT CTG      7428
Glu Met Phe Phe Gly Arg His Ile Gly Leu Asp Glu Glu Phe Asp Leu
    2400                2405                2410

GAA GAT GTG AGA AAC ATG GGA TTG TTT CAG AAG TGG TCT GTC ATT CCT      7476
Glu Asp Val Arg Asn Met Gly Leu Phe Gln Lys Trp Ser Val Ile Pro
2415                2420                2425

ATT CTG GGA CTA ATA GAG ACC TCT CTA TAT GAC AAC ATA CTC TTG CAT      7524
Ile Leu Gly Leu Ile Glu Thr Ser Leu Tyr Asp Asn Ile Leu Leu His
2430                2435                2440                2445

AAT GCT CTT TTA CTT CTT CCC CAT CAT GCA GTA GTT CAA AAG CGG AAA      7572
Asn Ala Leu Leu Leu Leu Pro His His Ala Val Val Gln Lys Arg Lys
            2450                2455                2460

AGC ATT GCT GGT CCT CGA AAA TTT CCC CTT GCT CAA ACT GAA TCG CTT      7620
Ser Ile Ala Gly Pro Arg Lys Phe Pro Leu Ala Gln Thr Glu Ser Leu
        2465                2470                2475

CTG ATG AAA ATG CGT TCA GTG GCA AAT GAT GAG CTT CAT GTG ATG ATG      7668
Leu Met Lys Met Arg Ser Val Ala Asn Asp Glu Leu His Val Met Met
    2480                2485                2490

CAA CGG AGA ATG AGC CAA GAG AAC CCT AGC CAA GCA ACT GAA ACG GAA      7716
Gln Arg Arg Met Ser Gln Glu Asn Pro Ser Gln Ala Thr Glu Thr Glu
2495                2500                2505

CTT GCG CAG AGA CTA CAG AGG CTC ACT GTT TTA GCA GTC AAC AGG ATT      7764
Leu Ala Gln Arg Leu Gln Arg Leu Thr Val Leu Ala Val Asn Arg Ile
2510                2515                2520                2525

ATT TAT CAA GAA TTT AAT TCA GAC ATT ATT GAC ATT TTG AGA ACT CCA      7812
Ile Tyr Gln Glu Phe Asn Ser Asp Ile Ile Asp Ile Leu Arg Thr Pro
            2530                2535                2540

GAA AAT GTA ACT CAA AGC AAG ACC TCA GTT TTC CAG ACC GAA ATT TCT      7860
Glu Asn Val Thr Gln Ser Lys Thr Ser Val Phe Gln Thr Glu Ile Ser
        2545                2550                2555

GAG GAA AAT ATT CAT CAT GAA CAG TCT TCT GTT TTC AAT CCA TTT CAG      7908
Glu Glu Asn Ile His His Glu Gln Ser Ser Val Phe Asn Pro Phe Gln
    2560                2565                2570

AAA GAA ATT TTT ACA TAT CTG GTA GAA GGA TTC AAA GTA TCT ATT GGT      7956
Lys Glu Ile Phe Thr Tyr Leu Val Glu Gly Phe Lys Val Ser Ile Gly
2575                2580                2585

TCA AGT AAA GCC AGT GGT TCC AAG CAG CAA TGG ACT AAA ATT CTG TGG      8004
Ser Ser Lys Ala Ser Gly Ser Lys Gln Gln Trp Thr Lys Ile Leu Trp
2590                2595                2600                2605

TCT TGT AAG GAG ACC TTC CGA ATG CAG CTT GGG AGA CTA CTA GTG CAT      8052
Ser Cys Lys Glu Thr Phe Arg Met Gln Leu Gly Arg Leu Leu Val His
            2610                2615                2620

ATT TTG TCG CCA GCC CAC GCT GCA CAA GAG AGA AAG CAA ATT TTT GAA      8100
Ile Leu Ser Pro Ala His Ala Ala Gln Glu Arg Lys Gln Ile Phe Glu
        2625                2630                2635
```

```
ATA GTT CAT GAA CCA AAT CAT CAG GAA ATA CTA CGA GAC TGT CTC AGC      8148
Ile Val His Glu Pro Asn His Gln Glu Ile Leu Arg Asp Cys Leu Ser
        2640                2645                2650

CCA TCC CTA CAA CAT GGA GCC AAG TTA GTT TTG TAT TTG TCA GAG TTG      8196
Pro Ser Leu Gln His Gly Ala Lys Leu Val Leu Tyr Leu Ser Glu Leu
        2655                2660                2665

ATA CAT AAT CAC CAA GGT GAA TTG ACT GAA GAA GAG CTA GGC ACA GCA      8244
Ile His Asn His Gln Gly Glu Leu Thr Glu Glu Glu Leu Gly Thr Ala
2670                2675                2680                2685

GAA CTG CTT ATG AAT GCT TTG AAG TTA TGT GGT CAC AAG TGC ATC CCT      8292
Glu Leu Leu Met Asn Ala Leu Lys Leu Cys Gly His Lys Cys Ile Pro
                2690                2695                2700

CCC AGT GCA TCA ACA AAA GCA GAC CTT ATT AAA ATG ATC AAA GAG GAA      8340
Pro Ser Ala Ser Thr Lys Ala Asp Leu Ile Lys Met Ile Lys Glu Glu
            2705                2710                2715

CAA AAG AAA TAT GAA ACT GAA GAA GGA GTG AAT AAA GCT GCT TGG CAG      8388
Gln Lys Lys Tyr Glu Thr Glu Glu Gly Val Asn Lys Ala Ala Trp Gln
        2720                2725                2730

AAA ACA GTT AAC AAT AAT CAA CAA AGT CTC TTT CAG CGT CTG GAT TCA      8436
Lys Thr Val Asn Asn Asn Gln Gln Ser Leu Phe Gln Arg Leu Asp Ser
        2735                2740                2745

AAA TCA AAG GAT ATA TCT AAA ATA GCT GCA GAT ATC ACC CAG GCA GTG      8484
Lys Ser Lys Asp Ile Ser Lys Ile Ala Ala Asp Ile Thr Gln Ala Val
2750                2755                2760                2765

TCT CTC TCC CAA GGA AAT GAG AGA AAA AAG GTG ATC CAG CAT ATT AGA      8532
Ser Leu Ser Gln Gly Asn Glu Arg Lys Lys Val Ile Gln His Ile Arg
                2770                2775                2780

GGA ATG TAT AAA GTA GAT TTG AGT GCC AGC AGA CAT TGG CAG GAA CTT      8580
Gly Met Tyr Lys Val Asp Leu Ser Ala Ser Arg His Trp Gln Glu Leu
        2785                2790                2795

ATT CAG CAG CTG ACA CAT GAT AGA GCA GTA TGG TAT GAC CCC ATC TAC      8628
Ile Gln Gln Leu Thr His Asp Arg Ala Val Trp Tyr Asp Pro Ile Tyr
            2800                2805                2810

TAT CCA ACC TCA TGG CAG TTG GAT CCA ACA GAA GGG CCA AAT CGA GAG      8676
Tyr Pro Thr Ser Trp Gln Leu Asp Pro Thr Glu Gly Pro Asn Arg Glu
        2815                2820                2825

AGG AGA CGT TTA CAG AGA TGT TAT TTA ACT ATT CCA AAT AAG TAT CTC      8724
Arg Arg Arg Leu Gln Arg Cys Tyr Leu Thr Ile Pro Asn Lys Tyr Leu
2830                2835                2840                2845

CTT AGG GAT AGA CAG AAA TCA GAA GAT GTT GTC AAA CCA CCA CTC TCT      8772
Leu Arg Asp Arg Gln Lys Ser Glu Asp Val Val Lys Pro Pro Leu Ser
                2850                2855                2860

TAC CTG TTT GAA GAC AAA ACT CAT TCT TCT TTC TCT ACT GTC AAA          8820
Tyr Leu Phe Glu Asp Lys Thr His Ser Ser Phe Ser Ser Thr Val Lys
        2865                2870                2875

GAC AAA GCT GCA AGT GAA TCT ATA AGA GTG AAT CGA AGA TGC ATC AGT      8868
Asp Lys Ala Ala Ser Glu Ser Ile Arg Val Asn Arg Arg Cys Ile Ser
            2880                2885                2890

GTT GCA CCA TCT AGA GAG ACA GCT GGT GAA TTG TTA CTA GGT AAA TGT      8916
Val Ala Pro Ser Arg Glu Thr Ala Gly Glu Leu Leu Leu Gly Lys Cys
        2895                2900                2905

GGA ATG TAT TTT GTG GAA GAT AAT GCT TCT GAT ACA GTT GAA AGT TCG      8964
Gly Met Tyr Phe Val Glu Asp Asn Ala Ser Asp Thr Val Glu Ser Ser
2910                2915                2920                2925

AGC CTT CAG GGA GAG TTG GAA CCA GCA TCA TTT TCC TGG ACA TAT GAA      9012
Ser Leu Gln Gly Glu Leu Glu Pro Ala Ser Phe Ser Trp Thr Tyr Glu
                2930                2935                2940

GAA ATT AAA GAA GTT CAC AAG CGT TGG TGG CAA TTG AGA GAT AAT GCT      9060
Glu Ile Lys Glu Val His Lys Arg Trp Trp Gln Leu Arg Asp Asn Ala
        2945                2950                2955
```

```
GTA GAA ATC TTT CTA ACA AAT GGC AGA ACA CTC CTG TTG GCA TTT GAT              9108
Val Glu Ile Phe Leu Thr Asn Gly Arg Thr Leu Leu Leu Ala Phe Asp
            2960                2965                2970

AAC ACC AAG GTT CGT GAT GAT GTA TAC CAC AAT ATA CTC ACA AAT AAC              9156
Asn Thr Lys Val Arg Asp Asp Val Tyr His Asn Ile Leu Thr Asn Asn
    2975                2980                2985

CTC CCT AAT CTT CTG GAA TAT GGT AAC ATC ACC GCT CTG ACA AAT TTA              9204
Leu Pro Asn Leu Leu Glu Tyr Gly Asn Ile Thr Ala Leu Thr Asn Leu
2990                2995                3000                3005

TGG TAT ACT GGG CAA ATT ACT AAT TTT GAA TAT TTG ACT CAC TTA AAC              9252
Trp Tyr Thr Gly Gln Ile Thr Asn Phe Glu Tyr Leu Thr His Leu Asn
            3010                3015                3020

AAA CAT GCT GGC CGA TCC TTC AAT GAT CTC ATG CAG TAT CCT GTG TTC              9300
Lys His Ala Gly Arg Ser Phe Asn Asp Leu Met Gln Tyr Pro Val Phe
    3025                3030                3035

CCA TTT ATA CTT GCT GAC TAC GTT AGT GAG ACA CTT GAC CTC AAT GAT              9348
Pro Phe Ile Leu Ala Asp Tyr Val Ser Glu Thr Leu Asp Leu Asn Asp
3040                3045                3050

CTG TTG ATA TAC AGA AAT CTC TCT AAA CCT ATA GCT GTT CAG TAT AAA              9396
Leu Leu Ile Tyr Arg Asn Leu Ser Lys Pro Ile Ala Val Gln Tyr Lys
            3055                3060                3065

GAA AAA GAA GAT CGT TAT GTG GAC ACA TAC AAG TAC TTG GAG GAA GAG              9444
Glu Lys Glu Asp Arg Tyr Val Asp Thr Tyr Lys Tyr Leu Glu Glu Glu
3070                3075                3080                3085

TAC CGC AAA GGA GCC AGA GAA GAT GAC CCC ATG CCT CCC GTG CAG CCC              9492
Tyr Arg Lys Gly Ala Arg Glu Asp Asp Pro Met Pro Pro Val Gln Pro
            3090                3095                3100

TAT CAC TAT GGC TCC CAC TAT TCC AAT AGC GGC ACT GTG CTT CAC TTC              9540
Tyr His Tyr Gly Ser His Tyr Ser Asn Ser Gly Thr Val Leu His Phe
    3105                3110                3115

CTG GTC AGG ATG CCT CCT TTC ACT AAA ATG TTT TTA GCC TAT CAA GAT              9588
Leu Val Arg Met Pro Pro Phe Thr Lys Met Phe Leu Ala Tyr Gln Asp
            3120                3125                3130

CAA AGT TTT GAC ATT CCA GAC AGA ACT TTT CAT TCT ACA AAT ACA ACT              9636
Gln Ser Phe Asp Ile Pro Asp Arg Thr Phe His Ser Thr Asn Thr Thr
    3135                3140                3145

TGG CGA CTC TCA TCT TTT GAA TCT ATG ACT GAT GTG AAA GAA CTT ATC              9684
Trp Arg Leu Ser Ser Phe Glu Ser Met Thr Asp Val Lys Glu Leu Ile
3150                3155                3160                3165

CCA GAG TTT TTC TAT CTT CCA GAG TTC CTA GTT AAC CGT GAA GGT TTT              9732
Pro Glu Phe Phe Tyr Leu Pro Glu Phe Leu Val Asn Arg Glu Gly Phe
            3170                3175                3180

GAT TTT GGT GTG CGT CAG AAT GGT GAA CGG GTT AAT CAC GTC AAC CTT              9780
Asp Phe Gly Val Arg Gln Asn Gly Glu Arg Val Asn His Val Asn Leu
    3185                3190                3195

CCC CCT TGG GCG CGT AAT GAT CCT CGT CTT TTT ATC CTC ATC CAT CGG              9828
Pro Pro Trp Ala Arg Asn Asp Pro Arg Leu Phe Ile Leu Ile His Arg
            3200                3205                3210

CAG GCT CTA GAG TCT GAC TAC GTG TCG CAG AAC ATC TGT CAG TGG ATT              9876
Gln Ala Leu Glu Ser Asp Tyr Val Ser Gln Asn Ile Cys Gln Trp Ile
    3215                3220                3225

GAC TTG GTG TTT GGG TAT AAG CAA AAG GGG AAG GCT TCT GTT CAA GCG              9924
Asp Leu Val Phe Gly Tyr Lys Gln Lys Gly Lys Ala Ser Val Gln Ala
3230                3235                3240                3245

ATC AAT GTT TTT CAT CCT GCT ACA TAT TTT GGA ATG GAT GTC TCT GCA              9972
Ile Asn Val Phe His Pro Ala Thr Tyr Phe Gly Met Asp Val Ser Ala
            3250                3255                3260

GTT GAA GAT CCA GTT CAG AGA CGA GCG CTA GAA ACC ATG ATA AAA ACC             10020
Val Glu Asp Pro Val Gln Arg Arg Ala Leu Glu Thr Met Ile Lys Thr
    3265                3270                3275
```

```
TAC GGG CAG ACT CCC CGT CAG CTG TTC CAC ATG GCC CAT GTG AGC AGA    10068
Tyr Gly Gln Thr Pro Arg Gln Leu Phe His Met Ala His Val Ser Arg
        3280                3285                3290

CCT GGA GCC AAG CTC AAT ATT GAA GGA GAG CTT CCA GCT GCT GTG GGG    10116
Pro Gly Ala Lys Leu Asn Ile Glu Gly Glu Leu Pro Ala Ala Val Gly
3295                3300                3305

TTG CTA GTG CAG TTT GCT TTC AGG GAG ACC CGA GAA CAG GTC AAA GAA    10164
Leu Leu Val Gln Phe Ala Phe Arg Glu Thr Arg Glu Gln Val Lys Glu
3310                3315                3320                3325

ATC ACC TAT CCG AGT CCT TTG TCA TGG ATA AAA GGC TTG AAA TGG GGG    10212
Ile Thr Tyr Pro Ser Pro Leu Ser Trp Ile Lys Gly Leu Lys Trp Gly
        3330                3335                3340

GAA TAC GTG GGT TCC CCC AGT GCT CCA GTA CCT GTG GTC TGC TTC AGC    10260
Glu Tyr Val Gly Ser Pro Ser Ala Pro Val Pro Val Val Cys Phe Ser
            3345                3350                3355

CAG CCC CAC GGA GAA AGA TTT GGC TCT CTC CAG GCT CTG CCC ACC AGA    10308
Gln Pro His Gly Glu Arg Phe Gly Ser Leu Gln Ala Leu Pro Thr Arg
        3360                3365                3370

GCA ATC TGT GGT TTG TCA CGG AAT TTC TGT CTT GTG ATG ACA TAT AGC    10356
Ala Ile Cys Gly Leu Ser Arg Asn Phe Cys Leu Val Met Thr Tyr Ser
        3375                3380                3385

AAG GAA CAA GGT GTG AGA AGC ATG AAC AGT ACG GAC ATT CAG TGG TCA    10404
Lys Glu Gln Gly Val Arg Ser Met Asn Ser Thr Asp Ile Gln Trp Ser
3390                3395                3400                3405

GCC ATC CTG AGC TGG GGA TAT GCT GAT AAT ATT TTA AGG TTG AAG AGT    10452
Ala Ile Leu Ser Trp Gly Tyr Ala Asp Asn Ile Leu Arg Leu Lys Ser
        3410                3415                3420

AAA CAA AGT GAG CCT CCA GTA AAC TTT ATT CAA AGT CAA CAG TAC        10500
Lys Gln Ser Glu Pro Pro Val Asn Phe Ile Gln Ser Gln Gln Tyr
        3425                3430                3435

CAG GTG ACT AGT TGT GCT TGG GTG CCT GAC AGT TGC CAG CTG TTT ACT    10548
Gln Val Thr Ser Cys Ala Trp Val Pro Asp Ser Cys Gln Leu Phe Thr
        3440                3445                3450

GGA AGC AAA TGC GGT GTC ATC ACA GCC TAC ACA AAC AGA TTT ACA AGC    10596
Gly Ser Lys Cys Gly Val Ile Thr Ala Tyr Thr Asn Arg Phe Thr Ser
        3455                3460                3465

AGC ACG CCA TCA GAA ATA GAA ATG GAG ACT CAA ATA CAT CTC TAT GGT    10644
Ser Thr Pro Ser Glu Ile Glu Met Glu Thr Gln Ile His Leu Tyr Gly
3470                3475                3480                3485

CAC ACA GAA GAG ATA ACC AGC TTA TTT GTT TGC AAA CCA TAC AGT ATA    10692
His Thr Glu Glu Ile Thr Ser Leu Phe Val Cys Lys Pro Tyr Ser Ile
            3490                3495                3500

CTG ATA AGT GTG AGC AGA GAC GGA ACC TGC ATC ATA TGG GAT TTA AAC    10740
Leu Ile Ser Val Ser Arg Asp Gly Thr Cys Ile Ile Trp Asp Leu Asn
        3505                3510                3515

AGG TTA TGC TAT GTA CAA AGT CTG GCG GGA CAC AAA AGC CCT GTC ACA    10788
Arg Leu Cys Tyr Val Gln Ser Leu Ala Gly His Lys Ser Pro Val Thr
        3520                3525                3530

GCT GTC TCT GCC AGT GAA ACC TCA GGT GAT ATT GCT ACT GTG TGT GAT    10836
Ala Val Ser Ala Ser Glu Thr Ser Gly Asp Ile Ala Thr Val Cys Asp
        3535                3540                3545

TCA GCT GGC GGA GGC AGT GAC CTC AGA CTC TGG ACG GTG AAC GGG GAT    10884
Ser Ala Gly Gly Gly Ser Asp Leu Arg Leu Trp Thr Val Asn Gly Asp
3550                3555                3560                3565

CTC GTT GGA CAT GTC CAC TGC AGG GAG ATC ATC TGT TCC GTG GCT TTC    10932
Leu Val Gly His Val His Cys Arg Glu Ile Ile Cys Ser Val Ala Phe
        3570                3575                3580

TCC AAC CAG CCT GAG GGA GTA TCT ATC AAT GTA ATC GCT GGG GGA TTA    10980
Ser Asn Gln Pro Glu Gly Val Ser Ile Asn Val Ile Ala Gly Gly Leu
        3585                3590                3595
```

```
GAA AAT GGA ATT GTT AGG TTA TGG AGC ACA TGG GAC TTA AAG CCT GTG    11028
Glu Asn Gly Ile Val Arg Leu Trp Ser Thr Trp Asp Leu Lys Pro Val
        3600                3605                3610

AGA GAA ATT ACA TTT CCC AAA TCA AAT AAG CCC ATC ATC AGC CTT ACA    11076
Arg Glu Ile Thr Phe Pro Lys Ser Asn Lys Pro Ile Ile Ser Leu Thr
    3615                3620                3625

TTT TCT TGT GAT GGC CAC CAT TTG TAC ACA GCA AAC AGT GAT GGG ACC    11124
Phe Ser Cys Asp Gly His His Leu Tyr Thr Ala Asn Ser Asp Gly Thr
3630                3635                3640                3645

GTG ATT GCC TGG TGT CGG AAG GAC CAG CAC CGC TTG AAA CAG CCA ATG    11172
Val Ile Ala Trp Cys Arg Lys Asp Gln His Arg Leu Lys Gln Pro Met
            3650                3655                3660

TTC TAT TCC TTC CTT AGC AGC TAT GCA GCC GGG TGA ATGCGAATGA         11218
Phe Tyr Ser Phe Leu Ser Ser Tyr Ala Ala Gly  *
        3665                3670

ACTTCATGTT CTCCAAAGCA CTTTAACTCC AAACTAGATT TGTTGACTTC ACCAGTTTTA  11278
GGAGGTTGAA CCTAAAGAAA TGGATGACTG GACAAACCAT CCAAATAATG ATAAAGTCTA  11338
TTCATCTGCA CAAAATTCTG AAGAGTCACA TGATCCTAAG AGGAAAGTTC TGTTCTATTT  11398
TAGTGATAAT CTGGAAGATT GTGTCAATAT GCACTAGCCA ACAAGTTTTA AGCCTCGCAT  11458
GGTACATTAA AATGATATTC TTAAAATTTT TTCCCACCAA GGTATTCCAA AGAAAATATT  11518
AAGGTCTCCC CTTTTTCTAT GATTCCAAAA GGACCAGTAG AATTTAAATT GGTTGGTTGA  11578
TGTTTATATA AAACACACTA AAATTATATT TTAAAAGTTT ATGCCTGAAA TACTCCTCCC  11638
ACCACACACA CATGCTCCAA AAGAGGAAAG AAAAAAAGAT AATTTTTAGG ACTTGATAAT  11698
TGCTTTCTTT GAGAAGCAAA TTATTCAGTA GGTGCCTCTG TACCAAATAT TTTATGGAAT  11758
ATCTAAATAC TAAAATAAAC TATGAATGAA TCTCAAAATT AGGCAGTTTT TGCCAGTTGC  11818
TTTCTTAGCT CAAAGGAGAA CCAGAATTTT TTTGACAGCC ACAAACAAGA ATACAGGTAT  11878
CTTGGATTTC AGACACATTC TGTTTCTTCA TAAAAATTTT ACTTAAAATC TGTAACGCTA  11938
GATATTGACT ATCCTTAGTT GAGTCACTGA GGTTTAAACA CAATGGTAAG TCTTAAAGTC  11998
TGCTATTTAC AGAGCATTGA ATCTGTACCA ATTTGCAATA GAAAGCCTTC AGTATGCAAG  12058
AAGTTTGCAT GGGTATTAAG AACACAGCCT AAATAAGGCA TTTGATTAAT CTGCAGGAAG  12118
AATTTTCTTC CCCAAAACAG AATTATAAAA GCTTACTTTA AACAGGAGGC AGAATAATTC  12178
TTTTAGGAAA CCATTTCATT CTGTTTCTAC TAACCTATAC CATCTGA               12225

(2) INFORMATION FOR SEQ ID NO:12:

(i) SEQUENCE CHARACTERISTICS:
        (A) LENGTH: 3672 amino acids
        (B) TYPE: amino acid
        (D) TOPOLOGY: unknown (ii) MOLECULE TYPE: protein (xi) SEQUENCE DESCRIPTION: SEQ ID NO:12:

Met Ser Thr Asp Ser Asn Ser Leu Ala Arg Glu Phe Leu Thr Asp Val
  1               5                  10                  15

Asn Arg Leu Cys Asn Ala Val Val Gln Arg Val Glu Ala Arg Glu Glu
                 20                  25                  30

Glu Glu Glu Glu Thr His Met Ala Thr Leu Gly Gln Tyr Leu Val His
             35                  40                  45

Gly Arg Gly Phe Leu Leu Leu Thr Lys Leu Asn Ser Ile Ile Asp Gln
         50                  55                  60

Ala Leu Thr Cys Arg Glu Glu Leu Leu Thr Leu Leu Leu Ser Leu Leu
```

```
         65                  70                  75                  80
Pro Leu Val Trp Lys Ile Pro Val Gln Glu Glu Lys Ala Thr Asp Phe
                    85                  90                  95
Asn Leu Pro Leu Ser Ala Asp Ile Ile Leu Thr Lys Glu Lys Asn Ser
                100                 105                 110
Ser Ser Gln Arg Ser Thr Gln Glu Lys Leu His Leu Glu Gly Ser Ala
                115                 120                 125
Leu Ser Ser Gln Val Ser Ala Lys Val Asn Val Phe Arg Lys Ser Arg
            130                 135                 140
Arg Gln Arg Lys Ile Thr His Arg Tyr Ser Val Arg Asp Ala Arg Lys
145                 150                 155                 160
Thr Gln Leu Ser Thr Ser Asp Ser Glu Ala Asn Ser Asp Glu Lys Gly
                165                 170                 175
Ile Ala Met Asn Lys His Arg Arg Pro His Leu Leu His His Phe Leu
                180                 185                 190
Thr Ser Phe Pro Lys Gln Asp His Pro Lys Ala Lys Leu Asp Arg Leu
            195                 200                 205
Ala Thr Lys Glu Gln Thr Pro Pro Asp Ala Met Ala Leu Glu Asn Ser
        210                 215                 220
Arg Glu Ile Ile Pro Arg Gln Gly Ser Asn Thr Asp Ile Leu Ser Glu
225                 230                 235                 240
Pro Ala Ala Leu Ser Val Ile Ser Asn Met Asn Asn Ser Pro Phe Asp
                245                 250                 255
Leu Cys His Val Leu Leu Ser Leu Leu Glu Lys Val Cys Lys Phe Asp
                260                 265                 270
Val Thr Leu Asn His Asn Ser Pro Leu Ala Ala Ser Val Val Pro Thr
            275                 280                 285
Leu Thr Glu Phe Leu Ala Gly Phe Gly Asp Cys Cys Ser Leu Ser Asp
        290                 295                 300
Asn Leu Glu Ser Arg Val Val Ser Ala Gly Trp Thr Glu Glu Pro Val
305                 310                 315                 320
Ala Leu Ile Gln Arg Met Leu Phe Arg Thr Val Leu His Leu Leu Ser
                325                 330                 335
Val Asp Val Ser Thr Ala Glu Met Met Pro Glu Asn Leu Arg Lys Asn
            340                 345                 350
Leu Thr Glu Leu Leu Arg Ala Ala Leu Lys Ile Arg Ile Cys Leu Glu
        355                 360                 365
Lys Gln Pro Asp Pro Phe Ala Pro Arg Gln Lys Lys Thr Leu Gln Glu
    370                 375                 380
Val Gln Glu Asp Phe Val Phe Ser Lys Tyr Arg His Arg Ala Leu Leu
385                 390                 395                 400
Leu Pro Glu Leu Leu Glu Gly Val Leu Gln Ile Leu Ile Cys Cys Leu
                405                 410                 415
Gln Ser Ala Ala Ser Asn Pro Phe Tyr Phe Ser Gln Ala Met Asp Leu
            420                 425                 430
Val Gln Glu Phe Ile Gln His His Gly Phe Asn Leu Phe Glu Thr Ala
        435                 440                 445
Val Leu Gln Met Glu Trp Leu Val Leu Arg Asp Gly Val Pro Pro Glu
    450                 455                 460
Ala Ser Glu His Leu Lys Ala Leu Ile Asn Ser Val Met Lys Ile Met
465                 470                 475                 480
Ser Thr Val Lys Lys Val Lys Ser Glu Gln Leu His His Ser Met Cys
                485                 490                 495
```

-continued

Thr Arg Lys Arg His Arg Arg Cys Glu Tyr Ser His Phe Met His His
            500                 505                 510

His Arg Asp Leu Ser Gly Leu Leu Val Ser Ala Phe Lys Asn Gln Val
            515                 520                 525

Ser Lys Asn Pro Phe Glu Glu Thr Ala Asp Gly Asp Val Tyr Tyr Pro
            530                 535                 540

Glu Arg Cys Cys Cys Ile Ala Val Cys Ala His Gln Cys Leu Arg Leu
545                 550                 555                 560

Leu Gln Gln Ala Ser Leu Ser Ser Thr Cys Val Gln Ile Leu Ser Gly
                565                 570                 575

Val His Asn Ile Gly Ile Cys Cys Cys Met Asp Pro Lys Ser Val Ile
            580                 585                 590

Ile Pro Leu Leu His Ala Phe Lys Leu Pro Ala Leu Lys Asn Phe Gln
            595                 600                 605

Gln His Ile Leu Asn Ile Leu Asn Lys Leu Ile Leu Asp Gln Leu Gly
            610                 615                 620

Gly Ala Glu Ile Ser Pro Lys Ile Lys Lys Ala Ala Cys Asn Ile Cys
625                 630                 635                 640

Thr Val Asp Ser Asp Gln Leu Ala Gln Leu Glu Glu Thr Leu Gln Gly
                645                 650                 655

Asn Leu Cys Asp Ala Glu Leu Ser Ser Ser Leu Ser Ser Pro Ser Tyr
            660                 665                 670

Arg Phe Gln Gly Ile Leu Pro Ser Ser Gly Ser Glu Asp Leu Leu Trp
            675                 680                 685

Lys Trp Asp Ala Leu Lys Ala Tyr Gln Asn Phe Val Phe Glu Glu Asp
690                 695                 700

Arg Leu His Ser Ile Gln Ile Ala Asn His Ile Cys Asn Leu Ile Gln
705                 710                 715                 720

Lys Gly Asn Ile Val Val Gln Trp Lys Leu Tyr Asn Tyr Ile Phe Asn
                725                 730                 735

Pro Val Leu Gln Arg Gly Val Glu Leu Ala His His Cys Gln His Leu
            740                 745                 750

Ser Val Thr Ser Ala Gln Ser His Val Cys Ser His His Asn Gln Cys
            755                 760                 765

Leu Pro Gln Asp Val Leu Gln Ile Tyr Val Lys Thr Leu Pro Ile Leu
            770                 775                 780

Leu Lys Ser Arg Val Ile Arg Asp Leu Phe Leu Ser Cys Asn Gly Val
785                 790                 795                 800

Ser Gln Ile Ile Glu Leu Asn Cys Leu Asn Gly Ile Arg Ser His Ser
                805                 810                 815

Leu Lys Ala Phe Glu Thr Leu Ile Ile Ser Leu Gly Glu Gln Gln Lys
            820                 825                 830

Asp Ala Ser Val Pro Asp Ile Asp Gly Ile Asp Ile Glu Gln Lys Glu
            835                 840                 845

Leu Ser Ser Val His Val Gly Thr Ser Phe His His Gln Gln Ala Tyr
            850                 855                 860

Ser Asp Ser Pro Gln Ser Leu Ser Lys Phe Tyr Ala Gly Leu Lys Glu
865                 870                 875                 880

Ala Tyr Pro Lys Arg Arg Lys Thr Val Asn Gln Asp Val His Ile Asn
                885                 890                 895

Thr Ile Asn Leu Phe Leu Cys Val Ala Phe Leu Cys Val Ser Lys Glu
            900                 905                 910

Ala Glu Ser Asp Arg Glu Ser Ala Asn Asp Ser Glu Asp Thr Ser Gly
            915                 920                 925

```
Tyr Asp Ser Thr Ala Ser Glu Pro Leu Ser His Met Leu Pro Cys Ile
    930                 935                 940

Ser Leu Glu Ser Leu Val Leu Pro Ser Pro Glu His Met His Gln Ala
945                 950                 955                 960

Ala Asp Ile Trp Ser Met Cys Arg Trp Ile Tyr Met Leu Ser Ser Val
                965                 970                 975

Phe Gln Lys Gln Phe Tyr Arg Leu Gly Gly Phe Arg Val Cys His Lys
            980                 985                 990

Leu Ile Phe Met Ile Ile Gln Lys Leu Phe Arg Ser His Lys Glu Glu
        995                 1000                1005

Gln Gly Lys Lys Glu Gly Asp Thr Ser Val Asn Glu Asn Gln Asp Leu
    1010                1015                1020

Asn Arg Ile Ser Gln Pro Lys Arg Thr Met Lys Glu Asp Leu Leu Ser
1025                1030                1035                1040

Leu Ala Ile Lys Ser Asp Pro Ile Pro Ser Glu Leu Gly Ser Leu Lys
                1045                1050                1055

Lys Ser Ala Asp Ser Leu Gly Lys Leu Glu Leu Gln His Ile Ser Ser
            1060                1065                1070

Ile Asn Val Glu Glu Val Ser Ala Thr Glu Ala Ala Pro Glu Glu Ala
        1075                1080                1085

Lys Leu Phe Thr Ser Gln Glu Ser Glu Thr Ser Leu Gln Ser Ile Arg
    1090                1095                1100

Leu Leu Glu Ala Leu Leu Ala Ile Cys Leu His Gly Ala Arg Thr Ser
1105                1110                1115                1120

Gln Gln Lys Met Glu Leu Glu Leu Pro Asn Gln Asn Leu Ser Val Glu
                1125                1130                1135

Ser Ile Leu Phe Glu Met Arg Asp His Leu Ser Gln Ser Lys Val Ile
            1140                1145                1150

Glu Thr Gln Leu Ala Lys Pro Leu Phe Asp Ala Leu Leu Arg Val Ala
        1155                1160                1165

Leu Gly Asn Tyr Ser Ala Asp Phe Glu His Asn Asp Ala Met Thr Glu
    1170                1175                1180

Lys Ser His Gln Ser Ala Glu Glu Leu Ser Ser Gln Pro Gly Asp Phe
1185                1190                1195                1200

Ser Glu Glu Ala Glu Asp Ser Gln Cys Cys Ser Phe Lys Leu Leu Val
                1205                1210                1215

Glu Glu Glu Gly Tyr Glu Ala Asp Ser Glu Ser Asn Pro Glu Asp Gly
            1220                1225                1230

Glu Thr Gln Asp Asp Gly Val Asp Leu Lys Ser Glu Thr Glu Gly Phe
        1235                1240                1245

Ser Ala Ser Ser Ser Pro Asn Asp Leu Leu Glu Asn Leu Thr Gln Gly
    1250                1255                1260

Glu Ile Ile Tyr Pro Glu Ile Cys Met Leu Glu Leu Asn Leu Leu Ser
1265                1270                1275                1280

Ala Ser Lys Ala Lys Leu Asp Val Leu Ala His Val Phe Glu Ser Phe
                1285                1290                1295

Leu Lys Ile Ile Arg Gln Lys Glu Lys Asn Val Phe Leu Leu Met Gln
            1300                1305                1310

Gln Gly Thr Val Lys Asn Leu Leu Gly Gly Phe Leu Ser Ile Leu Thr
        1315                1320                1325

Gln Asp Asp Ser Asp Phe Gln Ala Cys Gln Arg Val Leu Val Asp Leu
    1330                1335                1340

Leu Val Ser Leu Met Ser Ser Arg Thr Cys Ser Glu Glu Leu Thr Leu
```

```
                 1345                1350                1355                1360

Leu Leu Arg Ile Phe Leu Glu Lys Ser Pro Cys Thr Lys Ile Leu Leu
                 1365                1370                1375

Leu Gly Ile Leu Lys Ile Ile Glu Ser Asp Thr Thr Met Ser Pro Ser
                 1380                1385                1390

Gln Tyr Leu Thr Phe Pro Leu Leu His Ala Pro Asn Leu Ser Asn Gly
                 1395                1400                1405

Val Ser Ser Gln Lys Tyr Pro Gly Ile Leu Asn Ser Lys Ala Met Gly
                 1410                1415                1420

Leu Leu Arg Arg Ala Arg Val Ser Arg Ser Lys Lys Glu Ala Asp Arg
1425                 1430                1435                1440

Glu Ser Phe Pro His Arg Leu Leu Ser Ser Trp His Ile Ala Pro Val
                 1445                1450                1455

His Leu Pro Leu Leu Gly Gln Asn Cys Trp Pro His Leu Ser Glu Gly
                 1460                1465                1470

Phe Ser Val Ser Leu Trp Phe Asn Val Glu Cys Ile His Glu Ala Glu
                 1475                1480                1485

Ser Thr Thr Glu Lys Gly Lys Lys Ile Lys Lys Arg Asn Lys Ser Leu
                 1490                1495                1500

Ile Leu Pro Asp Ser Ser Phe Asp Gly Thr Glu Ser Asp Arg Pro Glu
1505                 1510                1515                1520

Gly Ala Glu Tyr Ile Asn Pro Gly Glu Arg Leu Ile Glu Glu Gly Cys
                 1525                1530                1535

Ile His Ile Ile Ser Leu Gly Ser Lys Ala Leu Met Ile Gln Val Trp
                 1540                1545                1550

Ala Asp Pro His Asn Ala Thr Leu Ile Phe Arg Val Cys Met Asp Ser
                 1555                1560                1565

Asn Asp Asp Met Lys Ala Val Leu Leu Ala Gln Val Glu Ser Gln Glu
                 1570                1575                1580

Asn Ile Phe Leu Pro Ser Lys Trp Gln His Leu Val Leu Thr Tyr Leu
1585                 1590                1595                1600

Gln Gln Pro Gln Gly Lys Arg Arg Ile His Gly Lys Ile Ser Ile Trp
                 1605                1610                1615

Val Ser Gly Gln Arg Lys Pro Asp Val Thr Leu Asp Phe Met Leu Pro
                 1620                1625                1630

Arg Lys Thr Ser Leu Ser Ser Asp Ser Asn Lys Thr Phe Cys Met Ile
                 1635                1640                1645

Gly His Cys Leu Ser Ser Gln Glu Glu Phe Leu Gln Leu Ala Gly Lys
                 1650                1655                1660

Trp Asp Leu Gly Asn Leu Leu Leu Phe Asn Gly Ala Lys Val Gly Ser
1665                 1670                1675                1680

Gln Glu Ala Phe Tyr Leu Tyr Ala Cys Gly Pro Asn His Thr Ser Val
                 1685                1690                1695

Met Pro Cys Lys Tyr Gly Lys Pro Val Asn Asp Tyr Ser Lys Tyr Ile
                 1700                1705                1710

Asn Lys Glu Ile Leu Arg Cys Glu Gln Ile Arg Glu Leu Phe Met Thr
                 1715                1720                1725

Lys Lys Asp Val Asp Ile Gly Leu Leu Ile Glu Ser Leu Ser Val Val
                 1730                1735                1740

Tyr Thr Thr Tyr Cys Pro Ala Gln Tyr Thr Ile Tyr Glu Pro Val Ile
1745                 1750                1755                1760

Arg Leu Lys Gly Gln Met Lys Thr Gln Leu Ser Gln Arg Pro Phe Ser
                 1765                1770                1775
```

-continued

```
Ser Lys Glu Val Gln Ser Ile Leu Leu Glu Pro His His Leu Lys Asn
            1780                1785                1790

Leu Gln Pro Thr Glu Tyr Lys Thr Ile Gln Gly Ile Leu His Glu Ile
        1795                1800                1805

Gly Gly Thr Gly Ile Phe Val Phe Leu Phe Ala Arg Val Val Glu Leu
    1810                1815                1820

Ser Ser Cys Glu Glu Thr Gln Ala Leu Ala Leu Arg Val Ile Leu Ser
1825                1830                1835                1840

Leu Ile Lys Tyr Asn Gln Gln Arg Val His Glu Leu Glu Asn Cys Asn
            1845                1850                1855

Gly Leu Ser Met Ile His Gln Val Leu Ile Lys Gln Lys Cys Ile Val
            1860                1865                1870

Gly Phe Tyr Ile Leu Lys Thr Leu Leu Glu Gly Cys Cys Gly Glu Asp
        1875                1880                1885

Ile Ile Tyr Met Asn Glu Asn Gly Glu Phe Lys Leu Asp Val Asp Ser
    1890                1895                1900

Asn Ala Ile Ile Gln Asp Val Lys Leu Leu Glu Glu Leu Leu Leu Asp
1905                1910                1915                1920

Trp Lys Ile Trp Ser Lys Ala Glu Gln Gly Val Trp Glu Thr Leu Leu
            1925                1930                1935

Ala Ala Leu Glu Val Leu Ile Arg Ala Asp His His Gln Gln Met Phe
        1940                1945                1950

Asn Ile Lys Gln Leu Leu Lys Ala Gln Val Val His His Phe Leu Leu
        1955                1960                1965

Thr Cys Gln Val Leu Gln Glu Tyr Lys Glu Gly Gln Leu Thr Pro Met
    1970                1975                1980

Pro Arg Glu Val Cys Arg Ser Phe Val Lys Ile Ile Ala Glu Val Leu
1985                1990                1995                2000

Gly Ser Pro Pro Asp Leu Glu Leu Leu Thr Ile Ile Phe Asn Phe Leu
            2005                2010                2015

Leu Ala Val His Pro Pro Thr Asn Thr Tyr Val Cys His Asn Pro Thr
        2020                2025                2030

Asn Phe Tyr Phe Ser Leu His Ile Asp Gly Lys Ile Phe Gln Glu Lys
        2035                2040                2045

Val Arg Ser Ile Met Tyr Leu Arg His Ser Ser Ser Gly Gly Arg Ser
    2050                2055                2060

Leu Met Ser Pro Gly Phe Met Val Ile Ser Pro Ser Gly Phe Thr Ala
2065                2070                2075                2080

Ser Pro Tyr Glu Gly Glu Asn Ser Ser Asn Ile Ile Pro Gln Gln Met
            2085                2090                2095

Ala Ala His Met Leu Arg Ser Arg Ser Leu Pro Ala Phe Pro Thr Ser
        2100                2105                2110

Ser Leu Leu Thr Gln Ser Gln Lys Leu Thr Gly Ser Leu Gly Cys Ser
        2115                2120                2125

Ile Asp Arg Leu Gln Asn Ile Ala Asp Thr Tyr Val Ala Thr Gln Ser
    2130                2135                2140

Lys Lys Gln Asn Ser Leu Gly Ser Ser Asp Thr Leu Lys Lys Gly Lys
2145                2150                2155                2160

Glu Asp Ala Phe Ile Ser Ser Cys Glu Ser Ala Lys Thr Val Cys Glu
            2165                2170                2175

Met Glu Ala Val Leu Ser Ala Gln Val Ser Val Ser Asp Val Pro Lys
        2180                2185                2190

Gly Val Leu Gly Phe Pro Val Val Lys Ala Asp His Lys Gln Leu Gly
        2195                2200                2205
```

```
Ala Glu Pro Arg Ser Glu Asp Asp Ser Pro Gly Asp Glu Ser Cys Pro
    2210                2215                2220

Arg Arg Pro Asp Tyr Leu Lys Gly Leu Ala Ser Phe Gln Arg Ser His
2225            2230                2235                2240

Ser Thr Ile Ala Ser Leu Gly Leu Ala Phe Pro Ser Gln Asn Gly Ser
            2245                2250                2255

Ala Ala Val Gly Arg Trp Pro Ser Leu Val Asp Arg Asn Thr Asp Asp
        2260                2265                2270

Trp Glu Asn Phe Ala Tyr Ser Leu Gly Tyr Glu Pro Asn Tyr Asn Arg
    2275                2280                2285

Thr Ala Ser Ala His Ser Val Thr Glu Asp Cys Leu Val Pro Ile Cys
2290                2295                2300

Cys Gly Leu Tyr Glu Leu Leu Ser Gly Val Leu Leu Ile Leu Pro Asp
2305            2310                2315                2320

Val Leu Leu Glu Asp Val Met Asp Lys Leu Ile Gln Ala Asp Thr Leu
            2325                2330                2335

Leu Val Leu Val Asn His Pro Ser Pro Ala Ile Gln Gln Gly Val Ile
        2340                2345                2350

Lys Leu Leu Asp Ala Tyr Phe Ala Arg Ala Ser Lys Glu Gln Lys Asp
    2355                2360                2365

Lys Phe Leu Lys Asn Arg Gly Phe Ser Leu Leu Ala Asn Gln Leu Tyr
2370                2375                2380

Leu His Arg Gly Thr Gln Glu Leu Leu Glu Cys Phe Ile Glu Met Phe
2385            2390                2395                2400

Phe Gly Arg His Ile Gly Leu Asp Glu Glu Phe Asp Leu Glu Asp Val
            2405                2410                2415

Arg Asn Met Gly Leu Phe Gln Lys Trp Ser Val Ile Pro Ile Leu Gly
        2420                2425                2430

Leu Ile Glu Thr Ser Leu Tyr Asp Asn Ile Leu Leu His Asn Ala Leu
    2435                2440                2445

Leu Leu Leu Pro His His Ala Val Val Gln Lys Arg Lys Ser Ile Ala
2450                2455                2460

Gly Pro Arg Lys Phe Pro Leu Ala Gln Thr Glu Ser Leu Leu Met Lys
2465            2470                2475                2480

Met Arg Ser Val Ala Asn Asp Glu Leu His Val Met Met Gln Arg Arg
            2485                2490                2495

Met Ser Gln Glu Asn Pro Ser Gln Ala Thr Glu Thr Glu Leu Ala Gln
        2500                2505                2510

Arg Leu Gln Arg Leu Thr Val Leu Ala Val Asn Arg Ile Ile Tyr Gln
    2515                2520                2525

Glu Phe Asn Ser Asp Ile Ile Asp Ile Leu Arg Thr Pro Glu Asn Val
    2530                2535                2540

Thr Gln Ser Lys Thr Ser Val Phe Gln Thr Glu Ile Ser Glu Glu Asn
2545            2550                2555                2560

Ile His His Glu Gln Ser Ser Val Phe Asn Pro Phe Gln Lys Glu Ile
            2565                2570                2575

Phe Thr Tyr Leu Val Glu Gly Phe Lys Val Ser Ile Gly Ser Ser Lys
        2580                2585                2590

Ala Ser Gly Ser Lys Gln Gln Trp Thr Lys Ile Leu Trp Ser Cys Lys
    2595                2600                2605

Glu Thr Phe Arg Met Gln Leu Gly Arg Leu Leu Val His Ile Leu Ser
2610                2615                2620

Pro Ala His Ala Ala Gln Glu Arg Lys Gln Ile Phe Glu Ile Val His
```

```
                2625                2630                2635                2640
Glu Pro Asn His Gln Glu Ile Leu Arg Asp Cys Leu Ser Pro Ser Leu
                    2645                2650                2655
Gln His Gly Ala Lys Leu Val Leu Tyr Leu Ser Glu Leu Ile His Asn
                2660                2665                2670
His Gln Gly Glu Leu Thr Glu Glu Leu Gly Thr Ala Glu Leu Leu
            2675                2680                2685
Met Asn Ala Leu Lys Leu Cys Gly His Lys Cys Ile Pro Pro Ser Ala
            2690                2695            2700
Ser Thr Lys Ala Asp Leu Ile Lys Met Ile Lys Glu Glu Gln Lys Lys
2705                2710                2715                2720
Tyr Glu Thr Glu Glu Gly Val Asn Lys Ala Ala Trp Gln Lys Thr Val
                2725                2730                2735
Asn Asn Asn Gln Gln Ser Leu Phe Gln Arg Leu Asp Ser Lys Ser Lys
                2740                2745                2750
Asp Ile Ser Lys Ile Ala Ala Asp Ile Thr Gln Ala Val Ser Leu Ser
            2755                2760                2765
Gln Gly Asn Glu Arg Lys Lys Val Ile Gln His Ile Arg Gly Met Tyr
            2770                2775                2780
Lys Val Asp Leu Ser Ala Ser Arg His Trp Gln Glu Leu Ile Gln Gln
2785                2790                2795                2800
Leu Thr His Asp Arg Ala Val Trp Tyr Asp Pro Ile Tyr Tyr Pro Thr
                2805                2810                2815
Ser Trp Gln Leu Asp Pro Thr Glu Gly Pro Asn Arg Glu Arg Arg Arg
            2820                2825                2830
Leu Gln Arg Cys Tyr Leu Thr Ile Pro Asn Lys Tyr Leu Leu Arg Asp
            2835                2840                2845
Arg Gln Lys Ser Glu Asp Val Val Lys Pro Pro Leu Ser Tyr Leu Phe
        2850                2855                2860
Glu Asp Lys Thr His Ser Ser Phe Ser Ser Thr Val Lys Asp Lys Ala
2865                2870                2875                2880
Ala Ser Glu Ser Ile Arg Val Asn Arg Arg Cys Ile Ser Val Ala Pro
                2885                2890                2895
Ser Arg Glu Thr Ala Gly Glu Leu Leu Leu Gly Lys Cys Gly Met Tyr
            2900                2905                2910
Phe Val Glu Asp Asn Ala Ser Asp Thr Val Glu Ser Ser Ser Leu Gln
            2915                2920                2925
Gly Glu Leu Glu Pro Ala Ser Phe Ser Trp Thr Tyr Glu Glu Ile Lys
            2930                2935                2940
Glu Val His Lys Arg Trp Trp Gln Leu Arg Asp Asn Ala Val Glu Ile
2945                2950                2955                2960
Phe Leu Thr Asn Gly Arg Thr Leu Leu Leu Ala Phe Asp Asn Thr Lys
                2965                2970                2975
Val Arg Asp Asp Val Tyr His Asn Ile Leu Thr Asn Asn Leu Pro Asn
            2980                2985                2990
Leu Leu Glu Tyr Gly Asn Ile Thr Ala Leu Thr Asn Leu Trp Tyr Thr
            2995                3000                3005
Gly Gln Ile Thr Asn Phe Glu Tyr Leu Thr His Leu Asn Lys His Ala
            3010                3015                3020
Gly Arg Ser Phe Asn Asp Leu Met Gln Tyr Pro Val Phe Pro Phe Ile
3025                3030                3035                3040
Leu Ala Asp Tyr Val Ser Glu Thr Leu Asp Leu Asn Asp Leu Leu Ile
                3045                3050                3055
```

-continued

Tyr Arg Asn Leu Ser Lys Pro Ile Ala Val Gln Tyr Lys Glu Lys Glu
                3060                3065                3070

Asp Arg Tyr Val Asp Thr Tyr Lys Tyr Leu Glu Glu Glu Tyr Arg Lys
                3075                3080                3085

Gly Ala Arg Glu Asp Asp Pro Met Pro Val Gln Pro Tyr His Tyr
            3090                3095                3100

Gly Ser His Tyr Ser Asn Ser Gly Thr Val Leu His Phe Leu Val Arg
3105                3110                3115                3120

Met Pro Pro Phe Thr Lys Met Phe Leu Ala Tyr Gln Asp Gln Ser Phe
                3125                3130                3135

Asp Ile Pro Asp Arg Thr Phe His Ser Thr Asn Thr Thr Trp Arg Leu
                3140                3145                3150

Ser Ser Phe Glu Ser Met Thr Asp Val Lys Glu Leu Ile Pro Glu Phe
            3155                3160                3165

Phe Tyr Leu Pro Glu Phe Leu Val Asn Arg Gly Phe Asp Phe Gly
            3170                3175                3180

Val Arg Gln Asn Gly Glu Arg Val Asn His Val Asn Leu Pro Pro Trp
3185                3190                3195                3200

Ala Arg Asn Asp Pro Arg Leu Phe Ile Leu Ile His Arg Gln Ala Leu
                3205                3210                3215

Glu Ser Asp Tyr Val Ser Gln Asn Ile Cys Gln Trp Ile Asp Leu Val
            3220                3225                3230

Phe Gly Tyr Lys Gln Lys Gly Lys Ala Ser Val Gln Ala Ile Asn Val
            3235                3240                3245

Phe His Pro Ala Thr Tyr Phe Gly Met Asp Val Ser Ala Val Glu Asp
            3250                3255                3260

Pro Val Gln Arg Arg Ala Leu Glu Thr Met Ile Lys Thr Tyr Gly Gln
3265                3270                3275                3280

Thr Pro Arg Gln Leu Phe His Met Ala His Val Ser Arg Pro Gly Ala
                3285                3290                3295

Lys Leu Asn Ile Glu Gly Glu Leu Pro Ala Ala Val Gly Leu Leu Val
                3300                3305                3310

Gln Phe Ala Phe Arg Glu Thr Arg Glu Gln Val Lys Glu Ile Thr Tyr
                3315                3320                3325

Pro Ser Pro Leu Ser Trp Ile Lys Gly Leu Lys Trp Gly Glu Tyr Val
                3330                3335                3340

Gly Ser Pro Ser Ala Pro Val Pro Val Val Cys Phe Ser Gln Pro His
3345                3350                3355                3360

Gly Glu Arg Phe Gly Ser Leu Gln Ala Leu Pro Thr Arg Ala Ile Cys
                3365                3370                3375

Gly Leu Ser Arg Asn Phe Cys Leu Val Met Thr Tyr Ser Lys Glu Gln
            3380                3385                3390

Gly Val Arg Ser Met Asn Ser Thr Asp Ile Gln Trp Ser Ala Ile Leu
            3395                3400                3405

Ser Trp Gly Tyr Ala Asp Asn Ile Leu Arg Leu Lys Ser Lys Gln Ser
    3410                3415                3420

Glu Pro Pro Val Asn Phe Ile Gln Ser Ser Gln Gln Tyr Gln Val Thr
3425                3430                3435                3440

Ser Cys Ala Trp Val Pro Asp Ser Cys Gln Leu Phe Thr Gly Ser Lys
                3445                3450                3455

Cys Gly Val Ile Thr Ala Tyr Thr Asn Arg Phe Thr Ser Ser Thr Pro
            3460                3465                3470

Ser Glu Ile Glu Met Glu Thr Gln Ile His Leu Tyr Gly His Thr Glu
            3475                3480                3485

```
Glu Ile Thr Ser Leu Phe Val Cys Lys Pro Tyr Ser Ile Leu Ile Ser
    3490                3495                3500

Val Ser Arg Asp Gly Thr Cys Ile Ile Trp Asp Leu Asn Arg Leu Cys
3505                3510                3515                3520

Tyr Val Gln Ser Leu Ala Gly His Lys Ser Pro Val Thr Ala Val Ser
                3525                3530                3535

Ala Ser Glu Thr Ser Gly Asp Ile Ala Thr Val Cys Asp Ser Ala Gly
            3540                3545                3550

Gly Gly Ser Asp Leu Arg Leu Trp Thr Val Asn Gly Asp Leu Val Gly
            3555                3560                3565

His Val His Cys Arg Glu Ile Ile Cys Ser Val Ala Phe Ser Asn Gln
    3570                3575                3580

Pro Glu Gly Val Ser Ile Asn Val Ile Ala Gly Gly Leu Glu Asn Gly
3585                3590                3595                3600

Ile Val Arg Leu Trp Ser Thr Trp Asp Leu Lys Pro Val Arg Glu Ile
            3605                3610                3615

Thr Phe Pro Lys Ser Asn Lys Pro Ile Ile Ser Leu Thr Phe Ser Cys
            3620                3625                3630

Asp Gly His His Leu Tyr Thr Ala Asn Ser Asp Gly Thr Val Ile Ala
            3635                3640                3645

Trp Cys Arg Lys Asp Gln His Arg Leu Lys Gln Pro Met Phe Tyr Ser
    3650                3655                3660

Phe Leu Ser Ser Tyr Ala Ala Gly
3665                3670

(2) INFORMATION FOR SEQ ID NO:13:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:13:

CAGTGGAATG ACCACCAGGC C                                               21

(2) INFORMATION FOR SEQ ID NO:14:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:14:

GTTGCAGGCA TGTACCACTA C                                               21

(2) INFORMATION FOR SEQ ID NO:15:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:15:
```

```
TATGAACCTA CCAAAGCAGA C                                              21

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

ACTTCGGAAG TAGTTGTCTC                                                20

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

CAAAGAAAGC GCTCAGAAAC                                                20

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

AAAGAGGAAA ACCCAAGACT                                                20

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

CAAAAACAAG ACACCCAAGT                                                20

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

TGTTGAATTG AGTGTTGTAG                                                20

(2) INFORMATION FOR SEQ ID NO:21:
```

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:21:

CCAGCCACAG AATACCATCC                                    20

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

GGACATACTC TGCTGCCATC                                    20

(2) INFORMATION FOR SEQ ID NO:23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

ACCCCAGAAC TTGAGAAATA G                                  21

(2) INFORMATION FOR SEQ ID NO:24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

TGCTGAGGTG ATAGGTTTAT G                                  21

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

ATTGGCTAGT GTGTGCAGAC                                    20

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:26:

GAAGCAGATG ACTGAGCAGA                20

(2) INFORMATION FOR SEQ ID NO:27:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

TCTTCTTGTC CTGCCTGATG CT                22

(2) INFORMATION FOR SEQ ID NO:28:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:28:

GTGCTTCACT TCCTCCAGAT C                21

(2) INFORMATION FOR SEQ ID NO:29:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

GCCTCATTCC AGCGAAGC                18

(2) INFORMATION FOR SEQ ID NO:30:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

CTGGATAGCA GGTGATGGGT GGTTA                25

(2) INFORMATION FOR SEQ ID NO:31:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

-continued

```
TGCTGTGGAT TATATGAACT C                                          21

(2) INFORMATION FOR SEQ ID NO:32:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

GGTCTCTATT AGTCCGAGAA C                                          21
```

COMPOSITIONS FOR THE DIAGNOSIS AND TREATMENT OF CHEDIAK-HIGASHI SYNDROME

This application claims priority under 35 U.S.C. § 119(e) to U.S. provisional application Serial No. 60/021,064, filed Jul. 1, 1996, U.S. provisional application Serial No. 60/015,673, filed Apr. 19, 1996 and U.S. provisional application Serial No. 60/013,883, filed Mar. 22, 1996, each of which is incorporated herein by reference in its entirety.

1. INTRODUCTION

The present invention relates to the identification of novel nucleic acid molecules and proteins encoded by such nucleic acid molecules or degenerate, especially naturally occurring, variants thereof, that, when mutated, lead to disorders involving abnormal intracellular vesicles, especially abnormal lysosomes, melanosomes, platelet dense granules and cytolytic granules, including Chediak-Higashi syndrome (CHS). The nucleic acid molecules of the present invention represent the genes corresponding to the mammalian bg gene, including the human bg gene, which are involved in the normal differentiation and/or function of such intracellular vesicles. Nucleic acid molecules representing loss-of-function alleles of the human bg gene bring about Chediak-Higashi syndrome (CHS), in individuals homozygous for such alleles.

In particular, the compositions of the present invention include nucleic acid molecules (e.g., bg gene), including recombinant DNA molecules, cloned genes or degenerate, especially naturally occurring, variants thereof, which encode novel bg gene products, and antibodies directed against such bg gene products or conserved variants or fragments thereof. The compositions of the present invention additionally include cloning vectors, including expression vectors, containing the nucleic acid molecules of the invention and hosts which have been transformed with such nucleic acid molecules.

In addition, this invention presents methods for the diagnostic evaluation and prognosis of disorders involving abnormal intracellular vesicles, especially abnormal lysosomes, melanosomes, platelet dense granules and cytolytic granules, including CHS, and for the identification of subjects having a predisposition to such conditions. For example, nucleic acid molecules of the invention can be used as diagnostic hybridization probes or as primers for diagnostic PCR analysis for the identification of bg gene mutations, allelic variations and regulatory defects in the bg gene.

Further, methods and compositions are presented for the treatment of disorders involving abnormal intracellular vesicles, especially abnormal lysosomes, melanosomes, platelet dense granules and cytolytic granules, including CHS. Such methods and compositions are capable of modulating the level of bg gene expression and/or the level of bg gene product activity.

Still further, the present invention relates to methods for the use of the bg gene, bg gene products and/or cells expressing wild type or mutant bg gene sequences for the identification of compounds which modulate bg gene expression and/or the activity of bg gene products. Such compounds can be used as agents to control disorders involving abnormal intracellular vesicles, especially abnormal lysosomes, melanosomes, platelet dense granules and cytolytic granules, in particular, therapeutic agents in the treatment of CHS.

2. BACKGROUND OF THE INVENTION

Chediak-Higashi syndrome (CHS) is a lethal autosomal recessive disorder of humans mapping to 1q43. The clinical manifestations of this disorder include hypopigmentation, defective immune cell function, including severely impaired natural killer cell activity, and defective antibody-dependent, lymphocyte-mediated cytolysis against tumor cell targets. Further, neural degeneration is observed and, finally, the occurrence of a mononuclear cell lymphoma develops, which causes the death of afflicted individuals.

As mentioned above, the disease is accompanied by a marked susceptibility to infections. Young children have repeated infections, usually with gram-positive organisms of the staphylococcal and streptococcal type. Further, during the course of the disease, children may develop a progressive peripheral neuropathy. Children surviving the early infectious episodes (8–18 years of age), most frequently develop terminal lymphoreticular malignancy. Few patients survive beyond twenty years.

Pathological manifestation of the syndrome includes enlarged vesicles affecting lysosomes, melanosomes, platelet dense granules, cytolytic granules and Schwann cell granules. The abnormal size of these vesicles is thought to result from a malregulation of vesicle fusion or fission. Abnormal membrane-bound lysosomal-like organelles have been found in cells of the buccal mucosa, Schwann cells, pancreas, liver, gastric and duodenal mucosa, adrenal, pituitary, spleen, kidney, bone marrow, hair skin, iris and conjunctiva. The giant granules observed resemble the normal granules of the specific cell type in both fine structure and cytochemic reactions and result from the fusion of small primary granules.

Similar phenotypes are found in other species, most notably the beige mouse and the Aleutian mink, but are also found in such species as the Persian cat, cattle and even the killer whale. Somatic cell fusion studies have suggested that mutations within the same gene in mouse, mink, and man were responsible for the CHS-like phenotype in each of these species. In mice, the gene responsible for such a phenotype is the beige (bg) gene. Such studies, however, were not able to elucidate either the function or the identity of the bg gene product.

Over the past thirty years numerous theories have been evoked to explain the nature of these disorders. For example, it has been suggested that the defect might be caused by alterations in membrane fluidity, defects in microtubules or microtubule associated proteins, or changes in cyclic nucleotides levels. Upon further examination, though, each of these theories has been found to be inadequate, thus highlighting the fact that a great need remains for the discovery of the causative agent of the lethal Chediak-Higashi syndrome genetic disorder.

3. SUMMARY OF THE INVENTION

The present invention relates to the identification of novel nucleic acid molecules and proteins encoded by such nucleic acid molecules or degenerate, especially naturally occurring, variants thereof, that, when mutated, lead to disorders involving abnormal intracellular vesicles, especially abnormal lysosomes, melanosomes, platelet dense granules and cytolytic granules, including Chediak-Higashi syndrome (CHS). The nucleic acid molecules of the present invention represent the genes corresponding to the mammalian bg gene, including the human bg gene, which are involved in the normal differentiation and/or function of such intracellular vesicles. Nucleic acid molecules representing loss-offunction alleles of the human bg gene bring about Chediak-Higashi syndrome (CHS), in individuals homozygous for such alleles.

In particular, the compositions of the present invention include nucleic acid molecules (e.g., bg gene), including recombinant DNA molecules, cloned genes or degenerate, especially naturally occurring, variants thereof, which encode novel bg gene products, and antibodies directed against such bg gene products or conserved variants or fragments thereof. The compositions of the present invention additionally include cloning vectors, including expression vectors, containing the nucleic acid molecules of the invention and hosts which have been transformed with such nucleic acid molecules.

Nucleic acid sequences of wild type and mutant forms of the murine bg gene are provided. Wild type murine bg gene produces a transcript of approximately 12–14 kb. The amino acid sequence of the predicted bg gene product indicates that the protein is novel.

Nucleic acid sequences of wild type forms of the human bg gene are also provided. The human bg gene produces alternatively spliced transcripts. The long, putatively full length bg transcript encodes a bg protein of 3801 amino acid residues, as shown in FIG. 7. A short form, alternatively spliced, human bg transcript encodes a bg protein of 3672 amino acid residues, as shown in FIG. 8. The amino acid sequence of the predicted human bg gene products indicates that the proteins are novel.

In addition, this invention presents methods for the diagnostic evaluation and prognosis of disorders involving abnormal intracellular vesicles, especially abnormal lysosomes, melanosomes, platelet dense granules and cytolytic granules, including CHS, and for the identification of subjects having a predisposition to such conditions. For example, nucleic acid molecules of the invention can be used as diagnostic hybridization probes or as primers for diagnostic PCR analysis for the identification of bg gene mutations, allelic variations and regulatory defects in the bg gene.

Further, methods and compositions are presented for the treatment of disorders involving abnormal intracellular vesicles, especially abnormal lysosomes, melanosomes, platelet dense granules and cytolytic granules, including CHS. Such methods and compositions are capable of modulating the level of bg gene expression and/or the level of bg gene product activity.

Still further, the present invention relates to methods for the use of the bg gene, bg gene products and/or cells expressing wild type or mutant bg gene sequences for the identification of compounds which modulate bg gene expression and/or the activity of bg gene products. Such compounds can be used as agents to control disorders involving abnormal intracellular vesicles, especially abnormal lysosomes, melanosomes, platelet dense granules and cytolytic granules, in particular, therapeutic agents in the treatment of CHS.

This invention is based, in part, on a combination of in vitro complementation using yeast artificial chromosomes (YACs), positional cloning techniques and mutation detection which, together, were used to successfully identify and clone the murine bg gene, as described in the Examples, below, presented in Sections 6–9. Such analyses included the identification and sequencing of two independent bg mutations, one an insertion of 117 base pairs and the other a point mutation which results in an in-frame, premature stop codon. Both mutations result in the product of transcripts encoding truncated BG proteins.

4. DESCRIPTION OF THE FIGURES

FIG. 1. Genetic and physical map of mouse chromosome 13 region containing the bg gene interval.

Figure 2A:
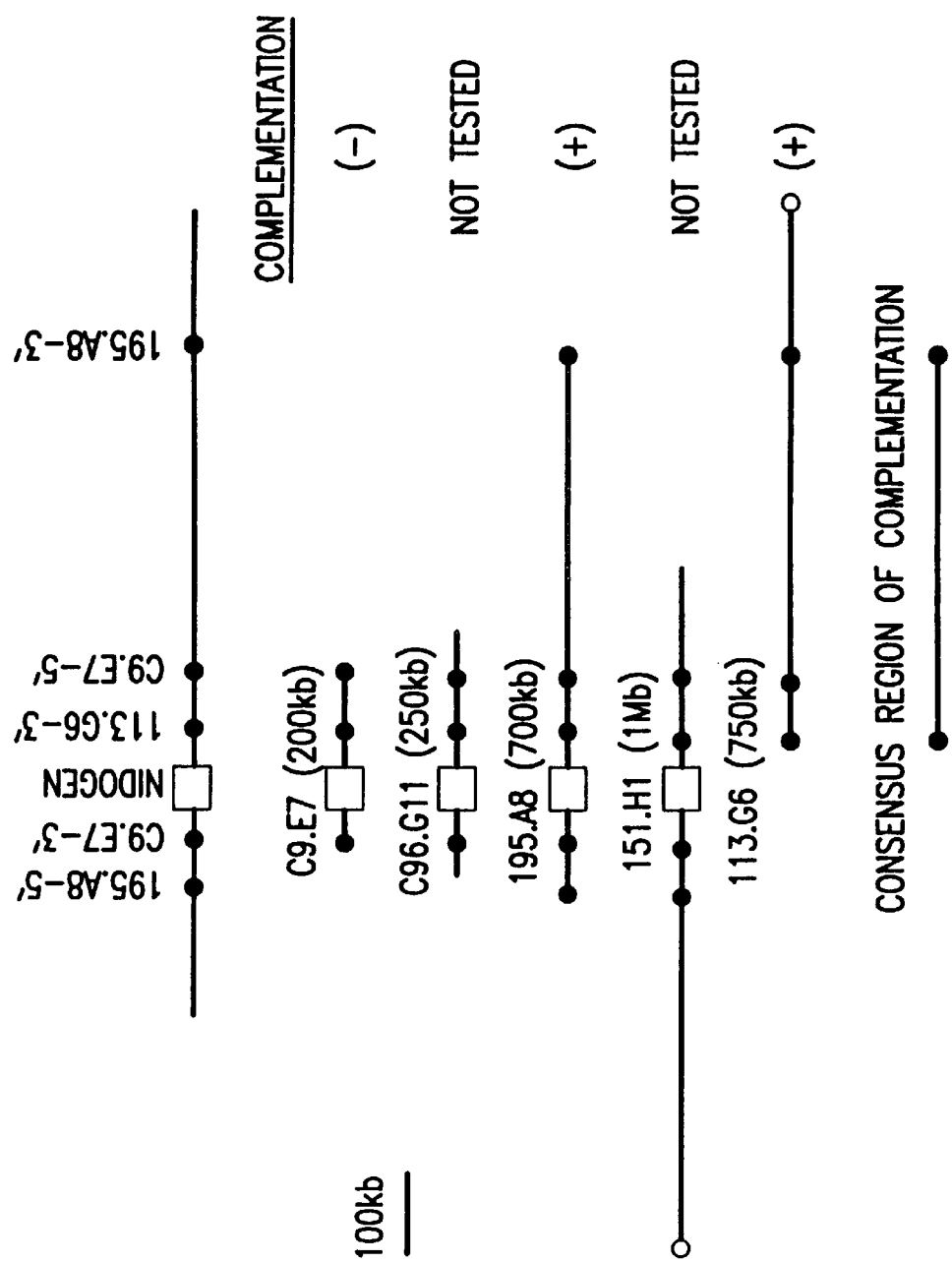

FIGS. 2A–2B. Diagram depicting yeast artificial chromosomes (YACs) spanning the minimal bg interval. Ability of YACs to complement the bg mutation is noted.

Figure 3A:
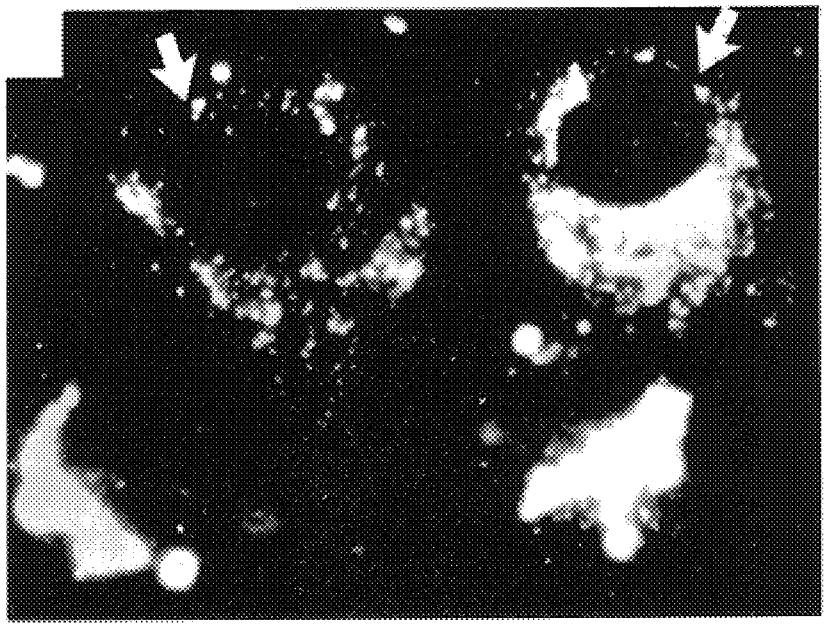

FIG. 3A. Wild type and bg mouse fibroblasts plated together to demonstrate differences in phenotypes between the two cell types. The arrows denote two wild type cells. Two bg cells are just below the indicated wild type cells. Note the difference in lysosome size and distribution. Magnification was approximately 500×.

Figure 3B:
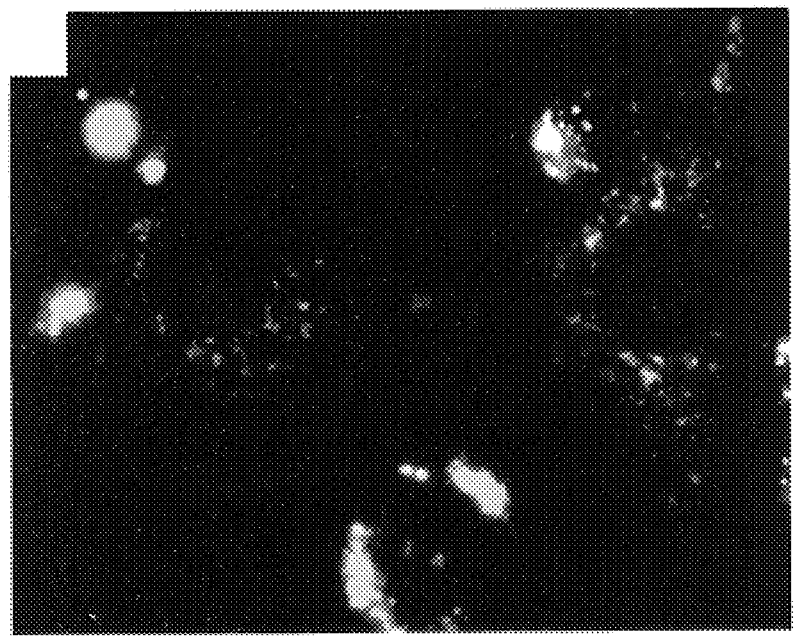

FIG. 3B. The initial mixed isolate of complemented colony 195-4, isolated from 400 μg/ml G418. This colony, as isolated from the plate contained complemented and uncomplemented bg cells. Magnification was approximately 500×.

Figure 3C:
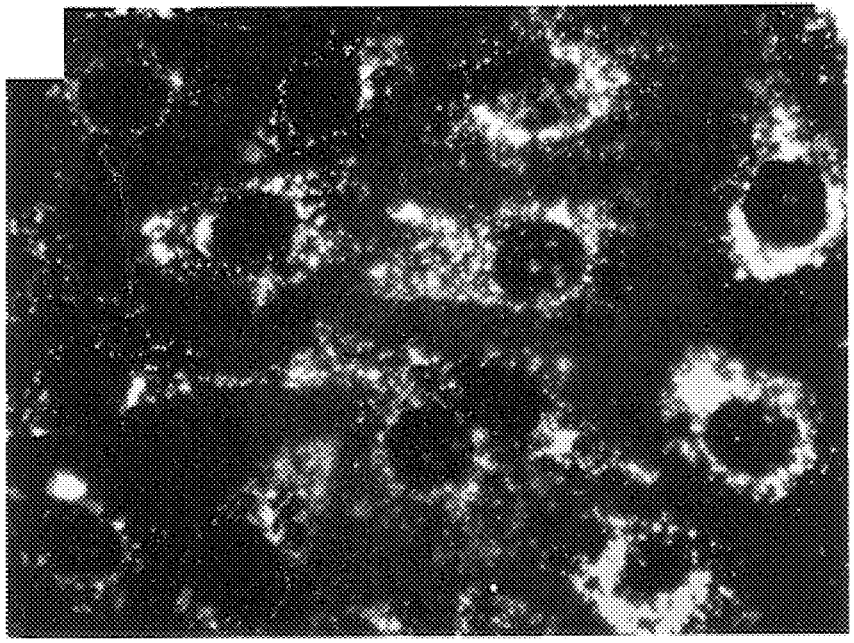

FIG. 3C. Colony 195-4 after 10 days in 800 μg/ml G418. Note that the colony after this period of time was homogeneously complemented (i.e., all of the bg cells appeared wild type with respect to the lysosomal morphology.) Magnification was approximately 500×.

Figure 3D:
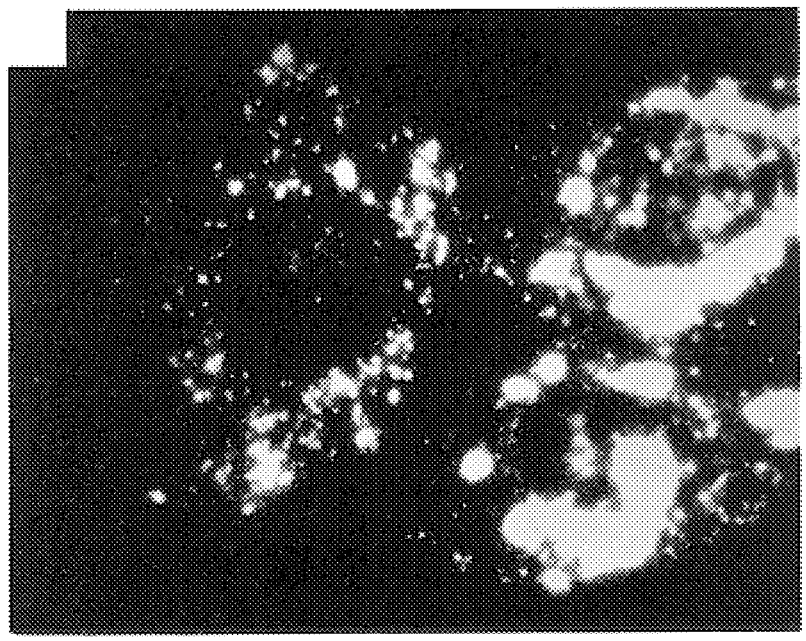
Figure 5A:
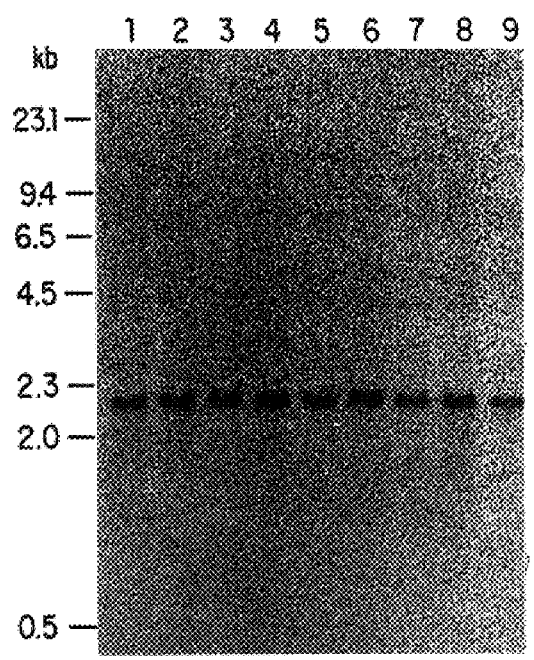
Figure 5B:
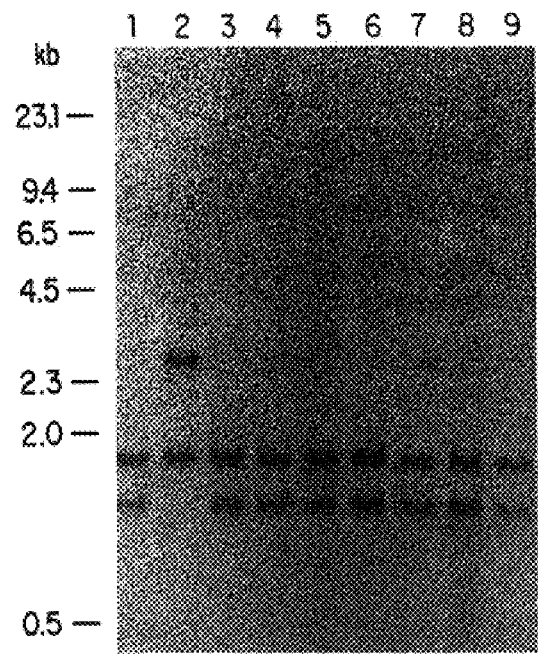
Figure 5C:
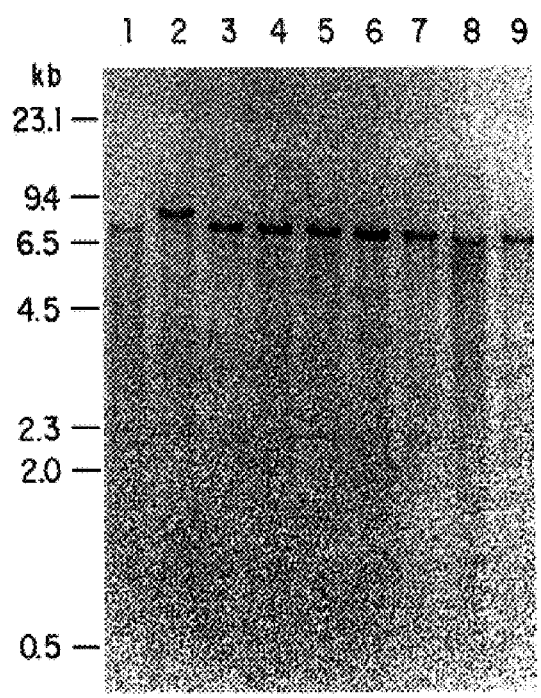
Figure 5D:
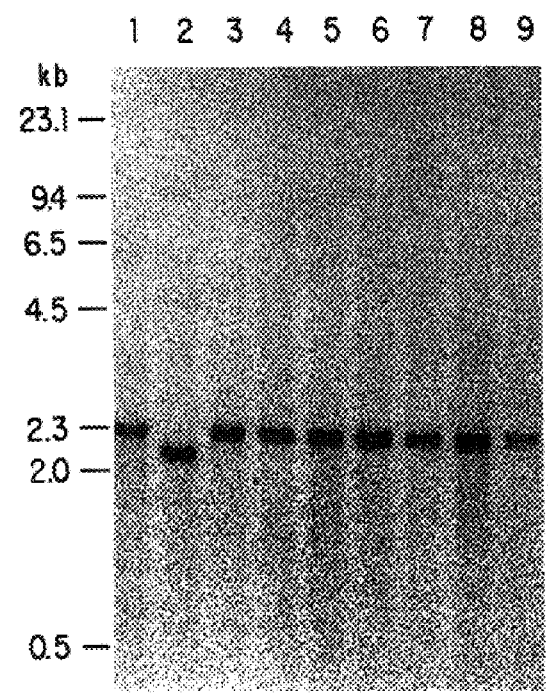

FIG. 3D. Colony 195-4 after culture i 800 μg/ml G418 for ten days, then cultured without G418 for thirty days. The result illustrated here demonstrates that the YAC was responsible for the complementation, in that, when the cells were cultured without G418, they lost the YAC and reverted back to the mutant bg morphology. Magnification was approximately 500×.

FIG. 4. Nucleotide sequence (bottom line; SEQ ID NO:1) and amino acid sequence (top line; SEQ ID NO:2) of the 22B/30B gene (the murine bg gene).

FIGS. 5A–5D. Southern blot analysis of a chromosomal rearrangement associated with the bg allele. Southern blot analysis of a 510 bp fragment of 22B/30B hybridized to lane (1) C57BL/6J; (2) C57BL/6J-bg; (3) C57BL/6J-bg$^J$; (4) C57BL/6J-bg$^{10J}$; (5) C57BL/6J-bg$^{11J}$; (6) C3H/HeJ; (7) C3H/H3J-bg$^{2J}$; (8) DBA/2J; and (9)DBA/2J-CO-bg$^{8J}$ DNAs digested with 5A: HindIII; 5B: PstI; 5C: BglII; and 5D: TaqI. Size markers are indicated.

Figure 6:
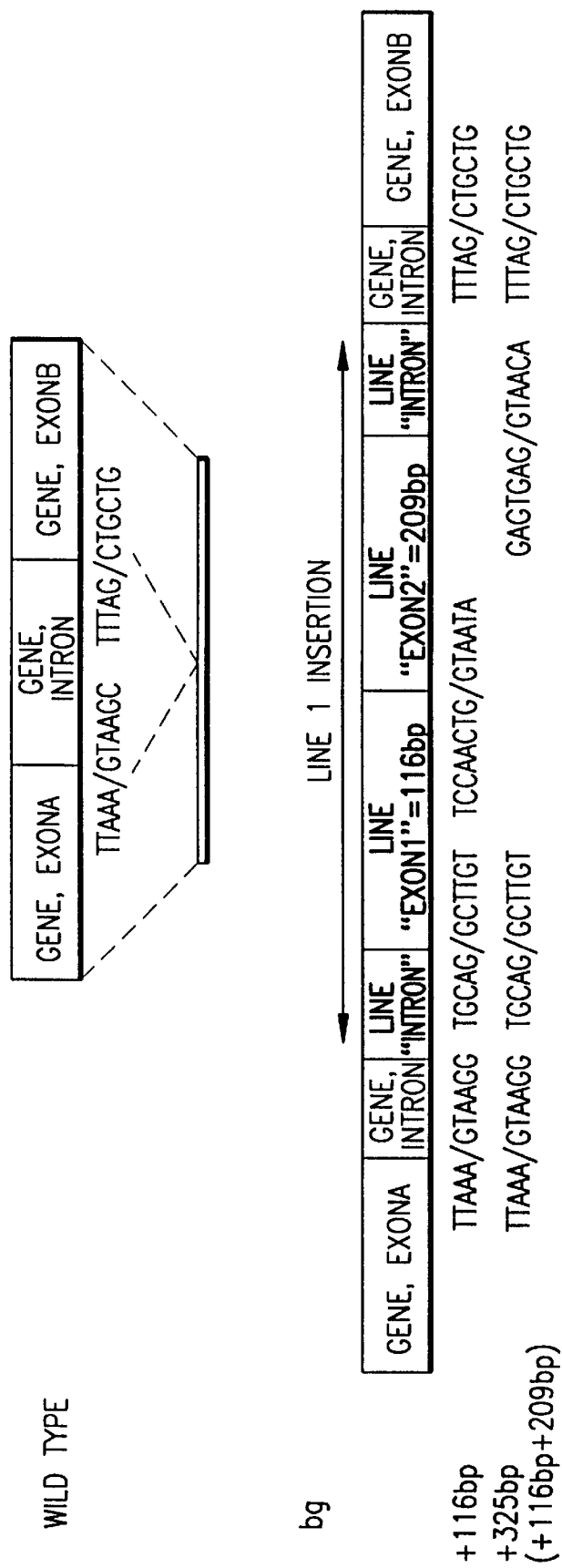

FIG. 6. Diagram illustrating the location and structure of a Line 1 insertion representing mutation within the bg gene yielding truncated BG proteins which leads to a mutant bg phenotype (SEQ ID NO:8).

FIG. 7. Human long form (putative full length) bg gene nucleotide (bottom line) (SEQ ID NO:9) and derived amino acid (top line) (SEQ ID NO:10) sequences.

FIG. 8. Human short form, alternatively spliced bg gene nucleotide (bottom line) (SEQ ID NO:11) and derived amino acid (top line) (SEQ ID NO:12) sequences.

5. DETAILED DESCRIPTION OF THE INVENTION

Described herein are novel mammalian genes, the beige (bg) genes, including the human bg gene. Such genes are involved in the normal differentiation and/or function of intracellular vesicles. When such sequences are mutated such that, for example, a functional beige gene product (BG) is no longer produced, disorders develop involving abnormal intracellular vesicles, especially abnormal lysosomes, melanosomes, platelet dense granules and cytolytic granules, including Chediak-Higashi syndrome. Also described are recombinant mammalian, including human, bg DNA molecules, cloned genes, or degenerate variants thereof. The compositions of the present invention further include bg gene products (e.g., proteins) that are encoded by the hg gene, and the modulation of bg gene expression and/or bg gene product activity in the treatment of disorders involving abnormal intracellular vesicles, including, but not limited to CHS. Also described herein are antibodies against bg gene products (e.g., proteins), or conserved variants or fragments thereof, and nucleic acid probes useful for the identification of bg gene mutations and the use of such nucleic acid probes in, for example, the identification of individuals predisposed to such disorders and/or individuals who carry mutant bg alleles. Further described are methods for the use of the bg gene and/or bg gene products in the identification of compounds which modulate the activity of the hg gene product.

Murine bg nucleic acid and amino acid compositions of the invention are demonstrated in the Examples presented, below, in Sections 6 through 9. A gene, referred to herein as the 22B/30B gene, representing a candidate for the murine bg gene was identified via a combination of genetic and physical mapping coupled with a yeast artificial chromosome (YAC) complementation assay by which complementation of the bg mutation was assessed via analysis of the morphological phenotype of YAC-transformed bg fibroblasts. Identification and sequencing of two independent bg mutations revealed that the mutations resided within the 22B/30B gene, representing compelling evidence that the 22B/30B gene was the bg gene. For clarity, it should, therefore, be noted that the murine bg gene is also referred to herein as the 22B/30B gene.

Human bg nucleic acid and amino acid compositions of the invention are demonstrated in Example 10, below.

5.1. THE bg GENE

The bg gene, murine nucleic acid sequence of which is shown in FIG. 4 (SEQ ID NO:1) and human nucleic acid sequences of which are shown in FIGS. 7 and 8, is a novel gene involved in the normal differentiation and/or function of intracellular vesicles. Nucleic acid sequences of the bg gene are described herein. As used herein, "bg gene" refers to (a) a gene containing the DNA sequence shown in FIG. 4, FIG. 7 or FIG. 8; (b) any DNA sequence that encodes the amino acid sequence shown in FIG. 4 (SEQ ID NO:2), FIG. 7 or FIG. 8; (c) any DNA sequence that hybridizes to the complement of the DNA sequences that encode the amino acid sequence shown in FIG. 4, FIG. 7 or FIG. 8, under highly stringent conditions, e.g hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3); and/or (d) any DNA sequence that hybridizes to the complement of the DNA sequences that encode the amino acid sequence shown in FIG. 4, FIG. 7 or FIG. 8, under less stringent conditions, such as moderately stringent conditions, e.g., washing in 0.2×SSC/0.1% SDS at 42° C. (Ausubel et al., 1989, supra), yet which still encodes a functional bg gene product. As used herein, bg gene may also refer to degenerate variants of DNA sequences (a) through (d), including naturally occurring variants. The term "functional bg gene product," as used herein, refers to a gene product encoded by a nucleic acid sequence capable of complementing a recessive, loss-of-function bg mutation.

The invention also includes nucleic acid molecules, preferably DNA molecules, that hybridize to, and are therefore the complements of, the DNA sequences (a) through (d), in the preceding paragraph, and to degenerate variants of the DNA sequences shown in (a) through (d) in the preceding paragraph. Hybridization conditions may be highly stringent or less highly stringent, as described above. In instances wherein the nucleic acid molecules are deoxyoligonucleotides ("oligos"), highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as bg gene antisense molecules, useful, for example, in bg gene regulation, as antisense primers in amplification reactions of bg gene nucleic acid sequences and/or as hybridization probes for the identification of bg nucleic acid sequences. With respect to diagnostic procedures, such molecules may be used as components of methods whereby, for example, the presence of a particular bg allele responsible for causing a disorder, such as CHS, may be detected.

The invention also encompasses (a) DNA vectors that contain any of the foregoing bg coding sequences and/or their complements (i.e., antisense); (b) DNA expression vectors that contain any of the foregoing bg coding sequences operatively associated with a regulatory element that directs the expression of the coding sequences; and (c) genetically engineered host cells that contain any of the foregoing bg coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors. The invention includes fragments of any of the DNA sequences disclosed herein.

bg gene sequences include, for example, alleles and homologs of genes containing the sequence depicted in FIG. 4, FIG. 7 or FIG. 8, wherein such alleles are present at the same locus as the sequence depicted in FIG. 4, FIG. 7 or FIG. 8 and homologs are genes at other genetic loci within the genome that encode proteins which have extensive homology to one or more domains of the bg gene product. Such bg gene alleles and homologs can be identified and readily isolated, without undue experimentation, by molecular biological techniques well known in the art.

As an example, in order to clone a human bg gene sequence using isolated murine bg gene sequences as disclosed herein, such murine bg gene sequences may be labeled and used to screen a cDNA library constructed from mRNA obtained from appropriate cells or tissues of interest (e.g., a cell or tissue known to express the bg gene in mouse, and/or a cell or tissue known to be affected by CHS in humans, such as, for example, a retinal library). The hybridization washing conditions used should normally be of a lower stringency when the cDNA library is derived from an organism different from the type of organism from which the labeled sequence was derived, but appropriate stringency conditions for the specific sequence and library being utilized will be apparent to those of skill in the art.

Low stringency conditions, for example, are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Springs Harbor Press, N.Y.; and Ausubel et al., 1989, Current Protocols in Molecular Biology, Green Publishing Associates and Wiley Interscience, N.Y.

Alternatively, the labeled fragment may be used to screen a genomic library derived from the organism of interest, again, using appropriately stringent conditions. Such a screening procedure could be utilized, for example, to identify either bg alleles or bg homolog genes located in different portions of the genome containing sequences encoding one or more domains exhibiting extensive homology to one or more domains encoded by the bg gene.

Further, a bg gene sequence may be isolated from nucleic acid of the organism of interest by performing PCR using two degenerate oligonucleotide primer pools designed on the basis of amino acid sequences within the bg gene product disclosed herein. The template for the reaction may be cDNA obtained by reverse transcription of mRNA prepared from, for example, human or non-human cell lines or tissue known or suspected to express a bg gene allele.

The PCR product may be subcloned and sequenced to ensure that the amplified sequences represent the sequences of a bg gene nucleic acid sequence. The PCR fragment may then be used to isolate a full length cDNA clone by a variety of methods. For example, the amplified fragment may be labeled and used to screen a cDNA library, such as a bacteriophage cDNA library. Alternatively, the labeled fragment may be used to isolate genomic clones via the screening of a genomic library.

PCR technology may also be utilized to isolate full length cDNA sequences. For example, RNA may be isolated, following standard procedures, from an appropriate cellular or tissue source (i.e., one known, or suspected, to express the bg gene, and/or one known to be affected by disorders caused by bg mutations). A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al., 1989, supra.

bg gene sequences may additionally be used to isolate mutant bg gene alleles. Such mutant alleles may be isolated from individuals either known or proposed to have a genotype which contributes to the symptoms of intracellular vesicle disorders, including CHS. Mutant alleles and mutant allele products may then be utilized in the therapeutic and diagnostic systems described below. Additionally, such bg gene sequences can be used to detect bg gene regulatory (e.g., promoter) defects which can affect intracellular vesicle differentiation and/or function.

A cDNA of a mutant bg gene may be isolated, for example, by using PCR, a technique which is well known to those of skill in the art. In this case, the first cDNA strand may be synthesized by hybridizing an oligo-dT oligonucleotide to mRNA isolated from tissue known or suspected to be expressed in an individual putatively carrying the mutant bg allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant bg allele to that of the normal bg allele, the mutation(s) responsible for the loss or alteration of function of the mutant bg gene product can be ascertained.

Alternatively, a genomic library can be constructed using DNA obtained from an individual suspected of or known to carry the mutant bg allele, or a cDNA library can be constructed using RNA from a tissue known, or suspected, to express the mutant bg allele. The normal bg gene or any suitable fragment thereof may then be labeled and used as a probe to identify the corresponding mutant bg allele in such libraries. Clones containing the mutant bg gene sequences may then be purified and subjected to sequence analysis according to methods well known to those of skill in the art.

Additionally, an expression library can be constructed utilizing cDNA synthesized from, for example, RNA isolated from a tissue known, or suspected, to express a mutant bg allele in an individual suspected of or known to carry such a mutant allele. In this manner, gene products made by the putatively mutant tissue may be expressed and screened using standard antibody screening techniques in conjunction with antibodies raised against the normal bg gene product, as described, below, in Section 5.3. (For screening techniques, see, for example, Harlow, E. and Lane, eds., 1988, "Antibodies: A Laboratory Manual", Cold Spring Harbor Press, Cold Spring Harbor.) In cases where a bg mutation results in an expressed gene product with altered function (e.g., as a result of a missense or a frameshift mutation), a polyclonal set of anti-bg gene product antibodies are likely to cross-react with the mutant bg gene product. Library clones detected via their reaction with such labeled antibodies can be purified and subjected to sequence analysis according to methods well known to those of skill in the art.

The Example presented in Section 9, below, demonstrates the successful isolation and sequencing of two bg mutations, each of which causes the production of truncated, non-functional BG proteins.

5.2. PROTEIN PRODUCTS OF THE bg GENE bg gene products, peptide fragments thereof or fusion proeins, can be prepared for a variety of uses. For example, such gene products, peptide fragments thereof or fusion proteins, can be used for the generation of antibodies, in diagnostic assays, or for the identification of other cellular gene products involved in the differentiation and/or function of intracellular vesicles.

FIG. 4 depicts murine bg gene product amino acid sequence. FIG. 7 depicts the long form, putative full length, human bg gene product amino acid sequence. As shown in FIG. 7, the long form human bg gene product contains 3801 amino acid residues. FIG. 8 depicts the short form human bg gene product encoded by an alternatively spliced short form of bg transcript. As shown in FIG. 8, the human bg gene product encoded by this short form transcript contains 3672 amino acid residues. The bg gene product, sometimes referred to herein as "BG", may additionally include those gene products encoded by the bg gene sequences described in Section 5.1, above.

In addition, bg gene products may include proteins that represent functionally equivalent bg gene products. The term "functionally equivalent bg gene product", as used herein, refers to a gene product encoded by a nucleic acid sequence capable of complementing a bg mutation. Such an equivalent bg gene product may contain deletions, additions or substitutions of amino acid residues within the amino acid sequence encoded by the bg gene sequences described, above, in Section 5.1, but which result in a silent change, thus producing a functionally equivalent bg gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

The bg gene products, peptide fragments thereof or fusion proteins, may be produced by recombinant DNA technology using techniques well known in the art. Thus, methods for preparing the bg gene polypeptides, peptides and fusion proteins of the invention by expressing nucleic acid containing bg gene sequences are described herein. Methods which are well known to those skilled in the art can be used to construct expression vectors containing bg gene product coding sequences and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, RNA capable of encoding bg gene product sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems may be utilized to express the bg gene coding sequences of the invention. Such host-expression systems represent vehicles by which the coding sequences of interest may be produced and subsequently purified, but also represent cells which may, when transformed or transfected with the appropriate nucleotide coding sequences, exhibit the bg gene product of the invention in situ. These include but are not limited to microorganisms such as bacteria (e.g., *E. coli, B. subtilis*) transformed with recombinant bacteriophage DNA, plasmid DNA or cosmid DNA expression vectors containing hg gene product coding sequences; yeast (e.g., Saccharomyces, Pichia) transformed with recombinant yeast expression vectors containing the bg gene product coding sequences; insect cell systems infected with recombinant virus expression vectors (e.g., baculovirus) containing the bg gene product coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing bg gene product coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the bg gene product being expressed. For example, when a large quantity of such a protein is to be produced, for the generation of pharmaceutical compositions of bg protein or for raising antibodies to bg protein, for example, vectors which direct the expression of high levels of fusion protein products that are readily purified may be desirable. Such vectors include, but are not limited to, the *E. coli* expression vector pUR278 (Ruther et al., 1983, EMBO J. 2:1791), in which the bg gene product coding sequence may be ligated individually into the vector in frame with the lac Z coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The bg gene coding sequence may be cloned individually into non-essential regions (for example the polyhedrin gene) of the virus and placed under control of an AcNPV promoter (for example the polyhedrin promoter). Successful insertion of bg gene coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed. (E.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the bg gene coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing bg gene product in infected hosts. (E.g., See Logan & Shenk, 1984, Proc. Natl. Acad. Sci. USA 81:3655–3659). Specific initiation signals may also be required for efficient translation of inserted bg gene product coding sequences. These signals include the ATG initiation codon and adjacent sequences. In cases where an entire bg gene, including its own initiation codon and adjacent sequences, is inserted into the appropriate expression vector, no additional translational control signals may be needed. However, in cases where only a portion of the bg gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3 and WI38 cell lines.

For long-term, high-yield production of recombinant proteins, stable expression is preferred. For example, cell lines which stably express the bg gene product may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the bg gene product. Such engineered cell lines may be particularly useful in screening and evaluation of compounds that affect the endogenous activity of the bg gene product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk-, hgprt- or aprt- cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88: 8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$-nitriloacetic acid-agarose columns and histidine-tagged proteins are selectively eluted with imidazole-containing buffers.

The bg gene products can also be expressed in transgenic animals. Animals of any species, including, but not limited to, mice, rats, rabbits, guinea pigs, pigs, micro-pigs, goats, and non-human primates, e.g., baboons, monkeys, and chimpanzees may be used to generate bg transgenic animals.

Any technique known in the art may be used to introduce the bg gene transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the bg transgene in all their cells, as well as animals which carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, M. et al., 1992, Proc. Natl. Acad. Sci. USA 89: 6232–6236). The regulatory sequences required for such a cell-type specific activation will depend upon the particular cell type of interest, and will be apparent to those of skill in the art. When it is desired that the bg gene transgene be integrated into the chromosomal site of the endogenous bg gene, gene targeting is preferred. Briefly, when such a technique is to be utilized, vectors containing some nucleotide sequences homologous to the endogenous bg gene are designed for the purpose of integrating, via homologous recombination with chromosomal sequences, into and disrupting the function of the nucleotide sequence of the endogenous bg gene. The transgene may also be selectively introduced into a particular cell type, thus inactivating the endogenous bg gene in only that cell type, by following, for example, the teaching of Gu et al. (Gu, et al., 1994, Science 265: 103–106). The regulatory sequences required for such a cell-type specific inactivation will depend upon the particular cell type of interest, and will be apparent to those of skill in the art.

Once transgenic animals have been generated, the expression of the recombinant bg gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of bg gene-expressing tissue, may also be evaluated immunocytochemically using antibodies specific for the bg transgene product.

5.3. ANTIBODIES TO bg GENE PRODUCTS

Described herein are methods for the production of antibodies capable of specifically recognizing one or more bg gene product epitopes or epitopes of conserved variants or peptide fragments of the bg gene products.

Such antibodies may include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Such antibodies may be used, for example, in the detection of a bg gene product in an biological sample and may, therefore, be utilized as part of a diagnostic or prognostic technique whereby patients may be tested for abnormal levels of bg gene products, and/or for the presence of abnormal forms of the such gene products. Such antibodies may also be utilized in conjunction with, for example, compound screening schemes, as described, below, in Section 5.4.2, for the evaluation of the effect of test compounds on bg gene product levels and/or activity. Additionally, such antibodies can be used in conjunction with the gene therapy techniques described, below, in Section 5.4.3, to, for example, evaluate the normal and/or engineered bg-expressing cells prior to their introduction into the patient.

Anti-bg gene product antibodies may additionally be used as a method for the inhibition of abnormal bg gene product activity, in, for example, instances in which such abnormal activity is due to an increased level of bg gene product or to the presence of mutant, gain-of-function mutant bg gene products. Thus, such antibodies may, therefore, be utilized as part of methods for the treatment of disorders caused by such abnormal bg gene product activity, including, for example, disorders involving abnormal intracellular vesicle differentiation and/or function.

For the production of antibodies against a bg gene product, various host animals may be immunized by injection with a bg gene product, or a portion thereof. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of animals immunized with an antigen, such as a bg gene product, or an antigenic functional derivative thereof. For the production of polyclonal antibodies, host animals such as those described above, may be immunized by injection with bg gene product supplemented with adjuvants as also described above.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against bg gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

5.4. USES OF THE bg GENE, GENE PRODUCTS, AND ANTIBODIES

Described herein are various applications of the bg gene, the bg gene product including peptide fragments thereof, and of antibodies directed against the bg gene product and peptide fragments thereof.

Such applications include, for example, prognostic and diagnostic evaluation of disorders involving abnormal intracellular vesicles, including, for example, abnormal lysosomes, melanosomes, platelet dense granules and cytolytic granules, including, but not limited to Chediak-Higashi syndrome (CHS), and methods for the identification of subjects with a predisposition to such disorders and the identification of individuals carrying mutant bg alleles.

Such methods may, for example, utilize reagents such as the bg gene nucleotide sequences described in Sections 5.1, and antibodies directed against bg gene products, including peptide fragments thereof, as described, above, in Section 5.3. Specifically, such reagents may be used, for example, for: (1) nucleic acid-based techniques for the detection of the presence of bg gene mutations, or the detection of either over- or under-expression of bg gene mRNA relative levels known to be found in the normal state; and (2) peptide-based techniques for the detection of mutant BG proteins or either an over- or an under-abundance of BG relative levels known to be found in the normal state.

The methods described herein may be performed, for example, by utilizing pre-packaged diagnostic kits comprising at least one specific bg gene nucleic acid or anti-bg gene antibody reagent described herein, which may be conveniently used, e.g., in clinical settings, to diagnose patients exhibiting intracellular vesicle disorder abnormalities.

Nucleic acid-based detection techniques are described, below, in Section 5.4.1. Peptide detection techniques are described, below, in Section 5.4.2.

Additionally, such applications include methods for the treatment of disorders involving abnormal intracellular vesicles, including CHS, as described, below, in Section 5.4.4, and for the identification of compounds which modulate the expression of the bg gene and/or the activity of the bg gene product, as described below, in Section 5.4.3. Such compounds can include, for example, other cellular products which are involved in normal differentiation and/or function of intracellular vesicles.

5.4.1. DETECTION OF bg GENE NUCLEIC ACID MOLECULES

Mutations within the bg gene can be detected by utilizing a number of techniques. Nucleic acid from any nucleated cell can be used as the starting point for such assay techniques, and may be isolated according to standard nucleic acid preparation procedures which are well known to those of skill in the art.

DNA may be used in hybridization or amplification assays of biological samples to detect abnormalities involving bg gene structure, including point mutations, insertions, deletions and chromosomal rearrangements. Such assays may include, but are not limited to, Southern analyses, single stranded conformational polymorphism analyses (SSCP), and PCR analyses.

Such diagnostic methods for the detection of bg gene-specific mutations can involve for example, contacting and incubating nucleic acids including recombinant DNA molecules, cloned genes or degenerate variants thereof, obtained from a sample, e.g., derived from a patient sample or other appropriate cellular source, with one or more labeled nucleic acid reagents including recombinant DNA molecules, cloned genes or degenerate variants thereof, as described in Section 5.1, under conditions favorable for the specific annealing of these reagents to their complementary sequences within the bg gene. Preferably, the lengths of these nucleic acid reagents are at least 15 to 30 nucleotides. After incubation, all non-annealed nucleic acids are removed from the nucleic acid:bg molecule hybrid. The presence of nucleic acids which have hybridized, if any such molecules exist, is then detected. Using such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid reagents of the type described in Section 5.1 are easily removed. Detection of the remaining, annealed, labeled bg nucleic acid reagents is accomplished using standard techniques well-known to those in the art. The bg gene sequences to which the nucleic acid reagents have annealed can be compared to the annealing pattern expected from a normal bg gene sequence in order to determine whether a bg gene mutation is present.

Alternative diagnostic methods for the detection of bg gene specific nucleic acid molecules, in patient samples or other appropriate cell sources, may involve their amplification, e.g., by PCR (the experimental embodiment set forth in Mullis, K. B., 1987, U.S. Pat. No. 4,683,202), followed by the detection of the amplified molecules using techniques well known to those of skill in the art. The resulting amplified sequences can be compared to those which would be expected if the nucleic acid being amplified contained only normal copies of the bg gene in order to determine whether a bg gene mutation exists.

Additionally, well-known genotyping techniques can be performed to identify individuals carrying bg gene mutations. Such techniques include, for example, the use of restriction fragment length polymorphisms (RFLPs), which involve sequence variations in one of the recognition sites for the specific restriction enzyme used.

Additionally, improved methods for analyzing DNA polymorphisms which can be utilized for the identification of bg gene mutations have been described which capitalize on the presence of variable numbers of short, tandemly repeated DNA sequences between the restriction enzyme sites. For example, Weber (U.S. Pat. No. 5,075,217, which is incorporated herein by reference in its entirety) describes a DNA marker based on length polymorphisms in blocks of (dC-dA)n-(dG-dT)n short tandem repeats. The average separation of (dC-dA)n-(dG-dT)n blocks is estimated to be 30,000–60,000 bp. Markers which are so closely spaced exhibit a high frequency co-inheritance, and are extremely useful in the identification of genetic mutations, such as, for example, mutations within the bg gene, and the diagnosis of diseases and disorders related to bg mutations.

Also, Caskey et al. (U.S. Pat. No. 5,364,759, which is incorporated herein by reference in its entirety) describe a DNA profiling assay for detecting short tri and tetra nucleotide repeat sequences. The process includes extracting the DNA of interest, such as the bg gene, amplifying the extracted DNA, and labelling the repeat sequences to form a genotypic map of the individual's DNA.

The level and/or type of bg gene expression can also be assayed. For example, RNA from a cell type or tissue known, or suspected, to express the bg gene, may be isolated and tested utilizing hybridization or PCR techniques such as are described, above. The isolated cells can be derived from cell culture or from a patient. The analysis of cells taken from culture may be a necessary step in the assessment of cells to be used as part of a cell-based gene therapy technique or, alternatively, to test the effect of compounds on the expression of the bg gene. Such analyses may reveal both quantitative and qualitative aspects of the expression pattern of the bg gene, including activation or inactivation of bg gene expression, as well as reveal the presence or absence of alternatively spliced forms of bg gene transcripts.

In one embodiment of such a detection scheme, a cDNA molecule is synthesized from an RNA molecule of interest (e.g., by reverse transcription of the RNA molecule into cDNA). A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the bg gene nucleic acid reagents described in Section 5.1. The preferred lengths of such nucleic acid reagents are at least 9–30 nucleotides. For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

Additionally, it is possible to perform such bg gene expression assays "in situ", i.e., directly upon tissue sections (fixed and/or frozen) of patient tissue obtained from biopsies or resections, such that no nucleic acid purification is necessary. Nucleic acid reagents such as those described in Section 5.1 may be used as probes and/or primers for such in situ procedures (see, for example, Nuovo, G. J., 1992, "PCR In Situ Hybridization: Protocols And Applications", Raven Press, NY).

Alternatively, if a sufficient quantity of the appropriate cells can be obtained, standard Northern analysis can be performed to determine the level of mRNA expression of the bg gene.

5.4.2. DETECTION OF bg GENE PRODUCTS

Antibodies directed against wild type or mutant bg gene products or conserved variants or peptide fragments thereof, which are discussed, above, in Section 5.3, may also be used as intracellular vesicle, including, but not limited to CHS, disorder diagnostics and prognostics, as described herein. Such diagnostic methods, may be used to detect abnormalities in the level of bg gene expression, or abnormalities in the structure and/or temporal, tissue, cellular, or subcellular location of bg gene product. Further, such assays can be utilized to detect the presence or absence of bg gene products encoded by alternatively spliced bg gene transcripts. Given the intracellular vesicles affected by bg mutations, it is possible that the bg gene product is an intracellular gene product. The antibodies and immunoassay methods described below, therefore, have important in vitro applications in assessing the efficacy of treatments for such disorders. Antibodies, or fragments of antibodies, such as those described below, may be used to screen potentially therapeutic compounds in vitro to determine their effects on bg gene expression and bg peptide production. The compounds which have beneficial effects on intracellular vesicle disorders, such as for example, CHS, can be identified, and a therapeutically effective dose determined.

In vitro immunoassays may also be used, for example, to assess the efficacy of cell-based gene therapy for intracellular vesicle disorder, including, for example, CHS. Antibodies directed against bg peptides may be used in vitro to determine the level of bg gene expression achieved in cells genetically engineered to produce bg peptides. Given that the bg gene product may represent an intracellular gene product, such an assessment is, preferably, done using cell lysates or extracts. Such analysis will allow for a determination of the number of transformed cells necessary to achieve therapeutic efficacy in vivo, as well as optimization of the gene replacement protocol.

The tissue or cell type to be analyzed will generally include those which are known, or suspected, to express the bg gene. The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, New York), which is incorporated herein by reference in its entirety. The isolated cells can be derived from cell culture or from a patient. The analysis of cell taken from culture may be a necessary step in the assessment of cells to be used as part of a cell-based gene therapy technique or, alternatively, to test the effect of compounds on the expression of the bg gene.

Preferred diagnostic methods for the detection of bg gene products or conserved variants or peptide fragments thereof, may involve, for example, immunoassays wherein the bg gene products or conserved variants or peptide fragments are detected by their interaction with an anti-bg gene product-specific antibody.

For example, antibodies, or fragments of antibodies, such as those described, above, in Section 5.3, useful in the present invention may be used to quantitatively or qualitatively detect the presence of bg gene products or conserved variants or peptide fragments thereof. This can be accomplished, for example, by immunofluorescence techniques employing a fluorescently labeled antibody (see below, this Section) coupled with light microscopic, flow cytometric, or fluorimetric detection. Such techniques are especially preferred if such bg gene products are expressed on the cell surface.

The antibodies (or fragments thereof) useful in the present invention may, additionally, be employed histologically, as in immunofluorescence or immunoelectron microscopy, for in situ detection of bg gene products or conserved variants or peptide fragments thereof. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the bg gene product, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

Immunoassays for bg gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of identifying bg gene products or conserved variants or peptide fragments thereof, and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled bg gene specific antibody. The solid phase support may then be washed with the buffer a second time to remove unbound antibody. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-bg gene product antibody may be determined according to well known methods. Those skilled in the art will be able to determine operative and optimal assay conditions for each determination by employing routine experimentation.

One of the ways in which the bg gene peptide-specific antibody can be detectably labeled is by linking the same to an enzyme and use in an enzyme immunoassay (EIA) (Voller, A., "The Enzyme Linked Immunosorbent Assay (ELISA)", 197, Diagnostic Horizons 2:1–7, Microbiological Associates Quarterly Publication, Walkersville, Md.); Voller, A. et al., 1978, J. Clin. Pathol. 31:507–520; Butler, J. E., 1981, Meth. Enzymol. 73:482–523; Maggio, E. (ed.), 1980, Enzyme Immunoassay, CRC Press, Boca Raton, Fla.,; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect bg gene peptides through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

5.4.3. SCREENING ASSAYS FOR COMPOUNDS THAT MODULATE bg GENE ACTIVITY

The following assays are designed to identify compounds that bind to bg gene products, bind to other intracellular proteins that interact with a bg gene product, to compounds that interfere with the interaction of the bg gene product with other intracellular proteins and to compounds which modulate the activity of bg gene (i.e., modulate the level of bg gene expression and/or modulate the level of bg gene product activity). Assays may additionally be utilized which identify compounds which bind to bg gene regulatory sequences (e.g., promoter sequences). See e.g., Platt, K. A., 1994, J. Biol. Chem. 269:28558–28562, which is incorporated herein by reference in its entirety, which may modulate the level of bg gene expression. Compounds may include, but are not limited to, small organic molecules which are able to cross the blood-brain barrier, gain entry into an appropriate cell and affect expression of the bg gene or some other gene involved in the pathway or pathways regulating intracellular vesicle differentiation and/or function, or other intracellular proteins. Methods for the identification of such intracellular proteins are described, below, in Section 5.4.3.1. Such intracellular proteins may be involved in the differentiation and/or function of intracellular vesicles, including, but not limited to, lysosomes, melanosomes, platelet dense granules and cytolytic granules. Further, among these compounds are compounds which affect the level of bg gene expression and/or bg gene product activity and which can be used in the therapeutic treatment of disorders involving abnormal intracellular vesicles, including, but not limited to, abnormal lysosomes, melanosomes, platelet dense granules and cytolytic granules, including CHS, as described, below, in Section 5.4.4.

Compounds may include, but are not limited to, peptides such as, for example, soluble peptides, including but not limited to, Ig-tailed fusion peptides, and members of random peptide libraries; (see, e.g., Lam, K. S. et al., 1991, Nature 354:82–84; Houghten, R. et al., 1991, Nature 354:84–86), and combinatorial chemistry-derived molecular library made of D- and/or L- configuration amino acids, phosphopeptides (including, but not limited to members of random or partially degenerate, directed phosphopeptide libraries; see, e.g., Songyang, Z. et al., 1993, Cell 72:767–778), antibodies (including, but not limited to, polyclonal, monoclonal, humanized, anti-idiotypic, chimeric or single chain antibodies, and FAb, F(ab')$_2$ and FAb expression library fragments, and epitope-binding fragments thereof), and small organic or inorganic molecules.

Compounds identified via assays such as those described herein may be useful, for example, in elaborating the biological function of the bg gene product, and for ameliorating intracellular vesicle disorders such as, for example, CHS. Assays for testing the effectiveness of compounds, identified by, for example, techniques such as those described in Section 5.4.3.1–5.4.3.3, are discussed, below, in Section 5.4.3.4.

5.4.3.1. IN VITRO SCREENING ASSAYS FOR COMPOUNDS THAT BIND TO THE bg GENE PRODUCT

In vitro systems may be designed to identify compounds capable of binding the bg gene products of the invention. Compounds identified may be useful, for example, in modulating the activity of wild type and/or mutant bg gene products, may be useful in elaborating the biological function of the bg gene product, may be utilized in screens for identifying compounds that disrupt normal bg gene product interactions, or may in themselves disrupt such interactions.

The principle of the assays used to identify compounds that bind to the bg gene product involves preparing a reaction mixture of the bg gene product and the test compound under conditions and for a time sufficient to allow the two components to interact and bind, thus forming a complex which can be removed and/or detected in the reaction mixture. These assays can be conducted in a variety of ways. For example, one method to conduct such an assay would involve anchoring bg gene product or the test substance onto a solid phase and detecting bg gene product/test compound complexes anchored on the solid phase at the end of the reaction. In one embodiment of such a method, the bg gene product may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for bg gene product or the test compound to anchor any complexes formed in solution, and a labeled antibody specific for the other component of the possible complex to detect anchored complexes.

5.4.3.2. ASSAYS FOR INTRACELLULAR PROTEINS THAT INTERACT WITH THE bg GENE PRODUCT

Any method suitable for detecting protein-protein interactions may be employed for identifying bg protein-intracellular protein interactions.

Among the traditional methods which may be employed are co-immunoprecipitation, crosslinking and co-purification through gradients or chromatographic columns. Utilizing procedures such as these allows for the identification of intracellular proteins which interact with ba gene products. Once isolated, such an intracellular protein can be identified and can, in turn, be used, in conjunction with standard techniques, to identify proteins it interacts with. For example, at least a portion of the amino acid sequence of the intracellular protein which interacts with the bg gene product can be ascertained using techniques well known to those of skill in the art, such as via the Edman degradation technique (see, e.g., Creighton, 1983, "Proteins: Structures and Molecular Principles", W. H. Freeman & Co., N.Y., pp.34–49). The amino acid sequence obtained may be used as a guide for the generation of oligonucleotide mixtures that can be used to screen for gene sequences encoding such intracellular proteins. Screening made be accomplished, for example, by standard hybridization or PCR techniques. Techniques for the generation of oligonucleotide mixtures and the screening are well-known. (See, e.g., Ausubel, supra., and PCR Protocols: A Guide to Methods and Applications, 1990, Innis, M. et al., eds. Academic Press, Inc., New York).

Additionally, methods may be employed which result in the simultaneous identification of genes which encode the intracellular protein interacting with the bg protein. These methods include, for example, probing expression libraries with labeled bg protein, using bg protein in a manner similar to the well known technique of antibody probing of λgt11 libraries.

One method which detects protein interactions in vivo, the two-hybrid system, is described in detail for illustration only and not by way of limitation. One version of this system has been described (Chien et al., 1991, Proc. Natl. Acad. Sci. USA, 88:9578–9582) and is commercially available from Clontech (Palo Alto, Calif.).

Briefly, utilizing such a system, plasmids are constructed that encode two hybrid proteins: one consists of the DNA-binding domain of a transcription activator protein fused to the bg gene product and the other consists of the transcription activator protein's activation domain fused to an unknown protein that is encoded by a cDNA which has been recombined into this plasmid as part of a cDNA library. The DNA-binding domain fusion plasmid and the cDNA library are transformed into a strain of the yeast *Saccharomvces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. By way of example, and not by way of limitation, bg gene products may be used as the bait gene product. Total genomic or cDNA sequences are fused to the DNA encoding an activation domain. This library and a plasmid encoding a hybrid of a bait bg gene product fused to the DNA-binding domain are cotransformed into a yeast reporter strain, and the resulting transformants are screened for those that express the reporter gene. For example, and not by way of limitation, a bait bg gene sequence, such as the bg open reading frame sequence in FIG. 4, can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait bg gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait bg gene-GAL4 fusion plasmid into a yeast strain which contains a lacZ gene driven by a promoter which contains GAL4 activation sequence. A cDNA encoded protein, fused to GAL4 transcriptional activation domain, that interacts with bait bg gene product will reconstitute an active GAL4 protein and thereby drive expression of the HIS3 gene. Colonies which express HIS3 can be detected by their growth on petri dishes containing semi-solid agar based media lacking histidine. The cDNA can then be purified from these strains, and used to produce and isolate the bait bg gene-interacting protein using techniques routinely practiced in the art.

5.4.3.3. ASSAYS FOR COMPOUNDS THAT INTERFERE WITH bg GENE PRODUCT/ INTRACELLULAR MACROMOLECULE INTERACTION

The bg gene products of the invention may, in vivo, interact with one or more intracellular macromolecules, such as proteins. Such macromolecules may include, but are not limited to, nucleic acid molecules and those proteins identified via methods such as those described, above, in Section 5.4.3.2. For purposes of this discussion, such intracellular macromolecules are referred to herein as "binding partners". Compounds that disrupt bg binding in this way may be useful in regulating the activity of the bg gene product, especially mutant bg gene products. Such compounds may include, but are not limited to molecules such as peptides, and the like, as described, for example, in Section 5.4.3.1. above, which would be capable of gaining access to the intracellular bg gene product.

The basic principle of the assay systems used to identify compounds that interfere with the interaction between the bg gene product and its intracellular binding partner or partners involves preparing a reaction mixture containing the bg gene product, and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of bg gene product and its intracellular binding partner. Control reaction mixtures are incubated without the test compound or with a placebo. The formation of any complexes between the bg gene protein and the intracellular binding partner is then detected. The formation of a complex in the control reaction, but not in the reaction mixture containing the test compound, indicates that the compound interferes with the interaction of the bg gene protein and the interactive binding partner. Additionally, complex formation within reaction mixtures containing the test compound and normal bg gene protein may also be compared to complex formation within reaction mixtures containing the test compound and a mutant bg gene protein. This comparison may be important in those cases wherein it is desirable to identify compounds that disrupt interactions of mutant but not normal bg gene proteins.

The assay for compounds that interfere with the interaction of the bg gene products and binding partners can be conducted in a heterogeneous or homogeneous format. Heterogeneous assays involve anchoring either the bg gene product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the bg gene products and the binding partners, e.g., by competition, can be identified by conducting the reaction in the presence of the test substance; i.e., by adding the test substance to the reaction mixture prior to or simultaneously with the bg gene protein and interactive intracellular binding partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either the bg gene product or the interactive intracellular binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the bg gene product or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the bg gene protein and the interactive intracellular binding partner is prepared in which either the bg gene product or its binding partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt bg gene protein/intracellular binding partner interaction can be identified.

In a particular embodiment, the bg gene product can be prepared for immobilization using recombinant DNA techniques described in Section 5.2. above. For example, the bg coding region can be fused to a glutathione-S-transferase (GST) gene using a fusion vector, such as pGEX-5X-1, in such a manner that its binding activity is maintained in the resulting fusion protein. The interactive intracellular binding partner can be purified and used to raise a monoclonal antibody, using methods routinely practiced in the art and described above, in Section 5.3. This antibody can be labeled with the radioactive isotope $^{125}$I, for example, by methods routinely practiced in the art. In a heterogeneous assay, e.g., the GST-bg fusion protein can be anchored to glutathione-agarose beads. The interactive intracellular binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the bg gene protein and the interactive intracellular binding partner can be detected by measuring the amount of radioactivity that remains associated with the glutathione-agarose beads. A successful inhibition of the interaction by the test compound will result in a decrease in measured radioactivity.

Alternatively, the GST-B gene fusion protein and the interactive intracellular binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the bg gene product/binding partner interaction can be detected by adding the labeled antibody and measuring the radioactivity associated with the beads.

In another embodiment of the invention, these same techniques can be employed using peptide fragments that correspond to the binding domains of the bg protein and/or the interactive intracellular or binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described in this Section above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the intracellular binding partner is obtained, short gene segments can be engineered to express peptide fragments of the protein, which can then be tested for binding activity and purified or synthesized.

For example, and not by way of limitation, a ba gene product can be anchored to a solid material as described, above, in this Section by making a GST-bg fusion protein and allowing it to bind to glutathione agarose beads. The interactive intracellular binding partner can be labeled with a radioactive isotope, such as $^{35}S$, and cleaved with a proteolytic enzyme such as trypsin. Cleavage products can then be added to the anchored GST-bg fusion protein and allowed to bind. After washing away unbound peptides, labeled bound material, representing the intracellular binding partner binding domain, can be eluted, purified, and analyzed for amino acid sequence by well-known methods. Peptides so identified can be produced synthetically or fused to appropriate facilitative proteins using recombinant DNA technology.

5.4.3.4. ASSAYS FOR IDENTIFICATION OF COMPOUNDS THAT AMELIORATE INTRACELLULAR VESICLE DISORDERS

Compounds, including but not limited to binding compounds identified via assay techniques such as those described, above, in Sections 5.4.3.1–5.4.3.3, can be tested for the ability to ameliorate intracellular vesicle disorder symptoms, including symptoms associated with CHS. It should be noted that although bg gene products may be intracellular molecules which are not secreted and have no transmembrane component, the assays described herein can identify compounds which affect bg gene activity by either affecting bg gene expression or by affecting the level of bg gene product activity. For example, compounds may be identified which are involved in another step in the pathway in which the bg gene and/or bg gene product is involved and, by affecting this same pathway may modulate the affect of bg on the development of intracellular vesicle disorders. Such compounds can be used as part of a therapeutic method for the treatment of intracellular vesicle disorders, including, for example, CHS.

Described below are cell-based and animal model-based assays for the identification of compounds exhibiting such an ability to intracellular vesicle disorder symptoms.

First, cell-based systems can be used to identify compounds which may act to ameliorate intracellular vesicle disorder symptoms. Such cell systems can include, for example, recombinant or non-recombinant cells, such as cell lines, which express the bg gene. Further, such cell systems can include, for example, recombinant or non-recombinant cell, such as cell lines, which express mutant forms of the bg gene and/or which exhibit elements of the bg phenotype. For example, bg fibroblast cells, Aleutian mink cells or human Chediak-Higashi cells, as described, below, in Sections 7 and 8, can be used.

In utilizing such cell systems, cells may be exposed to a compound, suspected of exhibiting an ability to ameliorate intracellular vesicle disorder symptoms, at a sufficient concentration and for a time sufficient to elicit such an amelioration in the exposed cells. After exposure, the cells can be assayed to measure alterations in the expression of the bg gene, e.g., by assaying cell lysates for bg MRNA transcripts (e.g., by Northern analysis) or for bg protein expressed in the cell; compounds which increase expression of the bg gene are good candidates as therapeutics. Alternatively, the cells are examined to determine whether one or more aspects of the bg cellular phenotype has been altered to resemble a more normal or more wild type, phenotype, or a phenotype more likely to produce a lower incidence or severity of intracellular disorder symptoms.

In addition, animal-based intracellular vesicle disorder systems, which may include, for example bg mice, may be used to identify compounds capable of ameliorating intracellular vesicle disorder-like symptoms (e.g., bg phenotype). Such animal models may be used as test substrates for the identification of drugs, pharmaceuticals, therapies and interventions which may be effective in treating such disorders. For example, animal models may be exposed to a compound, suspected of exhibiting an ability to ameliorate intracellular vesicle disorder symptoms, at a sufficient concentration and for a time sufficient to elicit such an amelioration of the symptoms in the exposed animals. The response of the animals to the exposure may be monitored by assessing the reversal of disorders associated with intracellular vesicle disorders such as CHS.

With regard to intervention, any treatments which reverse any aspect of the intracellular disorder-like symptoms should be considered as candidates for human intracellular disorder therapeutic intervention. Dosages of test agents may be determined by deriving dose-response curves, as discussed in Section 5.5.1, below.

5.4. COMPOUNDS AND METHODS FOR THE TREATMENT OF INTRACELLULAR VESICLE DISORDERS

Described below are methods and compositions whereby intracellular vesicle disorders, including, but not limited to, CHS may be treated. Loss of normal bg gene product function results in the development of a bg, or intracellular vesicle disorder, phenotype, an increase in bg gene product activity would facilitate progress towards a normal state in individuals exhibiting a deficient level of bg gene expression and/or bg gene product activity.

Alternatively, it is conceivable that symptoms of certain intracellular vesicle disorders may be ameliorated by decreasing the level of bg gene expression and/or bg gene product activity. For example, bg gene sequences may be utilized in conjunction with well-known antisense, gene "knock-out," ribozyme and/or triple helix methods to decrease the level of bg gene expression.

With respect to an increase in the level of normal bg gene expression and/or bg gene product activity, bg gene nucleic acid sequences, described, above, in Section 5.1, can, for example, be utilized for the treatment of intracellular vesicle disorders, including CHS. Such treatment can be administered, for example, in the form of gene replacement therapy. Specifically, one or more copies of a normal bg gene or a portion of the bg gene that directs the production of a bg gene product exhibiting normal bg gene function, may be inserted into the appropriate cells within a patient, using vectors which include, but are not limited to adenovirus, adeno-associated virus, and retrovirus vectors, in addition to other particles that introduce DNA into cells, such as liposomes.

It is conceivable that it may be advantageous to achieve bg gene expression in the brain, given the large number of cell type affected by the bg and CHS phenotypes. As such, gene replacement therapy techniques may be utilized which are capable delivering bg gene sequences to these cell types within patients. Thus, the techniques for delivery of hg gene sequences should be able to readily cross the blood-brain barrier, which are well known to those of skill in the art (see, e.g., PCT application, publication No. WO89/10134, which is incorporated herein by reference in its entirety), or, alternatively, should involve direct administration of such bg gene sequences to the site of the cells in which the bg gene sequences are to be expressed. With respect to delivery which is capable of crossing the blood-brain barrier, viral vectors such as, for example, those described above, are preferable.

Additional methods which may be utilized to increase the overall level of hg gene expression and/or bg gene product activity include the introduction of appropriate bg-expressing cells, preferably autologous cells, into a patient at positions and in numbers which are sufficient to ameliorate the symptoms of intracellular vesicle disorders, including CHS. Such cells may be either recombinant or non-recombinant.

Alternatively, cells, preferably autologous cells, can be engineered to express bg gene sequences which may then be introduced into a patient in positions appropriate for the amelioration of intracellular vesicle disorder symptoms. Alternately, cells which express the bg gene in a wild type in MHC matched individuals, i.e., non-bg individual, and may include, for example, hypothalamic cells. The expression of the bg gene sequences is controlled by the appropriate gene regulatory sequences to allow such expression in the necessary cell types. Such gene regulatory sequences are well known to the skilled artisan. Such cell-based gene therapy techniques are well known to those skilled in the art, see, e.g., Anderson, F., U.S. Pat. No. 5,399,349.

When the cells to be administered are non-autologous cells, they can be administered using well known techniques which prevent a host immune response against the introduced cells from developing. For example, the cells may be introduced in an encapsulated form which, while allowing for an exchange of components with the immediate extracellular environment, does not allow the introduced cells to be recognized by the host immune system.

Additionally, compounds, such as those identified via techniques such as those described, above, in Section 5.4.3, which are capable of modulating bg gene product activity can be administered using standard techniques which are well known to those of skill in the art.

5.5. PHARMACEUTICAL PREPARATIONS AND METHODS OF ADMINISTRATION

The compounds that are determined to affect bg gene expression or gene product activity can be administered to a patient at therapeutically effective doses to treat or ameliorate intracellular vesicle disorders, including CHS. A therapeutically effective dose refers to that amount of the compound sufficient to result in amelioration of symptoms of intracellular vesicle disorders, including elements associated with the bg phenotype and/or the CHS phenotype.

5.5.1. EFFECTIVE DOSE

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

5.5.2. FORMULATIONS AND USE

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

6. EXAMPLE

Genetic and Physical Mapping of the bg Gene

The Example presented in this Section describes genetic mapping of the murine bg locus into a minimal genetic interval of 0.41 cM+/−0.1 cM on murine chromosome 13. Physical mapping of this minimal bg genetic interval is established herein to be approximately 1 Mb.

6.1 MATERIALS AND METHODS

Mouse crosses segregating beige. Multiple strain crosses were established to maximize inter strain variation in order to facilitate detection of polymorphisms of mapping markers. These included i) (C57BL/6J-$bg^J$ X DBA/2J) X C57BL/6J-$bg^J$; ii) (DBA/2 Co-$bg^{8J}$ X C57BL/6J) X DBA/2 Co-$bg^{8J}$; iii) (C3H/HeJ-$bg^{2J}$ X CAST/Ei) X C3H/HeJ-$bg^{2J}$; iv) (C57BL/6J-$bg^J$ X CAST/Ei) X C57BL/6J-$bg^J$; v) (DBA/2 Co- $bg^{8J}$ X CAST/Ei) X DBA/2 Co- $bg^{8J}$. The offspring of each of these backcrosses were analyzed, by coat color, for their bg genotype. Genomic DNA was made from a tail clip from each and analyzed for multiple simple sequence length repeat polymorphisms (SSLP). Not all strain combinations were polymorphic for all markers. Additional loci, Nidogen (Nid) and Ras like protein1 (Rasl1) were also genotyped in mice from crosses utilizing CAST/Ei. CAST/Ei vs inbred strain polymorphisms were detected using Single Stranded Conformational polymorphism (SSCP). The primers used for Nid were; forward 5'-CAGTGGAATGACCACCAGGCC-3' (SEQ ID NO:13) and reverse 5'-GTTGCAGGCATGTACCACTAC-3' (SEQ ID NO:14) (from mouse cDNA sequence, NCBI GenInfo ID: 53383) The Rasl1 primers were: forward 5'-TATGAACCTACCAAAGCAGAC-3' (SEQ ID NO:15) and reverse 5'ACTTCGGAAGTAGTTGTCTC (SEQ ID NO:16) (from rat RALA cDNA sequence, GenBank Accession: L19698). The PCR amplification conditions were 94° C. for 2 minutes, 0.15U of AmpliTaq was added for a hot start, followed by 30 cycles of 94° C. for 40 secs, 55° C. for 50 secs, 72° C. for 30 secs. The products were run on either a nondenaturing 8% acrylamide gel at 45W, room temperature for 3 hours, for SSLP analysis or, for SSCP analysis, on a 10% acrylamide gel run at 20W, 4° C. for 2.5 hours. Both types of gel were stained, post running, with SYBR Green I and scanned on an MD Fluorimager.

A linkage map of all loci, including bg was constructed, manually, for proximal MMU Chr 13 by minimizing double and multiple cross overs.

Interspecific backcross mapping. One hundred and eighty eight (C57BL/6J X Mus spretus) X C57BL/6J backcross mice were generated and genomic DNA was prepared to create a BSB mapping panel. A framework map was established using 80 previously mapped SSLP markers which encompassed each chromosome. The conditions used for SSLP analysis were as described above. Linkage maps were constructed using Map manager v2.6.5 (Manley, K. F., 1993, Mammalian Genome 4:303–313).

Additional loci, Nid, Rasl1, Ryanodine receptor 2, (Ryr2) and Neutrophil oxidase factor 2-related sequence, (Ncf2-rs), were also placed on the Chr 13 map using SSCP as each gave a C57BL/6J vs Mus spretus polymorphism. Nid, Rasl, were typed as described above. Ryr2 was analyzed by SSCP using the following primers, (from mouse cDNA sequence, NCBI GenInfo ID: 516278): forward 5'-CAAAGAAAGCCCTCAGAAAC-3' (SEQ ID NO:17) and reverse 5'-AAAGAGGAAAACCCAAGACT-3' (SEQ ID NO:18). Ncf2-rs was also analyzed by SSCP using the following primers (designed from human cDNA sequence, GenBank Accession No. U00776): forward 5'-CAAAAACAAGACACCCAAGT-3' (SEQ ID NO:19) and reverse 5'-TGTGGAATTGAGTGTTGTAG-3' (SEQ ID NO:20).

Physical map of ba minimal interval. The Whitehead mouse YAC library (Research Genetics; Huntsville, Ala.) was screened using SSLP markers including D13Mit173, D13Mit44, D13Mit305 using the PCR conditions described above. The YAC end clones were isolated according to standard methods. The YAC end clones were sequenced on an ABI sequencer. PCR primers from each unique end clone were designed, and used to map the end clone back to the mouse genome on the BSB map to check for chimeric YAC's. Those ends that mapped to the correct region of MMU Chr 13 were subsequently used in further rounds of YAC library screening. Cross addressing of the various SSLP markers and YAC end clones allowed a full YAC contig across the bg minimal genetic interval to be established. BACs were also isolated across the physical region using markers from the region.

In order to size the YACs, yeast genomic DNA was prepared according to the New England Biolabs Imbed procedure. Contour clamped homogeneous electric field (CHEF) electrophoresis was carried out using a CHEF MAPPER electrophoresis apparatus (Bio-Rad Laboratories, Inc., Hercules, Calif.) for 28 hours on a 1% agarose gel with an electric field gradient of 6V/cm at 14° C. and a pulse time of 12.55 sec.

6.2 RESULTS

The mapping procedures described in Section 6.1, above, and depicted in FIG. 1, yielded a genetic map with gave a minimal genetic interval for the bg locus of 0.41±0.1 cM. The data giving this result are summarized herein.

The proximal interval, between bg and D13Mit173, was 2/690 recombinants which was 0.14±0.1 cM. The distal interval, between bg and D13Mit305, was 8/1496 recombinants which was 0.27±0.1 cM. The non-recombinant marker SSLP marker D13Mit44 was typed in 690 animals giving an upper genetic distance (at the 95% confidence limit) between bg and D13Mit44 of 0.4 cM.

The homologous genes Nid, which maps to human Chr 1q43, and Rasl, which maps to human Chr 7p, were also placed on the bg genetic map. Nid was non-recombinant in 690 mice putting it within (at the 95% confidence limit) 0.4 cM of bg. Rasl mapped 0.72 cM distal of bg. The homologous gene Ryr2, which maps to human Chr 1q43-q42, was not mapped in the bg segregating crosses as no polymorphism between any of the strains used was found but it was mapped in the BSB mapping panel. By inference from the BSB map, Ryr2 maps within 1.6 cM of Nid (95% confidence limit). The simplest interpretation of the mapping of homologous genes to the map of proximal mouse Chr 13 around the bg region was that bg is likely to fall within the 1q43 syntenic region on the human genetic map.

The mapping of the locus referred to herein as Ncf2-rs was done using primers designed to amplify human cDNA sequence. Ncf2 has been mapped to human Chr 1cen-q32 and to mouse chromosome 1 (Francke U., 1990, Am. J. Hum. Genet. 47:483–92). The primers designed produced a PCR fragment which mapped to the bg region of Chr13.

The YAC and BAC coverage across the minimal bg genetic interval gives an estimated physical distance of approximately 1 Mb.

7. EXAMPLE

YAC Complementation of the Beige Mutation

The experiments presented in this Section describe results which have localized the murine bg gene to a specific interval on murine chromosome 13. Specifically, a complementation-based strategy was utilized to identify two overlapping murine yeast artificial chromosomes (YACs) capable of complementing the murine bg mutation. One of these YACs was tested, via cell fusion studies, and found to be capable of complementing Aleutian mink and human Chediak-Higashi syndrome (CHS) mutant phenotypes, thus strongly suggesting that the mouse, human and mink mutant phenotypes are caused by defects in homologous genes.

7.1. MATERIALS AND METHODS

Isolation and Characterization of YACs. The primers F: 5'-CCAGCCACAGAATACCATCC-3' (SEQ ID NO:21) and R: 5'-GGACATACTCTGCTGCCATC-3' (SEQ ID NO:22) specific for Nidogen (Nid) amino terminal sequences were used to screen the Princeton and Whitehead mouse YAC libraries using the following conditions on an Idaho Technologies Thermal Cycler: 20 sec. 94° hot start, 94° 0 sec./50° 0 sec./72° 15 sec. for 35 cycles. To identify the positive pools, the PCR products were separated on 2% agarose gels, transferred to Nytran membranes and probed by standard hybridization techniques. This screen resulted in the isolation of YACs 195.A8, 151.H1, C9.E7, and C96.G11. YAC 113.G6 was isolated from the Whitehead library using the primers: F:5'-ACCCCAGAACTTGAGAAATAG-3' (SEQ ID NO:23)and R:5'-TGCTGAGGTGATAGGTTTATG-3' (SEQ ID NO:24) specific for the Sequence Tagged Site (STS) 195.A8-right end (R) using the above mentioned PCR conditions. Yeast plugs were prepared according to Gnirke et al. (Gnirke, A. et al., 1993, Genomics 15:659–667). YAC DNA was analyzed by Southern blots or PCR to determine STS and Nid content. The sizes of the YACs were determined using pulsed-field gel electrophoresis on a Bio-Rad CHEF DRII, with a pulse time of 10 to 100 seconds.

YAC End Isolation. One or both end fragments of YACs C9.E7, 195.A8 and 151.H1 were isolated and used to create STS. The end fragments were isolated using inverse PCR according to Joslyn et al. (Joslyn, G., et al., 1991, Cell 66:601–613). Each inverse PCR product was either directly sequenced using the M13-UP and RP sites engineered into the primers, or cloned using Invitrogen's TA cloning kit, and then sequenced using the T7 and SP6 sequencing primers. PCR primers specific for each unique end were created and tested on mouse genomic DNA to determine whether they amplified the expected size product.

YAC End Analysis. Each YAC end was tested to determine whether it was derived from mouse chromosome 13. For YAC end analysis, all STS were tested against a panel of mouse/hamster somatic cell hybrids, some of which harbored mouse chromosome 13 (Kozak, C. A. et al., 1975, Som. Cell Gen. 1:371–382). Each hybrid was tested with the dinucleotide repeat markers D13MIT44 and 173 from Research Genetics specific for the bg/Nid region of mouse chromosome 13 before use to determine whether the relevant region of mouse chromosome 13 was present. Southern blots of these hybrids were then probed with YAC end STS to determine if these markers were present in the mouse chromosome 13 positive hybrids. In some instances, YAC end STS were assayed by PCR. The ends of YAC 195.A8 were further analyzed by genetic mapping onto a panel of interspecific backcrossed beige mice (Jenkins, N. A. et al., 1991, Genomics 9:401–403). Genomic DNA blots of mice from this panel were prepared and hybridized with the single copy STS 195.A8-R and 195.A8-left end (L). The map positions of these two markers was then determined using the program Map Manager v2.6.3 (Manley, K. F., 1993, Mammalian Genome 4:303–313). This analysis placed these two markers on the same genetic interval as bg and Nid.

SpheroDlast fusion and YAC microiniection. All YACs were "retrofitted" with the neomycin resistance gene using the vector pRV1 and homologous recombination in yeast as described by Srivastava and Schlessinger (Srivastava, A. & Schlessinger, D., 1991, Gene 103:53–59). This protocol introduces the neomycin resistance gene and the LYS2 gene into the URA3 gene present in the YAC "right" arm. Spheroplast fusion using retrofitted YACs was performed according to Huxley et al. (Huxley, C. et al., 1991, Genomics 9:742–750) with the following modifications. A 100 ml culture of yeast was grown to an OD$_{600}$ of 3–4 in SD-Lys-Trp. Spheroplasts were prepared using Oxalyticase (Enzogenetics, Oregon) and resuspended in two milliliters of STC (1M Sorbitol, 10 mM CaCl$_2$, 10 mM Tris pH8). bg mouse fibroblasts (3×10$^6$ MCHSF2) were fused to 0.5 ml of the spheroplast preparation in 0.4 mls of 50% PEG/10 mM CaCl$_2$ (Boehringer Mannheim) for 100, 150 and 200 seconds. The fusion reaction, was diluted with 4.0 mls of serum-free Dulbecco's, incubated at room temperature for twenty minutes, centrifuged at loog and plated into four 100 mm plates. Microinjections were performed according to Gnirke et al. (Gnirke, A. et al., 1993, Genomics 15:659–667). Twenty-four hours after fusion or microinjection, the cells were washed twice with PBS and incubated with Dulbecco's minimal essential media containing 10% FCS and 400–500 µg/ml G418 for three to four weeks. Individual colonies were isolated and expanded to at least 1×10$^6$ cells. Genomic DNA was isolated from these colonies using Qiagen Genomic DNA Tips and the DNA used for Southern or PCR analysis. YAC vector sequences which are immediately adjacent to the genomic insert were assayed using PCR primers specific for YAC "left" and "right" arms (Peterson, K. R. et al., 1993, Proc. Natl, Acad. Sci. U.S.A. 90:7593–7597), or by Southern blotting using the YAC vector as a probe. For Southern blotting, ten µg of fibroblast DNA or 2 µg of yeast DNA was cut with HindIII, run on a 0.8% agarose gel, and then transferred to a Nytran membrane. This membrane was then hybridized with the 9.5 kb gel purified HindIII fragment of the retrofitting vector pRV1.

Fluorescent Microscopy. Cells were examined for lysosomal morphology using fluorescent labeling of lysosomes (Perou, C. M. & Kaplan, J., 1993, Som. Cell Mol. Gen. 19:459–468). Briefly, lysosomes were labeled by incubating cells overnight in Dulbecco's plus 10% FCS with 0.5 mg/ml Lucifer Yellow-CH, followed by two washes in culture medium, and a final 2–6 hour chase in medium alone. Lysosomes were visualized on live cells using standard fluorescent microscopy techniques.

Somatic Cell Fusions. Aleutian mink or Human CHS (GM02075A) fibroblast lysosomes were labeled with Lucifer Yellow-CH, while the complemented hg mouse fibroblast colony 195-4 lysosomes was separately labeled with dextran-Texas Red. The two cell populations were trypsinized, mixed together, and fused to one another using UV-inactivated Sendai virus (Perou, C. M. & Kaplan, J., 1993, Som. Cell Mol. Gen. 19:459–468; Schlegel, R. S. & Rechsteiner, M. C., 1975, Cell 5:371–379). The cells were plated and examined twenty-four hours later using fluorescent microscopy. Two photographs of the same field were taken, one to visualize the Lucifer Yellow fluorescence and a second to visualize the dextran-Texas Red. A heterokaryon could be identified by the presence of both dyes within all lysosomes of one cell.

7.2. RESULTS

The experiments reported herein describe, first, the isolation and characterization of murine YACs lying within the physical region in which the bg gene must reside. Further, a complementation-based strategy is utilized to identify which of the isolated YACs were able to complement the bg phenotype, thus significantly narrowing the region within which the bg gene must be located. Third, one of these murine YACs was tested, via cell fusion studies, and found to be capable of complementing the bg phenotype in cells of other species, namely those of Aleutian mink and human.

YAC Characterization. As discussed in Section 6, above, and in Jenkins et al. (Jenkins, N. A. et al., 1991, Genomics 9:401–403) the bg gene is located near Nid on chromosome 13. PCR primers specific for Nid were, therefore, utilized to isolate YACs from the bg/Nid region (FIG. 2A). The Princeton and Whitehead mouse YAC libraries were screened, yielding two YACs from each library. Inverse PCR was used to isolate YAC ends, which were sequenced and used to create STS. Each isolated YAC end was tested to determine if it was derived from mouse chromosome 13. Some of these STS were then used to develop a YAC contig across the bg interval. Of the four Nid positive YACs isolated, 151.H1 and C96.G11 were determined to be unstable and were not used. YACs C9.E7 and 195.A8 were both derived from chromosome 13, mapped to the bg interval, and remained stable with time. A fifth YAC, 113.G6, was isolated from the Whitehead Library using the STS 195.A8-R. It was determined that 113.G6 was chimeric, but had significant overlap (500 kb) with 195.A8. For all subsequent experiments, the retrofitted derivatives of YACs C9.E7, 195.A8, and 113.G6 were used.

Introduction of YACs into bg Mouse Fibroblasts.

Retrofitted YACs were introduced by spheroplast fusion (Huxley, C. et al., 1991, Genomics 9:742–750) or microinjection (Gnirke, A. et al., 1993, Genomics 15:659–667) into fibroblasts derived from a C57BL/6J beige mouse (Perou, C. M. & Kaplan, J., 1993, Som. Cell Mol. Gen. 19:459–468). These cells retained the bg phenotype of abnormally large lysosomes with a clustered perinuclear distribution. This phenotype could be corrected by somatic cell fusion with normal cells (Perou, C. M. & Kaplan, J., 1993, Som. Cell Mol. Gen. 19:459–468). Mutant cells containing YACs were selected for resistance to the neomycin analogue G418, and colonies were examined for lysosomal distribution and morphology by fluorescent microscopy using Lucifer Yellow labeling.

Seven G418 resistant colonies from several independent spheroplast fusions using YAC 195.A8 were obtained. The efficacy of YAC transfer using spheroplast fusion was extremely low as determined by G418-resistance. A frequency of colony formation of $10^7$ was calculated. Southern and PCR analyses (Peterson, K. R. et al., 1993, Proc. Natl, Acad. Sci. U.S.A. 90:7593–7597) confirmed that all resistant colonies contained YAC "right" arm vector sequences. Only three of the seven colonies, however, contained YAC "left" arm vector sequences, indicating that the other four colonies contained only a fragment of the YAC. Of the seven colonies, five showed a complemented phenotype (FIG. 3B). These five colonies included the three complete YAC colonies and two of the fragmented YACs. Complemented cells showed dramatically smaller lysosomes than the parental bg cells (FIGS. 3A and 3C). Other features indicating a corrected phenotype included lysosomes which were no longer clustered in the perinuclear region, and the disappearance of tubular lysosomes. Tubular lysosomes are frequently seen in macroblasts but are not observed in normal fibroblasts. Tubular lysosomes are seen, however, in bg mouse and Aleutian mink fibroblasts.

YAC 113.G6 was introduced into murine bg fibroblasts using spheroplast fusion and two independent colonies were obtained. One colony was complemented and contained sequences from both YAC arms. The other colony was not complemented and contained only a fragmented copy of the YAC. YAC C9.E7 was microinjected into the bg mouse cell line and thirty independent colonies were obtained, five of which contained both YAC vector arms as determined by PCR. All of these colonies retained the bg phenotype. Cells resistant to G418 due to YAC introduction, either uncomplemented cells carrying fragmented YACs or C9.E7 microinjected cells, showed no complemented features regardless of the concentration of G418 employed.

In the complemented colonies isolated using a G418 concentration of 400–500 μg/ml, it was observed that not all cells showed the complemented phenotype. Some colonies appeared to contain a mixture of bg and complemented cells (FIG. 3B). Two possibilities were considered. First, the colonies, as removed from the plate, might contain a mixture of G418-resistant complemented cells and G418-resistant bg cells. Second, the YAC might be unstable and, at the concentration of G418 employed, some cells may lose the YAC and revert to the bg phenotype. To distinguish between these possibilities, the cell line 195–4 was incubated in 800 μg/ml G418 and lysosomal morphology examined after 10 days. Examination of multiple fields and several hundred cells revealed very few (<1%) bg appearing cells (FIG. 3C). When these complemented cells were incubated in the absence of G418 there was a time-dependent return to the bg phenotype. Seven days after the removal of G418, approximately 1.0% of the cells showed the mutant phenotype, but after thirty days greater than 30% of the cells showed the bg phenotype (FIG. 3D). These results demonstrate that complementation of the mutant phenotype was YAC-dependent.

The fact that not all YACs complement, and that not all spheroplast fusion generated colonies were complemented, suggests that the act of introducing these YACs along with yeast DNA does not cause the reversion of the bg phenotype. Further, the fact that only certain fragmented YAC 195.A8 or 113.G6 YAC molecules failed to correct the phenotype, suggests that fragmented YACs can be utilized as part of a strategy to localize the relevant gene.

Complementation of the CHS Defect in Other Species by a Murine YAC. To analyze the nature of defective genes in different species exhibiting bg phenotypes, both complemented and uncomplemented 195.A8 YAC containing bg cells were fused with cultured Aleutian mink or human CHS derived cells (Perou, C. M. & Kaplan, J., 1993, Som. Cell Mol. Gen. 19:459–4682). When Aleutian mink cells were the recipient cell line, complementation occurred only when the complemented bg mouse cell lines were used. Identical results were obtained with the human CHS fibroblast cell line GM02075A. It was necessary to fuse complemented murine cells to mink and human cells as neither mink nor human cells will accept YACs using the spheroplast fusion or microinjection protocols. These results strongly support the hypothesis that a similar gene (or genes) is responsible for the Chediak phenotype.

It was found that the choice of cell lines was the most important parameter in determining the efficacy of YAC transfer. No G418-resistant colonies were ever obtained using primary human, mouse, or mink fibroblasts as the recipients. Colonies were obtained using the long term cultured bg mouse cell line MCHSF2. A ten to twenty fold increase in the frequency of transformants was obtained using mouse L-cells. These results suggest that increased chromosome instability resulting from long term culture may contribute to increased transformation efficiency.

8. EXAMPLE

Positional Cloning of a Candidate Beige Gene

The Example presented in this Section describes the cloning of a gene, referred to here as the 22B/30B gene, which represents a candidate murine beige (bg) gene. Extending the studies described in Sections 6 and 7, above, the 22B/30B gene was identified via a refinement of the YAC mapping data presented above, couple with a positional cloning strategy. Characterization of the 22B/30B gene indicated that the gene produces an approximately 12–14 kb mRNA that encodes a novel protein exhibiting strong nucleotide homology to multiple expressed sequence tags (ESTs), including human ESTS.

8.1. MATERIALS AND METHODS

YAC Characterization. The Princeton and Whitehead mouse YAC libraries were screened by PCR with primers specific for the right end sequence of YAC 195.A8, as described above. This screen resulted in the isolation of two additional YACS, 137.A10 and B27.F7. An additional YAC from this region was isolated from the Princeton library using primers from the end sequences of the cDNA clone 22B, described in Section 8, below. The F primer was 5'-ATTGGCTAGTGTGTGCAGAC-3' (SEQ ID NO:25)and the R primer was 5'-GAAGCAGATGACTGAGCAGA-3'

(SEQ ID NO:26). PCR reactions were performed on an Idaho Technologies Thermal Cycler under the following conditions: 20 sec. 94° C. hot start, 94° C. 0 sec./55° C. 0 sec./72° C. 30 sec. for 30 cycles.

All other YAC techniques were as described, above, in Section 7.1.

Isolation of cDNAs and Preparation of Plugs. Agarose blocks containing yeast chromosomal and YAC 195.A8 DNA were prepared as described in Gnirke et al (Gnirke, A. et al., 1993, Genomics 15:659–667), loaded in a 1%, 0.5× TBE gel and electrophoresed in a Bio-Rad DRII clamped homogeneous electric field (CHEF) apparatus (Bio-Rad Laboratories, Inc., Hercules, Calif.) at 200 V with a constant pulse time of 60 sec. for 24 hrs. The YAC was excised and purified using the GeneClean II Kit according to manufacturers instructions (Bio 101, Inc., La Jolla, Calif.). Gel-purified YAC DNA was radiolabelled with $^{32}$P-dCTP by random priming. The hybridization probe was pre-competed with 100 µg of sonicated genomic mouse DNA, 50 µg of mouse COT-1 DNA (GIBCO BRL, Gaithersburg, Md.) and 20 µg of sonicated pYAC55 DNA (Sigma, St. Louis, Mo.) for 2 hrs at 65° C. Filters containing plaques from a C57BL/6J mouse E16.5 cDNA library (Stratagene, La Jolla, Calif.) were prehybridized at 65° C. for 6–8 hrs in RapidHyb buffer (Amersham, Arlington Heights, Ill.) containing 100 µg/ml sonicated mouse genomic DNA, 4 µg/ml COT-1 DNA and 2 µg/ml sonicated pYAC55 DNA. Hybridization proceeded overnight at 65° C. Filters were washed to 0.1×SSC at 65° C. Clones positive after a secondary screen were recovered as phagemids.

Genomic DNA Isolation and Southern Blots. High molecular weight mouse DNA for Southern Blots and PCR analysis was either purchased from the Jackson Labs (Bar Harbour, Me.) or isolated using a Qiagen tip 2500 (Qiagen, Inc., Chatsworth, Calif.). Southern blots were prepared and hybridized according to (Jenkins, N. A. et al., 1982, J. Virol. 43:26–36), exposed to Fuji Imaging Plates, Type BAS-IIIS and visualized using a Fujix Bas 1000 Phosphoimager (Fuji Film I & I, Fuji Medical Systems U.S.A., Inc., Stamford, Conn.).

RNA Isolation, Northern Blots. Total RNA was isolated from various mouse tissues and cultured mouse and human melanoma cells using the RNA STAT-60 reagent (Tel-Test "B", Inc., Friendswood, Tex.) according to manufacturer's instructions. For Northern blot preparations, 25 µg of this RNA was run on a 1.5% denaturing gel and transferred overnight onto Zeta pore membrane (CUNO, Inc., Meriden, Conn.) in 10×SSC. Filters were hybridized with a gel purified 811 bp HindIII +Pst I fragment from the clone 30B that was radiolabeled with $^{32}$P-dCTP by random priming. Hybridization was performed at 65° C. overnight in QuikHybe Hybridization Solution (Stratagene, La Jolla, Calif.). Filters were washed to 0.1×SSC at 65° C. and visualized by X-ray film autoradiography.

8.2. RESULTS

YAC characterization. The minimal bg interval was refined by further in vitro complementation of bg murine fibroblasts with additional YACS (FIG. 2B). First, it was demonstrated that YAC151.H1, which contains restriction fragments in common with YAC195.A8, as defined by fingerprinting with COT-1 DNA, was not capable of complementing bg. Furthermore, YAC137.A10 which is nearly identical to that of YAC 113.G6, also failed to complement the bg phenotype. These studies, therefore, demonstrate that the minimal bg region must lie between the proximal end of YAC137.A10 and the distal end of YAC151.H1.

Isolation of candidate genes in the bg minimal region. The complementing YAC195.A8 (See Section 7, above) was gel purified, radiolabelled and used to isolate clones from an E16.5 day mouse embryo cDNA library. Forty five clones were isolated. Based on sequence analysis and mapping to the YAC-defined physical map, six genes were defined.

Of particular note was a gene, referred to herein as the 22B/30B gene, defined by two cDNA clones, 30B and 22B. These clones had 447 bp of overlap sequence, with 30B extending more 5' than 22B, and were located within the region predicted to contain the bg gene. In order to determine whether the cDNA clones 22B and 30B mapped physically to the interval predicted to contain the bg gene, the clones were used as probes against restriction enzyme digested YAC DNA. The non-complementing YAC137.A10 lacked two HindIII 30B hybridizing bands that were present in complementing YAC113.G8. Likewise, YAC151H.1 lacked some HindIII bands hybridizing with 22B.

Based upon the complementation data, it was predicted that the complete bg gene would lie in the region of overlap between YACs 113.G6 and 195.A8, but would be disrupted or absent from the non-complementing YACs 137.A10 and 151.H1. This was the pattern observed for the 22B/30B gene, making it a candidate for the bg gene.

Sequence of 22B/30B gene. Sequencing of the two overlapping cDNA clones, 22B and 30B, of the putative bg gene totaled 6831 bp of contiguous sequence (FIG. 4; SEQ ID NO:1). 6559 bp of this was open reading frame followed by a stop codon at nucleotide 6560 and 269 bp of the 3' untranslated region (with 30B present 5' of this contiguous sequence relative to 22B).

The 22B/30B protein sequence predicted from the 22B/30B nucleotide sequence is 2186 amino acids and encodes a novel protein (FIG. 4; SEQ ID NO:2). A BLASTX (1993, Nature Genetics 3:266–272) search with the 22B/30B protein amino acid sequence did, however, identify significant homologies to several sequences. Such sequences included an anonymous S.cerievisiae protein, YCRO32w, encoded by a 7 kb MRNA, two C. elegans novel proteins, T01H10.8 and F10F2.1 and a human gene, cell division control protein 4-related protein, CDC4L. Amino acid residues 1520–1807 of the 22B/30B protein sequence exhibited the highest level of amino acid conservation. Within this region, the S.cerievisiae and C. elegans proteins showed 50% identity and 75% similarity to murine 22B/30B. The homology to the human CDC4L protein spanned a shorter segment (22B/30B amino acid residues 1675–1806), but again showed 50% identity.

A known protein motif was found within the 22B/30B amino acid sequence. Specifically, a WD40 or G protein-beta subunit repeat motif (van der Voorn, L. & Ploegh, H. L., 1992, FEBS Lett. 307:131–134) was found to be located at amino acid residue 2016–2030. This motif was originally identified in the β-subunit of the G-protein transducin (Duronio, R. J. et a., 1992, Proteins 13:41–56), and is thought to be involved in mediating protein-protein interactions (Wang, D. S. et al., 1994, Biochem. Biophys. Res. Comm. 203:29–35). None of the proteins found to be homologous to the 22B/30B protein sequence contain such a motif.

Comparison of the 22B/30B DNA sequence to the dbEST database identified homologies to ESTs from two human cDNA libraries. Specifically, 22B/30B nucleotides 725–942 were 82% identical to human cDNA clone H51623 isolated from a fetal liver and spleen cDNA library, 22B/30B nucleotides 1530–1596 were 88% identical and 22B/30B nucleotides 1596–1842 were 74% identical to the human cDNA clone H50968 isolated from the same fetal cDNA library. 22B/30B nucleotides 1096–1269 were 89% identical to the cDNA clone Z21358 isolated from an adult human testis library. 22B/30B nucleotides 1092–1164 were 87% identical and nucleotides 1165–1302 were 91% identical to the human cDNA clone Z21296 isolated from the same testis cDNA library. In summary, the 22B/30B sequence from approximately nucleotide 725 to nucleotide 1842 appeared to be highly homologous at the nucleotide level to one or more human gene sequences.

Expression of the 22B/30B gene. PCR analysis from reverse transcribed murine mRNA was used for detecting expression of the 22B/30B gene. Such an analysis indicated that the 22B/30B message was expressed in each of the tissues tested, namely liver, spleen, kidney, thymus, muscle, fat, heart, lung, stomach, pancreas and cultured fibroblasts. Using an 811 bp probe from the most 5' end of the available cDNA 22B/30B sequence, a Northern blot of mRNA from two human melanoma cell lines, WM-115 and WM266-4 and from the mouse B16 melanoma cell line showed hybridization to an approximately 12–14 kb message. It should be noted that the 811 bp probe used overlapped with the portion of the 22B/30B sequence discussed above that exhibits 82% identity to a human EST.

9. EXAMPLE

Identification of the Beige Gene Via Beige Mutation Detection

The Example presented herein describes the successful identification of the bg gene, the homolog of the gene responsible for the human Chediak-Higashi syndrome (CHS), via the sequencing of two independent mutant bg alleles. The mutation detection analysis revealed that the bg gene corresponds to the 22B/30B gene described in Section 8, above.

9.1. MATERIALS AND METHODS

Southern blot/Genomic DNA isolation. The procedures utilized were as described in Section 8.1, above.

RT-PCR. RNA was isolated as described, above, in Section 8.1. Reverse transcription-polymerase chain reactions (RT-PCR) were carried out as follows: briefly, 0.5 μg of total RNA was reverse transcribed into cDNA using equal concentrations of random and oligo(dT)$_{15}$ primers and AMV reverse transcriptase (Promega Corp., Madison, Wis.) in a final volume of 200 μl. One μl of each reaction was amplified with 0.25 μM of each of the appropriate primers. The primers were as follows: 22B-5F—5'-TCTTCTTGTCCTGCCTGATGCT-3' (SEQ ID NO:27); 22B-D11— 5'-GTGCTTCACTTCCTCCAGATC-3' (SEQ ID NO:28); 22B-D6—5'-GCCTCATTCCAGCGAAGC-3' (SEQ ID NO:29); 22B-D10—5'-CTGGATAGCAGGTGATGGGTGGTTA-3' (SEQ ID NO:30). Amplifications were carried out in a final volume of 25 μl in 1×PCR buffer containing 1.5 mM MgCl$_2$, 0.5 Units Ampli Taq polymerase (Perkin-Elmer-Cetus). After an initial denaturation step at 94° C. for 2 mins, samples were subjected to 35 cycles of 40 sec at 94° C., 50 sec at 57° C., and 2 mins at 72° C. Following a 10 mins final extension at 72° C., samples were stored at 4° C. PCR products were separated by electrophoresis through 2%, 1×TBE agarose gels.

PCR: Mouse genomic DNA (C57BL/6J, C57BL/6J-ba/ba, Satin/Beige-bg/bg DNA) was amplified using the following primers: 228F: 5'-TGCTGTGGATTATATGAACTC-3' (SEQ ID NO:31) and 228R: 5'-GGTCTCTATTAGTCCGAGAAC-3' (SEQ ID NO:32). Amplification parameters were as follows: 2 minutes hot start 94° C., 94° C. 30 seconds/52° C. 30 seconds/72° C. 4 minutes, for 30 cycles on a Perkin-Elmer DNA Thermal Cycler.

9.2 RESULTS bg gene mutation detection. Described herein are bg gene mutation studies which reveal that the gene corresponding to the 22B/30B gene, described above, in Section 8, corresponds to the murine bg gene. Specifically, nucleotide defects within two bg mutant alleles are demonstrated to lie within the 22B/30B region and to result in the production of C terminally truncated proteins.

The original bg mutation arose in a radiation experiment at the Oak Ridge National Laboratory. Hence it was probably radiation induced and was either on a chromosome originating from the C3H/R1 or the 101/R1 inbred strains of mice. Because the original bg mutation was radiation-induced, it was possible that the mutation could be visible via Southern blot analysis. There have been many subsequent re-mutations of the mouse bg gene, all of which have arisen spontaneously. Some of these are extinct with no surviving tissues or DNA. For others, for example C57BL-bg$^{10J}$ and C57BL-bg$^{11J}$ although the mutation is extinct there is DNA available (Jackson Laboratories), and for others, the mutation is still available as a live mutant stock, e.g. SJL-bg, C57BL-bg$^J$, C3H/HeJ-bg$^{2J}$, and DBA/2J-Co-bg$^{8J}$. Southern blot analysis of these multiple bg alleles and their appropriate normal controls showed no polymorphic bands for probes from either the 5' or 3' regions of the 22B/30B gene sequence, although a probe, 22B/30B nucleotides 6489–6719, did make it possible to determine that the original bg allele arose on a C3H-like chromosome, not a 101/R1 derived chromosome. In contrast, when a 510 bp fragment, 22B/30B nucleotides 1618–2127, was used as a probe, the original mutant bg allele showed altered bands for 7 out of 9 enzymes (FIGS. 5A–5D).

PCR primers, as described above, in Section 9.1, were designed which surrounded and spanned the 510 bp region and were used to amplify genomic DNA and cDNA. One primer set, designated 228F and R, amplified a 2 kb genomic fragment from C57BL/6J but amplified a 3 kb genomic fragment from the strain carrying the original bg allele. A similar set of primers, 22B-5F and 22B-11, was used to amplify cDNA prepared from the kidneys of C57BL/6J, C3H/HeJ and SJL/J-bg. A single band of 312 bp was detected in both C57BL/6J and C3H/HeJ. cDNA from the SJL/J-bg, mouse, however, produced two bands, 428 bp and 637 bp.

Both the RT-PCR products, as well as the genomic DNA PCR products were isolated and directly sequenced using standard procedures. Sequencing of the amplified products revealed that the bg mutation was located within the 22B/30B gene. Specifically, analysis of the amplified sequences revealed that the increased size of the genomic product from the bg allele was the result of an incomplete LINE 1 element (Burton, F. H. et al., 1986, J. Mol. Biol. 187:291–304) insertion into an intron contained within the 30B/22B gene's genomic DNA. As this element contained adventitious splice donor and acceptor sites, two aberrant mRNAs were created that each result in a frame shift. The 428 bp RT-PCR product had a 116 bp LINE 1 insertion between 22B/30B nucleotides 2235 and 2236, while analysis of the larger product demonstrated a 325 bp LINE 1 insertion at this same location. Both of these two LINE 1 insertions results in the introduction of stop codons and in a 22B/30B protein product that is truncated by 1442 amino acids. See FIG. 6 for a diagram depicting the location of these insertions.

Analysis of another bg allele, $bg^{8J}$, by sequencing of an RT-PCR product produced using primers 22B-D6 and 22B-D10, identified a C to T base change creating a stop codon at 22B/30B bp 2027. The mutation resulted in the production of a truncated 22B/30B protein missing the last 1511 amino acids.

It should be noted that the truncated proteins produced by each of the bg (22B/30B) mutant alleles lack the amino acid sequence homologous to *S. cerevisiae*, *C. elegans* and human CDC4L genes and also delete the putative WD40 motif (described, above, in Section 8).

In summary, two independent bg gene mutations were revealed to lie within the sequence of the 22B/30B gene, thus presenting compelling evidence identifying the 22B/30B gene to, in fact, correspond the bg gene.

10. EXAMPLE

Identification and Characterization of the Humane bg Gene

The Example presented herein describes the successful identification and characterization of cDNA molecules corresponding to the human beige (bg) gene. Characterization of the isolated cDNA molecules revealed that the human bg gene undergoes alternative splicing, yielding long (putative full length) and short forms of bg transcripts and bg gene products, as described below.

10.1. MATERIALS AND METHODS cDNA cloning. A human retina λgt10 library (Cat. No. HL1132a; Clontech, Palo Alto Calif.) was screened with a mixture of three DNA fragments isolated from mouse beige clones. They were, in order from 5' to 3', 30B (bp 82–921 of FIG. 4), 22B (bp 1650–2160 of FIG. 4), and K2+K5 (bp 6520–6750 of FIG. 4).

The three probes were labeled with $^{32}$P by random priming and hybridized with filters representing $10^6$ clones overnight at 42° C. in Church's buffer (7% SDS, 250 mM NaHPO$_4$, 2 μM EDTA, 1% BSA). The filters were washed in 2×SSC, 1% SDS at 42° C. Positive plaques were replated and treated in the same manner. Phage DNA was prepped by a standard plate lysate method. After digestion of the phage DNA with EcoRI, cDNA inserts were isolated and subcloned into pBluescript (Stratagene; La Jolla Calif.) for DNA sequencing. DNA sequencing was performed according to standard techniques.

cDNA identified in the above screening was used to probe a λgt10 human fetal liver library (Cat. No. HL3020a; Clontech, Palo Alto Calif.) and the human retina library described above. Filters representing $10^6$ clones of each library were hybridized at 65° C. overnight with $^{32}$P labelled probe in Church's buffer and washed in 0.1×SSC, 0.1% SDS at 65° C. Positive plaques were replated and rescreened in the same manner. Phage DNA was prepared, and cDNA inserts were isolated and subcloned as described above.

10.2. RESULTS

In order to identify the human bg gene, murine bg gene sequences were used to screen human cDNA libraries. Screening, phage isolation and details are presented in Section 10.1, above.

First, a murine bg sequences were used to probe a human retina cDNA library. This screen resulted in the identification of a phage containing a 2 kb cDNA insert (designated fvhx004). The cDNA insert was isolated and subcloned. The fvhx004 cDNA insert was then used to rescreen the human retina cDNA library and to screen a λgt10 human fetal liver library, as described in Section 10.1, above. This screen yielded two positive phage from the human fetal liver library. One phage contained a 4.4 kb cDNA insert (designated fvh1006) and the second contained a 6.3 kb cDNA insert (designated fvh1009). A 3 kb subclone of fvh1006 which overlapped the fvh1009 clone was designated fvh1006a. Additional subclones of fvh1006 were designated fvh1006b (a 1 kb sublcone) and fvh1006c (a 400 bp subclone). An additional positive phage was also isolated from the human retina library. This phage contained a 2 kb cDNA insert (designated fvhx003a). A 1.1 kb HindIII/EcoRV fragment from fvh1009 was used to rescreen the human retina library. This screen resulted in one positive phage containing a 1.6 kb insert, designated fvhx015.

The isolated clones were sequenced according to standard procedures. A database search using human bg nucleotide sequence revealed extensive homology to human cDNA clones H51623 (96% identity), Z21358 (99% identify) and Z21296 (97% identity), as indicated in parentheses. These clones were described in Section 9, above.

Comparison of the human bg sequence with that of mouse bg sequences revealed a 378 base pair region present in mouse sequence which was absent from the sequence obtained from the isolated human clones. PCR of both the retina and liver libraries with primers flanking this sequence, however, revealed that the sequence was present in both these libraries. Sequencing of the resultant PCR products, coupled with the sequence obtained from the isolated clones, produced what is referred to below as the "long" form of bg gene sequence, while the sequence of the isolated clones, alone, yielded what is referred to below as the "short" form of bg gene sequence.

FIG. 7 presents the long form (putative full length) human hg gene nucleic acid sequence. FIG. 7 further depicts the derived amino acid sequence encoded by the long form (putative full length) human bg gene nucleic acid sequence shown therein. As shown in FIG. 7, the predicted long form human bg gene product contains 3801 amino acid residues. As in the mouse bg gene product described in Section 8, above, the human bg gene product contains a WD40 or G protein-beta subunit repeat motif. In the long form human bg gene product this motif is present at amino acid residues 3694–4708.

FIG. 8 presents the short form human bg gene nucleic acid sequence. FIG. 8 further depicts the derived amino acid sequence encoded by the short form human bg gene nucleic acid sequence shown therein. As shown in FIG. 8, the predicted short form human bg gene product contains 3672 amino acid residues. It is missing base pairs 7544–7921 of the long form depicted in FIG. 7. The short form bg nucleic acid sequence retains the same frame as the long form throughout its length and encodes a bg gene product which is missing amino acid residues 2451–2577 of the long form depicted in FIG. 7. The WD40 sequence motif is present in the short form bg gene product at amino acid residues 3565–3579 depicted in FIG. 8.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

---

What is claimed is:

1. An isolated nucleic acid molecule comprising:

(a) a nucleic acid molecule encoding a polypeptide comprising the amino acid sequence shown in SEQ ID NO:2;

(b) a nucleic acid molecule encoding a polypeptide comprising the amino acid sequence shown in SEQ ID NO:10; or (c) a nucleic acid molecule encoding a polypeptide comprising the amino acid sequence shown in SEQ ID NO:12.

2. The isolated nucleic acid molecule of claim 1 wherein the nucleic acid molecule is a cDNA molecule.

3. The isolated nucleic acid molecule of claim 1, wherein the nucleic acid molecule comprises a nucleotide sequence which encodes the polypeptide shown in SEQ ID NO:2.

4. The isolated nucleic acid molecule of claim 3 wherein the nucleic acid molecule comprises the nucleotide sequence shown in SEQ ID NO: 1.

5. The isolated nucleic acid molecule of claim 1, wherein the nucleic acid molecule comprises a nucleotide sequence which encodes the polypeptide shown in SEQ ID NO:10.

6. The isolated nucleic acid molecule of claim 5 wherein the nucleic acid molecule comprises the nucleotide sequence shown in SEQ ID NO:9.

7. The isolated nucleic acid molecule of claim 1, wherein the nucleic acid molecule comprises a nucleotide sequence which encodes the polypeptide shown in SEQ ID NO:12.

8. The isolated nucleic acid molecule of claim 7 wherein the nucleic acid molecule comprises the nucleotide sequence shown in SEQ ID NO:11.

9. A nucleotide vector comprising the nucleic acid molecule of claim 1.

10. An expression vector comprising the nucleic acid molecule of claim 1 in operative association with a nucleotide regulatory sequence that controls expression of the nucleic acid in a host cell.

11. An isolated host cell genetically engineered to contain the nucleic acid molecule of claim 1.

12. An isolated host cell genetically engineered to contain the nucleic acid molecule of claim 1 in operative association with a regulatory sequence that controls expression of the nucleic acid in the host cell.

13. An isolated nucleic acid molecule which comprises an allelic variant of a second nucleic acid molecule comprising the nucleotide sequence shown in SEQ ID NO:1, SEQ ID NO-9 or SEQ ID NO:11, wherein the nucleic acid molecule hybridizes under highly stringent conditions to the complement of the second nucleic acid molecule, said highly stringent conditions comprising hybridization to filter-bound DNA in 0.5 M $NaHPO_4$, 7% SDS, 1 mM EDTA at 65° C. and washing in 0.1×SSC/0.1% SDS at 68 ° C., and wherein the nucleic acid molecule is expressed at the same chromosomal locus as that expressing a nucleic acid molecule comprising SEQ ID NO: 1, SEQ ID NO:9 or SEQ ID NO-11.

14. A nucleotide vector comprising the nucleic acid molecule of claim 13.

15. An expression vector comprising the nucleic acid molecule of claim 5 in operative association with a nucleotide regulatory sequence that controls expression of the nucleic acid in a host cell.

16. An isolated host cell genetically engineered to contain the nucleic acid molecule of claim 13.

17. An isolated host cell genetically engineered to contain the nucleic acid molecule of claim 13 in operative association with a regulatory sequence that controls expression of the nucleic acid in the host cell.

18. The isolated nucleic acid molecule of claim 13, wherein the nucleic acid molecule comprises an allelic variant of a second nucleic acid molecule comprising the nucleotide sequence shown in SEQ ID NO: 1.

19. The isolated nucleic acid molecule of claim 13, wherein the nucleic acid molecule comprises an allelic variant of a second nucleic acid molecule comprising the nucleotide sequence shown in SEQ ID NO:9.

20. The isolated nucleic acid molecule of claim 13, wherein the nucleic acid molecule comprises an allelic variant of a second nucleic acid molecule comprising the nucleotide sequence shown in SEQ ID NO. 11.

* * * * *